(12) United States Patent
Lassen et al.

(10) Patent No.: US 7,923,232 B2
(45) Date of Patent: Apr. 12, 2011

(54) HAFNIA PHYTASE

(75) Inventors: Soeren Flensted Lassen, Farum (DK);
Carsten Sjoeholm, Alleroed (DK); Lars Kobberoee Skov, Ballerup (DK)

(73) Assignee: Novozymes A/S, Bagsvaerd (DK)

( * ) Notice: Subject to any disclaimer, the term of this patent is extended or adjusted under 35 U.S.C. 154(b) by 426 days.

(21) Appl. No.: 12/055,694

(22) Filed: Mar. 26, 2008

(65) Prior Publication Data

US 2008/0263688 A1   Oct. 23, 2008

Related U.S. Application Data

(60) Provisional application No. 60/908,705, filed on Mar. 29, 2007.

(30) Foreign Application Priority Data

Mar. 26, 2007   (EP) .................................... 07104870

(51) Int. Cl.
*C12N 9/16* (2006.01)
*A23J 1/00* (2006.01)
*A61K 38/46* (2006.01)

(52) U.S. Cl. ........................ 435/196; 435/19; 536/23.2

(58) Field of Classification Search ................. 435/196, 435/19; 536/23.2
See application file for complete search history.

(56) References Cited

FOREIGN PATENT DOCUMENTS

| WO | WO 2006/043178 | 4/2006 |
|---|---|---|
| WO | WO 2008/092901 A2 | 8/2008 |
| WO | WO 2008/097619 A2 | 8/2008 |
| WO | WO 2008/116878 A1 | 10/2008 |

OTHER PUBLICATIONS

Greaves et al, Nature, vol. 200, pp. 1231-1332 (1963).
Huang et al, Biochemical and Biophysical Research, vol. 350, No. 4, pp. 884-889 (2006).
Ryan et al, Computer Methods and Programs in Biomedicine, vol. 85, No. 1, pp. 69-76 (2006).
Yoon et al, Enzyme and Microbial Technology, vol. 18, No. 6, pp. 449-454 (1996).
Zinin et al, Database Biosis, Abstract—XP002392194. (2003).
Zinin et al, Phytase Activty of Several Bacteria Groups, Article in Russian XP008045468, pp. 3-10 (2003).
Gu et al., vol. 23, No. 6, pp. 1017-1021 (2007).
Kim et al., Applied Microbiol Biotechnology, vol. 79, pp. 751-758 (2008).
Lehmann et al., Current Opinion in Biotechnology, vol. 12, pp. 371-375 (2001).
Lim et al., Nature Structural Biology, vol. 7, No. 2, pp. 108-113 (2000).
Mullaney et al., Biochemical and Biophysical Research Communications, vol. 328, pp. 404-408 (2005).
Shi et al., Aquaculture, vol. 275, pp. 70-75 (2008).
Zinin et al., FEMS Microbiology Letters, vol. 236, pp. 283-290 (2004).

*Primary Examiner* — Tekchand Saidha
(74) *Attorney, Agent, or Firm* — Elias Lambiris

(57) ABSTRACT

The present invention relates to isolated polypeptides having phytase activity and isolated polynucleotides encoding the polypeptides. The polypeptides are related to a phytase derived from *Hafnia alvei*, the amino acid sequence of which is shown in the appended sequence listing as SEQ ID NO: 10. The invention also relates to nucleic acid constructs, vectors, and host cells comprising the polynucleotides as well as methods for producing and using the polypeptides, in particular within animal feed.

11 Claims, 54 Drawing Sheets

Residual inositol-phosphate bound phosphorous (mg IP-P/g feed) after *in vitro* incubation. Comparison of the *Hafnia alvei* phytase with a *Citrobacter braakii* phytases dosed from 125-500 FYT/kg feed.

Residual inositol-phosphate bound phosphorous (mg IP-P/g feed) after *in vitro* incubation. Comparison of the *Hafnia alvei* phytase with a *Peniophora lycii* phytases dosed from 250 FYT/kg feed and 500 FYT/kg feed.

Figure 3

Appendix

```
ATOM      1  N    ALA     4      20.713  17.796  42.010  1.00  12.63      PROT
ATOM      2  CA   ALA     4      21.283  17.898  40.629  1.00  11.99      PROT
ATOM      3  C    ALA     4      22.578  17.097  40.693  1.00  11.33      PROT
ATOM      4  O    ALA     4      23.356  17.160  41.635  1.00  11.74      PROT
ATOM      5  CB   ALA     4      21.506  19.352  40.251  1.00  12.29      PROT
ATOM     11  N    PRO     5      22.811  16.324  39.616  1.00  10.64      PROT
ATOM     12  CA   PRO     5      23.904  15.337  39.557  1.00   9.73      PROT
ATOM     13  C    PRO     5      25.274  15.935  39.877  1.00   6.97      PROT
ATOM     14  O    PRO     5      25.533  17.103  39.568  1.00   8.47      PROT
ATOM     15  CB   PRO     5      23.683  14.724  38.150  1.00   9.76      PROT
ATOM     16  CG   PRO     5      22.514  14.991  37.638  1.00   9.88      PROT
ATOM     17  CD   PRO     5      22.102  16.305  38.234  1.00  10.41      PROT
ATOM     25  N    ALA     6      26.125  15.130  40.618  1.00   8.17      PROT
ATOM     26  CA   ALA     6      27.464  15.547  40.907  1.00   7.59      PROT
ATOM     27  C    ALA     6      28.259  16.013  39.693  1.00   7.10      PROT
ATOM     28  O    ALA     6      28.357  15.305  38.687  1.00   6.94      PROT
ATOM     29  CB   ALA     6      28.196  14.414  41.635  1.00   7.58      PROT
ATOM     35  N    GLY     7      28.783  17.227  39.784  1.00   6.31      PROT
ATOM     36  CA   GLY     7      29.579  17.803  38.702  1.00   5.32      PROT
ATOM     37  C    GLY     7      28.790  18.675  37.748  1.00   4.11      PROT
ATOM     38  O    GLY     7      29.382  19.381  36.938  1.00   4.06      PROT
ATOM     42  N    PHE     8      27.455  18.603  37.835  1.00   3.50      PROT
ATOM     43  CA   PHE     8      26.572  19.411  36.970  1.00   2.73      PROT
ATOM     44  C    PHE     8      26.594  20.881  37.404  1.00   2.50      PROT
ATOM     45  O    PHE     8      26.353  21.169  38.592  1.00   2.39      PROT
ATOM     46  CB   PHE     8      25.134  18.885  37.036  1.00   2.80      PROT
ATOM     47  CG   PHE     8      24.777  17.897  35.952  1.00   3.44      PROT
ATOM     48  CD1  PHE     8      25.501  16.720  35.792  1.00   4.43      PROT
ATOM     49  CD2  PHE     8      23.681  18.135  35.119  1.00   3.41      PROT
ATOM     50  CE1  PHE     8      25.156  15.792  34.794  1.00   5.73      PROT
ATOM     51  CE2  PHE     8      23.329  17.221  34.119  1.00   4.46      PROT
ATOM     52  CZ   PHE     8      24.069  16.062  33.959  1.00   5.76      PROT
ATOM     62  N    GLN     9      26.679  21.789  36.436  1.00   2.00      PROT
ATOM     63  CA   GLN     9      26.688  23.217  36.709  1.00   2.46      PROT
ATOM     64  C    GLN     9      25.696  23.952  35.795  1.00   2.60      PROT
ATOM     65  O    GLN     9      25.713  23.744  34.581  1.00   2.00      PROT
ATOM     66  CB   GLN     9      26.093  23.796  36.904  1.00   2.76      PROT
ATOM     67  CG   GLN     9      26.175  25.296  36.808  1.00   6.29      PROT
ATOM     68  CD   GLN     9      27.709  25.628  38.220  1.00   9.39      PROT
ATOM     69  OE1  GLN     9      26.198  25.063  39.196  1.00  12.04      PROT
ATOM     70  NE2  GLN     9      26.766  26.656  38.329  1.00  10.33      PROT
ATOM     79  N    LEU    10      24.831  24.758  36.400  1.00   2.00      PROT
ATOM     80  CA   LEU    10      23.865  25.567  35.665  1.00   2.37      PROT
ATOM     81  C    LEU    10      24.649  26.702  35.027  1.00   2.28      PROT
ATOM     82  O    LEU    10      25.310  27.463  35.717  1.00   2.01      PROT
ATOM     83  CB   LEU    10      22.802  26.092  36.605  1.00   2.26      PROT
ATOM     84  CG   LEU    10      21.740  26.395  35.965  1.00   2.58      PROT
ATOM     85  CD1  LEU    10      20.990  26.242  34.696  1.00   3.29      PROT
ATOM     86  CD2  LEU    10      20.784  27.505  37.034  1.00   2.73      PROT
ATOM     98  N    GLU    11      24.574  26.808  33.704  1.00   2.72      PROT
ATOM     99  CA   GLU    11      25.355  27.805  32.994  1.00   3.42      PROT
ATOM    100  C    GLU    11      24.885  28.965  32.570  1.00   3.46      PROT
ATOM    101  O    GLU    11      24.933  30.107  32.569  1.00   3.40      PROT
ATOM    102  CB   GLU    11      26.033  27.195  31.754  1.00   2.69      PROT
ATOM    103  CG   GLU    11      27.260  26.342  32.091  1.00   4.83      PROT
ATOM    104  CD   GLU    11      28.231  26.239  30.933  1.00   5.70      PROT
ATOM    105  OE1  GLU    11      27.872  26.626  29.809  1.00   5.87      PROT
ATOM    106  OE2  GLU    11      29.362  25.728  31.152  1.00   6.82      PROT
ATOM    113  N    LYS    12      23.252  28.691  32.174  1.00   4.39      PROT
ATOM    114  CA   LYS    12      22.299  29.734  31.805  1.00   5.12      PROT
ATOM    115  C    LYS    12      20.843  29.299  31.738  1.00   4.51      PROT
```

Figure 3 cont.

```
ATOM    116  O   LYS    12      20.546  28.114  31.665  1.00  3.38      PROT
ATOM    117  CB  LYS    12      22.741  30.493  30.533  1.00  6.06      PROT
ATOM    118  CG  LYS    12      20.824  29.545  29.343  1.00  0.00      PROT
ATOM    119  CD  LYS    12      23.272  30.019  28.043  1.00  0.00      PROT
ATOM    120  CE  LYS    12      24.744  30.306  28.031  1.00  0.00      PROT
ATOM    121  NZ  LYS    12      25.124  31.346  26.980  1.00  0.00      PROT
ATOM    135  N   VAL    13      19.944  30.277  31.807  1.00  3.72      PROT
ATOM    136  CA  VAL    13      18.806  30.017  31.624  1.00  3.81      PROT
ATOM    137  C   VAL    13      17.762  30.933  30.363  1.00  3.54      PROT
ATOM    138  O   VAL    13      18.058  32.131  30.769  1.00  3.40      PROT
ATOM    139  CB  VAL    13      17.926  30.203  33.253  1.00  4.18      PROT
ATOM    140  CG1 VAL    13      16.420  30.153  33.230  1.00  5.07      PROT
ATOM    141  CG2 VAL    13      18.472  29.147  34.206  1.00  3.43      PROT
ATOM    151  N   VAL    14      16.795  30.356  30.189  1.00  3.81      PROT
ATOM    152  CA  VAL    14      15.846  31.114  29.340  1.00  3.97      PROT
ATOM    153  C   VAL    14      14.448  30.887  29.693  1.00  2.90      PROT
ATOM    154  O   VAL    14      13.988  29.706  29.999  1.00  2.68      PROT
ATOM    155  CB  VAL    14      15.926  30.756  27.834  1.00  3.65      PROT
ATOM    156  CG1 VAL    14      15.019  31.697  26.989  1.00  4.56      PROT
ATOM    157  CG2 VAL    14      17.352  30.826  27.342  1.00  4.20      PROT
ATOM    167  N   ILE    15      13.789  31.945  30.066  1.00  2.11      PROT
ATOM    168  CA  ILE    15      12.460  31.691  30.869  1.00  2.32      PROT
ATOM    169  C   ILE    15      11.498  32.482  29.897  1.00  2.00      PROT
ATOM    170  O   ILE    15      11.396  33.682  29.320  1.00  2.00      PROT
ATOM    171  CB  ILE    15      12.467  30.687  33.197  1.00  2.00      PROT
ATOM    172  CG1 ILE    15      13.546  32.176  33.126  1.00  2.94      PROT
ATOM    173  CG2 ILE    15      11.059  32.605  32.856  1.00  2.63      PROT
ATOM    174  CD  ILE    15      13.825  33.060  34.295  1.00  3.09      PROT
ATOM    186  N   LEU    16      10.549  31.655  29.430  1.00  2.00      PROT
ATOM    187  CA  LEU    16       9.439  32.102  28.609  1.00  2.00      PROT
ATOM    188  C   LEU    16       8.204  32.176  29.304  1.00  2.00      PROT
ATOM    189  O   LEU    16       7.566  31.159  29.313  1.00  2.00      PROT
ATOM    190  CB  LEU    16       9.193  31.161  27.450  1.00  2.00      PROT
ATOM    191  CG  LEU    16       8.039  31.504  26.506  1.00  2.70      PROT
ATOM    192  CD1 LEU    16       8.204  32.656  25.899  1.00  2.00      PROT
ATOM    193  CD2 LEU    16       7.873  30.500  25.429  1.00  2.02      PROT
ATOM    205  N   SER    17       7.861  33.389  29.887  1.00  2.02      PROT
ATOM    206  CA  SER    17       6.840  33.601  30.897  1.00  2.08      PROT
ATOM    207  C   SER    17       5.592  34.235  30.330  1.00  2.37      PROT
ATOM    208  O   SER    17       5.669  35.118  29.476  1.00  3.13      PROT
ATOM    209  CB  SER    17       7.400  34.559  31.987  1.00  2.09      PROT
ATOM    210  OG  SER    17       6.447  34.740  33.005  1.00  2.68      PROT
ATOM    215  N   ARG    18       4.431  33.799  30.818  1.00  2.00      PROT
ATOM    216  CA  ARG    18       3.214  34.353  30.369  1.00  2.00      PROT
ATOM    217  C   ARG    18       3.201  35.825  31.413  1.00  2.00      PROT
ATOM    218  O   ARG    18       3.763  35.857  32.543  1.00  2.00      PROT
ATOM    219  CB  ARG    18       1.985  33.726  30.870  1.00  2.00      PROT
ATOM    220  CG  ARG    18       0.860  34.426  30.517  1.00  2.00      PROT
ATOM    221  CD  ARG    18      -0.511  33.466  30.647  1.00  2.00      PROT
ATOM    222  NE  ARG    18      -1.741  34.129  30.234  1.00  3.19      PROT
ATOM    223  CZ  ARG    18      -2.925  33.925  30.789  1.00  4.18      PROT
ATOM    224  NH1 ARG    18      -3.063  33.065  31.783  1.00  3.39      PROT
ATOM    225  NH2 ARG    18      -3.974  34.599  30.344  1.00  7.02      PROT
ATOM    239  N   HSD    19       2.620  36.870  30.857  1.00  2.00      PROT
ATOM    240  CA  HSD    19       2.293  38.099  31.594  1.00  2.00      PROT
ATOM    241  C   HSD    19       1.303  37.780  32.857  1.00  2.00      PROT
ATOM    242  O   HSD    19       0.957  36.681  32.983  1.00  2.00      PROT
ATOM    243  CB  HSD    19       1.503  39.067  30.692  1.00  2.00      PROT
ATOM    244  CG  HSD    19       0.192  38.504  30.208  1.00  2.00      PROT
ATOM    245  CG2 HSD    19      -0.036  38.193  29.383  1.00  2.94      PROT
ATOM    246  ND1 HSD    19      -0.966  38.269  30.860  1.00  2.00      PROT
ATOM    247  NE2 HSD    19      -1.266  37.730  28.751  1.00  2.00      PROT
ATOM    248  CE1 HSD    19      -1.848  37.750  29.939  1.00  2.04      PROT
ATOM    256  N   GLY    20       1.428  38.789  33.766  1.00  2.00      PROT
```

Figure 3 cont.

```
ATOM    257  CA   GLY   20     0.713  38.891  35.034  1.00   2.00      PROT
ATOM    258  C    GLY   20    -0.785  38.760  34.891  1.00   2.00      PROT
ATOM    259  O    GLY   20    -1.294  38.867  33.780  1.00   2.26      PROT
ATOM    263  N    VAL   21    -1.483  38.756  36.019  1.00   2.50      PROT
ATOM    264  CA   VAL   21    -2.945  38.897  36.084  1.00   3.01      PROT
ATOM    265  C    VAL   21    -3.369  40.196  35.402  1.00   3.18      PROT
ATOM    266  O    VAL   21    -2.797  41.267  35.654  1.00   3.58      PROT
ATOM    267  CB   VAL   21    -3.487  38.868  37.516  1.00   2.78      PROT
ATOM    268  CG1  VAL   21    -3.003  39.106  37.848  1.00   3.47      PROT
ATOM    269  CG2  VAL   21    -3.174  37.327  38.169  1.00   2.20      PROT
ATOM    279  N    ARG   22    -4.383  40.088  34.564  1.00   3.11      PROT
ATOM    280  CA   ARG   22    -4.814  41.201  33.748  1.00   4.01      PROT
ATOM    281  C    ARG   22    -6.333  41.241  33.667  1.00   3.73      PROT
ATOM    282  O    ARG   22    -6.991  40.232  33.881  1.00   3.14      PROT
ATOM    283  CB   ARG   22    -4.241  41.021  32.346  1.00   4.08      PROT
ATOM    284  CG   ARG   22    -4.698  39.755  31.718  1.00   6.73      PROT
ATOM    285  CD   ARG   22    -5.092  39.946  30.298  1.00  10.71      PROT
ATOM    286  NE   ARG   22    -4.715  38.779  29.526  1.00  16.61      PROT
ATOM    287  CZ   ARG   22    -5.500  37.751  29.239  1.00  17.99      PROT
ATOM    288  NH1  ARG   22    -6.774  37.726  29.628  1.00  19.11      PROT
ATOM    289  NH2  ARG   22    -4.991  36.748  28.531  1.00  19.82      PROT
ATOM    303  N    ALA   23    -6.875  42.417  33.353  1.00   4.55      PROT
ATOM    304  CA   ALA   23    -8.294  42.565  33.096  1.00   4.90      PROT
ATOM    305  C    ALA   23    -8.667  41.839  31.798  1.00   5.65      PROT
ATOM    306  O    ALA   23    -7.813  41.618  30.937  1.00   5.74      PROT
ATOM    307  CB   ALA   23    -8.675  44.068  33.048  1.00   4.90      PROT
ATOM    313  N    PRO   24    -9.927  41.394  31.668  1.00   6.59      PROT
ATOM    314  CA   PRO   24   -10.337  40.783  30.410  1.00   7.05      PROT
ATOM    315  C    PRO   24    -9.879  41.613  29.206  1.00   8.04      PROT
ATOM    316  O    PRO   24    -9.363  42.843  29.232  1.00   7.72      PROT
ATOM    317  CB   PRO   24   -11.859  40.796  30.510  1.00   7.08      PROT
ATOM    318  CG   PRO   24   -12.114  40.624  31.943  1.00   6.76      PROT
ATOM    319  CD   PRO   24   -11.032  41.418  32.642  1.00   6.35      PROT
ATOM    327  N    THR   25    -9.366  40.938  28.190  1.00   8.78      PROT
ATOM    328  CA   THR   25    -8.315  41.612  26.954  1.00   9.25      PROT
ATOM    329  C    THR   25   -10.104  42.397  26.257  1.00  10.25      PROT
ATOM    330  O    THR   25    -9.995  43.432  25.774  1.00  10.55      PROT
ATOM    331  CB   THR   25    -8.210  40.600  26.011  1.00  10.17      PROT
ATOM    332  OG1  THR   25    -7.092  40.609  26.700  1.00  12.82      PROT
ATOM    333  CG2  THR   25    -7.698  41.267  24.748  1.00  12.25      PROT
ATOM    340  N    LYS   26   -11.240  41.809  26.235  1.00   9.88      PROT
ATOM    341  CA   LYS   26   -12.457  42.140  25.633  1.00  10.27      PROT
ATOM    342  C    LYS   26   -13.567  41.729  26.452  1.00   9.40      PROT
ATOM    343  O    LYS   26   -13.638  40.722  27.164  1.00   8.76      PROT
ATOM    344  CB   LYS   26   -12.602  41.672  24.175  1.00  10.05      PROT
ATOM    345  CG   LYS   26   -12.540  40.155  23.989  1.00  12.65      PROT
ATOM    346  CD   LYS   26   -12.847  39.707  22.554  1.00  13.17      PROT
ATOM    347  CE   LYS   26   -12.136  40.561  21.511  1.00  15.68      PROT
ATOM    348  NZ   LYS   26   -13.445  40.105  20.119  1.00  18.10      PROT
ATOM    362  N    MET   27   -14.721  42.331  26.355  1.00   8.63      PROT
ATOM    363  CA   MET   27   -15.988  42.217  26.971  1.00   8.61      PROT
ATOM    364  C    MET   27   -17.044  42.491  25.899  1.00   7.95      PROT
ATOM    365  O    MET   27   -17.493  43.609  25.720  1.00   8.61      PROT
ATOM    366  CB   MET   27   -16.190  43.048  28.251  1.00   9.07      PROT
ATOM    367  CG   MET   27   -17.470  42.757  29.049  1.00  10.49      PROT
ATOM    368  SD   MET   27   -17.795  41.019  29.436  1.00  13.25      PROT
ATOM    369  CE   MET   27   -16.353  40.540  30.368  1.00   9.60      PROT
ATOM    378  N    THR   28   -17.391  41.430  25.171  1.00   6.47      PROT
ATOM    380  CA   THR   28   -18.244  41.501  23.991  1.00   5.05      PROT
ATOM    381  C    THR   28   -19.699  41.490  24.395  1.00   4.62      PROT
ATOM    382  O    THR   28   -20.027  41.144  25.544  1.00   3.85      PROT
ATOM    383  CB   THR   28   -18.003  40.298  23.044  1.00   5.05      PROT
ATOM    384  OG1  THR   28   -18.536  39.106  23.633  1.00   2.00      PROT
ATOM    385  CG2  THR   28   -16.532  40.103  22.782  1.00   4.28      PROT
```

Figure 3 cont.

```
ATOM    392  N    GLN   29     -20.876  41.623  23.449  1.00   4.28      PROT
ATOM    393  CA   GLN   29     -22.004  41.757  23.699  1.00   3.94      PROT
ATOM    394  C    GLN   29     -22.452  40.343  24.044  1.00   3.99      PROT
ATOM    395  O    GLN   29     -23.229  40.153  24.998  1.00   4.23      PROT
ATOM    396  CB   GLN   29     -22.827  42.329  22.528  1.00   4.43      PROT
ATOM    397  CG   GLN   29     -24.285  42.567  25.906  1.00   4.28      PROT
ATOM    398  CD   GLN   29     -24.421  43.545  24.083  1.00   5.08      PROT
ATOM    399  OE1  GLN   29     -23.819  44.608  24.094  1.00   5.80      PROT
ATOM    400  NE2  GLN   29     -25.211  43.152  25.064  1.00   6.12      PROT
ATOM    409  N    THR   30     -21.965  39.397  23.293  1.00   4.21      PROT
ATOM    410  CA   THR   30     -22.272  37.950  23.575  1.00   4.98      PROT
ATOM    411  C    THR   30     -21.914  37.579  25.023  1.00   4.96      PROT
ATOM    412  O    THR   30     -22.752  37.042  25.753  1.00   4.22      PROT
ATOM    413  CB   THR   30     -21.898  36.977  22.856  1.00   5.04      PROT
ATOM    414  OG1  THR   30     -22.127  37.214  21.244  1.00   7.16      PROT
ATOM    415  CG2  THR   30     -21.867  35.508  22.924  1.00   6.76      PROT
ATOM    422  N    MET   31     -20.689  37.893  25.434  1.00   5.01      PROT
ATOM    423  CA   MET   31     -20.223  37.644  26.806  1.00   5.36      PROT
ATOM    424  C    MET   31     -21.156  38.242  27.861  1.00   5.38      PROT
ATOM    425  O    MET   31     -21.374  37.649  28.918  1.00   5.89      PROT
ATOM    426  CB   MET   31     -18.802  38.175  27.003  1.00   5.35      PROT
ATOM    427  CG   MET   31     -17.722  37.353  26.301  1.00   5.61      PROT
ATOM    428  SD   MET   31     -16.176  38.271  26.202  1.00   8.17      PROT
ATOM    429  CE   MET   31     -15.303  37.353  24.959  1.00   7.03      PROT
ATOM    439  N    ARG   32     -21.709  39.413  27.567  1.00   6.15      PROT
ATOM    440  CA   ARG   32     -22.697  40.037  28.448  1.00   6.96      PROT
ATOM    441  C    ARG   32     -24.050  39.335  28.371  1.00   6.30      PROT
ATOM    442  O    ARG   32     -24.731  39.182  29.387  1.00   7.23      PROT
ATOM    443  CB   ARG   32     -22.850  41.531  28.134  1.00   6.82      PROT
ATOM    444  CG   ARG   32     -21.569  42.327  28.343  1.00   8.67      PROT
ATOM    445  CD   ARG   32     -21.859  43.739  28.824  1.00  13.26      PROT
ATOM    446  NE   ARG   32     -20.766  44.223  29.664  1.00  16.64      PROT
ATOM    447  CZ   ARG   32     -20.662  43.990  30.971  1.00  17.47      PROT
ATOM    448  NH1  ARG   32     -21.595  43.289  31.621  1.00  18.77      PROT
ATOM    449  NH2  ARG   32     -19.620  44.462  31.630  1.00  18.21      PROT
ATOM    463  N    ASP   33     -24.421  38.905  27.169  1.00   6.38      PROT
ATOM    464  CA   ASP   33     -25.746  38.347  26.876  1.00   5.81      PROT
ATOM    465  C    ASP   33     -25.889  36.949  27.479  1.00   5.40      PROT
ATOM    466  O    ASP   33     -27.126  36.612  27.826  1.00   5.43      PROT
ATOM    467  CB   ASP   33     -26.011  38.342  25.347  1.00   6.20      PROT
ATOM    468  CG   ASP   33     -26.242  39.753  24.765  1.00   7.59      PROT
ATOM    469  OD1  ASP   33     -26.339  40.733  25.534  1.00   7.92      PROT
ATOM    470  OD2  ASP   33     -26.313  39.894  23.519  1.00   8.93      PROT
ATOM    475  N    VAL   34     -24.907  36.154  27.626  1.00   4.41      PROT
ATOM    476  CA   VAL   34     -25.036  34.753  28.078  1.00   3.47      PROT
ATOM    477  C    VAL   34     -25.260  34.594  29.598  1.00   3.40      PROT
ATOM    478  O    VAL   34     -25.376  33.479  30.114  1.00   3.09      PROT
ATOM    479  CB   VAL   34     -23.822  33.909  27.624  1.00   3.46      PROT
ATOM    480  CG1  VAL   34     -23.711  33.915  26.100  1.00   3.28      PROT
ATOM    481  CG2  VAL   34     -22.502  34.396  28.279  1.00   3.10      PROT
ATOM    491  N    THR   35     -25.324  35.716  30.301  1.00   2.99      PROT
ATOM    492  CA   THR   35     -25.647  35.697  31.708  1.00   2.95      PROT
ATOM    493  C    THR   35     -26.552  36.865  32.107  1.00   3.14      PROT
ATOM    494  O    THR   35     -26.887  37.979  31.675  1.00   2.76      PROT
ATOM    495  CB   THR   35     -24.369  35.642  32.619  1.00   3.13      PROT
ATOM    496  OG1  THR   35     -24.733  35.672  34.009  1.00   2.29      PROT
ATOM    497  CG2  THR   35     -23.399  36.697  32.311  1.00   2.99      PROT
ATOM    504  N    PRO   36     -27.535  36.615  33.007  1.00   3.31      PROT
ATOM    505  CA   PRO   36     -28.334  37.697  33.587  1.00   3.89      PROT
ATOM    506  C    PRO   36     -27.836  39.491  34.831  1.00   4.01      PROT
ATOM    507  O    PRO   36     -27.977  39.566  35.064  1.00   4.34      PROT
ATOM    508  CB   PRO   36     -29.482  36.954  34.271  1.00   3.57      PROT
ATOM    509  CG   PRO   36     -28.889  35.651  34.661  1.00   3.53      PROT
ATOM    510  CD   PRO   36     -27.949  35.890  33.535  1.00   2.96      PROT
ATOM    518  N    HSD   37     -26.382  37.954  35.026  1.00   4.16      PROT
```

Figure 3 cont.

```
ATOM    519  CA   HSD    37     -25.505   39.598   36.006  1.00   4.65      PROT
ATOM    520  C    HSD    37     -24.622   39.659   35.380  1.00   4.84      PROT
ATOM    521  O    HSD    37     -24.291   39.562   34.170  1.00   4.87      PROT
ATOM    522  CB   HSD    37     -24.694   37.552   36.715  1.00   4.50      PROT
ATOM    523  CG   HSD    37     -25.398   36.399   37.276  1.00   6.78      PROT
ATOM    524  CD2  HSD    37     -25.232   35.108   36.820  1.00   7.57      PROT
ATOM    525  ND1  HSD    37     -26.330   36.334   38.287  1.00   7.61      PROT
ATOM    526  NE2  HSD    37     -26.021   34.297   37.502  1.00   7.73      PROT
ATOM    527  CE1  HSD    37     -26.699   35.014   38.390  1.00   8.20      PROT
ATOM    535  N    GLN    38     -24.256   40.670   36.128  1.00   4.87      PROT
ATOM    536  CA   GLN    38     -23.381   41.734   35.668  1.00   4.88      PROT
ATOM    537  C    GLN    38     -21.918   41.356   35.893  1.00   4.90      PROT
ATOM    538  O    GLN    38     -21.526   40.234   36.198  1.00   4.84      PROT
ATOM    539  CB   GLN    38     -23.711   43.042   36.379  1.00   5.48      PROT
ATOM    540  CG   GLN    38     -25.285   43.369   36.613  1.00   7.42      PROT
ATOM    541  CD   GLN    38     -26.017   42.762   37.806  1.00  10.27      PROT
ATOM    542  OE1  GLN    38     -25.890   41.745   38.384  1.00  11.02      PROT
ATOM    543  NE2  GLN    38     -27.142   43.387   38.178  1.00   8.29      PROT
ATOM    552  N    TRP    39     -21.123   41.464   34.832  1.00   4.55      PROT
ATOM    553  CA   TRP    39     -19.672   41.301   34.934  1.00   4.68      PROT
ATOM    554  C    TRP    39     -19.038   42.413   35.787  1.00   4.54      PROT
ATOM    555  O    TRP    39     -19.312   43.568   35.579  1.00   4.25      PROT
ATOM    556  CB   TRP    39     -19.032   41.268   33.551  1.00   4.76      PROT
ATOM    557  CG   TRP    39     -19.382   40.048   32.801  1.00   4.40      PROT
ATOM    558  CD1  TRP    39     -20.381   39.699   31.883  1.00   5.28      PROT
ATOM    559  CD2  TRP    39     -18.739   38.773   32.905  1.00   5.11      PROT
ATOM    560  NE1  TRP    39     -20.409   38.612   31.407  1.00   3.73      PROT
ATOM    561  CE2  TRP    39     -19.399   37.903   32.016  1.00   4.98      PROT
ATOM    562  CE3  TRP    39     -17.656   38.294   33.659  1.00   5.42      PROT
ATOM    563  CZ2  TRP    39     -19.019   36.567   31.863  1.00   5.75      PROT
ATOM    564  CZ3  TRP    39     -17.283   36.968   33.509  1.00   4.53      PROT
ATOM    565  CH2  TRP    39     -17.959   36.120   32.611  1.00   5.11      PROT
ATOM    576  N    PRO    40     -18.161   42.023   36.751  1.00   4.95      PROT
ATOM    577  CA   PRO    40     -17.560   42.985   37.660  1.00   5.49      PROT
ATOM    578  C    PRO    40     -16.374   43.322   36.956  1.00   5.93      PROT
ATOM    579  O    PRO    40     -15.976   43.501   36.026  1.00   5.79      PROT
ATOM    580  CB   PRO    40     -16.836   42.092   38.674  1.00   5.53      PROT
ATOM    581  CG   PRO    40     -16.553   40.826   37.350  1.00   6.07      PROT
ATOM    582  CD   PRO    40     -17.685   40.646   36.366  1.00   4.85      PROT
ATOM    590  N    GLU    41     -16.329   45.187   37.370  1.00   6.05      PROT
ATOM    591  CA   GLU    41     -15.525   46.093   36.811  1.00   7.01      PROT
ATOM    592  C    GLU    41     -14.141   45.863   37.383  1.00   5.93      PROT
ATOM    593  O    GLU    41     -13.960   45.625   38.583  1.00   6.33      PROT
ATOM    594  CB   GLU    41     -15.929   47.570   36.920  1.00   7.71      PROT
ATOM    595  CG   GLU    41     -16.406   48.192   35.585  1.00  11.21      PROT
ATOM    596  CD   GLU    41     -15.298   48.375   34.523  1.00  16.08      PROT
ATOM    597  OE1  GLU    41     -14.093   48.142   34.802  1.00  18.62      PROT
ATOM    598  OE2  GLU    41     -15.640   48.774   33.394  1.00  16.73      PROT
ATOM    605  N    TRP    42     -13.185   45.926   36.509  1.00   5.39      PROT
ATOM    606  CA   TRP    42     -11.772   45.799   36.915  1.00   4.35      PROT
ATOM    607  C    TRP    42     -11.177   47.175   37.202  1.00   4.25      PROT
ATOM    608  O    TRP    42     -11.600   48.164   36.613  1.00   3.94      PROT
ATOM    609  CB   TRP    42     -10.985   45.046   35.839  1.00   3.64      PROT
ATOM    610  CG   TRP    42     -11.207   43.564   35.894  1.00   3.85      PROT
ATOM    611  CD1  TRP    42     -12.371   42.888   35.604  1.00   3.07      PROT
ATOM    612  CD2  TRP    42     -10.353   42.569   36.276  1.00   2.95      PROT
ATOM    613  NE1  TRP    42     -12.183   41.540   35.779  1.00   2.90      PROT
ATOM    614  CE2  TRP    42     -10.900   41.316   36.198  1.00   2.03      PROT
ATOM    615  CE3  TRP    42      -8.907   42.615   36.674  1.00   2.96      PROT
ATOM    616  CZ2  TRP    42     -10.246   40.108   36.509  1.00   2.75      PROT
ATOM    617  CZ3  TRP    42      -8.264   41.430   36.985  1.00   3.10      PROT
ATOM    618  CH2  TRP    42      -8.935   40.198   36.895  1.00   3.42      PROT
ATOM    629  N    PRO    43     -10.198   47.240   38.122  1.00   4.47      PROT
ATOM    630  CA   PRO    43      -9.609   48.485   38.464  1.00   4.28      PROT
ATOM    631  C    PRO    43      -8.697   49.006   37.363  1.00   4.85      PROT
```

Figure 3 cont.

```
ATOM    632  O    PRO   43      -7.985  50.105  37.883  1.00   4.76      PROT
ATOM    633  CB   PRO   43      -8.689  48.095  39.707  1.00   4.40      PROT
ATOM    634  CG   PRO   43      -8.466  46.613  39.565  1.00   4.95      PROT
ATOM    635  CD   PRO   43      -9.697  46.090  38.906  1.00   3.52      PROT
ATOM    643  N    VAL   44      -8.490  48.415  36.197  1.00   5.33      PROT
ATOM    644  CA   VAL   44      -7.643  48.925  35.100  1.00   5.83      PROT
ATOM    645  C    VAL   44      -8.383  48.849  33.746  1.00   6.09      PROT
ATOM    646  O    VAL   44      -9.456  48.318  33.643  1.00   5.41      PROT
ATOM    647  CB   VAL   44      -6.259  48.194  34.987  1.00   6.61      PROT
ATOM    648  CG1  VAL   44      -6.442  46.711  34.656  1.00   6.04      PROT
ATOM    649  CG2  VAL   44      -5.401  48.401  36.260  1.00   6.72      PROT
ATOM    659  H    LYS   45      -7.691  49.372  32.722  1.00   5.96      PROT
ATOM    660  CA   LYS   45      -8.127  49.257  31.335  1.00   6.89      PROT
ATOM    661  C    LYS   45      -8.202  47.779  30.916  1.00   6.26      PROT
ATOM    662  O    LYS   45      -7.383  46.984  31.356  1.00   5.53      PROT
ATOM    663  CB   LYS   45      -7.112  50.003  30.462  1.00   7.49      PROT
ATOM    664  CG   LYS   45      -7.153  49.653  28.991  1.00  10.33      PROT
ATOM    665  CD   LYS   45      -8.228  50.423  28.258  1.00  13.76      PROT
ATOM    666  CE   LYS   45      -7.670  51.725  27.683  1.00  14.41      PROT
ATOM    667  NZ   LYS   45      -6.643  51.519  26.610  1.00  16.40      PROT
ATOM    681  N    LEU   46      -9.167  47.415  30.069  1.00   5.86      PROT
ATOM    682  CA   LEU   46      -9.227  46.057  29.508  1.00   6.20      PROT
ATOM    683  C    LEU   46      -7.867  45.636  28.913  1.00   5.80      PROT
ATOM    684  O    LEU   46      -7.253  46.393  28.187  1.00   5.53      PROT
ATOM    685  CB   LEU   46     -10.326  45.954  28.429  1.00   6.49      PROT
ATOM    686  CG   LEU   46     -11.801  46.115  28.807  1.00   7.73      PROT
ATOM    687  CD1  LEU   46     -12.637  46.121  27.542  1.00  12.17      PROT
ATOM    688  CD2  LEU   46     -12.280  45.022  29.759  1.00   9.52      PROT
ATOM    700  N    GLY   47      -7.387  44.453  29.279  1.00   5.97      PROT
ATOM    701  CA   GLY   47      -6.110  43.931  28.772  1.00   6.38      PROT
ATOM    702  C    GLY   47      -4.850  44.379  29.508  1.00   6.04      PROT
ATOM    703  O    GLY   47      -3.751  43.895  29.233  1.00   6.46      PROT
ATOM    707  N    TYR   48      -4.898  45.327  30.409  1.00   5.50      PROT
ATOM    708  CA   TYR   48      -3.864  45.799  31.338  1.00   4.86      PROT
ATOM    709  C    TYR   48      -3.594  44.874  32.405  1.00   4.19      PROT
ATOM    710  O    TYR   48      -4.526  44.289  32.960  1.00   3.87      PROT
ATOM    711  CB   TYR   48      -4.139  47.197  31.803  1.00   5.44      PROT
ATOM    712  CG   TYR   48      -3.805  48.358  30.889  1.00   6.31      PROT
ATOM    713  CD1  TYR   48      -3.853  48.220  29.507  1.00   6.51      PROT
ATOM    714  CD2  TYR   48      -3.483  49.612  31.419  1.00   6.97      PROT
ATOM    715  CE1  TYR   48      -3.553  49.280  28.667  1.00   7.62      PROT
ATOM    716  CE2  TYR   48      -3.136  50.688  30.567  1.00   7.42      PROT
ATOM    717  CZ   TYR   48      -3.232  50.505  29.211  1.00   7.57      PROT
ATOM    718  OH   TYR   48      -2.855  51.550  28.376  1.00   7.06      PROT
ATOM    727  H    ILE   49      -2.322  44.757  32.772  1.00   3.12      PROT
ATOM    728  CA   ILE   49      -1.943  44.106  34.024  1.00   2.56      PROT
ATOM    729  C    ILE   49      -2.464  44.959  35.199  1.00   2.39      PROT
ATOM    730  O    ILE   49      -2.527  46.198  35.127  1.00   2.00      PROT
ATOM    731  CB   ILE   49      -0.377  43.803  34.094  1.00   3.10      PROT
ATOM    732  CG1  ILE   49      -0.027  42.859  35.224  1.00   2.27      PROT
ATOM    733  CG2  ILE   49       0.447  45.082  34.192  1.00   3.29      PROT
ATOM    734  CD   ILE   49       1.423  43.284  35.162  1.00   2.61      PROT
ATOM    746  N    THR   50      -2.892  44.296  36.263  1.00   2.00      PROT
ATOM    747  CA   THR   50      -3.295  45.020  37.473  1.00   2.00      PROT
ATOM    748  C    THR   50      -2.071  45.240  38.382  1.00   2.00      PROT
ATOM    749  O    THR   50      -1.030  44.533  38.251  1.00   2.00      PROT
ATOM    750  CB   THR   50      -4.368  44.248  38.233  1.00   2.00      PROT
ATOM    751  OG1  THR   50      -3.904  42.998  38.652  1.00   3.05      PROT
ATOM    752  CG2  THR   50      -5.679  43.993  37.323  1.00   2.00      PROT
ATOM    759  H    PRO   51      -2.110  46.243  39.282  1.00   2.00      PROT
ATOM    760  CA   PRO   51      -1.003  46.327  40.259  1.00   2.00      PROT
ATOM    761  C    PRO   51      -0.765  45.009  41.041  1.00   2.00      PROT
ATOM    762  O    PRO   51       0.366  44.663  41.347  1.00   2.00      PROT
ATOM    763  CB   PRO   51      -1.443  47.452  41.210  1.00   2.38      PROT
ATOM    764  CG   PRO   51      -2.434  48.297  40.402  1.00   2.06      PROT
```

Figure 3 cont.

```
ATOM    765  CD  PRO   51      -3.081  47.347  39.414  1.00  2.16      PROT
ATOM    773  N   ARG   52      -1.839  44.298  41.371  1.00  2.00      PROT
ATOM    774  CA  ARG   52      -1.741  42.979  42.019  1.00  2.00      PROT
ATOM    775  C   ARG   52      -3.059  41.946  41.114  1.00  2.00      PROT
ATOM    776  O   ARG   52      -0.248  41.153  41.600  1.00  2.00      PROT
ATOM    777  CB  ARG   52      -3.124  42.489  42.437  1.00  2.00      PROT
ATOM    778  CG  ARG   52      -3.372  41.047  42.893  1.00  2.00      PROT
ATOM    779  CD  ARG   52      -4.387  40.796  43.732  1.00  5.06      PROT
ATOM    780  NE  ARG   52      -4.517  39.381  44.081  1.00  5.77      PROT
ATOM    781  CZ  ARG   52      -5.064  38.836  45.206  1.00  7.20      PROT
ATOM    782  NH1 ARG   52      -5.526  39.789  46.116  1.00  6.08      PROT
ATOM    783  NH2 ARG   52      -5.342  37.636  45.436  1.00  4.67      PROT
ATOM    797  N   GLY   53      -1.385  41.969  39.820  1.00  2.00      PROT
ATOM    798  CA  GLY   53      -0.706  41.181  38.781  1.00  2.00      PROT
ATOM    799  C   GLY   53       0.783  41.440  38.790  1.00  2.00      PROT
ATOM    800  O   GLY   53       1.584  40.507  38.746  1.00  2.00      PROT
ATOM    804  N   GLU   54       1.169  42.716  38.875  1.00  2.00      PROT
ATOM    805  CA  GLU   54       2.581  43.101  38.960  1.00  2.00      PROT
ATOM    806  C   GLU   54       3.253  42.571  40.232  1.00  2.00      PROT
ATOM    807  O   GLU   54       4.335  41.982  40.170  1.00  2.00      PROT
ATOM    808  CB  GLU   54       2.719  44.617  38.861  1.00  2.00      PROT
ATOM    809  CG  GLU   54       2.353  45.194  37.503  1.00  2.46      PROT
ATOM    810  CD  GLU   54       2.408  46.712  37.500  1.00  6.68      PROT
ATOM    811  OE1 GLU   54       1.503  47.353  38.065  1.00  7.39      PROT
ATOM    812  OE2 GLU   54       3.398  47.266  36.924  1.00 11.95      PROT
ATOM    819  N   HSD   55       2.607  42.764  41.376  1.00  2.00      PROT
ATOM    820  CA  HSD   55       3.310  42.239  42.649  1.00  2.00      PROT
ATOM    821  C   HSD   55       3.314  40.733  42.577  1.00  2.00      PROT
ATOM    822  O   HSD   55       4.327  40.214  43.035  1.00  2.00      PROT
ATOM    823  CB  HSD   55       2.156  42.566  43.615  1.00  2.00      PROT
ATOM    824  CG  HSD   55       2.642  42.027  45.128  1.00  2.00      PROT
ATOM    825  ND1 HSD   55       3.635  42.421  45.637  1.00  2.22      PROT
ATOM    826  CD2 HSD   55       2.197  41.109  45.972  1.00  2.60      PROT
ATOM    827  CE1 HSD   55       4.012  41.772  46.836  1.00  5.06      PROT
ATOM    828  NE2 HSD   55       2.980  40.968  47.024  1.00  4.14      PROT
ATOM    836  N   LEU   56       2.332  40.044  42.014  1.00  2.00      PROT
ATOM    837  CA  LEU   56       2.410  38.588  41.886  1.00  2.00      PROT
ATOM    838  C   LEU   56       3.604  38.145  41.027  1.00  2.00      PROT
ATOM    839  O   LEU   56       4.266  37.152  41.361  1.00  2.00      PROT
ATOM    840  CB  LEU   56       1.100  38.042  41.291  1.00  2.12      PROT
ATOM    841  CG  LEU   56      -0.031  38.012  42.308  1.00  2.16      PROT
ATOM    842  CD1 LEU   56      -1.378  37.761  41.657  1.00  2.32      PROT
ATOM    843  CD2 LEU   56       0.246  36.950  43.398  1.00  4.12      PROT
ATOM    855  N   ILE   57       3.850  38.863  39.924  1.00  2.00      PROT
ATOM    856  CA  ILE   57       5.031  38.643  39.076  1.00  2.00      PROT
ATOM    857  C   ILE   57       6.327  38.892  39.851  1.00  2.00      PROT
ATOM    858  O   ILE   57       7.291  38.124  39.745  1.00  2.00      PROT
ATOM    859  CB  ILE   57       5.019  39.526  37.783  1.00  2.00      PROT
ATOM    860  CG1 ILE   57       3.891  39.099  36.825  1.00  2.00      PROT
ATOM    861  CG2 ILE   57       6.343  39.378  36.979  1.00  2.39      PROT
ATOM    862  CD  ILE   57       3.963  37.606  36.469  1.00  2.00      PROT
ATOM    874  N   SER   58       6.356  39.962  40.639  1.00  2.00      PROT
ATOM    875  CA  SER   58       7.596  40.272  41.375  1.00  2.17      PROT
ATOM    876  C   SER   58       7.659  39.209  42.456  1.00  2.00      PROT
ATOM    877  O   SER   58       9.017  38.903  42.753  1.00  2.34      PROT
ATOM    878  CB  SER   58       7.569  41.694  41.930  1.00  2.12      PROT
ATOM    879  OG  SER   58       6.913  41.731  43.178  1.00  7.69      PROT
ATOM    884  N   LEU   59       6.800  38.625  43.012  1.00  2.00      PROT
ATOM    885  CA  LEU   59       6.953  37.478  43.923  1.00  2.00      PROT
ATOM    886  C   LEU   59       7.615  36.283  43.229  1.00  2.00      PROT
ATOM    887  O   LEU   59       8.495  35.642  43.809  1.00  2.00      PROT
ATOM    888  CB  LEU   59       5.617  37.076  44.559  1.00  2.00      PROT
ATOM    889  CG  LEU   59       4.969  38.048  45.563  1.00  2.14      PROT
ATOM    890  CD1 LEU   59       3.621  37.504  45.959  1.00  2.00      PROT
ATOM    891  CD2 LEU   59       5.830  38.328  46.793  1.00  4.93      PROT
```

Figure 3 cont.

| | | | | | | | | |
|---|---|---|---|---|---|---|---|---|
| ATOM | 903 | N | MET | 60 | 7.213 | 36.016 | 41.982 | 1.00 | 2.00 | PROT |
| ATOM | 904 | CA | MET | 60 | 7.317 | 35.048 | 41.126 | 1.00 | 2.00 | PROT |
| ATOM | 905 | C | MET | 60 | 8.378 | 35.412 | 40.882 | 1.00 | 2.00 | PROT |
| ATOM | 906 | O | MET | 60 | 10.341 | 34.546 | 40.371 | 1.00 | 2.00 | PROT |
| ATOM | 907 | CB | MET | 60 | 7.224 | 34.859 | 39.756 | 1.00 | 2.23 | PROT |
| ATOM | 908 | CG | MET | 60 | 6.035 | 33.308 | 39.732 | 1.00 | 5.39 | PROT |
| ATOM | 909 | SD | MET | 60 | 6.233 | 32.152 | 40.171 | 1.00 | 9.67 | PROT |
| ATOM | 910 | CE | MET | 60 | 7.383 | 31.814 | 40.061 | 1.00 | 3.93 | PROT |
| ATOM | 920 | N | GLY | 61 | 9.606 | 36.682 | 40.973 | 1.00 | 2.00 | PROT |
| ATOM | 921 | CA | GLY | 61 | 11.042 | 37.183 | 40.404 | 1.00 | 2.00 | PROT |
| ATOM | 922 | C | GLY | 61 | 11.933 | 36.895 | 41.618 | 1.00 | 2.00 | PROT |
| ATOM | 923 | O | GLY | 61 | 13.102 | 36.514 | 41.461 | 1.00 | 2.00 | PROT |
| ATOM | 927 | N | GLY | 62 | 11.363 | 37.070 | 42.804 | 1.00 | 2.00 | PROT |
| ATOM | 928 | CA | GLY | 62 | 12.035 | 36.776 | 44.073 | 1.00 | 2.00 | PROT |
| ATOM | 929 | C | GLY | 62 | 12.843 | 35.297 | 44.225 | 1.00 | 2.00 | PROT |
| ATOM | 930 | O | GLY | 62 | 13.398 | 34.326 | 44.757 | 1.00 | 2.00 | PROT |
| ATOM | 934 | N | PHE | 63 | 11.433 | 34.455 | 43.732 | 1.00 | 2.16 | PROT |
| ATOM | 935 | CA | PHE | 63 | 11.653 | 33.014 | 43.740 | 1.00 | 2.22 | PROT |
| ATOM | 936 | C | PHE | 63 | 12.798 | 32.645 | 42.805 | 1.00 | 2.90 | PROT |
| ATOM | 937 | O | PHE | 63 | 13.683 | 31.877 | 43.190 | 1.00 | 2.46 | PROT |
| ATOM | 938 | CB | PHE | 63 | 10.390 | 32.211 | 43.420 | 1.00 | 2.94 | PROT |
| ATOM | 939 | CG | PHE | 63 | 10.628 | 30.726 | 43.333 | 1.00 | 3.29 | PROT |
| ATOM | 940 | CD1 | PHE | 63 | 10.946 | 29.997 | 44.461 | 1.00 | 3.85 | PROT |
| ATOM | 941 | CD2 | PHE | 63 | 10.621 | 30.077 | 42.112 | 1.00 | 4.03 | PROT |
| ATOM | 942 | CE1 | PHE | 63 | 11.216 | 28.623 | 44.400 | 1.00 | 4.11 | PROT |
| ATOM | 943 | CE2 | PHE | 63 | 10.880 | 28.709 | 42.038 | 1.00 | 5.69 | PROT |
| ATOM | 944 | CZ | PHE | 63 | 11.183 | 27.992 | 43.185 | 1.00 | 3.33 | PROT |
| ATOM | 954 | N | TYR | 64 | 12.772 | 33.136 | 41.582 | 1.00 | 3.92 | PROT |
| ATOM | 955 | CA | TYR | 64 | 13.862 | 33.040 | 40.618 | 1.00 | 4.54 | PROT |
| ATOM | 956 | C | TYR | 64 | 15.215 | 33.458 | 41.011 | 1.00 | 4.67 | PROT |
| ATOM | 957 | O | TYR | 64 | 16.191 | 32.715 | 41.112 | 1.00 | 4.47 | PROT |
| ATOM | 958 | CB | TYR | 64 | 13.571 | 33.803 | 39.322 | 1.00 | 5.31 | PROT |
| ATOM | 959 | CG | TYR | 64 | 12.500 | 33.169 | 38.454 | 1.00 | 6.18 | PROT |
| ATOM | 960 | CD1 | TYR | 64 | 12.566 | 31.829 | 38.090 | 1.00 | 4.36 | PROT |
| ATOM | 961 | CD2 | TYR | 64 | 11.420 | 33.911 | 37.984 | 1.00 | 6.56 | PROT |
| ATOM | 962 | CE1 | TYR | 64 | 11.620 | 31.226 | 37.198 | 1.00 | 8.27 | PROT |
| ATOM | 963 | CE2 | TYR | 64 | 10.440 | 33.318 | 37.175 | 1.00 | 8.92 | PROT |
| ATOM | 964 | CZ | TYR | 64 | 10.554 | 31.974 | 36.845 | 1.00 | 7.72 | PROT |
| ATOM | 965 | OH | TYR | 64 | 9.621 | 31.359 | 36.052 | 1.00 | 10.78 | PROT |
| ATOM | 974 | N | ARG | 65 | 15.248 | 34.624 | 41.843 | 1.00 | 4.87 | PROT |
| ATOM | 975 | CA | ARG | 65 | 16.456 | 35.143 | 42.517 | 1.00 | 5.63 | PROT |
| ATOM | 976 | C | ARG | 65 | 17.062 | 34.313 | 43.486 | 1.00 | 4.96 | PROT |
| ATOM | 977 | O | ARG | 65 | 18.225 | 33.752 | 43.349 | 1.00 | 5.23 | PROT |
| ATOM | 978 | CB | ARG | 65 | 16.160 | 36.480 | 43.219 | 1.00 | 6.01 | PROT |
| ATOM | 979 | CG | ARG | 65 | 17.154 | 36.839 | 44.348 | 1.00 | 6.81 | PROT |
| ATOM | 980 | CD | ARG | 65 | 16.931 | 38.249 | 44.886 | 1.00 | 7.76 | PROT |
| ATOM | 981 | NE | ARG | 65 | 17.598 | 39.186 | 43.975 | 1.00 | 14.22 | PROT |
| ATOM | 982 | CZ | ARG | 65 | 18.891 | 39.493 | 43.998 | 1.00 | 13.94 | PROT |
| ATOM | 983 | NH1 | ARG | 65 | 19.697 | 38.986 | 44.915 | 1.00 | 17.72 | PROT |
| ATOM | 984 | NH2 | ARG | 65 | 19.373 | 40.325 | 43.092 | 1.00 | 12.46 | PROT |
| ATOM | 998 | N | GLU | 66 | 16.272 | 33.638 | 44.440 | 1.00 | 4.36 | PROT |
| ATOM | 999 | CA | GLU | 66 | 16.756 | 32.652 | 45.390 | 1.00 | 4.71 | PROT |
| ATOM | 1000 | C | GLU | 66 | 17.236 | 31.352 | 44.726 | 1.00 | 4.38 | PROT |
| ATOM | 1001 | O | GLU | 66 | 18.277 | 30.813 | 45.039 | 1.00 | 3.86 | PROT |
| ATOM | 1002 | CB | GLU | 66 | 15.686 | 32.292 | 46.404 | 1.00 | 4.46 | PROT |
| ATOM | 1003 | CG | GLU | 66 | 15.453 | 33.333 | 47.420 | 1.00 | 6.83 | PROT |
| ATOM | 1004 | CD | GLU | 66 | 14.617 | 32.826 | 48.566 | 1.00 | 9.34 | PROT |
| ATOM | 1005 | OE1 | GLU | 66 | 14.695 | 31.610 | 48.885 | 1.00 | 9.67 | PROT |
| ATOM | 1006 | OE2 | GLU | 66 | 13.908 | 33.659 | 49.161 | 1.00 | 11.89 | PROT |
| ATOM | 1013 | N | ARG | 67 | 16.463 | 30.875 | 43.763 | 1.00 | 4.19 | PROT |
| ATOM | 1014 | CA | ARG | 67 | 16.790 | 29.654 | 43.037 | 1.00 | 5.20 | PROT |
| ATOM | 1015 | C | ARG | 67 | 18.107 | 29.795 | 42.273 | 1.00 | 4.98 | PROT |
| ATOM | 1016 | O | ARG | 67 | 18.955 | 28.903 | 42.327 | 1.00 | 5.04 | PROT |
| ATOM | 1017 | CB | ARG | 67 | 15.647 | 29.268 | 42.093 | 1.00 | 5.59 | PROT |
| ATOM | 1018 | CG | ARG | 67 | 15.784 | 27.807 | 41.470 | 1.00 | 9.26 | PROT |

Figure 3 cont.

| | | | | | | | | | |
|---|---|---|---|---|---|---|---|---|---|
| ATOM | 1019 | CD | ARG | 67 | 15.408 | 26.797 | 42.444 | 1.00 14.02 | PROT |
| ATOM | 1020 | NE | ARG | 67 | 15.480 | 25.489 | 41.807 | 1.00 18.33 | PROT |
| ATOM | 1021 | CZ | ARG | 67 | 16.416 | 24.571 | 42.050 | 1.00 19.85 | PROT |
| ATOM | 1022 | NH1 | ARG | 67 | 16.380 | 23.417 | 41.404 | 1.00 21.89 | PROT |
| ATOM | 1023 | NH2 | ARG | 67 | 17.384 | 24.799 | 42.930 | 1.00 21.56 | PROT |
| ATOM | 1037 | N | PHE | 68 | 18.084 | 30.920 | 41.584 | 1.00 4.63 | PROT |
| ATOM | 1038 | CA | PHE | 68 | 19.486 | 31.127 | 40.767 | 1.00 5.23 | PROT |
| ATOM | 1039 | C | PHE | 68 | 20.733 | 31.443 | 41.601 | 1.00 5.51 | PROT |
| ATOM | 1040 | O | PHE | 68 | 21.846 | 31.148 | 41.170 | 1.00 5.25 | PROT |
| ATOM | 1041 | CB | PHE | 68 | 19.294 | 32.180 | 39.681 | 1.00 5.29 | PROT |
| ATOM | 1042 | CG | PHE | 68 | 18.177 | 31.736 | 38.687 | 1.00 6.33 | PROT |
| ATOM | 1043 | CD1 | PHE | 68 | 17.994 | 30.468 | 38.325 | 1.00 6.76 | PROT |
| ATOM | 1044 | CD2 | PHE | 68 | 17.359 | 32.762 | 38.122 | 1.00 8.13 | PROT |
| ATOM | 1045 | CE1 | PHE | 68 | 16.908 | 30.105 | 37.419 | 1.00 8.41 | PROT |
| ATOM | 1046 | CE2 | PHE | 68 | 16.367 | 32.419 | 37.200 | 1.00 7.26 | PROT |
| ATOM | 1047 | CZ | PHE | 68 | 16.175 | 31.084 | 36.863 | 1.00 8.28 | PROT |
| ATOM | 1057 | N | GLN | 69 | 20.534 | 32.029 | 42.766 | 1.00 5.99 | PROT |
| ATOM | 1058 | CA | GLN | 69 | 21.608 | 32.186 | 43.761 | 1.00 7.65 | PROT |
| ATOM | 1059 | C | GLN | 69 | 22.065 | 30.830 | 44.329 | 1.00 7.80 | PROT |
| ATOM | 1060 | O | GLN | 69 | 23.263 | 30.588 | 44.465 | 1.00 7.84 | PROT |
| ATOM | 1061 | CB | GLN | 69 | 21.176 | 33.102 | 44.938 | 1.00 7.41 | PROT |
| ATOM | 1062 | CG | GLN | 69 | 21.119 | 34.613 | 44.669 | 1.00 8.97 | PROT |
| ATOM | 1063 | CD | GLN | 69 | 20.607 | 35.452 | 45.790 | 1.00 8.31 | PROT |
| ATOM | 1064 | OE1 | GLN | 69 | 20.955 | 36.601 | 45.943 | 1.00 13.38 | PROT |
| ATOM | 1065 | NE2 | GLN | 69 | 19.747 | 34.870 | 46.604 | 1.00 12.25 | PROT |
| ATOM | 1074 | N | GLN | 70 | 21.108 | 29.962 | 44.663 | 1.00 8.00 | PROT |
| ATOM | 1075 | CA | GLN | 70 | 21.395 | 28.595 | 45.135 | 1.00 8.76 | PROT |
| ATOM | 1076 | C | GLN | 70 | 22.240 | 27.755 | 44.157 | 1.00 8.73 | PROT |
| ATOM | 1077 | O | GLN | 70 | 23.143 | 27.015 | 44.567 | 1.00 8.76 | PROT |
| ATOM | 1078 | CB | GLN | 70 | 20.063 | 27.867 | 45.442 | 1.00 8.31 | PROT |
| ATOM | 1079 | CG | GLN | 70 | 20.252 | 26.470 | 46.050 | 1.00 9.36 | PROT |
| ATOM | 1080 | CD | GLN | 70 | 18.930 | 25.746 | 46.237 | 1.00 9.94 | PROT |
| ATOM | 1081 | OE1 | GLN | 70 | 18.093 | 25.711 | 45.343 | 1.00 10.89 | PROT |
| ATOM | 1082 | NE2 | GLN | 70 | 18.747 | 25.156 | 47.413 | 1.00 12.48 | PROT |
| ATOM | 1091 | N | GLN | 71 | 21.942 | 27.882 | 40.867 | 1.00 8.75 | PROT |
| ATOM | 1092 | CA | GLN | 71 | 22.617 | 27.113 | 41.823 | 1.00 9.45 | PROT |
| ATOM | 1093 | C | GLN | 71 | 23.898 | 27.808 | 41.291 | 1.00 9.61 | PROT |
| ATOM | 1094 | O | GLN | 71 | 24.543 | 27.307 | 40.369 | 1.00 9.03 | PROT |
| ATOM | 1095 | CB | GLN | 71 | 21.624 | 26.789 | 40.703 | 1.00 9.50 | PROT |
| ATOM | 1096 | CG | GLN | 71 | 20.393 | 26.046 | 41.214 | 1.00 10.91 | PROT |
| ATOM | 1097 | CD | GLN | 71 | 19.300 | 25.887 | 40.161 | 1.00 11.43 | PROT |
| ATOM | 1098 | OE1 | GLN | 71 | 18.757 | 26.871 | 39.666 | 1.00 12.06 | PROT |
| ATOM | 1099 | NE2 | GLN | 71 | 18.947 | 24.636 | 39.888 | 1.00 13.08 | PROT |
| ATOM | 1108 | N | GLY | 72 | 24.299 | 28.968 | 41.850 | 1.00 10.16 | PROT |
| ATOM | 1109 | CA | GLY | 72 | 25.476 | 29.663 | 41.591 | 1.00 11.22 | PROT |
| ATOM | 1110 | C | GLY | 72 | 25.479 | 30.584 | 40.393 | 1.00 11.79 | PROT |
| ATOM | 1111 | O | GLY | 72 | 26.537 | 31.079 | 39.979 | 1.00 11.92 | PROT |
| ATOM | 1115 | N | LEU | 73 | 24.291 | 30.823 | 39.843 | 1.00 11.63 | PROT |
| ATOM | 1116 | CA | LEU | 73 | 24.142 | 31.570 | 38.601 | 1.00 11.35 | PROT |
| ATOM | 1117 | C | LEU | 73 | 24.007 | 33.078 | 38.826 | 1.00 11.82 | PROT |
| ATOM | 1118 | O | LEU | 73 | 24.879 | 33.680 | 38.004 | 1.00 11.93 | PROT |
| ATOM | 1119 | CB | LEU | 73 | 22.953 | 31.015 | 37.804 | 1.00 11.17 | PROT |
| ATOM | 1120 | CG | LEU | 73 | 22.759 | 31.445 | 36.357 | 1.00 11.20 | PROT |
| ATOM | 1121 | CD1 | LEU | 73 | 23.915 | 30.983 | 35.493 | 1.00 10.42 | PROT |
| ATOM | 1122 | CD2 | LEU | 73 | 21.415 | 30.947 | 35.834 | 1.00 10.49 | PROT |
| ATOM | 1134 | N | LEU | 74 | 23.357 | 33.456 | 39.924 | 1.00 11.69 | PROT |
| ATOM | 1135 | CA | LEU | 74 | 23.375 | 34.831 | 40.415 | 1.00 12.06 | PROT |
| ATOM | 1136 | C | LEU | 74 | 24.196 | 34.993 | 41.695 | 1.00 12.50 | PROT |
| ATOM | 1137 | O | LEU | 74 | 24.223 | 34.029 | 42.498 | 1.00 11.85 | PROT |
| ATOM | 1138 | CB | LEU | 74 | 21.966 | 35.362 | 40.683 | 1.00 11.36 | PROT |
| ATOM | 1139 | CG | LEU | 74 | 21.078 | 35.823 | 39.522 | 1.00 13.15 | PROT |
| ATOM | 1140 | CD1 | LEU | 74 | 19.703 | 36.195 | 40.049 | 1.00 13.13 | PROT |
| ATOM | 1141 | CD2 | LEU | 74 | 21.873 | 36.999 | 38.763 | 1.00 14.79 | PROT |
| ATOM | 1153 | N | PRO | 75 | 24.849 | 36.113 | 41.871 | 1.00 13.04 | PROT |
| ATOM | 1154 | CA | PRO | 75 | 25.649 | 36.436 | 43.043 | 1.00 13.81 | PROT |

Figure 3 cont.

| | | | | | | | | | |
|---|---|---|---|---|---|---|---|---|---|
| ATOM | 1155 | C | PRO | 75 | 24.793 | 36.557 | 44.303 | 1.00 14.26 | PROT |
| ATOM | 1156 | O | PRO | 75 | 23.639 | 36.990 | 44.255 | 1.00 14.74 | PROT |
| ATOM | 1157 | CB | PRO | 75 | 26.084 | 37.990 | 42.829 | 1.00 17.17 | PROT |
| ATOM | 1158 | CG | PRO | 75 | 25.303 | 38.476 | 41.656 | 1.00 17.10 | PROT |
| ATOM | 1159 | CD | PRO | 75 | 25.013 | 37.256 | 40.851 | 1.00 16.76 | PROT |
| ATOM | 1167 | H | LYS | 76 | 25.381 | 36.143 | 45.422 | 1.00 14.55 | PROT |
| ATOM | 1168 | CA | LYS | 76 | 24.781 | 36.389 | 46.729 | 1.00 14.97 | PROT |
| ATOM | 1169 | C | LYS | 76 | 25.095 | 37.804 | 47.140 | 1.00 15.01 | PROT |
| ATOM | 1170 | O | LYS | 76 | 24.268 | 38.673 | 47.523 | 1.00 15.08 | PROT |
| ATOM | 1171 | CB | LYS | 76 | 25.363 | 35.379 | 47.761 | 1.00 15.25 | PROT |
| ATOM | 1172 | CG | LYS | 76 | 25.579 | 33.934 | 47.284 | 1.00 15.58 | PROT |
| ATOM | 1173 | CD | LYS | 76 | 24.890 | 33.027 | 47.535 | 1.00 15.07 | PROT |
| ATOM | 1174 | CE | LYS | 76 | 24.869 | 31.563 | 47.710 | 1.00 15.35 | PROT |
| ATOM | 1175 | NZ | LYS | 76 | 25.497 | 30.984 | 46.513 | 1.00 16.66 | PROT |
| ATOM | 1189 | H | ASP | 77 | 25.014 | 38.165 | 47.360 | 1.00 37.09 | PROT |
| ATOM | 1190 | CA | ASP | 77 | 24.883 | 39.549 | 47.761 | 1.00 37.81 | PROT |
| ATOM | 1191 | C | ASP | 77 | 25.035 | 40.380 | 46.498 | 1.00 37.73 | PROT |
| ATOM | 1192 | O | ASP | 77 | 25.566 | 39.885 | 45.494 | 1.00 37.70 | PROT |
| ATOM | 1193 | CB | ASP | 77 | 25.357 | 39.911 | 48.725 | 1.00 38.34 | PROT |
| ATOM | 1194 | CG | ASP | 77 | 25.594 | 41.130 | 49.632 | 1.00 39.50 | PROT |
| ATOM | 1195 | OD1 | ASP | 77 | 24.509 | 41.730 | 49.403 | 1.00 41.09 | PROT |
| ATOM | 1196 | OD2 | ASP | 77 | 26.389 | 41.468 | 50.524 | 1.00 41.62 | PROT |
| ATOM | 1201 | N | ASN | 78 | 24.583 | 41.619 | 46.538 | 1.00 37.41 | PROT |
| ATOM | 1202 | CA | ASN | 78 | 24.783 | 42.569 | 45.439 | 1.00 37.23 | PROT |
| ATOM | 1203 | C | ASN | 78 | 23.886 | 42.382 | 44.238 | 1.00 36.77 | PROT |
| ATOM | 1204 | O | ASN | 78 | 23.461 | 41.224 | 43.903 | 1.00 36.84 | PROT |
| ATOM | 1205 | CB | ASN | 78 | 26.253 | 42.612 | 44.987 | 1.00 37.97 | PROT |
| ATOM | 1206 | CG | ASN | 78 | 27.163 | 43.081 | 46.081 | 1.00 37.74 | PROT |
| ATOM | 1207 | OD1 | ASN | 78 | 27.389 | 42.377 | 47.067 | 1.00 38.55 | PROT |
| ATOM | 1208 | ND2 | ASN | 78 | 27.730 | 44.271 | 45.903 | 1.00 37.98 | PROT |
| ATOM | 1215 | N | CYS | 79 | 23.397 | 43.243 | 43.214 | 1.00 16.19 | PROT |
| ATOM | 1216 | CA | CYS | 79 | 22.832 | 43.532 | 42.605 | 1.00 16.26 | PROT |
| ATOM | 1217 | C | CYS | 79 | 23.597 | 42.781 | 41.510 | 1.00 16.22 | PROT |
| ATOM | 1218 | O | CYS | 79 | 24.836 | 42.753 | 41.526 | 1.00 16.10 | PROT |
| ATOM | 1219 | CB | CYS | 79 | 22.825 | 45.043 | 42.332 | 1.00 16.20 | PROT |
| ATOM | 1220 | SG | CYS | 79 | 21.462 | 45.968 | 43.104 | 1.00 17.58 | PROT |
| ATOM | 1225 | N | PRO | 80 | 22.865 | 42.209 | 40.548 | 1.00 16.04 | PROT |
| ATOM | 1226 | CA | PRO | 80 | 23.566 | 41.462 | 39.506 | 1.00 15.97 | PROT |
| ATOM | 1227 | C | PRO | 80 | 24.155 | 42.393 | 38.455 | 1.00 15.86 | PROT |
| ATOM | 1228 | O | PRO | 80 | 23.637 | 43.493 | 38.239 | 1.00 15.75 | PROT |
| ATOM | 1229 | CB | PRO | 80 | 22.472 | 40.599 | 38.877 | 1.00 15.93 | PROT |
| ATOM | 1230 | CG | PRO | 80 | 21.191 | 41.279 | 39.120 | 1.00 16.32 | PROT |
| ATOM | 1231 | CD | PRO | 80 | 21.401 | 42.197 | 40.359 | 1.00 15.83 | PROT |
| ATOM | 1239 | N | THR | 81 | 25.243 | 41.938 | 37.839 | 1.00 15.11 | PROT |
| ATOM | 1240 | CA | THR | 81 | 25.784 | 42.613 | 36.613 | 1.00 14.98 | PROT |
| ATOM | 1241 | C | THR | 81 | 24.649 | 42.736 | 35.604 | 1.00 14.03 | PROT |
| ATOM | 1242 | O | THR | 81 | 23.858 | 41.828 | 35.355 | 1.00 14.74 | PROT |
| ATOM | 1243 | CB | THR | 81 | 26.897 | 41.873 | 36.059 | 1.00 14.99 | PROT |
| ATOM | 1244 | OG1 | THR | 81 | 28.173 | 42.023 | 36.521 | 1.00 16.45 | PROT |
| ATOM | 1245 | CG2 | THR | 81 | 26.906 | 41.521 | 34.561 | 1.00 15.70 | PROT |
| ATOM | 1252 | H | PRO | 82 | 24.527 | 43.966 | 35.057 | 1.00 13.18 | PROT |
| ATOM | 1253 | CA | PRO | 82 | 23.515 | 44.336 | 34.036 | 1.00 12.07 | PROT |
| ATOM | 1254 | C | PRO | 82 | 23.628 | 43.384 | 32.792 | 1.00 11.01 | PROT |
| ATOM | 1255 | O | PRO | 82 | 22.628 | 43.098 | 32.114 | 1.00 10.30 | PROT |
| ATOM | 1256 | CB | PRO | 82 | 23.793 | 45.694 | 33.648 | 1.00 12.12 | PROT |
| ATOM | 1257 | CG | PRO | 82 | 24.421 | 46.277 | 34.830 | 1.00 13.06 | PROT |
| ATOM | 1258 | CD | PRO | 82 | 25.298 | 45.169 | 35.399 | 1.00 13.38 | PROT |
| ATOM | 1266 | N | ASP | 83 | 24.832 | 42.862 | 32.493 | 1.00 9.26 | PROT |
| ATOM | 1267 | CA | ASP | 83 | 25.069 | 41.989 | 31.354 | 1.00 8.37 | PROT |
| ATOM | 1268 | C | ASP | 83 | 24.413 | 40.568 | 31.665 | 1.00 7.22 | PROT |
| ATOM | 1269 | O | ASP | 83 | 23.280 | 39.870 | 30.765 | 1.00 7.05 | PROT |
| ATOM | 1270 | CB | ASP | 83 | 26.486 | 41.867 | 30.978 | 1.00 8.54 | PROT |
| ATOM | 1271 | CG | ASP | 83 | 27.001 | 43.100 | 30.241 | 1.00 10.63 | PROT |
| ATOM | 1272 | OD1 | ASP | 83 | 26.186 | 43.945 | 29.808 | 1.00 12.62 | PROT |
| ATOM | 1273 | OD2 | ASP | 83 | 28.234 | 43.224 | 30.098 | 1.00 12.07 | PROT |

Figure 3 cont.

```
ATOM   1278  N    ALA   84      24.370  40.253  32.953  1.00   6.02    PROT
ATOM   1279  CA   ALA   84      23.876  38.959  33.440  1.00   4.89    PROT
ATOM   1280  C    ALA   84      22.375  38.717  33.258  1.00   3.61    PROT
ATOM   1281  O    ALA   84      21.996  37.583  33.065  1.00   3.69    PROT
ATOM   1282  CB   ALA   84      24.267  38.775  34.910  1.00   4.25    PROT
ATOM   1288  N    VAL   85      21.561  39.766  33.347  1.00   3.41    PROT
ATOM   1289  CA   VAL   85      20.110  39.604  33.194  1.00   2.73    PROT
ATOM   1290  C    VAL   85      19.608  40.423  32.012  1.00   2.79    PROT
ATOM   1291  O    VAL   85      19.955  41.598  31.878  1.00   2.49    PROT
ATOM   1292  CB   VAL   85      19.338  40.014  34.489  1.00   3.07    PROT
ATOM   1293  CG1  VAL   85      17.851  39.679  34.358  1.00   2.00    PROT
ATOM   1294  CG2  VAL   85      19.945  39.324  35.722  1.00   3.73    PROT
ATOM   1304  N    TYR   86      18.774  39.812  31.171  1.00   2.33    PROT
ATOM   1305  CA   TYR   86      18.154  40.529  30.052  1.00   2.23    PROT
ATOM   1306  C    TYR   86      16.683  40.203  29.904  1.00   2.27    PROT
ATOM   1307  O    TYR   86      16.284  39.028  29.918  1.00   2.01    PROT
ATOM   1308  CB   TYR   86      18.935  40.205  28.765  1.00   2.41    PROT
ATOM   1309  CG   TYR   86      18.526  40.952  27.511  1.00   2.00    PROT
ATOM   1310  CD1  TYR   86      19.306  42.001  27.026  1.00   2.14    PROT
ATOM   1311  CD2  TYR   86      17.383  40.565  26.794  1.00   2.00    PROT
ATOM   1312  CE1  TYR   86      18.961  42.675  25.871  1.00   2.91    PROT
ATOM   1313  CE2  TYR   86      17.017  41.271  25.612  1.00   2.00    PROT
ATOM   1314  CZ   TYR   86      17.813  42.301  25.161  1.00   3.15    PROT
ATOM   1315  OH   TYR   86      17.505  42.982  24.012  1.00   2.37    PROT
ATOM   1324  N    VAL   87      15.859  41.240  29.763  1.00   2.00    PROT
ATOM   1325  CA   VAL   87      14.422  41.021  29.549  1.00   2.00    PROT
ATOM   1326  C    VAL   87      14.020  41.529  28.193  1.00   2.00    PROT
ATOM   1327  O    VAL   87      14.320  42.677  27.829  1.00   2.00    PROT
ATOM   1328  CB   VAL   87      13.592  41.734  30.617  1.00   2.00    PROT
ATOM   1329  CG1  VAL   87      12.060  41.591  30.800  1.00   2.00    PROT
ATOM   1330  CG2  VAL   87      13.889  41.243  32.021  1.00   2.00    PROT
ATOM   1340  N    TRP   88      13.362  40.652  27.413  1.00   2.00    PROT
ATOM   1341  CA   TRP   88      12.676  41.029  26.201  1.00   2.00    PROT
ATOM   1342  C    TRP   88      11.173  40.796  26.413  1.00   2.00    PROT
ATOM   1343  O    TRP   88      10.729  39.683  26.716  1.00   2.00    PROT
ATOM   1344  CB   TRP   88      13.196  40.275  24.971  1.00   2.00    PROT
ATOM   1345  CG   TRP   88      12.630  40.807  23.672  1.00   2.09    PROT
ATOM   1346  CD1  TRP   88      11.587  40.278  22.959  1.00   2.63    PROT
ATOM   1347  CD2  TRP   88      13.066  41.966  22.948  1.00   2.00    PROT
ATOM   1348  NE1  TRP   88      11.347  41.039  21.836  1.00   2.61    PROT
ATOM   1349  CE2  TRP   88      12.232  42.087  21.810  1.00   2.00    PROT
ATOM   1350  CE3  TRP   88      14.074  42.925  23.155  1.00   2.00    PROT
ATOM   1351  CZ2  TRP   88      12.391  43.113  20.866  1.00   2.62    PROT
ATOM   1352  CZ3  TRP   88      14.221  43.951  22.242  1.00   2.08    PROT
ATOM   1353  CH2  TRP   88      13.391  44.036  21.092  1.00   3.02    PROT
ATOM   1364  N    ALA   89      10.405  41.871  26.281  1.00   2.00    PROT
ATOM   1365  CA   ALA   89       8.974  41.845  26.500  1.00   2.00    PROT
ATOM   1366  C    ALA   89       8.268  42.148  25.197  1.00   2.00    PROT
ATOM   1367  O    ALA   89       8.772  42.938  24.375  1.00   2.00    PROT
ATOM   1368  CB   ALA   89       8.608  42.895  27.556  1.00   2.00    PROT
ATOM   1374  N    ASP   90       7.096  41.540  25.014  1.00   2.00    PROT
ATOM   1375  CA   ASP   90       6.230  41.890  23.905  1.00   2.00    PROT
ATOM   1376  C    ASP   90       5.762  43.321  24.123  1.00   2.00    PROT
ATOM   1377  O    ASP   90       5.980  43.905  25.201  1.00   2.00    PROT
ATOM   1378  CB   ASP   90       5.038  40.939  23.806  1.00   2.02    PROT
ATOM   1379  CG   ASP   90       4.386  40.927  22.419  1.00   3.28    PROT
ATOM   1380  OD1  ASP   90       4.904  41.530  21.427  1.00   2.00    PROT
ATOM   1381  OD2  ASP   90       3.366  40.234  22.305  1.00   4.44    PROT
ATOM   1386  N    VAL   91       5.145  43.864  23.089  1.00   2.00    PROT
ATOM   1387  CA   VAL   91       4.839  45.312  23.046  1.00   2.00    PROT
ATOM   1388  C    VAL   91       3.708  45.743  23.983  1.00   2.00    PROT
ATOM   1389  O    VAL   91       3.607  46.933  24.307  1.00   2.00    PROT
ATOM   1390  CB   VAL   91       4.491  45.789  21.610  1.00   2.00    PROT
ATOM   1391  CG1  VAL   91       5.703  45.611  20.703  1.00   2.00    PROT
ATOM   1392  CG2  VAL   91       3.283  44.938  21.063  1.00   2.00    PROT
```

Figure 3 cont.

| | | | | | | | | | |
|---|---|---|---|---|---|---|---|---|---|
| ATOM | 1402 | N | ASP | 92 | 2.865 | 44.784 | 24.380 | 1.00 | 2.00 | PROT |
| ATOM | 1403 | CA | ASP | 92 | 1.653 | 45.051 | 25.160 | 1.00 | 2.44 | PROT |
| ATOM | 1404 | C | ASP | 92 | 2.039 | 45.637 | 26.509 | 1.00 | 2.47 | PROT |
| ATOM | 1405 | O | ASP | 92 | 3.096 | 45.290 | 27.059 | 1.00 | 2.00 | PROT |
| ATOM | 1406 | CB | ASP | 92 | 0.830 | 43.773 | 25.409 | 1.00 | 2.85 | PROT |
| ATOM | 1407 | CG | ASP | 92 | 0.335 | 43.110 | 24.117 | 1.00 | 6.94 | PROT |
| ATOM | 1408 | OD1 | ASP | 92 | -0.731 | 43.495 | 23.587 | 1.00 | 7.72 | PROT |
| ATOM | 1409 | OD2 | ASP | 92 | 1.008 | 42.172 | 23.644 | 1.00 | 11.14 | PROT |
| ATOM | 1414 | N | GLN | 93 | 1.177 | 46.869 | 27.064 | 1.00 | 2.72 | PROT |
| ATOM | 1415 | CA | GLN | 93 | 1.454 | 46.986 | 28.408 | 1.00 | 3.30 | PROT |
| ATOM | 1416 | C | GLN | 93 | 1.531 | 45.656 | 29.444 | 1.00 | 3.26 | PROT |
| ATOM | 1417 | O | GLN | 93 | 2.402 | 45.897 | 30.502 | 1.00 | 2.71 | PROT |
| ATOM | 1418 | CB | GLN | 93 | 0.587 | 48.198 | 28.820 | 1.00 | 5.15 | PROT |
| ATOM | 1419 | CG | GLN | 93 | -0.668 | 48.007 | 29.653 | 1.00 | 5.19 | PROT |
| ATOM | 1420 | CD | GLN | 93 | -0.470 | 47.899 | 31.123 | 1.00 | 4.49 | PROT |
| ATOM | 1421 | OE1 | GLN | 93 | -0.305 | 48.431 | 32.046 | 1.00 | 7.38 | PROT |
| ATOM | 1422 | NE2 | GLN | 93 | -0.602 | 46.329 | 31.346 | 1.00 | 2.00 | PROT |
| ATOM | 1431 | N | ARG | 94 | 0.874 | 44.833 | 29.320 | 1.00 | 2.89 | PROT |
| ATOM | 1432 | CA | ARG | 94 | 0.890 | 43.683 | 30.240 | 1.00 | 2.30 | PROT |
| ATOM | 1433 | C | ARG | 94 | 2.030 | 42.923 | 30.263 | 1.00 | 2.13 | PROT |
| ATOM | 1434 | O | ARG | 94 | 2.490 | 42.522 | 31.326 | 1.00 | 2.00 | PROT |
| ATOM | 1435 | CB | ARG | 94 | -0.495 | 42.730 | 30.018 | 1.00 | 2.00 | PROT |
| ATOM | 1436 | CG | ARG | 94 | -0.562 | 42.008 | 28.643 | 1.00 | 2.96 | PROT |
| ATOM | 1437 | CD | ARG | 94 | -1.826 | 41.136 | 28.462 | 1.00 | 4.83 | PROT |
| ATOM | 1438 | NE | ARG | 94 | -2.869 | 41.869 | 27.755 | 1.00 | 13.79 | PROT |
| ATOM | 1439 | CZ | ARG | 94 | -3.314 | 41.610 | 26.528 | 1.00 | 13.85 | PROT |
| ATOM | 1440 | NH1 | ARG | 94 | -2.869 | 40.563 | 25.897 | 1.00 | 13.84 | PROT |
| ATOM | 1441 | NH2 | ARG | 94 | -4.349 | 42.395 | 26.002 | 1.00 | 17.58 | PROT |
| ATOM | 1455 | N | THR | 95 | 2.634 | 42.734 | 29.095 | 1.00 | 2.00 | PROT |
| ATOM | 1456 | CA | THR | 95 | 3.967 | 42.087 | 28.989 | 1.00 | 2.00 | PROT |
| ATOM | 1457 | C | THR | 95 | 5.125 | 42.993 | 29.397 | 1.00 | 2.00 | PROT |
| ATOM | 1458 | O | THR | 95 | 6.019 | 42.544 | 30.318 | 1.00 | 2.00 | PROT |
| ATOM | 1459 | CB | THR | 95 | 4.190 | 41.458 | 27.564 | 1.00 | 2.00 | PROT |
| ATOM | 1460 | OG1 | THR | 95 | 3.868 | 42.400 | 26.560 | 1.00 | 2.00 | PROT |
| ATOM | 1461 | CG2 | THR | 95 | 3.302 | 40.241 | 27.407 | 1.00 | 2.00 | PROT |
| ATOM | 1468 | N | ARG | 96 | 5.134 | 44.256 | 28.961 | 1.00 | 2.00 | PROT |
| ATOM | 1469 | CA | ARG | 96 | 6.308 | 45.173 | 29.375 | 1.00 | 2.00 | PROT |
| ATOM | 1470 | C | ARG | 96 | 6.265 | 45.331 | 30.900 | 1.00 | 2.00 | PROT |
| ATOM | 1471 | O | ARG | 96 | 7.342 | 45.239 | 31.498 | 1.00 | 2.00 | PROT |
| ATOM | 1472 | CB | ARG | 96 | 6.073 | 46.550 | 28.792 | 1.00 | 2.00 | PROT |
| ATOM | 1473 | CG | ARG | 96 | 6.334 | 46.523 | 27.195 | 1.00 | 2.00 | PROT |
| ATOM | 1474 | CD | ARG | 96 | 6.262 | 47.911 | 26.602 | 1.00 | 3.41 | PROT |
| ATOM | 1475 | NE | ARG | 96 | 4.837 | 48.356 | 26.337 | 1.00 | 2.27 | PROT |
| ATOM | 1476 | CZ | ARG | 96 | 4.239 | 49.279 | 27.044 | 1.00 | 3.34 | PROT |
| ATOM | 1477 | NH1 | ARG | 96 | 4.789 | 49.871 | 28.093 | 1.00 | 2.00 | PROT |
| ATOM | 1478 | NH2 | ARG | 96 | 3.011 | 49.609 | 26.691 | 1.00 | 4.75 | PROT |
| ATOM | 1492 | N | LYS | 97 | 5.097 | 45.561 | 31.510 | 1.00 | 2.00 | PROT |
| ATOM | 1493 | CA | LYS | 97 | 4.970 | 45.685 | 32.964 | 1.00 | 2.15 | PROT |
| ATOM | 1494 | C | LYS | 97 | 5.305 | 44.389 | 33.698 | 1.00 | 2.00 | PROT |
| ATOM | 1495 | O | LYS | 97 | 5.894 | 44.405 | 34.779 | 1.00 | 2.00 | PROT |
| ATOM | 1496 | CB | LYS | 97 | 3.566 | 46.131 | 33.373 | 1.00 | 2.09 | PROT |
| ATOM | 1497 | CG | LYS | 97 | 3.225 | 47.581 | 32.358 | 1.00 | 4.19 | PROT |
| ATOM | 1498 | CD | LYS | 97 | 3.935 | 48.612 | 33.816 | 1.00 | 9.00 | PROT |
| ATOM | 1499 | CE | LYS | 97 | 3.701 | 50.013 | 33.260 | 1.00 | 11.25 | PROT |
| ATOM | 1500 | NZ | LYS | 97 | 3.956 | 51.008 | 34.350 | 1.00 | 16.81 | PROT |
| ATOM | 1514 | N | THR | 98 | 5.047 | 43.251 | 33.058 | 1.00 | 2.00 | PROT |
| ATOM | 1515 | CA | THR | 98 | 5.477 | 41.950 | 33.602 | 1.00 | 2.10 | PROT |
| ATOM | 1516 | C | THR | 98 | 7.011 | 41.867 | 33.667 | 1.00 | 2.00 | PROT |
| ATOM | 1517 | O | THR | 98 | 7.574 | 41.530 | 34.691 | 1.00 | 2.00 | PROT |
| ATOM | 1518 | CB | THR | 98 | 4.894 | 40.779 | 32.802 | 1.00 | 2.41 | PROT |
| ATOM | 1519 | OG1 | THR | 98 | 3.466 | 40.757 | 32.353 | 1.00 | 2.10 | PROT |
| ATOM | 1520 | CG2 | THR | 98 | 5.480 | 39.437 | 33.293 | 1.00 | 4.45 | PROT |
| ATOM | 1527 | N | GLY | 99 | 7.669 | 42.268 | 32.571 | 1.00 | 2.00 | PROT |
| ATOM | 1528 | CA | GLY | 99 | 9.132 | 42.372 | 32.552 | 1.00 | 2.00 | PROT |
| ATOM | 1529 | C | GLY | 99 | 9.865 | 43.275 | 33.639 | 1.00 | 2.00 | PROT |

Figure 3 cont.

```
ATOM   1533  O    GLY    99      10.609  42.906  34.359  1.00   2.00      PROT
ATOM   1534  N    GLU   100       9.051  44.449  33.784  1.00   2.00      PROT
ATOM   1535  CA   GLU   100       9.460  45.396  34.826  1.00   2.05      PROT
ATOM   1536  C    GLU   100       9.293  44.767  36.213  1.00   2.00      PROT
ATOM   1537  O    GLU   100      10.213  44.802  37.024  1.00   2.00      PROT
ATOM   1538  CB   GLU   100       8.713  46.701  34.703  1.00   2.00      PROT
ATOM   1539  CG   GLU   100       9.129  47.307  33.444  1.00   3.36      PROT
ATOM   1540  CD   GLU   100       8.469  48.665  33.348  1.00   6.20      PROT
ATOM   1541  OE1  GLU   100       8.560  49.652  34.303  1.00  10.98      PROT
ATOM   1542  OE2  GLU   100       7.853  49.169  32.307  1.00  13.47      PROT
ATOM   1549  N    ALA   101       8.126  44.172  36.459  1.00   2.00      PROT
ATOM   1550  CA   ALA   101       7.860  43.482  37.745  1.00   2.00      PROT
ATOM   1551  C    ALA   101       9.011  42.304  38.036  1.00   2.00      PROT
ATOM   1552  O    ALA   101       9.177  42.093  39.194  1.00   2.00      PROT
ATOM   1553  CB   ALA   101       6.412  43.033  37.817  1.00   2.00      PROT
ATOM   1559  N    PHE   102       9.205  41.567  37.004  1.00   2.00      PROT
ATOM   1560  CA   PHE   102      10.183  40.463  37.165  1.00   2.00      PROT
ATOM   1561  C    PHE   102      11.506  41.008  37.708  1.00   2.00      PROT
ATOM   1562  O    PHE   102      12.078  40.461  38.651  1.00   2.00      PROT
ATOM   1563  CB   PHE   102      10.413  39.696  35.845  1.00   2.00      PROT
ATOM   1564  CG   PHE   102      11.708  38.891  35.801  1.00   2.00      PROT
ATOM   1565  CD1  PHE   102      11.805  37.638  36.417  1.00   2.31      PROT
ATOM   1566  CD2  PHE   102      12.813  39.379  35.108  1.00   2.00      PROT
ATOM   1567  CE1  PHE   102      12.992  36.895  36.380  1.00   2.00      PROT
ATOM   1568  CE2  PHE   102      14.001  38.656  35.062  1.00   2.98      PROT
ATOM   1569  CZ   PHE   102      14.090  37.405  35.677  1.00   2.00      PROT
ATOM   1579  N    LEU   103      11.959  42.110  37.119  1.00   2.00      PROT
ATOM   1580  CA   LEU   103      13.195  42.755  37.548  1.00   2.00      PROT
ATOM   1581  C    LEU   103      13.104  43.264  38.992  1.00   2.00      PROT
ATOM   1582  O    LEU   103      14.070  43.171  39.735  1.00   2.00      PROT
ATOM   1583  CB   LEU   103      13.620  43.855  36.559  1.00   2.00      PROT
ATOM   1584  CG   LEU   103      14.007  43.457  35.125  1.00   2.00      PROT
ATOM   1585  CD1  LEU   103      14.503  44.694  34.349  1.00   2.53      PROT
ATOM   1586  CD2  LEU   103      15.084  42.375  35.133  1.00   2.00      PROT
ATOM   1598  N    ALA   104      11.926  43.789  39.378  1.00   2.00      PROT
ATOM   1599  CA   ALA   104      11.671  44.317  40.709  1.00   2.00      PROT
ATOM   1600  C    ALA   104      11.822  43.270  41.789  1.00   2.00      PROT
ATOM   1601  O    ALA   104      12.226  43.575  42.930  1.00   2.40      PROT
ATOM   1602  CB   ALA   104      10.262  44.906  40.760  1.00   3.11      PROT
ATOM   1608  N    GLY   105      11.474  42.039  41.425  1.00   2.00      PROT
ATOM   1609  CA   GLY   105      11.554  40.915  42.325  1.00   2.36      PROT
ATOM   1610  C    GLY   105      12.863  40.164  42.270  1.00   2.19      PROT
ATOM   1611  O    GLY   105      13.355  39.725  43.304  1.00   2.00      PROT
ATOM   1615  N    LEU   106      13.426  40.001  41.070  1.00   2.74      PROT
ATOM   1616  CA   LEU   106      14.717  39.336  40.866  1.00   3.45      PROT
ATOM   1617  C    LEU   106      15.858  40.160  41.457  1.00   4.64      PROT
ATOM   1618  O    LEU   106      16.849  39.608  41.946  1.00   4.33      PROT
ATOM   1619  CB   LEU   106      14.997  39.092  39.396  1.00   3.80      PROT
ATOM   1620  CG   LEU   106      16.280  38.341  39.031  1.00   3.13      PROT
ATOM   1621  CD1  LEU   106      16.014  36.859  39.049  1.00   3.36      PROT
ATOM   1622  CD2  LEU   106      16.808  38.856  37.714  1.00   3.16      PROT
ATOM   1634  N    ALA   107      15.722  41.478  41.384  1.00   5.01      PROT
ATOM   1635  CA   ALA   107      16.807  42.366  41.747  1.00   6.45      PROT
ATOM   1636  C    ALA   107      16.269  43.669  42.271  1.00   6.30      PROT
ATOM   1637  O    ALA   107      16.396  44.715  41.605  1.00   6.73      PROT
ATOM   1638  CB   ALA   107      17.720  42.533  40.543  1.00   6.01      PROT
ATOM   1644  N    PRO   108      15.669  43.677  43.465  1.00   8.33      PROT
ATOM   1645  CA   PRO   108      15.052  44.972  44.037  1.00   9.44      PROT
ATOM   1646  C    PRO   108      16.064  45.979  44.282  1.00  10.34      PROT
ATOM   1647  O    PRO   108      17.180  45.706  44.720  1.00  10.41      PROT
ATOM   1648  CB   PRO   108      14.474  44.585  45.370  1.00   9.24      PROT
ATOM   1649  CG   PRO   108      14.475  43.001  45.260  1.00   9.66      PROT
ATOM   1650  CD   PRO   108      15.630  42.581  44.430  1.00   8.13      PROT
ATOM   1658  N    GLN   109      15.671  47.213  43.982  1.00  11.29      PROT
ATOM   1659  CA   GLN   109      16.346  48.367  44.132  1.00  12.67      PROT
```

Figure 3 cont.

| | | | | | | | | | |
|---|---|---|---|---|---|---|---|---|---|
| ATOM | 1660 | C | GLN | 109 | 17.626 | 48.299 | 43.287 | 1.00 | 12.75 | PROT |
| ATOM | 1661 | O | GLN | 109 | 18.837 | 48.322 | 43.619 | 1.00 | 13.13 | PROT |
| ATOM | 1662 | CB | GLN | 109 | 16.904 | 48.643 | 45.612 | 1.00 | 13.03 | PROT |
| ATOM | 1663 | CG | GLN | 109 | 15.785 | 48.393 | 46.633 | 1.00 | 15.36 | PROT |
| ATOM | 1664 | CD | GLN | 109 | 14.513 | 49.161 | 46.357 | 1.00 | 18.56 | PROT |
| ATOM | 1665 | OE1 | GLN | 109 | 14.529 | 50.223 | 45.699 | 1.00 | 19.89 | PROT |
| ATOM | 1666 | NE2 | GLN | 109 | 13.400 | 48.689 | 46.847 | 1.00 | 19.67 | PROT |
| ATOM | 1675 | N | CYS | 110 | 17.787 | 47.499 | 42.219 | 1.00 | 12.66 | PROT |
| ATOM | 1676 | CA | CYS | 110 | 18.857 | 47.466 | 41.239 | 1.00 | 12.26 | PROT |
| ATOM | 1677 | C | CYS | 110 | 18.376 | 48.198 | 39.995 | 1.00 | 11.36 | PROT |
| ATOM | 1678 | O | CYS | 110 | 17.204 | 48.084 | 39.695 | 1.00 | 11.75 | PROT |
| ATOM | 1679 | CB | CYS | 110 | 19.288 | 46.024 | 40.920 | 1.00 | 12.49 | PROT |
| ATOM | 1680 | SG | CYS | 110 | 19.778 | 45.068 | 42.410 | 1.00 | 13.69 | PROT |
| ATOM | 1685 | N | ASP | 111 | 19.278 | 48.957 | 39.381 | 1.00 | 11.33 | PROT |
| ATOM | 1686 | CA | ASP | 111 | 18.909 | 49.879 | 38.305 | 1.00 | 11.30 | PROT |
| ATOM | 1687 | C | ASP | 111 | 18.925 | 49.204 | 36.941 | 1.00 | 10.16 | PROT |
| ATOM | 1688 | O | ASP | 111 | 19.773 | 49.490 | 36.087 | 1.00 | 10.47 | PROT |
| ATOM | 1689 | CB | ASP | 111 | 19.822 | 51.102 | 38.317 | 1.00 | 12.10 | PROT |
| ATOM | 1690 | CG | ASP | 111 | 19.128 | 52.360 | 37.836 | 1.00 | 13.34 | PROT |
| ATOM | 1691 | OD1 | ASP | 111 | 17.909 | 52.325 | 37.563 | 1.00 | 14.20 | PROT |
| ATOM | 1692 | OD2 | ASP | 111 | 19.817 | 53.396 | 37.743 | 1.00 | 17.04 | PROT |
| ATOM | 1697 | N | LEU | 112 | 17.973 | 48.295 | 36.756 | 1.00 | 8.69 | PROT |
| ATOM | 1698 | CA | LEU | 112 | 17.884 | 47.508 | 35.546 | 1.00 | 6.78 | PROT |
| ATOM | 1699 | C | LEU | 112 | 16.579 | 47.909 | 34.795 | 1.00 | 5.58 | PROT |
| ATOM | 1700 | O | LEU | 112 | 15.632 | 48.421 | 35.394 | 1.00 | 5.83 | PROT |
| ATOM | 1701 | CB | LEU | 112 | 17.844 | 46.004 | 35.880 | 1.00 | 7.06 | PROT |
| ATOM | 1702 | CG | LEU | 112 | 19.012 | 45.458 | 36.725 | 1.00 | 7.52 | PROT |
| ATOM | 1703 | CD1 | LEU | 112 | 20.331 | 45.536 | 35.970 | 1.00 | 5.79 | PROT |
| ATOM | 1704 | CD2 | LEU | 112 | 18.757 | 44.036 | 37.212 | 1.00 | 6.06 | PROT |
| ATOM | 1716 | N | ALA | 113 | 16.579 | 47.672 | 33.496 | 1.00 | 3.63 | PROT |
| ATOM | 1717 | CA | ALA | 113 | 15.482 | 48.053 | 32.611 | 1.00 | 2.79 | PROT |
| ATOM | 1718 | C | ALA | 113 | 15.235 | 46.956 | 31.601 | 1.00 | 2.00 | PROT |
| ATOM | 1719 | O | ALA | 113 | 16.164 | 46.211 | 31.254 | 1.00 | 2.00 | PROT |
| ATOM | 1720 | CB | ALA | 113 | 15.807 | 49.371 | 31.894 | 1.00 | 2.36 | PROT |
| ATOM | 1726 | N | ILE | 114 | 13.993 | 46.878 | 31.125 | 1.00 | 2.00 | PROT |
| ATOM | 1727 | CA | ILE | 114 | 13.588 | 45.913 | 30.101 | 1.00 | 2.00 | PROT |
| ATOM | 1728 | C | ILE | 114 | 13.952 | 46.388 | 28.685 | 1.00 | 2.00 | PROT |
| ATOM | 1729 | O | ILE | 114 | 14.258 | 47.561 | 28.406 | 1.00 | 2.00 | PROT |
| ATOM | 1730 | CB | ILE | 114 | 12.059 | 45.692 | 30.175 | 1.00 | 2.00 | PROT |
| ATOM | 1731 | CG1 | ILE | 114 | 11.209 | 46.763 | 29.701 | 1.00 | 2.00 | PROT |
| ATOM | 1732 | CG2 | ILE | 114 | 11.676 | 45.354 | 31.697 | 1.00 | 2.00 | PROT |
| ATOM | 1733 | CD | ILE | 114 | 9.700 | 46.471 | 29.563 | 1.00 | 2.00 | PROT |
| ATOM | 1745 | N | HSD | 115 | 13.982 | 45.445 | 27.749 | 1.00 | 2.00 | PROT |
| ATOM | 1746 | CA | HSD | 115 | 14.074 | 45.727 | 26.333 | 1.00 | 2.00 | PROT |
| ATOM | 1747 | C | HSD | 115 | 12.756 | 45.349 | 25.659 | 1.00 | 2.00 | PROT |
| ATOM | 1748 | O | HSD | 115 | 12.042 | 44.448 | 26.126 | 1.00 | 2.00 | PROT |
| ATOM | 1749 | CB | HSD | 115 | 15.239 | 44.938 | 25.734 | 1.00 | 2.00 | PROT |
| ATOM | 1750 | CG | HSD | 115 | 16.579 | 45.398 | 26.216 | 1.00 | 2.00 | PROT |
| ATOM | 1751 | ND1 | HSD | 115 | 17.142 | 44.954 | 27.390 | 1.00 | 2.04 | PROT |
| ATOM | 1752 | CD2 | HSD | 115 | 17.449 | 46.293 | 25.699 | 1.00 | 2.00 | PROT |
| ATOM | 1753 | CE1 | HSD | 115 | 18.312 | 45.540 | 27.569 | 1.00 | 2.00 | PROT |
| ATOM | 1754 | NE2 | HSD | 115 | 18.526 | 46.349 | 26.546 | 1.00 | 2.21 | PROT |
| ATOM | 1762 | N | HSD | 116 | 12.425 | 46.047 | 24.577 | 1.00 | 2.00 | PROT |
| ATOM | 1763 | CA | HSD | 116 | 11.242 | 45.700 | 23.774 | 1.00 | 2.00 | PROT |
| ATOM | 1764 | C | HSD | 116 | 11.350 | 46.370 | 22.402 | 1.00 | 2.00 | PROT |
| ATOM | 1765 | O | HSD | 116 | 12.160 | 47.270 | 22.221 | 1.00 | 2.00 | PROT |
| ATOM | 1766 | CB | HSD | 116 | 9.911 | 46.039 | 24.463 | 1.00 | 2.00 | PROT |
| ATOM | 1767 | CG | HSD | 116 | 9.625 | 47.507 | 24.663 | 1.00 | 2.00 | PROT |
| ATOM | 1768 | CD2 | HSD | 116 | 9.723 | 48.192 | 25.834 | 1.00 | 2.12 | PROT |
| ATOM | 1769 | ND1 | HSD | 116 | 9.231 | 48.425 | 23.719 | 1.00 | 2.00 | PROT |
| ATOM | 1770 | NE2 | HSD | 116 | 9.410 | 49.453 | 25.650 | 1.00 | 2.00 | PROT |
| ATOM | 1771 | CE1 | HSD | 116 | 9.109 | 49.628 | 24.375 | 1.00 | 3.14 | PROT |
| ATOM | 1779 | N | GLN | 117 | 10.545 | 45.903 | 21.448 | 1.00 | 2.00 | PROT |
| ATOM | 1780 | CA | GLN | 117 | 10.493 | 46.476 | 20.108 | 1.00 | 2.44 | PROT |
| ATOM | 1781 | C | GLN | 117 | 10.198 | 47.973 | 20.207 | 1.00 | 2.34 | PROT |

Figure 3 cont.

| | | | | | | | | |
|---|---|---|---|---|---|---|---|---|
| ATOM | 1782 | O | GLN | 117 | 9.301 | 48.385 | 20.950 | 1.00 | 2.66 | PROT |
| ATOM | 1783 | CB | GLN | 117 | 7.426 | 45.769 | 19.273 | 1.00 | 2.08 | PROT |
| ATOM | 1784 | CG | GLN | 117 | 9.238 | 46.301 | 17.870 | 1.00 | 3.58 | PROT |
| ATOM | 1785 | CD | GLN | 117 | 8.402 | 45.390 | 17.021 | 1.00 | 3.37 | PROT |
| ATOM | 1786 | OE1 | GLN | 117 | 8.895 | 44.358 | 16.536 | 1.00 | 2.60 | PROT |
| ATOM | 1787 | NE2 | GLN | 117 | 7.159 | 45.739 | 16.818 | 1.00 | 3.63 | PROT |
| ATOM | 1796 | N | GLN | 118 | 10.365 | 49.767 | 19.465 | 1.00 | 2.94 | PROT |
| ATOM | 1797 | CA | GLN | 118 | 10.839 | 50.231 | 19.871 | 1.00 | 4.36 | PROT |
| ATOM | 1798 | C | GLN | 118 | 9.416 | 50.735 | 19.236 | 1.00 | 4.23 | PROT |
| ATOM | 1799 | O | GLN | 118 | 8.823 | 51.585 | 19.982 | 1.00 | 4.27 | PROT |
| ATOM | 1800 | CB | GLN | 118 | 11.789 | 50.862 | 18.446 | 1.00 | 4.57 | PROT |
| ATOM | 1801 | CG | GLN | 118 | 13.234 | 51.016 | 18.915 | 1.00 | 7.90 | PROT |
| ATOM | 1802 | CD | GLN | 118 | 13.453 | 52.158 | 19.930 | 1.00 | 10.01 | PROT |
| ATOM | 1803 | OE1 | GLN | 118 | 12.523 | 52.627 | 20.599 | 1.00 | 11.52 | PROT |
| ATOM | 1804 | NE2 | GLN | 118 | 14.696 | 52.566 | 20.080 | 1.00 | 12.05 | PROT |
| ATOM | 1813 | N | ASN | 119 | 8.772 | 50.211 | 18.196 | 1.00 | 4.34 | PROT |
| ATOM | 1814 | CA | ASN | 119 | 7.373 | 50.532 | 17.873 | 1.00 | 3.91 | PROT |
| ATOM | 1815 | C | ASN | 119 | 6.407 | 49.344 | 18.509 | 1.00 | 3.28 | PROT |
| ATOM | 1816 | O | ASN | 119 | 6.334 | 48.391 | 18.077 | 1.00 | 2.33 | PROT |
| ATOM | 1817 | CB | ASN | 119 | 7.179 | 50.528 | 16.351 | 1.00 | 4.16 | PROT |
| ATOM | 1818 | CG | ASN | 119 | 5.887 | 51.197 | 15.910 | 1.00 | 5.04 | PROT |
| ATOM | 1819 | OD1 | ASN | 119 | 4.809 | 50.873 | 16.391 | 1.00 | 7.49 | PROT |
| ATOM | 1820 | ND2 | ASN | 119 | 5.994 | 52.111 | 14.960 | 1.00 | 6.10 | PROT |
| ATOM | 1827 | N | THR | 120 | 5.676 | 50.004 | 19.519 | 1.00 | 3.07 | PROT |
| ATOM | 1828 | CA | THR | 120 | 4.763 | 49.153 | 20.265 | 1.00 | 4.87 | PROT |
| ATOM | 1829 | C | THR | 120 | 3.377 | 49.154 | 19.610 | 1.00 | 5.02 | PROT |
| ATOM | 1830 | O | THR | 120 | 2.465 | 48.483 | 20.063 | 1.00 | 5.27 | PROT |
| ATOM | 1831 | CB | THR | 120 | 4.691 | 49.567 | 21.763 | 1.00 | 4.46 | PROT |
| ATOM | 1832 | OG1 | THR | 120 | 4.106 | 50.875 | 21.874 | 1.00 | 3.87 | PROT |
| ATOM | 1833 | CG2 | THR | 120 | 6.076 | 49.605 | 22.365 | 1.00 | 4.19 | PROT |
| ATOM | 1840 | N | GLN | 121 | 3.236 | 49.869 | 18.512 | 1.00 | 6.52 | PROT |
| ATOM | 1841 | CA | GLN | 121 | 1.939 | 49.972 | 17.849 | 1.00 | 7.59 | PROT |
| ATOM | 1842 | C | GLN | 121 | 1.860 | 48.936 | 16.726 | 1.00 | 7.98 | PROT |
| ATOM | 1843 | O | GLN | 121 | 0.851 | 48.841 | 16.015 | 1.00 | 9.07 | PROT |
| ATOM | 1844 | CB | GLN | 121 | 1.676 | 51.391 | 17.346 | 1.00 | 8.37 | PROT |
| ATOM | 1845 | CG | GLN | 121 | 1.799 | 52.462 | 18.423 | 1.00 | 9.82 | PROT |
| ATOM | 1846 | CD | GLN | 121 | 0.733 | 52.391 | 19.517 | 1.00 | 12.79 | PROT |
| ATOM | 1847 | OE1 | GLN | 121 | -0.348 | 51.841 | 19.311 | 1.00 | 14.41 | PROT |
| ATOM | 1848 | NE2 | GLN | 121 | 1.047 | 52.935 | 20.687 | 1.00 | 12.67 | PROT |
| ATOM | 1857 | N | GLN | 122 | 2.939 | 49.167 | 16.876 | 1.00 | 7.19 | PROT |
| ATOM | 1858 | CA | GLN | 122 | 3.034 | 47.097 | 15.584 | 1.00 | 6.63 | PROT |
| ATOM | 1859 | C | GLN | 122 | 3.405 | 45.795 | 16.284 | 1.00 | 5.51 | PROT |
| ATOM | 1860 | O | GLN | 122 | 4.132 | 45.809 | 17.275 | 1.00 | 4.57 | PROT |
| ATOM | 1861 | CB | GLN | 122 | 4.093 | 47.423 | 14.530 | 1.00 | 6.79 | PROT |
| ATOM | 1862 | CG | GLN | 122 | 3.795 | 48.631 | 13.691 | 1.00 | 9.40 | PROT |
| ATOM | 1863 | CD | GLN | 122 | 4.278 | 48.806 | 12.277 | 1.00 | 12.32 | PROT |
| ATOM | 1864 | OE1 | GLN | 122 | 4.437 | 47.391 | 11.776 | 1.00 | 14.95 | PROT |
| ATOM | 1865 | NE2 | GLN | 122 | 4.802 | 49.636 | 11.609 | 1.00 | 13.56 | PROT |
| ATOM | 1874 | N | ALA | 123 | 2.901 | 44.674 | 15.769 | 1.00 | 4.39 | PROT |
| ATOM | 1875 | CA | ALA | 123 | 3.224 | 43.366 | 16.327 | 1.00 | 3.92 | PROT |
| ATOM | 1876 | C | ALA | 123 | 4.740 | 43.145 | 16.352 | 1.00 | 3.61 | PROT |
| ATOM | 1877 | O | ALA | 123 | 5.454 | 43.612 | 15.467 | 1.00 | 2.39 | PROT |
| ATOM | 1878 | CB | ALA | 123 | 2.537 | 40.258 | 15.528 | 1.00 | 4.62 | PROT |
| ATOM | 1884 | N | ASP | 124 | 5.238 | 42.477 | 17.393 | 1.00 | 3.00 | PROT |
| ATOM | 1885 | CA | ASP | 124 | 6.619 | 42.021 | 17.434 | 1.00 | 2.70 | PROT |
| ATOM | 1886 | C | ASP | 124 | 6.651 | 40.631 | 16.794 | 1.00 | 2.31 | PROT |
| ATOM | 1887 | O | ASP | 124 | 6.051 | 39.707 | 17.332 | 1.00 | 2.50 | PROT |
| ATOM | 1888 | CB | ASP | 124 | 7.107 | 41.984 | 18.901 | 1.00 | 3.22 | PROT |
| ATOM | 1889 | CG | ASP | 124 | 8.564 | 41.497 | 19.026 | 1.00 | 2.93 | PROT |
| ATOM | 1890 | OD1 | ASP | 124 | 9.121 | 40.907 | 18.068 | 1.00 | 3.58 | PROT |
| ATOM | 1891 | OD2 | ASP | 124 | 9.162 | 41.732 | 20.087 | 1.00 | 3.75 | PROT |
| ATOM | 1896 | N | PRO | 125 | 7.374 | 40.464 | 15.661 | 1.00 | 2.33 | PROT |
| ATOM | 1897 | CA | PRO | 125 | 7.386 | 39.193 | 14.934 | 1.00 | 2.64 | PROT |
| ATOM | 1898 | C | PRO | 125 | 7.301 | 38.001 | 15.736 | 1.00 | 2.17 | PROT |
| ATOM | 1899 | O | PRO | 125 | 7.657 | 36.859 | 15.369 | 1.00 | 2.28 | PROT |

Figure 3 cont.

| | | | | | | | | | |
|---|---|---|---|---|---|---|---|---|---|
| ATOM | 1900 | CB | PRO | 125 | 8.310 | 39.478 | 13.739 | 1.00 | 2.31 | PROT |
| ATOM | 1901 | CG | PRO | 125 | 9.151 | 40.596 | 14.144 | 1.00 | 3.16 | PROT |
| ATOM | 1902 | CD | PRO | 125 | 8.249 | 41.459 | 15.023 | 1.00 | 2.63 | PROT |
| ATOM | 1910 | N | LEU | 126 | 8.688 | 38.265 | 16.787 | 1.00 | 2.21 | PROT |
| ATOM | 1911 | CA | LEU | 126 | 9.104 | 37.200 | 17.718 | 1.00 | 2.06 | PROT |
| ATOM | 1912 | C | LEU | 126 | 7.920 | 36.492 | 18.387 | 1.00 | 2.03 | PROT |
| ATOM | 1913 | O | LEU | 126 | 7.925 | 35.266 | 18.552 | 1.00 | 2.00 | PROT |
| ATOM | 1914 | CB | LEU | 126 | 10.038 | 37.770 | 18.794 | 1.00 | 2.27 | PROT |
| ATOM | 1915 | CG | LEU | 126 | 10.662 | 36.746 | 19.750 | 1.00 | 2.85 | PROT |
| ATOM | 1916 | CD1 | LEU | 126 | 11.671 | 35.870 | 19.025 | 1.00 | 4.52 | PROT |
| ATOM | 1917 | CD2 | LEU | 126 | 11.314 | 37.453 | 20.921 | 1.00 | 2.00 | PROT |
| ATOM | 1929 | N | PHE | 127 | 6.900 | 37.064 | 18.760 | 1.00 | 2.00 | PROT |
| ATOM | 1930 | CA | PHE | 127 | 5.759 | 36.729 | 19.501 | 1.00 | 2.00 | PROT |
| ATOM | 1931 | C | PHE | 127 | 4.574 | 36.382 | 19.613 | 1.00 | 2.00 | PROT |
| ATOM | 1932 | O | PHE | 127 | 3.739 | 38.473 | 19.930 | 1.00 | 2.00 | PROT |
| ATOM | 1933 | CB | PHE | 127 | 5.296 | 37.743 | 20.543 | 1.00 | 2.00 | PROT |
| ATOM | 1934 | CG | PHE | 127 | 6.392 | 38.010 | 21.611 | 1.00 | 2.00 | PROT |
| ATOM | 1935 | CD1 | PHE | 127 | 6.416 | 37.165 | 22.703 | 1.00 | 2.00 | PROT |
| ATOM | 1936 | CD2 | PHE | 127 | 7.136 | 39.131 | 21.528 | 1.00 | 2.00 | PROT |
| ATOM | 1937 | CE1 | PHE | 127 | 7.347 | 37.422 | 23.731 | 1.00 | 2.00 | PROT |
| ATOM | 1938 | CE2 | PHE | 127 | 8.062 | 39.394 | 22.514 | 1.00 | 2.00 | PROT |
| ATOM | 1939 | CZ | PHE | 127 | 8.369 | 38.547 | 23.615 | 1.00 | 2.00 | PROT |
| ATOM | 1949 | N | HSD | 128 | 4.425 | 37.146 | 17.838 | 1.00 | 2.00 | PROT |
| ATOM | 1950 | CA | HSD | 128 | 3.306 | 37.008 | 16.813 | 1.00 | 2.00 | PROT |
| ATOM | 1951 | C | HSD | 128 | 3.764 | 37.146 | 15.186 | 1.00 | 2.00 | PROT |
| ATOM | 1952 | O | HSD | 128 | 3.434 | 38.133 | 14.501 | 1.00 | 2.69 | PROT |
| ATOM | 1953 | CB | HSD | 128 | 2.211 | 38.039 | 16.951 | 1.00 | 2.11 | PROT |
| ATOM | 1954 | CG | HSD | 128 | 1.713 | 37.969 | 18.362 | 1.00 | 3.31 | PROT |
| ATOM | 1955 | ND1 | HSD | 128 | 2.139 | 38.822 | 19.354 | 1.00 | 5.46 | PROT |
| ATOM | 1956 | CD2 | HSD | 128 | 0.613 | 37.144 | 18.947 | 1.00 | 4.58 | PROT |
| ATOM | 1957 | CE1 | HSD | 128 | 1.631 | 38.530 | 20.487 | 1.00 | 3.86 | PROT |
| ATOM | 1958 | NE2 | HSD | 128 | 0.717 | 37.513 | 20.265 | 1.00 | 5.27 | PROT |
| ATOM | 1966 | N | PRO | 129 | 4.529 | 36.185 | 14.661 | 1.00 | 2.00 | PROT |
| ATOM | 1967 | CA | PRO | 129 | 5.059 | 36.245 | 13.286 | 1.00 | 2.01 | PROT |
| ATOM | 1968 | C | PRO | 129 | 3.984 | 36.299 | 12.185 | 1.00 | 2.75 | PROT |
| ATOM | 1969 | O | PRO | 129 | 4.206 | 36.830 | 11.149 | 1.00 | 2.09 | PROT |
| ATOM | 1970 | CB | PRO | 129 | 5.925 | 34.991 | 13.139 | 1.00 | 2.40 | PROT |
| ATOM | 1971 | CG | PRO | 129 | 5.546 | 34.077 | 14.243 | 1.00 | 2.00 | PROT |
| ATOM | 1972 | CD | PRO | 129 | 4.989 | 34.923 | 15.347 | 1.00 | 2.00 | PROT |
| ATOM | 1980 | N | VAL | 130 | 2.845 | 35.647 | 12.427 | 1.00 | 3.60 | PROT |
| ATOM | 1981 | CA | VAL | 130 | 1.705 | 35.628 | 11.503 | 1.00 | 5.10 | PROT |
| ATOM | 1982 | C | VAL | 130 | 1.063 | 37.015 | 11.337 | 1.00 | 5.72 | PROT |
| ATOM | 1983 | O | VAL | 130 | 0.845 | 37.477 | 10.202 | 1.00 | 6.14 | PROT |
| ATOM | 1984 | CB | VAL | 130 | 0.636 | 34.575 | 11.950 | 1.00 | 4.93 | PROT |
| ATOM | 1985 | CG1 | VAL | 130 | -0.599 | 34.634 | 11.089 | 1.00 | 5.21 | PROT |
| ATOM | 1986 | CG2 | VAL | 130 | 1.227 | 33.166 | 11.934 | 1.00 | 5.30 | PROT |
| ATOM | 1996 | N | LYS | 131 | 0.759 | 37.664 | 12.465 | 1.00 | 6.37 | PROT |
| ATOM | 1997 | CA | LYS | 131 | 0.211 | 39.013 | 12.512 | 1.00 | 7.63 | PROT |
| ATOM | 1998 | C | LYS | 131 | 1.168 | 40.012 | 11.887 | 1.00 | 7.65 | PROT |
| ATOM | 1999 | O | LYS | 131 | 0.799 | 40.825 | 11.037 | 1.00 | 7.82 | PROT |
| ATOM | 2000 | CB | LYS | 131 | -0.130 | 39.391 | 13.965 | 1.00 | 7.17 | PROT |
| ATOM | 2001 | CG | LYS | 131 | -0.973 | 40.667 | 14.132 | 1.00 | 8.64 | PROT |
| ATOM | 2002 | CD | LYS | 131 | -2.306 | 40.720 | 13.428 | 1.00 | 13.01 | PROT |
| ATOM | 2003 | CE | LYS | 131 | -2.930 | 42.115 | 13.438 | 1.00 | 13.65 | PROT |
| ATOM | 2004 | NZ | LYS | 131 | -4.389 | 42.090 | 12.995 | 1.00 | 16.78 | PROT |
| ATOM | 2018 | N | ALA | 132 | 2.462 | 39.812 | 12.275 | 1.00 | 7.95 | PROT |
| ATOM | 2019 | CA | ALA | 132 | 3.525 | 40.770 | 11.735 | 1.00 | 8.15 | PROT |
| ATOM | 2020 | C | ALA | 132 | 3.842 | 40.533 | 10.252 | 1.00 | 8.44 | PROT |
| ATOM | 2021 | O | ALA | 132 | 4.630 | 41.273 | 9.657 | 1.00 | 8.27 | PROT |
| ATOM | 2022 | CB | ALA | 132 | 4.783 | 40.656 | 12.574 | 1.00 | 7.91 | PROT |
| ATOM | 2028 | N | GLY | 133 | 3.233 | 39.501 | 9.668 | 1.00 | 8.62 | PROT |
| ATOM | 2029 | CA | GLY | 133 | 3.329 | 39.246 | 8.231 | 1.00 | 8.97 | PROT |
| ATOM | 2030 | C | GLY | 133 | 4.598 | 38.549 | 7.783 | 1.00 | 9.39 | PROT |
| ATOM | 2031 | O | GLY | 133 | 5.050 | 38.748 | 6.654 | 1.00 | 9.35 | PROT |
| ATOM | 2035 | N | ILE | 134 | 5.160 | 37.736 | 8.660 | 1.00 | 9.31 | PROT |

Figure 3 cont.

```
ATOM   2036  CA   ILE   134       6.385  36.979   8.309  1.00   9.99      PROT
ATOM   2037  C    ILE   134       6.026  35.742   7.472  1.00   9.68      PROT
ATOM   2038  O    ILE   134       6.738  35.382   6.532  1.00   9.47      PROT
ATOM   2039  CB   ILE   134       7.207  36.616   9.678  1.00  10.04      PROT
ATOM   2040  CG1  ILE   134       7.846  37.888  10.139  1.00  10.17      PROT
ATOM   2041  CG2  ILE   134       8.280  35.569   9.283  1.00  10.44      PROT
ATOM   2042  CD   ILE   134       8.764  37.645  11.282  1.00  11.79      PROT
ATOM   2054  N    CYS   135       4.917  35.102   7.835  1.00   9.34      PROT
ATOM   2055  CA   CYS   135       4.417  33.939   7.110  1.00  10.07      PROT
ATOM   2056  C    CYS   135       2.909  33.849   7.291  1.00   9.85      PROT
ATOM   2057  O    CYS   135       2.328  34.526   8.155  1.00   9.01      PROT
ATOM   2058  CB   CYS   135       5.106  32.651   7.591  1.00  10.48      PROT
ATOM   2059  SG   CYS   135       4.902  32.261   9.378  1.00  11.84      PROT
ATOM   2064  N    SER   136       2.275  33.015   6.474  1.00   9.55      PROT
ATOM   2065  CA   SER   136       0.833  32.942   6.548  1.00   9.94      PROT
ATOM   2066  C    SER   136       0.487  31.367   6.244  1.00   9.82      PROT
ATOM   2067  O    SER   136       1.240  30.531   6.111  1.00   8.34      PROT
ATOM   2068  CB   SER   136       0.153  33.563   5.383  1.00   9.92      PROT
ATOM   2069  OG   SER   136      -1.148  33.971   5.758  1.00  10.83      PROT
ATOM   2074  N    MET   137      -0.731  31.055   7.053  1.00   9.66      PROT
ATOM   2075  CA   MET   137      -1.216  29.677   7.059  1.00   9.39      PROT
ATOM   2076  C    MET   137      -2.259  29.465   5.971  1.00   9.79      PROT
ATOM   2077  O    MET   137      -2.913  30.409   5.506  1.00   9.77      PROT
ATOM   2078  CB   MET   137      -1.790  29.295   8.421  1.00   9.87      PROT
ATOM   2079  CG   MET   137      -0.760  29.233   9.549  1.00  10.04      PROT
ATOM   2080  SD   MET   137      -1.523  28.727  11.094  1.00  10.76      PROT
ATOM   2081  CE   MET   137      -2.309  30.239  11.619  1.00  11.00      PROT
ATOM   2091  N    ASP   138      -2.405  28.215   5.558  1.00   9.73      PROT
ATOM   2092  CA   ASP   138      -3.364  27.877   4.519  1.00   9.45      PROT
ATOM   2093  C    ASP   138      -4.627  27.343   5.177  1.00   9.32      PROT
ATOM   2094  O    ASP   138      -4.572  26.367   5.920  1.00   8.95      PROT
ATOM   2095  CB   ASP   138      -2.774  26.645   3.574  1.00   9.87      PROT
ATOM   2096  CG   ASP   138      -3.754  26.407   2.524  1.00   9.74      PROT
ATOM   2097  OD1  ASP   138      -4.155  27.253   1.689  1.00   9.34      PROT
ATOM   2098  OD2  ASP   138      -4.131  25.200   2.855  1.00   9.76      PROT
ATOM   2103  N    LYS   139      -5.758  27.989   4.897  1.00   9.83      PROT
ATOM   2104  CA   LYS   139      -7.031  27.680   5.560  1.00   9.57      PROT
ATOM   2105  C    LYS   139      -7.378  26.190   5.552  1.00   9.23      PROT
ATOM   2106  O    LYS   139      -7.841  25.656   6.555  1.00   9.35      PROT
ATOM   2107  CB   LYS   139      -8.176  28.470   4.930  1.00  10.02      PROT
ATOM   2108  CG   LYS   139      -8.031  29.984   4.987  1.00  10.44      PROT
ATOM   2109  CD   LYS   139      -8.828  30.640   3.855  1.00  13.87      PROT
ATOM   2110  CE   LYS   139     -10.332  30.663   4.108  1.00  14.28      PROT
ATOM   2111  NZ   LYS   139     -11.034  31.459   3.053  1.00  14.34      PROT
ATOM   2125  N    SER   140      -7.152  25.532   4.420  1.00   6.74      PROT
ATOM   2126  CA   SER   140      -7.443  24.110   4.274  1.00   8.37      PROT
ATOM   2127  C    SER   140      -6.585  23.063   5.200  1.00   7.51      PROT
ATOM   2128  O    SER   140      -7.049  22.338   5.849  1.00   7.42      PROT
ATOM   2129  CB   SER   140      -7.295  23.676   2.822  1.00   6.29      PROT
ATOM   2130  OG   SER   140      -7.696  22.441   2.675  1.00  10.39      PROT
ATOM   2135  N    GLN   141      -5.276  23.589   5.247  1.00   6.85      PROT
ATOM   2136  CA   GLN   141      -4.333  21.890   6.111  1.00   6.00      PROT
ATOM   2137  C    GLN   141      -4.607  23.122   7.589  1.00   5.09      PROT
ATOM   2138  O    GLN   141      -4.299  22.254   8.415  1.00   4.38      PROT
ATOM   2139  CB   GLN   141      -2.893  23.273   5.786  1.00   6.20      PROT
ATOM   2140  CG   GLN   141      -2.382  22.657   4.501  1.00   7.20      PROT
ATOM   2141  CD   GLN   141      -3.135  21.624   4.724  1.00   9.60      PROT
ATOM   2142  OE1  GLN   141      -6.108  22.316   5.227  1.00  10.33      PROT
ATOM   2143  NE2  GLN   141      -1.198  20.351   4.344  1.00  10.78      PROT
ATOM   2152  N    VAL   142      -5.163  24.292   7.921  1.00   4.17      PROT
ATOM   2153  CA   VAL   142      -5.501  24.017   9.311  1.00   3.52      PROT
ATOM   2154  C    VAL   142      -6.674  23.756   9.764  1.00   3.86      PROT
ATOM   2155  O    VAL   142      -6.616  23.159  10.843  1.00   3.43      PROT
ATOM   2156  CB   VAL   142      -5.838  26.131   9.941  1.00   3.49      PROT
ATOM   2157  CG1  VAL   142      -6.237  26.363  11.012  1.00   3.00      PROT
```

Figure 3 cont.

| | | | | | | | | | |
|---|---|---|---|---|---|---|---|---|---|
| ATOM | 2158 | CG2 | VAL | 142 | -4.644 | 27.017 | 3.212 | 1.00 | 2.63 | PROT |
| ATOM | 2168 | N | HSD | 143 | -7.723 | 23.690 | 8.934 | 1.00 | 4.22 | PROT |
| ATOM | 2169 | CA | HSD | 143 | -8.906 | 22.394 | 9.247 | 1.00 | 5.30 | PROT |
| ATOM | 2170 | C | HSD | 143 | -8.529 | 21.439 | 9.481 | 1.00 | 5.26 | PROT |
| ATOM | 2171 | O | HSD | 143 | -8.913 | 20.857 | 10.484 | 1.00 | 5.56 | PROT |
| ATOM | 2172 | CB | HSD | 143 | -9.975 | 22.986 | 8.153 | 1.00 | 6.01 | PROT |
| ATOM | 2173 | CG | HSD | 143 | -10.923 | 24.134 | 8.316 | 1.00 | 6.01 | PROT |
| ATOM | 2174 | CD2 | HSD | 143 | -11.333 | 24.136 | 9.255 | 1.00 | 10.34 | PROT |
| ATOM | 2175 | ND1 | HSD | 143 | -11.031 | 25.303 | 7.641 | 1.00 | 9.95 | PROT |
| ATOM | 2176 | NE2 | HSD | 143 | -12.613 | 25.267 | 9.156 | 1.00 | 10.38 | PROT |
| ATOM | 2177 | CE1 | HSD | 143 | -12.084 | 25.893 | 8.191 | 1.00 | 10.32 | PROT |
| ATOM | 2185 | N | ALA | 144 | -7.774 | 20.859 | 8.546 | 1.00 | 5.66 | PROT |
| ATOM | 2186 | CA | ALA | 144 | -7.294 | 19.486 | 8.675 | 1.00 | 5.46 | PROT |
| ATOM | 2187 | C | ALA | 144 | -6.507 | 19.236 | 9.976 | 1.00 | 5.81 | PROT |
| ATOM | 2188 | O | ALA | 144 | -6.716 | 19.222 | 10.653 | 1.00 | 5.68 | PROT |
| ATOM | 2189 | CB | ALA | 144 | -6.456 | 19.103 | 7.460 | 1.00 | 5.37 | PROT |
| ATOM | 2195 | N | ALA | 145 | -5.606 | 20.152 | 10.327 | 1.00 | 5.35 | PROT |
| ATOM | 2196 | CA | ALA | 145 | -4.727 | 19.951 | 11.491 | 1.00 | 5.18 | PROT |
| ATOM | 2197 | C | ALA | 145 | -5.471 | 20.069 | 12.827 | 1.00 | 5.04 | PROT |
| ATOM | 2198 | O | ALA | 145 | -5.232 | 19.396 | 13.755 | 1.00 | 4.85 | PROT |
| ATOM | 2199 | CB | ALA | 145 | -3.863 | 20.905 | 11.438 | 1.00 | 5.49 | PROT |
| ATOM | 2205 | N | VAL | 146 | -6.372 | 21.042 | 12.905 | 1.00 | 5.06 | PROT |
| ATOM | 2206 | CA | VAL | 146 | -7.250 | 21.216 | 14.062 | 1.00 | 5.19 | PROT |
| ATOM | 2207 | C | VAL | 146 | -8.130 | 19.963 | 14.279 | 1.00 | 5.61 | PROT |
| ATOM | 2208 | O | VAL | 146 | -8.196 | 19.438 | 15.394 | 1.00 | 5.70 | PROT |
| ATOM | 2209 | CB | VAL | 146 | -8.075 | 20.524 | 13.954 | 1.00 | 4.89 | PROT |
| ATOM | 2210 | CG1 | VAL | 146 | -9.089 | 22.624 | 15.075 | 1.00 | 5.89 | PROT |
| ATOM | 2211 | CG2 | VAL | 146 | -7.140 | 33.743 | 14.013 | 1.00 | 4.56 | PROT |
| ATOM | 2221 | N | GLU | 147 | -8.767 | 19.473 | 13.213 | 1.00 | 5.93 | PROT |
| ATOM | 2222 | CA | GLU | 147 | -9.564 | 18.236 | 13.283 | 1.00 | 6.70 | PROT |
| ATOM | 2223 | C | GLU | 147 | -8.703 | 17.058 | 13.780 | 1.00 | 6.58 | PROT |
| ATOM | 2224 | O | GLU | 147 | -9.144 | 16.279 | 14.635 | 1.00 | 6.69 | PROT |
| ATOM | 2225 | CB | GLU | 147 | -10.196 | 17.696 | 11.923 | 1.00 | 6.31 | PROT |
| ATOM | 2226 | CG | GLU | 147 | -10.981 | 16.576 | 11.915 | 1.00 | 7.34 | PROT |
| ATOM | 2227 | CD | GLU | 147 | -11.708 | 16.311 | 10.623 | 1.00 | 7.06 | PROT |
| ATOM | 2228 | OE1 | GLU | 147 | -12.017 | 17.258 | 9.851 | 1.00 | 8.18 | PROT |
| ATOM | 2229 | OE2 | GLU | 147 | -12.120 | 15.139 | 10.382 | 1.00 | 8.64 | PROT |
| ATOM | 2236 | N | LYS | 148 | -7.493 | 16.954 | 13.240 | 1.00 | 6.53 | PROT |
| ATOM | 2237 | CA | LYS | 148 | -6.522 | 15.935 | 13.638 | 1.00 | 6.46 | PROT |
| ATOM | 2238 | C | LYS | 148 | -6.164 | 16.002 | 15.130 | 1.00 | 6.29 | PROT |
| ATOM | 2239 | O | LYS | 148 | -6.136 | 14.971 | 15.816 | 1.00 | 5.65 | PROT |
| ATOM | 2240 | CB | LYS | 148 | -5.282 | 16.029 | 12.740 | 1.00 | 6.96 | PROT |
| ATOM | 2241 | CG | LYS | 148 | -3.993 | 15.484 | 13.326 | 1.00 | 7.83 | PROT |
| ATOM | 2242 | CD | LYS | 148 | -2.928 | 15.360 | 12.246 | 1.00 | 10.37 | PROT |
| ATOM | 2243 | CE | LYS | 148 | -1.695 | 14.872 | 12.565 | 1.00 | 15.37 | PROT |
| ATOM | 2244 | NZ | LYS | 148 | -1.339 | 14.689 | 13.999 | 1.00 | 16.10 | PROT |
| ATOM | 2258 | N | GLN | 149 | -5.808 | 17.215 | 15.616 | 1.00 | 5.59 | PROT |
| ATOM | 2259 | CA | GLN | 149 | -5.627 | 17.470 | 17.036 | 1.00 | 6.00 | PROT |
| ATOM | 2260 | C | GLN | 149 | -6.613 | 17.139 | 17.943 | 1.00 | 6.22 | PROT |
| ATOM | 2261 | O | GLN | 149 | -6.620 | 16.660 | 19.065 | 1.00 | 7.19 | PROT |
| ATOM | 2262 | CB | GLN | 149 | -5.203 | 18.929 | 17.257 | 1.00 | 5.96 | PROT |
| ATOM | 2263 | CG | GLN | 149 | -4.564 | 19.221 | 18.652 | 1.00 | 4.72 | PROT |
| ATOM | 2264 | CD | GLN | 149 | -3.099 | 18.813 | 18.745 | 1.00 | 4.43 | PROT |
| ATOM | 2265 | OE1 | GLN | 149 | -2.509 | 18.331 | 17.773 | 1.00 | 4.32 | PROT |
| ATOM | 2266 | NE2 | GLN | 149 | -3.498 | 19.015 | 19.922 | 1.00 | 4.63 | PROT |
| ATOM | 2275 | N | ALA | 150 | -8.024 | 17.443 | 17.480 | 1.00 | 6.27 | PROT |
| ATOM | 2276 | CA | ALA | 150 | -9.243 | 17.137 | 18.245 | 1.00 | 6.03 | PROT |
| ATOM | 2277 | C | ALA | 150 | -9.560 | 15.666 | 18.228 | 1.00 | 6.09 | PROT |
| ATOM | 2278 | O | ALA | 150 | -10.169 | 15.153 | 19.164 | 1.00 | 6.04 | PROT |
| ATOM | 2279 | CB | ALA | 150 | -10.421 | 17.954 | 17.694 | 1.00 | 6.22 | PROT |
| ATOM | 2285 | N | GLY | 151 | -9.143 | 14.990 | 17.157 | 1.00 | 5.81 | PROT |
| ATOM | 2286 | CA | GLY | 151 | -9.402 | 13.559 | 16.975 | 1.00 | 6.64 | PROT |
| ATOM | 2287 | C | GLY | 151 | -10.811 | 13.275 | 16.492 | 1.00 | 6.92 | PROT |
| ATOM | 2288 | O | GLY | 151 | -11.247 | 12.126 | 16.475 | 1.00 | 6.89 | PROT |
| ATOM | 2292 | N | THR | 152 | -11.521 | 14.332 | 16.103 | 1.00 | 7.29 | PROT |

Figure 3 cont.

```
ATOM   2293 CA   THR  152   -12.926  14.251  15.709  1.00   8.38      PROT
ATOM   2294 C    THR  152   -13.325  15.562  15.010  1.00   8.07      PROT
ATOM   2295 O    THR  152   -12.725  16.603  15.280  1.00   8.24      PROT
ATOM   2296 CB   THR  152   -13.849  13.913  16.943  1.00   8.33      PROT
ATOM   2297 OG1  THR  152   -15.230  14.076  16.595  1.00   9.67      PROT
ATOM   2298 CG2  THR  152   -13.533  14.799  18.126  1.00   9.36      PROT
ATOM   2305 N    PRO  153   -14.313  15.619  14.090  1.00   8.15      PROT
ATOM   2306 CA   PRO  153   -14.776  16.768  13.475  1.00   8.02      PROT
ATOM   2307 C    PRO  153   -15.041  17.868  14.503  1.00   7.92      PROT
ATOM   2308 O    PRO  153   -15.646  17.615  15.544  1.00   7.36      PROT
ATOM   2309 CB   PRO  153   -16.080  16.346  12.789  1.00   7.99      PROT
ATOM   2310 CG   PRO  153   -15.826  14.939  12.403  1.00   8.33      PROT
ATOM   2311 CD   PRO  153   -15.040  14.353  13.546  1.00   7.92      PROT
ATOM   2319 N    ILE  154   -14.577  19.081  14.209  1.00   8.44      PROT
ATOM   2320 CA   ILE  154   -14.710  20.206  15.140  1.00   8.44      PROT
ATOM   2321 C    ILE  154   -16.167  20.561  15.384  1.00   9.05      PROT
ATOM   2322 O    ILE  154   -16.520  21.606  16.474  1.00   9.66      PROT
ATOM   2323 CB   ILE  154   -13.871  21.431  14.690  1.00   8.93      PROT
ATOM   2324 CG1  ILE  154   -12.375  21.109  14.799  1.00   9.95      PROT
ATOM   2325 CG2  ILE  154   -14.162  22.682  15.838  1.00   9.37      PROT
ATOM   2326 CD   ILE  154   -11.865  20.914  16.235  1.00  11.85      PROT
ATOM   2338 N    GLU  155   -17.016  19.378  14.383  1.00   7.69      PROT
ATOM   2339 CA   GLU  155   -18.447  19.647  14.512  1.00   7.38      PROT
ATOM   2340 C    GLU  155   -19.136  19.743  15.546  1.00   6.57      PROT
ATOM   2341 O    GLU  155   -20.213  20.671  16.080  1.00   6.19      PROT
ATOM   2342 CB   GLU  155   -19.143  20.595  13.144  1.00   7.87      PROT
ATOM   2343 CG   GLU  155   -18.531  19.606  12.143  1.00  10.89      PROT
ATOM   2344 CD   GLU  155   -17.323  20.179  11.397  1.00  13.73      PROT
ATOM   2345 OE1  GLU  155   -16.269  19.502  11.353  1.00  13.73      PROT
ATOM   2346 OE2  GLU  155   -17.425  21.306  10.856  1.00  16.16      PROT
ATOM   2353 N    THR  156   -18.486  18.631  15.876  1.00   5.93      PROT
ATOM   2354 CA   THR  156   -18.982  17.703  16.907  1.00   5.89      PROT
ATOM   2355 C    THR  156   -18.312  17.964  18.295  1.00   5.13      PROT
ATOM   2356 O    THR  156   -18.543  17.220  19.247  1.00   5.29      PROT
ATOM   2357 CB   THR  156   -18.718  16.225  16.475  1.00   5.87      PROT
ATOM   2358 OG1  THR  156   -18.913  16.074  15.056  1.00   7.17      PROT
ATOM   2359 CG2  THR  156   -19.676  15.278  17.194  1.00   7.44      PROT
ATOM   2366 N    LEU  157   -17.534  18.938  18.415  1.00   4.31      PROT
ATOM   2367 CA   LEU  157   -16.666  19.253  19.600  1.00   3.66      PROT
ATOM   2368 C    LEU  157   -17.397  19.304  20.947  1.00   3.43      PROT
ATOM   2369 O    LEU  157   -16.905  18.753  21.937  1.00   3.45      PROT
ATOM   2370 CB   LEU  157   -15.821  20.530  19.438  1.00   3.36      PROT
ATOM   2371 CG   LEU  157   -14.329  20.603  19.803  1.00   3.43      PROT
ATOM   2372 CD1  LEU  157   -13.963  21.977  20.359  1.00   2.00      PROT
ATOM   2373 CD2  LEU  157   -13.861  19.490  20.727  1.00   3.10      PROT
ATOM   2385 N    ASN  158   -18.542  19.980  20.982  1.00   3.12      PROT
ATOM   2386 CA   ASN  158   -19.342  20.151  22.202  1.00   3.97      PROT
ATOM   2387 C    ASN  158   -19.700  18.829  22.902  1.00   4.30      PROT
ATOM   2388 O    ASN  158   -19.862  18.788  24.118  1.00   4.18      PROT
ATOM   2389 CB   ASN  158   -20.639  20.903  21.895  1.00   3.81      PROT
ATOM   2390 CG   ASN  158   -20.406  22.370  21.585  1.00   3.63      PROT
ATOM   2391 OD1  ASN  158   -19.279  22.799  21.332  1.00   3.58      PROT
ATOM   2392 ND2  ASN  158   -21.494  23.136  21.443  1.00   4.72      PROT
ATOM   2399 N    GLN  159   -19.922  17.768  22.114  1.00   5.33      PROT
ATOM   2400 CA   GLN  159   -20.170  16.433  22.602  1.00   6.24      PROT
ATOM   2401 C    GLN  159   -19.089  15.755  23.419  1.00   6.68      PROT
ATOM   2402 O    GLN  159   -19.314  14.800  24.158  1.00   9.81      PROT
ATOM   2403 CB   GLN  159   -20.591  15.559  21.416  1.00   6.56      PROT
ATOM   2404 CG   GLN  159   -22.096  15.515  21.139  1.00   8.56      PROT
ATOM   2405 CD   GLN  159   -22.746  16.876  20.937  1.00  11.86      PROT
ATOM   2406 OE1  GLN  159   -22.254  17.717  20.183  1.00  13.25      PROT
ATOM   2407 NE2  GLN  159   -23.880  17.090  21.602  1.00  13.29      PROT
ATOM   2416 N    ARG  160   -17.830  16.242  23.273  1.00   7.14      PROT
ATOM   2417 CA   ARG  160   -16.711  15.819  24.111  1.00   8.01      PROT
ATOM   2418 C    ARG  160   -16.764  16.465  25.502  1.00   7.68      PROT
```

Figure 3 cont.

```
ATOM   2419  O    ARG  160   -16.123  15.979  26.441  1.00   7.37   PROT
ATOM   2420  CB   ARG  160   -15.373  16.181  23.453  1.00   8.27   PROT
ATOM   2421  CG   ARG  160   -15.246  15.627  21.965  1.00  11.38   PROT
ATOM   2422  CD   ARG  160   -14.941  14.304  21.769  1.00  14.83   PROT
ATOM   2423  NE   ARG  160   -15.476  13.385  21.709  1.00  17.77   PROT
ATOM   2424  CZ   ARG  160   -15.148  12.123  21.967  1.00  19.18   PROT
ATOM   2425  NH1  ARG  160   -13.904  11.808  22.316  1.00  20.08   PROT
ATOM   2426  NH2  ARG  160   -16.063  11.172  21.881  1.00  19.75   PROT
ATOM   2440  N    TYR  161   -17.532  17.381  25.631  1.00   7.10   PROT
ATOM   2441  CA   TYR  161   -17.459  18.406  26.835  1.00   6.58   PROT
ATOM   2442  C    TYR  161   -16.798  19.724  27.467  1.00   6.14   PROT
ATOM   2443  O    TYR  161   -16.976  19.789  28.051  1.00   5.81   PROT
ATOM   2444  CB   TYR  161   -16.721  19.705  26.490  1.00   6.57   PROT
ATOM   2445  CG   TYR  161   -15.309  19.448  26.072  1.00   6.84   PROT
ATOM   2446  CD1  TYR  161   -14.338  19.091  27.014  1.00   5.28   PROT
ATOM   2447  CD2  TYR  161   -14.943  19.513  24.737  1.00   5.67   PROT
ATOM   2448  CE1  TYR  161   -13.041  18.827  26.625  1.00   6.48   PROT
ATOM   2449  CE2  TYR  161   -13.652  19.255  24.333  1.00   7.24   PROT
ATOM   2450  CZ   TYR  161   -12.701  18.917  25.290  1.00   7.32   PROT
ATOM   2451  OH   TYR  161   -11.413  18.656  24.897  1.00   7.83   PROT
ATOM   2460  N    GLN  162   -19.722  17.773  27.387  1.00   5.85   PROT
ATOM   2461  CA   GLN  162   -21.303  17.960  27.635  1.00   5.64   PROT
ATOM   2462  C    GLN  162   -21.238  18.398  29.292  1.00   5.23   PROT
ATOM   2463  O    GLN  162   -21.957  19.365  29.590  1.00   4.79   PROT
ATOM   2464  CB   GLN  162   -21.957  16.746  27.494  1.00   6.07   PROT
ATOM   2465  CG   GLN  162   -22.276  16.626  26.002  1.00   7.19   PROT
ATOM   2466  CD   GLN  162   -23.083  17.604  25.469  1.00   9.89   PROT
ATOM   2467  OE1  GLN  162   -22.590  18.657  24.754  1.00  12.00   PROT
ATOM   2468  NE2  GLN  162   -24.355  17.868  25.897  1.00  10.47   PROT
ATOM   2477  N    ALA  163   -20.592  17.665  30.198  1.00   4.95   PROT
ATOM   2478  CA   ALA  163   -20.605  18.042  31.625  1.00   5.07   PROT
ATOM   2479  C    ALA  163   -19.969  19.422  31.924  1.00   4.84   PROT
ATOM   2480  O    ALA  163   -20.490  20.138  32.736  1.00   5.08   PROT
ATOM   2481  CB   ALA  163   -19.929  16.969  32.438  1.00   5.22   PROT
ATOM   2487  N    SER  164   -18.838  19.713  31.287  1.00   4.33   PROT
ATOM   2488  CA   SER  164   -18.154  21.010  31.434  1.00   3.93   PROT
ATOM   2489  C    SER  164   -18.985  22.178  30.925  1.00   3.60   PROT
ATOM   2490  O    SER  164   -18.940  23.293  31.471  1.00   3.72   PROT
ATOM   2491  CB   SER  164   -16.821  20.989  30.694  1.00   3.77   PROT
ATOM   2492  OG   SER  164   -15.861  20.224  31.389  1.00   5.27   PROT
ATOM   2497  N    LEU  165   -19.716  21.933  29.849  1.00   3.10   PROT
ATOM   2498  CA   LEU  165   -20.547  22.971  29.264  1.00   2.60   PROT
ATOM   2499  C    LEU  165   -21.775  23.160  30.129  1.00   2.63   PROT
ATOM   2500  O    LEU  165   -22.204  24.290  30.356  1.00   2.36   PROT
ATOM   2501  CB   LEU  165   -20.925  22.620  27.829  1.00   2.45   PROT
ATOM   2502  CG   LEU  165   -19.806  22.707  26.795  1.00   2.09   PROT
ATOM   2503  CD1  LEU  165   -20.337  22.399  25.426  1.00   2.00   PROT
ATOM   2504  CD2  LEU  165   -19.223  24.196  26.773  1.00   2.00   PROT
ATOM   2516  N    ALA  166   -22.312  22.046  30.503  1.00   2.53   PROT
ATOM   2517  CA   ALA  166   -23.439  22.076  31.557  1.00   2.86   PROT
ATOM   2518  C    ALA  166   -23.106  23.901  32.796  1.00   2.61   PROT
ATOM   2519  O    ALA  166   -23.896  23.766  33.193  1.00   2.92   PROT
ATOM   2520  CB   ALA  166   -23.869  20.664  31.953  1.00   2.37   PROT
ATOM   2526  N    LEU  167   -21.939  22.438  33.391  1.00   2.61   PROT
ATOM   2527  CA   LEU  167   -21.466  23.387  34.554  1.00   2.48   PROT
ATOM   2528  C    LEU  167   -21.286  24.895  34.247  1.00   2.34   PROT
ATOM   2529  O    LEU  167   -21.697  25.728  35.037  1.00   2.09   PROT
ATOM   2530  CB   LEU  167   -20.176  22.777  35.140  1.00   2.38   PROT
ATOM   2531  CG   LEU  167   -19.553  23.473  36.358  1.00   2.09   PROT
ATOM   2532  CD1  LEU  167   -20.461  23.405  37.608  1.00   2.51   PROT
ATOM   2533  CD2  LEU  167   -18.171  22.819  36.668  1.00   2.62   PROT
ATOM   2545  N    MET  168   -20.680  25.213  33.107  1.00   3.61   PROT
ATOM   2546  CA   MET  168   -20.564  26.619  32.676  1.00   3.63   PROT
ATOM   2547  C    MET  168   -21.944  27.280  32.546  1.00   3.83   PROT
ATOM   2548  O    MET  168   -22.329  28.438  32.944  1.00   3.71   PROT
```

Figure 3 cont.

```
ATOM   2549  CB   MET  168    -19.749  26.749  31.373  1.00   3.75    PROT
ATOM   2550  CG   MET  168    -19.644  28.174  30.811  1.00   4.17    PROT
ATOM   2551  SD   MET  168    -18.816  29.333  31.939  1.00   3.11    PROT
ATOM   2552  CE   MET  168    -17.096  28.868  31.742  1.00   4.61    PROT
ATOM   2562  N    SER  169    -22.910  26.543  32.011  1.00   4.84    PROT
ATOM   2563  CA   SER  169    -24.292  27.043  31.904  1.00   5.24    PROT
ATOM   2564  C    SER  169    -24.938  27.396  33.262  1.00   5.82    PROT
ATOM   2565  O    SER  169    -26.612  28.423  33.389  1.00   6.44    PROT
ATOM   2566  CB   SER  169    -25.168  26.060  31.133  1.00   5.03    PROT
ATOM   2567  OG   SER  169    -24.468  26.987  30.969  1.00   5.10    PROT
ATOM   2572  N    SER  170    -24.718  26.573  34.281  1.00   5.93    PROT
ATOM   2573  CA   SER  170    -25.290  26.880  35.593  1.00   6.38    PROT
ATOM   2574  C    SER  170    -24.539  28.012  36.316  1.00   5.95    PROT
ATOM   2575  O    SER  170    -25.172  28.857  36.944  1.00   5.72    PROT
ATOM   2576  CB   SER  170    -25.458  25.625  36.466  1.00   6.14    PROT
ATOM   2577  OG   SER  170    -24.233  24.956  36.660  1.00   8.41    PROT
ATOM   2582  N    VAL  171    -23.210  28.039  36.191  1.00   6.01    PROT
ATOM   2583  CA   VAL  171    -22.382  29.133  36.725  1.00   5.64    PROT
ATOM   2584  C    VAL  171    -22.877  30.487  36.186  1.00   5.62    PROT
ATOM   2585  O    VAL  171    -23.000  31.458  36.936  1.00   5.35    PROT
ATOM   2586  CB   VAL  171    -20.865  28.902  36.381  1.00   5.79    PROT
ATOM   2587  CG1  VAL  171    -20.043  30.193  36.611  1.00   5.78    PROT
ATOM   2588  CG2  VAL  171    -20.286  27.763  37.176  1.00   5.14    PROT
ATOM   2598  N    LEU  172    -23.160  30.522  34.887  1.00   5.19    PROT
ATOM   2599  CA   LEU  172    -23.710  31.704  34.212  1.00   5.27    PROT
ATOM   2600  C    LEU  172    -25.199  31.987  34.449  1.00   5.48    PROT
ATOM   2601  O    LEU  172    -25.627  33.110  34.219  1.00   5.62    PROT
ATOM   2602  CB   LEU  172    -23.521  31.582  32.693  1.00   5.01    PROT
ATOM   2603  CG   LEU  172    -22.105  31.635  32.103  1.00   5.33    PROT
ATOM   2604  CD1  LEU  172    -22.199  31.213  30.637  1.00   5.43    PROT
ATOM   2605  CD2  LEU  172    -21.481  33.006  32.269  1.00   5.50    PROT
ATOM   2617  N    ASP  173    -25.951  30.975  34.866  1.00   5.59    PROT
ATOM   2618  CA   ASP  173    -27.433  30.977  34.778  1.00   5.99    PROT
ATOM   2619  C    ASP  173    -27.895  31.308  33.352  1.00   5.68    PROT
ATOM   2620  O    ASP  173    -28.846  32.065  33.140  1.00   5.09    PROT
ATOM   2621  CB   ASP  173    -28.071  31.919  35.804  1.00   6.51    PROT
ATOM   2622  CG   ASP  173    -29.256  31.296  36.522  1.00   8.87    PROT
ATOM   2623  OD1  ASP  173    -30.077  30.601  35.878  1.00   9.09    PROT
ATOM   2624  OD2  ASP  173    -29.361  31.496  37.753  1.00  11.68    PROT
ATOM   2629  N    PHE  174    -27.201  30.721  32.360  1.00   5.67    PROT
ATOM   2630  CA   PHE  174    -27.473  30.322  30.952  1.00   6.15    PROT
ATOM   2631  C    PHE  174    -28.950  30.796  30.516  1.00   6.35    PROT
ATOM   2632  O    PHE  174    -29.393  31.549  29.638  1.00   6.68    PROT
ATOM   2633  CB   PHE  174    -26.561  30.062  30.126  1.00   5.77    PROT
ATOM   2634  CG   PHE  174    -26.868  29.394  28.656  1.00   5.76    PROT
ATOM   2635  CD1  PHE  174    -26.800  31.006  27.826  1.00   5.71    PROT
ATOM   2636  CD2  PHE  174    -27.621  28.963  28.099  1.00   5.78    PROT
ATOM   2637  CE1  PHE  174    -26.684  30.996  26.463  1.00   5.85    PROT
ATOM   2638  CE2  PHE  174    -27.913  28.949  26.733  1.00   6.26    PROT
ATOM   2639  CZ   PHE  174    -27.443  29.364  25.918  1.00   5.74    PROT
ATOM   2649  N    PRO  175    -29.712  29.846  31.104  1.00   6.82    PROT
ATOM   2650  CA   PRO  175    -31.141  29.704  30.769  1.00   7.25    PROT
ATOM   2651  C    PRO  175    -32.013  30.944  31.008  1.00   7.70    PROT
ATOM   2652  O    PRO  175    -33.022  31.132  30.323  1.00   7.59    PROT
ATOM   2653  CB   PRO  175    -31.590  28.584  31.708  1.00   6.97    PROT
ATOM   2654  CG   PRO  175    -30.378  27.786  31.922  1.00   6.59    PROT
ATOM   2655  CD   PRO  175    -29.312  28.812  32.078  1.00   6.49    PROT
ATOM   2663  N    LYS  176    -31.620  31.779  31.967  1.00   8.14    PROT
ATOM   2664  CA   LYS  176    -32.376  32.975  32.328  1.00   9.62    PROT
ATOM   2665  C    LYS  176    -31.738  34.247  31.768  1.00   8.84    PROT
ATOM   2666  O    LYS  176    -32.118  35.359  30.137  1.00   8.74    PROT
ATOM   2667  CB   LYS  176    -32.496  33.065  33.853  1.00   9.04    PROT
ATOM   2668  CG   LYS  176    -33.399  31.986  34.468  1.00   9.70    PROT
ATOM   2669  CD   LYS  176    -33.030  31.722  35.919  1.00  10.80    PROT
ATOM   2670  CE   LYS  176    -33.976  30.743  36.588  1.00  12.09    PROT
```

Figure 3 cont.

| | | | | | | | | | |
|---|---|---|---|---|---|---|---|---|---|
| ATOM | 2673 | NZ | LYS | 176 | -35.322 | 31.314 | 36.898 | 1.00 12.43 | PROT |
| ATOM | 2685 | N | SER | 177 | -30.772 | 34.067 | 30.874 | 1.00 8.39 | PROT |
| ATOM | 2686 | CA | SER | 177 | -30.008 | 35.171 | 30.393 | 1.00 9.04 | PROT |
| ATOM | 2687 | C | SER | 177 | -30.783 | 35.810 | 29.133 | 1.00 9.25 | PROT |
| ATOM | 2688 | O | SER | 177 | -31.610 | 35.163 | 28.533 | 1.00 9.85 | PROT |
| ATOM | 2689 | CB | SER | 177 | -28.651 | 34.660 | 29.819 | 1.00 8.59 | PROT |
| ATOM | 2690 | OG | SER | 177 | -28.811 | 33.794 | 28.704 | 1.00 9.38 | PROT |
| ATOM | 2695 | N | PRO | 178 | -30.482 | 37.092 | 28.831 | 1.00 9.58 | PROT |
| ATOM | 2696 | CA | PRO | 178 | -30.905 | 37.764 | 27.610 | 1.00 9.76 | PROT |
| ATOM | 2697 | C | PRO | 178 | -30.762 | 36.908 | 26.342 | 1.00 10.11 | PROT |
| ATOM | 2698 | O | PRO | 178 | -31.660 | 36.928 | 25.487 | 1.00 9.94 | PROT |
| ATOM | 2699 | CB | PRO | 178 | -29.999 | 38.991 | 27.544 | 1.00 9.85 | PROT |
| ATOM | 2700 | CG | PRO | 178 | -29.786 | 39.327 | 28.978 | 1.00 9.78 | PROT |
| ATOM | 2701 | CD | PRO | 178 | -29.684 | 38.009 | 29.698 | 1.00 9.89 | PROT |
| ATOM | 2709 | N | TYR | 179 | -29.662 | 36.158 | 26.232 | 1.00 10.33 | PROT |
| ATOM | 2710 | CA | TYR | 179 | -29.466 | 35.195 | 25.138 | 1.00 10.76 | PROT |
| ATOM | 2711 | C | TYR | 179 | -30.584 | 34.154 | 25.110 | 1.00 10.92 | PROT |
| ATOM | 2712 | O | TYR | 179 | -31.061 | 33.706 | 26.156 | 1.00 10.56 | PROT |
| ATOM | 2713 | CB | TYR | 179 | -28.106 | 34.495 | 25.259 | 1.00 11.42 | PROT |
| ATOM | 2714 | CG | TYR | 179 | -27.595 | 33.893 | 23.966 | 1.00 11.90 | PROT |
| ATOM | 2715 | CD1 | TYR | 179 | -28.733 | 34.610 | 23.136 | 1.00 12.65 | PROT |
| ATOM | 2716 | CD2 | TYR | 179 | -27.975 | 32.605 | 23.568 | 1.00 12.33 | PROT |
| ATOM | 2717 | CE1 | TYR | 179 | -26.266 | 34.068 | 21.948 | 1.00 13.68 | PROT |
| ATOM | 2718 | CE2 | TYR | 179 | -27.514 | 32.052 | 22.387 | 1.00 12.06 | PROT |
| ATOM | 2719 | CZ | TYR | 179 | -26.666 | 32.786 | 21.660 | 1.00 13.14 | PROT |
| ATOM | 2720 | OH | TYR | 179 | -26.205 | 32.236 | 20.419 | 1.00 13.39 | PROT |
| ATOM | 2729 | N | CYS | 180 | -31.106 | 33.670 | 26.393 | 1.00 0.00 | PROT |
| ATOM | 2730 | CA | CYS | 180 | -32.625 | 32.710 | 26.347 | 1.00 0.00 | PROT |
| ATOM | 2731 | C | CYS | 180 | -33.851 | 33.571 | 25.960 | 1.00 0.00 | PROT |
| ATOM | 2732 | O | CYS | 180 | -34.664 | 33.246 | 25.039 | 1.00 0.00 | PROT |
| ATOM | 2733 | CB | CYS | 180 | -32.981 | 31.556 | 27.199 | 1.00 0.00 | PROT |
| ATOM | 2734 | SG | CYS | 180 | -34.226 | 30.414 | 26.438 | 1.00 0.00 | PROT |
| ATOM | 2739 | N | GLN | 181 | -34.012 | 34.723 | 26.636 | 1.00 0.00 | PROT |
| ATOM | 2740 | CA | GLN | 181 | -35.190 | 35.564 | 26.459 | 1.00 0.00 | PROT |
| ATOM | 2741 | C | GLN | 181 | -35.343 | 36.159 | 25.053 | 1.00 0.00 | PROT |
| ATOM | 2742 | O | GLN | 181 | -36.462 | 36.400 | 24.594 | 1.00 0.00 | PROT |
| ATOM | 2743 | CB | GLN | 181 | -35.244 | 36.676 | 27.541 | 1.00 0.00 | PROT |
| ATOM | 2744 | CG | GLN | 181 | -35.447 | 36.125 | 28.977 | 1.00 0.00 | PROT |
| ATOM | 2745 | CD | GLN | 181 | -36.842 | 35.513 | 29.159 | 1.00 0.00 | PROT |
| ATOM | 2746 | OE1 | GLN | 181 | -37.855 | 36.033 | 28.699 | 1.00 0.00 | PROT |
| ATOM | 2747 | NE2 | GLN | 181 | -36.918 | 34.371 | 29.681 | 1.00 0.00 | PROT |
| ATOM | 2756 | N | GLN | 182 | -34.250 | 36.376 | 24.309 | 1.00 0.00 | PROT |
| ATOM | 2757 | CA | GLN | 182 | -34.302 | 36.781 | 22.911 | 1.00 0.00 | PROT |
| ATOM | 2758 | C | GLN | 182 | -34.071 | 35.622 | 21.937 | 1.00 0.00 | PROT |
| ATOM | 2759 | O | GLN | 182 | -33.681 | 35.826 | 20.790 | 1.00 0.00 | PROT |
| ATOM | 2760 | CB | GLN | 182 | -33.240 | 37.879 | 22.632 | 1.00 0.00 | PROT |
| ATOM | 2761 | CG | GLN | 182 | -33.339 | 39.118 | 23.567 | 1.00 0.00 | PROT |
| ATOM | 2762 | CD | GLN | 182 | -34.727 | 39.756 | 23.495 | 1.00 0.00 | PROT |
| ATOM | 2763 | OE1 | GLN | 182 | -35.168 | 40.265 | 22.465 | 1.00 0.00 | PROT |
| ATOM | 2764 | NE2 | GLN | 182 | -35.460 | 39.731 | 24.630 | 1.00 0.00 | PROT |
| ATOM | 2773 | N | HSD | 183 | -34.301 | 34.360 | 22.345 | 1.00 2.18 | PROT |
| ATOM | 2774 | CA | HSD | 183 | -33.937 | 33.212 | 21.530 | 1.00 2.18 | PROT |
| ATOM | 2775 | C | HSD | 183 | -35.131 | 32.628 | 20.765 | 1.00 2.18 | PROT |
| ATOM | 2776 | O | HSD | 183 | -35.956 | 31.918 | 21.335 | 1.00 2.18 | PROT |
| ATOM | 2777 | CB | HSD | 183 | -33.072 | 32.129 | 20.414 | 1.00 2.18 | PROT |
| ATOM | 2778 | CG | HSD | 183 | -32.290 | 31.238 | 21.708 | 1.00 2.18 | PROT |
| ATOM | 2779 | ND1 | HSD | 183 | -32.503 | 30.632 | 20.489 | 1.00 2.18 | PROT |
| ATOM | 2780 | CD2 | HSD | 183 | -31.048 | 30.848 | 22.096 | 1.00 2.18 | PROT |
| ATOM | 2781 | CE1 | HSD | 183 | -31.387 | 29.922 | 20.138 | 1.00 2.18 | PROT |
| ATOM | 2782 | NE2 | HSD | 183 | -30.480 | 30.020 | 21.145 | 1.00 2.18 | PROT |
| ATOM | 2790 | N | ASN | 184 | -35.061 | 32.806 | 19.463 | 1.00 7.42 | PROT |
| ATOM | 2791 | CA | ASN | 184 | -36.389 | 32.409 | 18.661 | 1.00 7.42 | PROT |
| ATOM | 2792 | C | ASN | 184 | -36.373 | 30.908 | 18.340 | 1.00 7.42 | PROT |
| ATOM | 2793 | O | ASN | 184 | -36.242 | 30.503 | 17.186 | 1.00 7.42 | PROT |
| ATOM | 2794 | CB | ASN | 184 | -36.467 | 33.143 | 17.231 | 1.00 7.42 | PROT |

Figure 3 cont.

| | | | | | | | | | |
|---|---|---|---|---|---|---|---|---|---|
| ATOM | 2795 | CG | ASN | 184 | -36.424 | 34.656 | 17.432 | 1.00 | 7.42 | PROT |
| ATOM | 2796 | OD1 | ASN | 184 | -35.478 | 35.300 | 16.983 | 1.00 | 7.42 | PROT |
| ATOM | 2797 | ND2 | ASN | 184 | -37.465 | 35.254 | 18.055 | 1.00 | 7.42 | PROT |
| ATOM | 2804 | N | ILE | 185 | -36.528 | 30.035 | 19.350 | 1.00 | 9.23 | PROT |
| ATOM | 2805 | CA | ILE | 185 | -36.596 | 28.597 | 19.160 | 1.00 | 9.23 | PROT |
| ATOM | 2806 | C | ILE | 185 | -37.853 | 28.016 | 19.761 | 1.00 | 9.23 | PROT |
| ATOM | 2807 | O | ILE | 185 | -38.264 | 28.323 | 20.875 | 1.00 | 9.23 | PROT |
| ATOM | 2808 | CB | ILE | 185 | -35.390 | 27.832 | 19.713 | 1.00 | 9.23 | PROT |
| ATOM | 2809 | CG1 | ILE | 185 | -35.058 | 28.206 | 21.181 | 1.00 | 9.23 | PROT |
| ATOM | 2810 | CG2 | ILE | 185 | -34.216 | 28.060 | 18.738 | 1.00 | 9.23 | PROT |
| ATOM | 2811 | CD | ILE | 185 | -33.898 | 27.301 | 21.763 | 1.00 | 9.23 | PROT |
| ATOM | 2823 | N | GLY | 186 | -38.493 | 27.080 | 19.027 | 1.00 | 2.38 | PROT |
| ATOM | 2824 | CA | GLY | 186 | -39.502 | 26.184 | 19.593 | 1.00 | 2.38 | PROT |
| ATOM | 2825 | C | GLY | 186 | -38.841 | 24.905 | 20.038 | 1.00 | 2.38 | PROT |
| ATOM | 2826 | O | GLY | 186 | -39.069 | 23.940 | 19.462 | 1.00 | 2.38 | PROT |
| ATOM | 2830 | N | LYS | 187 | -37.958 | 25.004 | 21.043 | 1.00 | 0.00 | PROT |
| ATOM | 2831 | CA | LYS | 187 | -37.185 | 23.937 | 21.652 | 1.00 | 0.00 | PROT |
| ATOM | 2832 | C | LYS | 187 | -36.869 | 24.470 | 23.032 | 1.00 | 0.00 | PROT |
| ATOM | 2833 | O | LYS | 187 | -37.276 | 25.581 | 23.360 | 1.00 | 0.00 | PROT |
| ATOM | 2834 | CB | LYS | 187 | -35.833 | 23.619 | 20.932 | 1.00 | 0.00 | PROT |
| ATOM | 2835 | CG | LYS | 187 | -35.926 | 23.091 | 19.497 | 1.00 | 0.00 | PROT |
| ATOM | 2836 | CD | LYS | 187 | -36.582 | 21.686 | 19.416 | 1.00 | 0.00 | PROT |
| ATOM | 2837 | CE | LYS | 187 | -37.039 | 21.248 | 18.031 | 1.00 | 0.00 | PROT |
| ATOM | 2838 | NZ | LYS | 187 | -38.067 | 20.193 | 17.540 | 1.00 | 0.00 | PROT |
| ATOM | 2852 | N | LEU | 188 | -36.108 | 23.720 | 23.869 | 1.00 | 0.00 | PROT |
| ATOM | 2853 | CA | LEU | 188 | -35.630 | 24.120 | 25.120 | 1.00 | 0.00 | PROT |
| ATOM | 2854 | C | LEU | 188 | -34.268 | 24.863 | 24.865 | 1.00 | 0.00 | PROT |
| ATOM | 2855 | O | LEU | 188 | -33.491 | 24.376 | 24.064 | 1.00 | 0.00 | PROT |
| ATOM | 2856 | CB | LEU | 188 | -35.478 | 23.145 | 26.195 | 1.00 | 0.00 | PROT |
| ATOM | 2857 | CG | LEU | 188 | -36.794 | 22.443 | 26.593 | 1.00 | 0.00 | PROT |
| ATOM | 2858 | CD1 | LEU | 188 | -36.427 | 21.236 | 27.492 | 1.00 | 0.00 | PROT |
| ATOM | 2859 | CD2 | LEU | 188 | -37.768 | 23.393 | 27.308 | 1.00 | 0.00 | PROT |
| ATOM | 2871 | N | CYS | 189 | -33.926 | 26.000 | 25.539 | 1.00 | 0.00 | PROT |
| ATOM | 2872 | CA | CYS | 189 | -32.590 | 26.577 | 25.446 | 1.00 | 0.00 | PROT |
| ATOM | 2873 | C | CYS | 189 | -31.562 | 25.706 | 26.148 | 1.00 | 0.00 | PROT |
| ATOM | 2874 | O | CYS | 189 | -31.818 | 25.166 | 27.214 | 1.00 | 0.00 | PROT |
| ATOM | 2875 | CB | CYS | 189 | -32.487 | 27.996 | 26.074 | 1.00 | 0.00 | PROT |
| ATOM | 2876 | SG | CYS | 189 | -33.232 | 29.308 | 25.066 | 1.00 | 0.00 | PROT |
| ATOM | 2881 | N | ASP | 190 | -30.386 | 25.569 | 25.528 | 1.00 | 12.16 | PROT |
| ATOM | 2882 | CA | ASP | 190 | -29.246 | 24.757 | 25.939 | 1.00 | 12.21 | PROT |
| ATOM | 2883 | C | ASP | 190 | -27.959 | 25.403 | 25.429 | 1.00 | 11.72 | PROT |
| ATOM | 2884 | O | ASP | 190 | -27.870 | 25.765 | 24.253 | 1.00 | 11.77 | PROT |
| ATOM | 2885 | CB | ASP | 190 | -29.403 | 23.330 | 25.393 | 1.00 | 12.34 | PROT |
| ATOM | 2886 | CG | ASP | 190 | -28.337 | 22.380 | 25.912 | 1.00 | 12.95 | PROT |
| ATOM | 2887 | OD1 | ASP | 190 | -27.404 | 22.063 | 25.146 | 1.00 | 13.80 | PROT |
| ATOM | 2888 | OD2 | ASP | 190 | -28.431 | 21.955 | 27.081 | 1.00 | 11.81 | PROT |
| ATOM | 2893 | N | PHE | 191 | -26.982 | 25.555 | 26.322 | 1.00 | 11.05 | PROT |
| ATOM | 2894 | CA | PHE | 191 | -25.706 | 26.215 | 26.015 | 1.00 | 10.27 | PROT |
| ATOM | 2895 | C | PHE | 191 | -24.959 | 25.548 | 24.861 | 1.00 | 9.72 | PROT |
| ATOM | 2896 | O | PHE | 191 | -24.542 | 26.208 | 23.924 | 1.00 | 9.18 | PROT |
| ATOM | 2897 | CB | PHE | 191 | -24.823 | 26.289 | 27.274 | 1.00 | 10.13 | PROT |
| ATOM | 2898 | CG | PHE | 191 | -23.640 | 27.213 | 27.157 | 1.00 | 10.27 | PROT |
| ATOM | 2899 | CD1 | PHE | 191 | -23.804 | 28.597 | 27.154 | 1.00 | 10.30 | PROT |
| ATOM | 2900 | CD2 | PHE | 191 | -22.348 | 26.696 | 27.096 | 1.00 | 10.43 | PROT |
| ATOM | 2901 | CE1 | PHE | 191 | -23.702 | 29.449 | 27.075 | 1.00 | 10.91 | PROT |
| ATOM | 2902 | CE2 | PHE | 191 | -21.235 | 27.540 | 27.014 | 1.00 | 11.48 | PROT |
| ATOM | 2903 | CZ | PHE | 191 | -21.412 | 28.921 | 26.998 | 1.00 | 9.94 | PROT |
| ATOM | 2913 | N | SER | 192 | -24.815 | 24.023 | 24.930 | 1.00 | 9.46 | PROT |
| ATOM | 2914 | CA | SER | 192 | -24.131 | 23.436 | 23.693 | 1.00 | 9.21 | PROT |
| ATOM | 2915 | C | SER | 192 | -24.880 | 23.444 | 22.563 | 1.00 | 9.27 | PROT |
| ATOM | 2916 | O | SER | 192 | -24.375 | 23.529 | 21.495 | 1.00 | 9.24 | PROT |
| ATOM | 2917 | CB | SER | 192 | -23.934 | 21.989 | 24.354 | 1.00 | 9.47 | PROT |
| ATOM | 2918 | OG | SER | 192 | -23.376 | 21.186 | 23.321 | 1.00 | 8.08 | PROT |
| ATOM | 2923 | N | GLN | 193 | -26.202 | 23.360 | 22.653 | 1.00 | 9.43 | PROT |
| ATOM | 2924 | CA | GLN | 193 | -27.092 | 23.303 | 21.502 | 1.00 | 9.52 | PROT |

Figure 3 cont.

```
ATOM   2925 C    GLN 193   -27.195  24.654  20.785  1.00  9.04      PROT
ATOM   2926 O    GLN 193   -27.181  24.703  19.558  1.00  9.14      PROT
ATOM   2927 CB   GLN 193   -28.457  22.825  21.982  1.00  9.57      PROT
ATOM   2928 CG   GLN 193   -29.687  23.182  21.128  1.00 10.55      PROT
ATOM   2929 CD   GLN 193   -30.935  22.613  21.694  1.00 11.20      PROT
ATOM   2930 OE1  GLN 193   -32.005  23.209  21.550  1.00 14.63      PROT
ATOM   2931 NE2  GLN 193   -30.840  21.452  22.344  1.00 12.34      PROT
ATOM   2940 N    ALA 194   -27.301  25.735  21.053  1.00  8.50      PROT
ATOM   2941 CA   ALA 194   -27.391  27.074  20.596  1.00  7.80      PROT
ATOM   2942 C    ALA 194   -26.127  27.433  20.227  1.00  7.21      PROT
ATOM   2943 O    ALA 194   -26.197  28.146  19.226  1.00  6.73      PROT
ATOM   2944 CB   ALA 194   -27.675  28.108  22.079  1.00  7.72      PROT
ATOM   2950 N    MET 195   -24.979  26.924  20.664  1.00  6.87      PROT
ATOM   2951 CA   MET 195   -23.696  27.304  20.096  1.00  6.66      PROT
ATOM   2952 C    MET 195   -22.779  26.143  19.711  1.00  5.61      PROT
ATOM   2953 O    MET 195   -23.802  25.870  20.409  1.00  5.29      PROT
ATOM   2954 CB   MET 195   -22.941  26.262  21.033  1.00  6.66      PROT
ATOM   2955 CG   MET 195   -23.713  29.493  21.397  1.00  7.00      PROT
ATOM   2956 SD   MET 195   -22.762  30.422  22.586  1.00  8.48      PROT
ATOM   2957 CE   MET 195   -23.955  30.565  23.909  1.00  9.43      PROT
ATOM   2967 N    PRO 196   -23.057  25.497  18.570  1.00  5.22      PROT
ATOM   2968 CA   PRO 196   -22.198  24.431  18.075  1.00  5.06      PROT
ATOM   2969 C    PRO 196   -20.785  24.943  17.807  1.00  4.80      PROT
ATOM   2970 O    PRO 196   -20.610  26.107  17.436  1.00  4.49      PROT
ATOM   2971 CB   PRO 196   -22.967  24.036  16.755  1.00  5.23      PROT
ATOM   2972 CG   PRO 196   -23.679  25.220  16.367  1.00  4.79      PROT
ATOM   2973 CD   PRO 196   -24.184  25.751  17.651  1.00  4.86      PROT
ATOM   2981 N    SER 197   -19.791  24.084  18.008  1.00  4.86      PROT
ATOM   2982 CA   SER 197   -18.403  24.426  17.703  1.00  6.96      PROT
ATOM   2983 C    SER 197   -18.147  24.961  16.195  1.00  5.23      PROT
ATOM   2984 O    SER 197   -18.730  25.836  15.384  1.00  5.02      PROT
ATOM   2985 CB   SER 197   -17.459  23.402  18.334  1.00  4.94      PROT
ATOM   2986 OG   SER 197   -17.338  23.590  19.736  1.00  4.42      PROT
ATOM   2991 N    ARG 198   -17.277  25.497  15.902  1.00  5.56      PROT
ATOM   2992 CA   ARG 198   -16.926  25.721  14.419  1.00  6.03      PROT
ATOM   2993 C    ARG 198   -15.865  26.417  14.303  1.00  6.32      PROT
ATOM   2994 O    ARG 198   -15.270  27.320  15.108  1.00  5.70      PROT
ATOM   2995 CB   ARG 198   -18.018  26.577  13.746  1.00  6.15      PROT
ATOM   2996 CG   ARG 198   -17.843  26.836  12.268  1.00  6.81      PROT
ATOM   2997 CD   ARG 198   -18.993  27.696  11.678  1.00  6.37      PROT
ATOM   2998 NE   ARG 198   -19.098  29.020  12.283  1.00  8.01      PROT
ATOM   2999 CZ   ARG 198   -18.392  30.085  11.908  1.00  7.33      PROT
ATOM   3000 NH1  ARG 198   -17.495  30.006  10.989  1.00  5.92      PROT
ATOM   3001 NH2  ARG 198   -18.577  31.242  12.518  1.00  9.37      PROT
ATOM   3015 N    LEU 199   -14.745  26.008  13.358  1.00  6.60      PROT
ATOM   3016 CA   LEU 199   -13.488  26.703  13.093  1.00  7.26      PROT
ATOM   3017 C    LEU 199   -13.694  27.820  12.067  1.00  7.72      PROT
ATOM   3018 O    LEU 199   -14.039  27.562  10.969  1.00  6.34      PROT
ATOM   3019 CB   LEU 199   -12.389  25.732  12.625  1.00  7.16      PROT
ATOM   3020 CG   LEU 199   -10.979  26.318  12.483  1.00  7.44      PROT
ATOM   3021 CD1  LEU 199   -10.368  26.730  13.790  1.00  9.06      PROT
ATOM   3022 CD2  LEU 199   -10.060  25.336  11.741  1.00  7.76      PROT
ATOM   3034 N    ALA 200   -13.483  29.057  12.509  1.00  8.41      PROT
ATOM   3035 CA   ALA 200   -13.617  30.228  11.644  1.00  9.34      PROT
ATOM   3036 C    ALA 200   -12.233  30.747  11.284  1.00 10.27      PROT
ATOM   3037 O    ALA 200   -11.403  31.026  12.164  1.00  9.85      PROT
ATOM   3038 CB   ALA 200   -14.434  31.309  12.355  1.00  8.51      PROT
ATOM   3044 N    ILE 201   -11.960  30.846   9.968  1.00 11.92      PROT
ATOM   3045 CA   ILE 201   -10.681  31.366   9.496  1.00 13.65      PROT
ATOM   3046 C    ILE 201   -10.920  32.530   8.531  1.00 14.75      PROT
ATOM   3047 O    ILE 201   -11.327  32.488   7.391  1.00 14.62      PROT
ATOM   3048 CB   ILE 201    -9.821  30.272   8.890  1.00 13.79      PROT
ATOM   3049 CG1  ILE 201    -9.842  28.961   9.536  1.00 14.01      PROT
ATOM   3050 CG2  ILE 201    -8.376  30.780   8.612  1.00 13.88      PROT
ATOM   3051 CD   ILE 201    -9.148  27.813   8.907  1.00 13.98      PROT
```

Figure 3 cont.

```
ATOM   3063  N    ASN  202    -10.093  33.560   8.647  1.00  16.40      PROT
ATOM   3064  CA   ASN  202    -10.227  34.757   7.833  1.00  17.93      PROT
ATOM   3065  C    ASN  202     -9.639  34.620   6.441  1.00  16.75      PROT
ATOM   3066  O    ASN  202     -9.990  33.623   6.108  1.00  16.41      PROT
ATOM   3067  CB   ASN  202     -9.545  35.942   8.538  1.00  18.43      PROT
ATOM   3068  CG   ASN  202     -8.008  35.913   8.363  1.00  19.42      PROT
ATOM   3069  OD1  ASN  202     -7.406  34.849   8.396  1.00  20.35      PROT
ATOM   3070  ND2  ASN  202     -7.432  37.084   8.192  1.00  20.23      PROT
ATOM   3077  N    ASP  203     -9.912  35.649   5.646  1.00  19.96      PROT
ATOM   3078  CA   ASP  203     -9.136  36.025   4.483  1.00  20.78      PROT
ATOM   3079  C    ASP  203     -7.971  36.859   5.052  1.00  21.20      PROT
ATOM   3080  O    ASP  203     -8.219  37.694   5.792  1.00  21.59      PROT
ATOM   3081  CB   ASP  203    -10.030  36.873   3.573  1.00  20.96      PROT
ATOM   3082  CG   ASP  203     -9.536  36.934   2.145  1.00  21.50      PROT
ATOM   3083  OD1  ASP  203    -10.169  36.298   1.271  1.00  22.64      PROT
ATOM   3084  OD2  ASP  203     -8.531  37.609   1.893  1.00  22.64      PROT
ATOM   3089  N    ASP  204     -6.710  36.454   4.852  1.00  21.80      PROT
ATOM   3090  CA   ASP  204     -6.286  35.387   3.931  1.00  21.87      PROT
ATOM   3091  C    ASP  204     -6.635  33.943   4.357  1.00  21.70      PROT
ATOM   3092  O    ASP  204     -7.484  33.329   3.710  1.00  21.69      PROT
ATOM   3093  CB   ASP  204     -4.792  35.536   3.877  1.00  22.16      PROT
ATOM   3094  CG   ASP  204     -4.464  36.863   3.324  1.00  22.96      PROT
ATOM   3095  OD1  ASP  204     -5.323  37.795   2.948  1.00  23.28      PROT
ATOM   3096  OD2  ASP  204     -3.336  37.027   2.393  1.00  22.93      PROT
ATOM   3101  N    GLY  205     -5.979  33.383   5.396  1.00  21.41      PROT
ATOM   3102  CA   GLY  205     -4.796  33.983   6.006  1.00  21.25      PROT
ATOM   3103  C    GLY  205     -4.483  33.847   7.488  1.00  21.03      PROT
ATOM   3104  O    GLY  205     -4.042  32.793   7.963  1.00  21.30      PROT
ATOM   3108  N    ASN  206     -4.713  34.935   8.213  1.00  20.47      PROT
ATOM   3109  CA   ASN  206     -3.939  35.243   9.416  1.00  19.96      PROT
ATOM   3110  C    ASN  206     -4.702  35.241  10.745  1.00  19.07      PROT
ATOM   3111  O    ASN  206     -4.105  35.433  11.802  1.00  19.05      PROT
ATOM   3112  CB   ASN  206     -3.207  36.594   9.217  1.00  20.09      PROT
ATOM   3113  CG   ASN  206     -2.662  36.763   7.806  1.00  21.25      PROT
ATOM   3114  OD1  ASN  206     -2.173  35.807   7.197  1.00  22.03      PROT
ATOM   3115  ND2  ASN  206     -2.729  37.989   7.263  1.00  21.50      PROT
ATOM   3122  N    LYS  207     -6.015  35.028  10.683  1.00  17.84      PROT
ATOM   3123  CA   LYS  207     -6.864  35.012  11.871  1.00  16.59      PROT
ATOM   3124  C    LYS  207     -7.659  33.715  11.949  1.00  15.36      PROT
ATOM   3125  O    LYS  207     -8.433  33.397  11.044  1.00  15.17      PROT
ATOM   3126  CB   LYS  207     -7.819  36.215  11.863  1.00  16.63      PROT
ATOM   3127  CG   LYS  207     -7.129  37.577  11.930  1.00  17.64      PROT
ATOM   3128  CD   LYS  207     -7.743  38.570  10.943  1.00  17.75      PROT
ATOM   3129  CE   LYS  207     -9.220  38.877  11.323  1.00  18.73      PROT
ATOM   3130  NZ   LYS  207     -9.747  39.911  10.276  1.00  18.65      PROT
ATOM   3144  N    VAL  208     -7.458  30.979  13.040  1.00  13.76      PROT
ATOM   3145  CA   VAL  208     -8.101  31.699  13.265  1.00  12.10      PROT
ATOM   3146  C    VAL  208     -6.803  31.730  14.662  1.00  11.80      PROT
ATOM   3147  O    VAL  208     -6.235  32.257  15.633  1.00  11.34      PROT
ATOM   3148  CB   VAL  208     -7.096  30.524  13.202  1.00  12.32      PROT
ATOM   3149  CG1  VAL  208     -7.716  29.296  13.626  1.00  11.62      PROT
ATOM   3150  CG2  VAL  208     -6.523  30.403  11.792  1.00  11.10      PROT
ATOM   3160  N    ALA  209    -10.022  31.202  14.750  1.00   9.53      PROT
ATOM   3161  CA   ALA  209    -10.705  31.182  16.034  1.00   8.69      PROT
ATOM   3162  C    ALA  209    -11.713  29.999  16.168  1.00   7.69      PROT
ATOM   3163  O    ALA  209    -12.354  29.600  15.202  1.00   7.52      PROT
ATOM   3164  CB   ALA  209    -11.419  32.481  16.324  1.00   8.81      PROT
ATOM   3170  N    LEU  210    -11.820  29.485  17.396  1.00   6.93      PROT
ATOM   3171  CA   LEU  210    -12.816  28.482  17.744  1.00   6.00      PROT
ATOM   3172  C    LEU  210    -14.104  29.162  18.178  1.00   5.69      PROT
ATOM   3173  O    LEU  210    -14.180  29.696  19.281  1.00   5.74      PROT
ATOM   3174  CB   LEU  210    -13.289  27.589  18.860  1.00   5.94      PROT
ATOM   3175  CG   LEU  210    -13.147  26.392  19.293  1.00   5.64      PROT
ATOM   3176  CD1  LEU  210    -13.227  25.363  18.175  1.00   3.02      PROT
ATOM   3177  CD2  LEU  210    -12.621  25.734  20.573  1.00   4.91      PROT
```

Figure 3 cont.

| ATOM | 3189 | N   | GLN | 211 | -15.165 | 29.155 | 17.302 | 1.00 | 5.20 | PROT |
|------|------|-----|-----|-----|---------|--------|--------|------|------|------|
| ATOM | 3190 | CA  | GLN | 211 | -16.412 | 29.735 | 17.615 | 1.00 | 4.60 | PROT |
| ATOM | 3191 | C   | GLN | 211 | -17.308 | 28.687 | 18.255 | 1.00 | 4.10 | PROT |
| ATOM | 3192 | O   | GLN | 211 | -17.154 | 27.638 | 17.987 | 1.00 | 3.35 | PROT |
| ATOM | 3193 | CB  | GLN | 211 | -17.095 | 30.274 | 16.351 | 1.00 | 4.35 | PROT |
| ATOM | 3194 | CG  | GLN | 211 | -16.283 | 31.280 | 15.535 | 1.00 | 4.28 | PROT |
| ATOM | 3195 | CD  | GLN | 211 | -16.023 | 32.603 | 16.324 | 1.00 | 6.19 | PROT |
| ATOM | 3196 | OE1 | GLN | 211 | -16.818 | 33.045 | 17.090 | 1.00 | 5.53 | PROT |
| ATOM | 3197 | OE2 | GLN | 211 | -14.953 | 33.224 | 15.882 | 1.00 | 8.01 | PROT |
| ATOM | 3204 | N   | GLY | 212 | -18.235 | 29.139 | 19.094 | 1.00 | 3.36 | PROT |
| ATOM | 3205 | CA  | GLY | 212 | -19.038 | 28.261 | 19.710 | 1.00 | 4.12 | PROT |
| ATOM | 3206 | C   | GLY | 212 | -19.048 | 28.106 | 21.212 | 1.00 | 3.93 | PROT |
| ATOM | 3207 | O   | GLY | 212 | -18.259 | 28.823 | 21.815 | 1.00 | 3.55 | PROT |
| ATOM | 3211 | N   | ALA | 213 | -19.758 | 27.138 | 21.795 | 1.00 | 3.67 | PROT |
| ATOM | 3212 | CA  | ALA | 213 | -19.830 | 26.940 | 23.245 | 1.00 | 3.61 | PROT |
| ATOM | 3213 | C   | ALA | 213 | -18.479 | 26.715 | 23.924 | 1.00 | 3.45 | PROT |
| ATOM | 3214 | O   | ALA | 213 | -18.224 | 27.277 | 24.977 | 1.00 | 3.73 | PROT |
| ATOM | 3215 | CB  | ALA | 213 | -20.789 | 25.798 | 23.577 | 1.00 | 3.67 | PROT |
| ATOM | 3221 | N   | VAL | 214 | -17.623 | 25.897 | 23.316 | 1.00 | 3.68 | PROT |
| ATOM | 3222 | CA  | VAL | 214 | -16.315 | 25.577 | 23.900 | 1.00 | 3.04 | PROT |
| ATOM | 3223 | C   | VAL | 214 | -15.366 | 26.773 | 23.820 | 1.00 | 3.14 | PROT |
| ATOM | 3224 | O   | VAL | 214 | -14.745 | 27.113 | 24.838 | 1.00 | 2.91 | PROT |
| ATOM | 3225 | CB  | VAL | 214 | -15.688 | 24.282 | 23.311 | 1.00 | 3.26 | PROT |
| ATOM | 3226 | CG1 | VAL | 214 | -14.237 | 24.121 | 23.770 | 1.00 | 2.87 | PROT |
| ATOM | 3227 | CG2 | VAL | 214 | -16.504 | 23.066 | 23.728 | 1.00 | 2.17 | PROT |
| ATOM | 3237 | N   | GLY | 215 | -15.273 | 27.417 | 22.663 | 1.00 | 2.68 | PROT |
| ATOM | 3238 | CA  | GLY | 215 | -14.533 | 28.686 | 22.543 | 1.00 | 2.77 | PROT |
| ATOM | 3239 | C   | GLY | 215 | -14.948 | 29.774 | 23.520 | 1.00 | 2.71 | PROT |
| ATOM | 3240 | O   | GLY | 215 | -14.120 | 30.280 | 24.310 | 1.00 | 3.19 | PROT |
| ATOM | 3244 | N   | LEU | 216 | -16.227 | 30.124 | 23.567 | 1.00 | 2.08 | PROT |
| ATOM | 3245 | CA  | LEU | 216 | -16.761 | 31.074 | 24.492 | 1.00 | 2.00 | PROT |
| ATOM | 3246 | C   | LEU | 216 | -16.479 | 30.690 | 25.960 | 1.00 | 2.00 | PROT |
| ATOM | 3247 | O   | LEU | 216 | -15.390 | 31.527 | 26.714 | 1.00 | 2.00 | PROT |
| ATOM | 3248 | CB  | LEU | 216 | -18.260 | 31.330 | 24.263 | 1.00 | 2.00 | PROT |
| ATOM | 3249 | CG  | LEU | 216 | -19.013 | 32.124 | 25.341 | 1.00 | 2.00 | PROT |
| ATOM | 3250 | CD1 | LEU | 216 | -18.481 | 33.558 | 25.449 | 1.00 | 2.00 | PROT |
| ATOM | 3251 | CD2 | LEU | 216 | -20.517 | 32.128 | 25.065 | 1.00 | 2.00 | PROT |
| ATOM | 3263 | N   | ALA | 217 | -16.774 | 29.444 | 26.344 | 1.00 | 2.00 | PROT |
| ATOM | 3264 | CA  | ALA | 217 | -16.570 | 28.970 | 27.722 | 1.00 | 2.00 | PROT |
| ATOM | 3265 | C   | ALA | 217 | -15.097 | 29.075 | 28.112 | 1.00 | 2.00 | PROT |
| ATOM | 3266 | O   | ALA | 217 | -14.762 | 29.360 | 29.241 | 1.00 | 2.00 | PROT |
| ATOM | 3267 | CB  | ALA | 217 | -17.205 | 27.575 | 27.956 | 1.00 | 2.00 | PROT |
| ATOM | 3273 | N   | SER | 218 | -14.213 | 28.646 | 27.175 | 1.00 | 2.00 | PROT |
| ATOM | 3274 | CA  | SER | 218 | -12.770 | 28.803 | 27.400 | 1.00 | 2.24 | PROT |
| ATOM | 3275 | C   | SER | 218 | -12.389 | 30.221 | 27.835 | 1.00 | 2.21 | PROT |
| ATOM | 3276 | O   | SER | 218 | -11.598 | 30.415 | 28.765 | 1.00 | 2.00 | PROT |
| ATOM | 3277 | CB  | SER | 218 | -11.978 | 28.424 | 26.148 | 1.00 | 2.00 | PROT |
| ATOM | 3278 | OG  | SER | 218 | -10.673 | 28.990 | 26.209 | 1.00 | 4.20 | PROT |
| ATOM | 3283 | N   | THR | 219 | -12.963 | 31.214 | 27.171 | 1.00 | 2.27 | PROT |
| ATOM | 3284 | CA  | THR | 219 | -12.691 | 32.618 | 27.512 | 1.00 | 2.60 | PROT |
| ATOM | 3285 | C   | THR | 219 | -13.226 | 32.946 | 28.896 | 1.00 | 2.43 | PROT |
| ATOM | 3286 | O   | THR | 219 | -12.505 | 33.479 | 29.746 | 1.00 | 2.00 | PROT |
| ATOM | 3287 | CB  | THR | 219 | -13.230 | 33.594 | 26.434 | 1.00 | 3.51 | PROT |
| ATOM | 3288 | OG1 | THR | 219 | -12.593 | 33.302 | 25.191 | 1.00 | 3.71 | PROT |
| ATOM | 3289 | CG2 | THR | 219 | -12.917 | 35.049 | 26.803 | 1.00 | 4.31 | PROT |
| ATOM | 3296 | N   | LEU | 220 | -14.497 | 32.630 | 29.125 | 1.00 | 2.00 | PROT |
| ATOM | 3297 | CA  | LEU | 220 | -15.148 | 32.885 | 30.421 | 1.00 | 2.00 | PROT |
| ATOM | 3298 | C   | LEU | 220 | -14.560 | 32.179 | 31.609 | 1.00 | 2.00 | PROT |
| ATOM | 3299 | O   | LEU | 220 | -14.370 | 32.765 | 32.666 | 1.00 | 2.00 | PROT |
| ATOM | 3300 | CB  | LEU | 220 | -16.643 | 32.552 | 30.356 | 1.00 | 2.00 | PROT |
| ATOM | 3301 | CG  | LEU | 220 | -17.466 | 33.137 | 29.228 | 1.00 | 2.00 | PROT |
| ATOM | 3302 | CD1 | LEU | 220 | -16.944 | 32.808 | 29.350 | 1.00 | 3.45 | PROT |
| ATOM | 3303 | CD2 | LEU | 220 | -17.293 | 34.714 | 29.118 | 1.00 | 2.74 | PROT |
| ATOM | 3315 | N   | ALA | 221 | -14.114 | 30.917 | 31.418 | 1.00 | 2.00 | PROT |
| ATOM | 3316 | CA  | ALA | 221 | -13.398 | 30.150 | 32.440 | 1.00 | 2.27 | PROT |

Figure 3 cont.

| | | | | | | | | | |
|---|---|---|---|---|---|---|---|---|---|
| ATOM | 3317 | C | ALA | 221 | -10.080 | 35.795 | 32.644 | 1.00 | 2.17 | PROT |
| ATOM | 3318 | O | ALA | 221 | -11.761 | 35.856 | 34.032 | 1.00 | 2.00 | PROT |
| ATOM | 3319 | CB | ALA | 221 | -13.157 | 28.723 | 31.971 | 1.00 | 2.20 | PROT |
| ATOM | 3325 | N | GLU | 222 | -11.303 | 31.230 | 31.353 | 1.00 | 2.19 | PROT |
| ATOM | 3326 | CA | GLU | 222 | -10.080 | 32.012 | 32.098 | 1.00 | 2.98 | PROT |
| ATOM | 3327 | C | GLU | 222 | -10.368 | 33.321 | 32.847 | 1.00 | 2.60 | PROT |
| ATOM | 3328 | O | GLU | 222 | -9.652 | 33.719 | 33.752 | 1.00 | 2.00 | PROT |
| ATOM | 3329 | CB | GLU | 222 | -9.340 | 32.272 | 30.776 | 1.00 | 3.21 | PROT |
| ATOM | 3330 | CG | GLU | 222 | -9.064 | 33.120 | 30.876 | 1.00 | 6.23 | PROT |
| ATOM | 3331 | CD | GLU | 222 | -6.966 | 32.461 | 31.693 | 1.00 | 9.36 | PROT |
| ATOM | 3332 | OE1 | GLU | 222 | -7.086 | 31.262 | 32.049 | 1.00 | 9.61 | PROT |
| ATOM | 3333 | OE2 | GLU | 222 | -5.982 | 33.165 | 32.006 | 1.00 | 10.00 | PROT |
| ATOM | 3340 | N | ILE | 223 | -11.485 | 33.969 | 32.482 | 1.00 | 2.69 | PROT |
| ATOM | 3341 | CA | ILE | 223 | -11.864 | 35.218 | 33.196 | 1.00 | 2.62 | PROT |
| ATOM | 3342 | C | ILE | 223 | -12.137 | 34.930 | 34.667 | 1.00 | 2.28 | PROT |
| ATOM | 3343 | O | ILE | 223 | -11.697 | 35.681 | 35.563 | 1.00 | 2.00 | PROT |
| ATOM | 3344 | CB | ILE | 223 | -13.050 | 35.968 | 32.512 | 1.00 | 2.92 | PROT |
| ATOM | 3345 | CG1 | ILE | 223 | -12.628 | 36.483 | 31.118 | 1.00 | 2.45 | PROT |
| ATOM | 3346 | CG2 | ILE | 223 | -13.514 | 37.115 | 33.392 | 1.00 | 2.75 | PROT |
| ATOM | 3347 | CD | ILE | 223 | -13.781 | 37.189 | 30.269 | 1.00 | 3.70 | PROT |
| ATOM | 3359 | N | PHE | 224 | -12.838 | 33.836 | 34.974 | 1.00 | 2.54 | PROT |
| ATOM | 3360 | CA | PHE | 224 | -13.060 | 33.440 | 36.373 | 1.00 | 2.24 | PROT |
| ATOM | 3361 | C | PHE | 224 | -11.772 | 33.194 | 37.121 | 1.00 | 2.01 | PROT |
| ATOM | 3362 | O | PHE | 224 | -11.596 | 33.693 | 38.026 | 1.00 | 2.00 | PROT |
| ATOM | 3363 | CB | PHE | 224 | -13.958 | 32.184 | 36.463 | 1.00 | 2.01 | PROT |
| ATOM | 3364 | CG | PHE | 224 | -15.309 | 32.330 | 35.830 | 1.00 | 2.00 | PROT |
| ATOM | 3365 | CD1 | PHE | 224 | -15.389 | 33.555 | 35.941 | 1.00 | 3.21 | PROT |
| ATOM | 3366 | CD2 | PHE | 224 | -16.903 | 31.253 | 35.224 | 1.00 | 2.00 | PROT |
| ATOM | 3367 | CE1 | PHE | 224 | -17.248 | 33.691 | 35.255 | 1.00 | 2.00 | PROT |
| ATOM | 3368 | CE2 | PHE | 224 | -17.188 | 31.353 | 34.643 | 1.00 | 2.00 | PROT |
| ATOM | 3369 | CZ | PHE | 224 | -17.846 | 32.595 | 34.652 | 1.00 | 2.00 | PROT |
| ATOM | 3379 | N | LEU | 225 | -10.866 | 32.428 | 36.522 | 1.00 | 2.00 | PROT |
| ATOM | 3380 | CA | LEU | 225 | -9.564 | 32.178 | 37.155 | 1.00 | 2.44 | PROT |
| ATOM | 3381 | C | LEU | 225 | -8.805 | 33.476 | 37.447 | 1.00 | 2.00 | PROT |
| ATOM | 3382 | O | LEU | 225 | -8.200 | 33.612 | 38.513 | 1.00 | 2.01 | PROT |
| ATOM | 3383 | CB | LEU | 225 | -8.723 | 31.211 | 36.316 | 1.00 | 3.03 | PROT |
| ATOM | 3384 | CG | LEU | 225 | -7.435 | 30.746 | 36.995 | 1.00 | 4.44 | PROT |
| ATOM | 3385 | CD1 | LEU | 225 | -7.255 | 29.246 | 36.823 | 1.00 | 6.20 | PROT |
| ATOM | 3386 | CD2 | LEU | 225 | -6.248 | 31.526 | 36.427 | 1.00 | 6.69 | PROT |
| ATOM | 3398 | N | LEU | 226 | -6.866 | 34.429 | 36.517 | 1.00 | 2.00 | PROT |
| ATOM | 3399 | CA | LEU | 226 | -6.243 | 35.744 | 36.699 | 1.00 | 2.19 | PROT |
| ATOM | 3400 | C | LEU | 226 | -8.901 | 36.583 | 37.799 | 1.00 | 2.16 | PROT |
| ATOM | 3401 | O | LEU | 226 | -9.182 | 37.262 | 38.554 | 1.00 | 2.00 | PROT |
| ATOM | 3402 | CB | LEU | 226 | -8.181 | 36.525 | 35.356 | 1.00 | 2.81 | PROT |
| ATOM | 3403 | CG | LEU | 226 | -7.214 | 35.953 | 34.314 | 1.00 | 4.36 | PROT |
| ATOM | 3404 | CD1 | LEU | 226 | -7.327 | 36.609 | 32.916 | 1.00 | 5.59 | PROT |
| ATOM | 3405 | CD2 | LEU | 226 | -5.787 | 35.960 | 34.834 | 1.00 | 4.87 | PROT |
| ATOM | 3417 | N | GLU | 227 | -10.240 | 36.542 | 37.861 | 1.00 | 2.00 | PROT |
| ATOM | 3418 | CA | GLU | 227 | -10.997 | 37.156 | 38.996 | 1.00 | 2.26 | PROT |
| ATOM | 3419 | C | GLU | 227 | -10.505 | 36.620 | 40.344 | 1.00 | 2.00 | PROT |
| ATOM | 3420 | O | GLU | 227 | -10.335 | 37.374 | 41.307 | 1.00 | 2.00 | PROT |
| ATOM | 3421 | CB | GLU | 227 | -12.502 | 36.868 | 38.881 | 1.00 | 2.48 | PROT |
| ATOM | 3422 | CG | GLU | 227 | -13.241 | 37.635 | 37.750 | 1.00 | 3.00 | PROT |
| ATOM | 3423 | CD | GLU | 227 | -14.688 | 37.182 | 37.552 | 1.00 | 3.47 | PROT |
| ATOM | 3424 | OE1 | GLU | 227 | -15.197 | 36.302 | 38.295 | 1.00 | 6.37 | PROT |
| ATOM | 3425 | OE2 | GLU | 227 | -15.343 | 37.723 | 36.639 | 1.00 | 5.01 | PROT |
| ATOM | 3432 | N | HSD | 228 | -10.279 | 35.310 | 40.404 | 1.00 | 2.00 | PROT |
| ATOM | 3433 | CA | HSD | 228 | -9.613 | 34.667 | 41.636 | 1.00 | 2.00 | PROT |
| ATOM | 3434 | C | HSD | 228 | -8.358 | 35.016 | 41.918 | 1.00 | 2.00 | PROT |
| ATOM | 3435 | O | HSD | 228 | -7.963 | 35.299 | 43.059 | 1.00 | 2.22 | PROT |
| ATOM | 3436 | CB | HSD | 228 | -10.048 | 33.148 | 41.567 | 1.00 | 2.00 | PROT |
| ATOM | 3437 | CG | HSD | 228 | -9.896 | 32.476 | 40.314 | 1.00 | 2.40 | PROT |
| ATOM | 3438 | ND1 | HSD | 228 | -8.758 | 31.787 | 43.270 | 1.00 | 5.23 | PROT |
| ATOM | 3439 | CD2 | HSD | 228 | -10.727 | 32.400 | 43.977 | 1.00 | 3.56 | PROT |
| ATOM | 3440 | CE1 | HSD | 228 | -8.896 | 31.310 | 44.491 | 1.00 | 2.61 | PROT |

Figure 3 cont.

```
ATOM   3441  NE2  HSD  228   -10.076  31.680  44.951  1.00   3.92      PROT
ATOM   3449  N    ALA  229    -7.537  35.030  40.874  1.00   2.00      PROT
ATOM   3450  CA   ALA  229    -6.139  35.625  41.010  1.00   2.00      PROT
ATOM   3451  C    ALA  229    -5.984  36.828  41.406  1.00   2.00      PROT
ATOM   3452  O    ALA  229    -5.009  37.272  42.068  1.00   2.04      PROT
ATOM   3453  CB   ALA  229    -5.386  35.120  39.713  1.00   2.00      PROT
ATOM   3459  N    GLN  230    -6.985  37.726  41.061  1.00   2.00      PROT
ATOM   3460  CA   GLN  230    -7.006  39.136  41.330  1.00   2.75      PROT
ATOM   3461  C    GLN  230    -7.536  39.346  42.743  1.00   3.94      PROT
ATOM   3462  O    GLN  230    -7.423  40.438  43.297  1.00   4.74      PROT
ATOM   3463  CB   GLN  230    -7.916  39.870  40.332  1.00   2.31      PROT
ATOM   3464  CG   GLN  230    -8.106  41.386  40.559  1.00   2.00      PROT
ATOM   3465  CD   GLN  230    -6.810  42.168  40.458  1.00   2.00      PROT
ATOM   3466  OE1  GLN  230    -6.813  41.669  39.955  1.00   2.00      PROT
ATOM   3467  NE2  GLN  230    -6.815  43.401  40.967  1.00   2.00      PROT
ATOM   3476  N    GLY  231    -8.134  38.306  43.312  1.00   4.89      PROT
ATOM   3477  CA   GLY  231    -8.737  38.364  44.628  1.00   7.20      PROT
ATOM   3478  C    GLY  231    -9.927  39.306  44.639  1.00   9.03      PROT
ATOM   3479  O    GLY  231   -10.097  40.073  45.592  1.00   9.60      PROT
ATOM   3483  N    MET  232   -10.731  39.253  43.577  1.00  10.20      PROT
ATOM   3484  CA   MET  232   -11.959  40.047  43.471  1.00  11.96      PROT
ATOM   3485  C    MET  232   -11.962  39.581  44.912  1.00  11.63      PROT
ATOM   3486  O    MET  232   -12.988  38.390  44.838  1.00  11.93      PROT
ATOM   3487  CB   MET  232   -12.616  39.682  42.106  1.00  11.85      PROT
ATOM   3488  CG   MET  232   -11.757  40.152  40.921  1.00  12.75      PROT
ATOM   3489  SD   MET  232   -12.629  41.023  39.789  1.00  16.78      PROT
ATOM   3490  CE   MET  232   -11.894  42.770  40.269  1.00  10.26      PROT
ATOM   3500  N    PRO  233   -13.823  40.501  44.999  1.00  11.66      PROT
ATOM   3501  CA   PRO  233   -14.789  40.142  46.037  1.00  11.78      PROT
ATOM   3502  C    PRO  233   -15.754  39.080  45.476  1.00  11.86      PROT
ATOM   3503  O    PRO  233   -16.091  38.161  46.352  1.00  12.02      PROT
ATOM   3504  CB   PRO  233   -15.530  41.460  46.325  1.00  11.48      PROT
ATOM   3505  CG   PRO  233   -15.285  42.336  45.170  1.00  11.93      PROT
ATOM   3506  CD   PRO  233   -13.983  41.902  44.590  1.00  11.61      PROT
ATOM   3514  N    LYS  234   -16.170  39.103  44.313  1.00  11.27      PROT
ATOM   3515  CA   LYS  234   -17.080  38.060  43.772  1.00  10.91      PROT
ATOM   3516  C    LYS  234   -16.482  37.446  42.514  1.00  10.37      PROT
ATOM   3517  O    LYS  234   -16.269  38.127  41.505  1.00   9.97      PROT
ATOM   3518  CB   LYS  234   -18.449  38.645  43.510  1.00  11.04      PROT
ATOM   3519  CG   LYS  234   -19.347  38.649  44.752  1.00  12.37      PROT
ATOM   3520  CD   LYS  234   -19.906  36.370  44.997  1.00  25.75      PROT
ATOM   3521  CE   LYS  234   -19.135  35.110  45.534  1.00  25.07      PROT
ATOM   3522  NZ   LYS  234   -17.572  34.867  45.360  1.00  21.97      PROT
ATOM   3536  N    VAL  235   -16.346  36.134  42.595  1.00   9.38      PROT
ATOM   3537  CA   VAL  235   -15.716  35.342  41.486  1.00   8.21      PROT
ATOM   3538  C    VAL  235   -16.846  34.497  40.899  1.00   7.30      PROT
ATOM   3539  O    VAL  235   -17.465  33.694  41.609  1.00   7.42      PROT
ATOM   3540  CB   VAL  235   -14.551  34.408  41.939  1.00   8.69      PROT
ATOM   3541  CG1  VAL  235   -13.375  35.217  42.485  1.00   9.22      PROT
ATOM   3542  CG2  VAL  235   -14.086  33.498  40.794  1.00   7.04      PROT
ATOM   3552  N    ALA  236   -17.124  34.685  39.607  1.00   6.92      PROT
ATOM   3553  CA   ALA  236   -18.181  33.938  38.922  1.00   6.04      PROT
ATOM   3554  C    ALA  236   -19.496  34.023  39.708  1.00   5.79      PROT
ATOM   3555  O    ALA  236   -20.252  33.044  39.791  1.00   4.79      PROT
ATOM   3556  CB   ALA  236   -17.772  32.488  38.737  1.00   6.17      PROT
ATOM   3562  N    TRP  237   -19.732  35.199  40.298  1.00   5.43      PROT
ATOM   3563  CA   TRP  237   -20.937  35.516  41.077  1.00   5.65      PROT
ATOM   3564  C    TRP  237   -21.211  34.542  42.234  1.00   5.73      PROT
ATOM   3565  O    TRP  237   -22.372  34.272  42.569  1.00   5.65      PROT
ATOM   3566  CB   TRP  237   -23.167  35.674  40.163  1.00   5.62      PROT
ATOM   3567  CG   TRP  237   -21.862  36.503  38.965  1.00   6.72      PROT
ATOM   3568  CD1  TRP  237   -21.827  37.865  38.894  1.00   6.98      PROT
ATOM   3569  CD2  TRP  237   -21.493  36.020  37.679  1.00   6.01      PROT
ATOM   3570  NE1  TRP  237   -21.476  38.260  37.632  1.00   7.13      PROT
ATOM   3571  CE2  TRP  237   -21.265  37.167  36.861  1.00   8.16      PROT
```

Figure 3 cont.

```
ATOM    3572  CE3 TRP   237     -21.344  34.743  37.128  1.00  6.02      PROT
ATOM    3573  CZ2 TRP   237     -20.863  37.036  35.523  1.00  6.55      PROT
ATOM    3574  CZ3 TRP   237     -20.963  34.630  35.800  1.00  6.46      PROT
ATOM    3575  CH2 TRP   237     -20.741  35.771  35.013  1.00  6.77      PROT
ATOM    3586  N   GLY   238     -20.132  34.025  42.824  1.00  5.45      PROT
ATOM    3587  CA  GLY   238     -20.202  33.083  43.937  1.00  5.24      PROT
ATOM    3588  C   GLY   238     -20.454  31.629  43.569  1.00  5.65      PROT
ATOM    3589  O   GLY   238     -20.635  30.802  44.457  1.00  5.14      PROT
ATOM    3593  N   ASN   239     -20.406  31.300  42.274  1.00  5.32      PROT
ATOM    3594  CA  ASN   239     -20.307  30.004  41.781  1.00  5.87      PROT
ATOM    3595  C   ASN   239     -19.907  29.871  41.576  1.00  5.89      PROT
ATOM    3596  O   ASN   239     -20.810  27.760  41.224  1.00  5.93      PROT
ATOM    3597  CB  ASN   239     -21.740  30.185  40.505  1.00  5.58      PROT
ATOM    3598  CG  ASN   239     -23.035  30.930  40.758  1.00  6.11      PROT
ATOM    3599  OD1 ASN   239     -23.612  30.836  41.837  1.00  6.76      PROT
ATOM    3600  ND2 ASN   239     -23.502  31.667  39.756  1.00  6.82      PROT
ATOM    3607  N   ILE   240     -18.621  29.349  41.781  1.00  6.14      PROT
ATOM    3608  CA  ILE   240     -17.601  28.102  41.786  1.00  6.09      PROT
ATOM    3609  C   ILE   240     -17.274  27.779  43.246  1.00  6.58      PROT
ATOM    3610  O   ILE   240     -16.827  28.640  44.007  1.00  7.29      PROT
ATOM    3611  CB  ILE   240     -16.305  28.489  41.013  1.00  5.88      PROT
ATOM    3612  CG1 ILE   240     -16.632  29.054  39.622  1.00  5.79      PROT
ATOM    3613  CG2 ILE   240     -15.399  27.274  40.888  1.00  5.36      PROT
ATOM    3614  CD  ILE   240     -15.421  29.613  38.891  1.00  5.45      PROT
ATOM    3626  N   HSD   241     -17.519  26.535  43.693  1.00  7.26      PROT
ATOM    3627  CA  HSD   241     -17.391  26.132  45.025  1.00  7.62      PROT
ATOM    3628  C   HSD   241     -16.229  25.180  45.263  1.00  7.39      PROT
ATOM    3629  O   HSD   241     -15.580  25.249  46.311  1.00  7.30      PROT
ATOM    3630  CB  HSD   241     -18.698  25.503  45.515  1.00  8.36      PROT
ATOM    3631  CG  HSD   241     -19.873  26.435  45.460  1.00  9.94      PROT
ATOM    3632  ND1 HSD   241     -20.845  26.347  44.466  1.00 11.72      PROT
ATOM    3633  CD2 HSD   241     -20.226  27.465  46.298  1.00 11.00      PROT
ATOM    3634  CE1 HSD   241     -21.752  27.297  44.693  1.00 11.28      PROT
ATOM    3635  NE2 HSD   241     -21.394  27.983  45.756  1.00 12.05      PROT
ATOM    3643  N   THR   242     -15.974  24.291  44.314  1.00  6.92      PROT
ATOM    3644  CA  THR   242     -15.036  23.391  44.536  1.00  7.02      PROT
ATOM    3645  C   THR   242     -13.886  23.156  43.542  1.00  6.93      PROT
ATOM    3646  O   THR   242     -13.063  23.695  42.445  1.00  7.23      PROT
ATOM    3647  CB  THR   242     -15.742  21.809  44.527  1.00  6.55      PROT
ATOM    3648  OG1 THR   242     -16.076  21.444  43.184  1.00  5.56      PROT
ATOM    3649  CG2 THR   242     -16.999  21.820  45.392  1.00  7.90      PROT
ATOM    3656  N   GLU   243     -12.890  22.503  43.944  1.00  7.09      PROT
ATOM    3657  CA  GLU   243     -11.680  22.226  43.053  1.00  6.85      PROT
ATOM    3658  C   GLU   243     -12.163  21.463  41.921  1.00  6.38      PROT
ATOM    3659  O   GLU   243     -11.759  21.761  40.692  1.00  5.51      PROT
ATOM    3660  CB  GLU   243     -10.615  21.420  43.799  1.00  7.39      PROT
ATOM    3661  CG  GLU   243      -9.663  20.676  42.867  1.00  8.63      PROT
ATOM    3662  CD  GLU   243      -8.794  19.803  43.633  1.00  9.49      PROT
ATOM    3663  OE1 GLU   243      -8.930  18.589  43.691  1.00  7.07      PROT
ATOM    3664  OE2 GLU   243      -7.741  20.362  44.199  1.00 11.16      PROT
ATOM    3671  N   GLN   244     -13.041  20.495  42.042  1.00  5.14      PROT
ATOM    3672  CA  GLN   244     -13.617  19.717  40.945  1.00  4.68      PROT
ATOM    3673  C   GLN   244     -14.089  20.612  39.881  1.00  3.99      PROT
ATOM    3674  O   GLN   244     -14.139  20.367  38.676  1.00  3.31      PROT
ATOM    3675  CB  GLN   244     -14.603  18.674  41.474  1.00  4.43      PROT
ATOM    3676  CG  GLN   244     -13.122  17.733  40.401  1.00  4.63      PROT
ATOM    3677  CD  GLN   244     -15.469  16.362  40.733  1.00 10.22      PROT
ATOM    3678  OE1 GLN   244     -16.675  16.076  40.539  1.00 13.93      PROT
ATOM    3679  NE2 GLN   244     -14.680  15.349  41.318  1.00 14.14      PROT
ATOM    3688  N   GLN   245     -15.095  21.642  40.339  1.00  3.48      PROT
ATOM    3689  CA  GLN   245     -15.657  22.621  39.457  1.00  3.56      PROT
ATOM    3690  C   GLN   245     -14.669  23.525  38.753  1.00  3.07      PROT
ATOM    3691  O   GLN   245     -14.865  23.870  37.569  1.00  2.89      PROT
ATOM    3692  CB  GLN   245     -16.687  23.484  40.232  1.00  3.63      PROT
ATOM    3693  CG  GLN   245     -17.999  22.813  40.436  1.00  5.02      PROT
```

Figure 3 cont.

```
ATOM   3694  CD   GLN   245    -18.810  23.415  41.566  1.00   6.61   PROT
ATOM   3695  OE1  GLN   245    -18.346  24.371  42.313  1.00   7.06   PROT
ATOM   3696  NE2  GLN   245    -20.043  22.953  41.694  1.00   8.44   PROT
ATOM   3705  N    TRP   246    -13.593  23.911  39.454  1.00   2.79   PROT
ATOM   3706  CA   TRP   246    -12.539  24.684  38.823  1.00   2.54   PROT
ATOM   3707  C    TRP   246    -11.933  23.991  37.670  1.00   2.35   PROT
ATOM   3708  O    TRP   246    -11.725  24.435  36.580  1.00   2.00   PROT
ATOM   3709  CB   TRP   246    -11.445  25.067  39.803  1.00   2.58   PROT
ATOM   3710  CG   TRP   246    -11.695  26.339  40.537  1.00   3.39   PROT
ATOM   3711  CD1  TRP   246    -11.934  26.476  41.869  1.00   2.89   PROT
ATOM   3712  CD2  TRP   246    -11.712  27.665  39.982  1.00   3.44   PROT
ATOM   3713  NE1  TRP   246    -12.107  27.803  42.182  1.00   6.09   PROT
ATOM   3714  CE2  TRP   246    -11.981  28.553  41.039  1.00   2.93   PROT
ATOM   3715  CE3  TRP   246    -11.548  28.182  38.684  1.00   2.71   PROT
ATOM   3716  CZ2  TRP   246    -12.077  29.946  40.851  1.00   3.61   PROT
ATOM   3717  CZ3  TRP   246    -11.654  29.557  38.493  1.00   2.47   PROT
ATOM   3718  CH2  TRP   246    -11.913  30.403  39.569  1.00   2.84   PROT
ATOM   3729  N    ASN   247    -11.663  22.608  37.919  1.00   2.00   PROT
ATOM   3730  CA   ASN   247    -10.992  21.769  36.939  1.00   2.50   PROT
ATOM   3731  C    ASN   247    -11.888  21.575  35.705  1.00   2.01   PROT
ATOM   3732  O    ASN   247    -11.417  21.678  34.580  1.00   2.60   PROT
ATOM   3733  CB   ASN   247    -10.616  20.409  37.549  1.00   2.50   PROT
ATOM   3734  CG   ASN   247     -9.361  20.473  38.426  1.00   3.92   PROT
ATOM   3735  OD1  ASN   247     -8.663  21.484  38.483  1.00   7.36   PROT
ATOM   3736  ND2  ASN   247     -9.073  19.376  39.107  1.00   5.56   PROT
ATOM   3743  N    SER   248    -13.169  21.302  35.945  1.00   2.00   PROT
ATOM   3744  CA   SER   248    -14.173  21.135  34.894  1.00   2.00   PROT
ATOM   3745  C    SER   248    -14.284  22.357  33.949  1.00   2.10   PROT
ATOM   3746  O    SER   248    -14.343  22.199  32.722  1.00   2.30   PROT
ATOM   3747  CB   SER   248    -15.531  20.749  35.596  1.00   2.00   PROT
ATOM   3748  OG   SER   248    -16.535  20.480  34.633  1.00   2.40   PROT
ATOM   3753  N    LEU   249    -14.305  23.562  34.526  1.00   2.00   PROT
ATOM   3754  CA   LEU   249    -14.346  24.807  33.744  1.00   2.00   PROT
ATOM   3755  C    LEU   249    -13.064  25.020  32.953  1.00   2.00   PROT
ATOM   3756  O    LEU   249    -13.111  25.269  31.748  1.00   2.00   PROT
ATOM   3757  CB   LEU   249    -14.632  26.027  34.636  1.00   2.00   PROT
ATOM   3758  CG   LEU   249    -16.038  26.035  35.252  1.00   2.37   PROT
ATOM   3759  CD1  LEU   249    -16.198  27.198  36.223  1.00   3.63   PROT
ATOM   3760  CD2  LEU   249    -17.132  26.089  34.188  1.00   2.00   PROT
ATOM   3772  N    LEU   250    -11.920  24.890  33.620  1.00   2.00   PROT
ATOM   3773  CA   LEU   250    -10.636  25.116  32.946  1.00   2.51   PROT
ATOM   3774  C    LEU   250    -10.283  24.056  31.914  1.00   2.05   PROT
ATOM   3775  O    LEU   250     -9.466  24.302  31.051  1.00   2.38   PROT
ATOM   3776  CB   LEU   250     -9.491  25.289  33.948  1.00   2.33   PROT
ATOM   3777  CG   LEU   250     -9.173  26.716  34.416  1.00   3.60   PROT
ATOM   3778  CD1  LEU   250    -10.329  27.303  35.221  1.00   4.09   PROT
ATOM   3779  CD2  LEU   250     -8.798  27.642  33.220  1.00   3.17   PROT
ATOM   3791  N    LYS   251    -10.907  22.879  32.012  1.00   2.58   PROT
ATOM   3792  CA   LYS   251    -10.734  21.642  31.000  1.00   3.10   PROT
ATOM   3793  C    LYS   251    -11.104  22.384  29.606  1.00   2.88   PROT
ATOM   3794  O    LYS   251    -10.459  22.094  28.615  1.00   2.97   PROT
ATOM   3795  CB   LYS   251    -11.572  20.803  31.356  1.00   3.79   PROT
ATOM   3796  CG   LYS   251    -11.673  19.566  30.242  1.00   5.55   PROT
ATOM   3797  CD   LYS   251    -11.927  18.159  30.794  1.00   8.54   PROT
ATOM   3798  CE   LYS   251    -13.399  17.823  30.804  1.00  10.50   PROT
ATOM   3799  NZ   LYS   251    -13.603  16.364  31.026  1.00  11.77   PROT
ATOM   3813  N    LEU   252    -12.156  23.193  29.850  1.00   2.97   PROT
ATOM   3814  CA   LEU   252    -12.601  23.835  28.305  1.00   2.99   PROT
ATOM   3815  C    LEU   252    -11.526  24.770  27.746  1.00   2.76   PROT
ATOM   3816  O    LEU   252    -11.266  24.788  26.541  1.00   2.86   PROT
ATOM   3817  CB   LEU   252    -13.962  24.604  28.547  1.00   2.00   PROT
ATOM   3818  CG   LEU   252    -15.136  23.760  28.905  1.00   4.13   PROT
ATOM   3819  CD1  LEU   252    -16.194  24.614  29.604  1.00   4.74   PROT
ATOM   3820  CD2  LEU   252    -15.729  23.040  27.664  1.00   4.65   PROT
ATOM   3832  N    HSD   253    -10.896  25.523  28.644  1.00   2.58   PROT
```

Figure 3 cont.

| | | | | | | | | | |
|---|---|---|---|---|---|---|---|---|---|
| ATOM | 3833 | CA | HSD | 253 | -6.837 | 26.448 | 28.295 | 1.00 | 2.90 | PROT |
| ATOM | 3834 | C | HSD | 253 | -8.571 | 25.761 | 27.804 | 1.00 | 2.67 | PROT |
| ATOM | 3835 | O | HSD | 253 | -7.992 | 26.162 | 26.795 | 1.00 | 3.21 | PROT |
| ATOM | 3836 | CB | HSD | 253 | -9.535 | 27.356 | 29.486 | 1.00 | 2.97 | PROT |
| ATOM | 3837 | CG | HSD | 253 | -8.384 | 28.284 | 29.275 | 1.00 | 4.58 | PROT |
| ATOM | 3838 | ND1 | HSD | 253 | -8.518 | 29.610 | 28.658 | 1.00 | 4.97 | PROT |
| ATOM | 3839 | CD2 | HSD | 253 | -7.098 | 28.197 | 29.660 | 1.00 | 5.22 | PROT |
| ATOM | 3840 | CE1 | HSD | 253 | -7.353 | 30.131 | 28.661 | 1.00 | 4.54 | PROT |
| ATOM | 3841 | NE2 | HSD | 253 | -6.467 | 29.352 | 29.263 | 1.00 | 5.30 | PROT |
| ATOM | 3849 | N | ASN | 254 | -9.119 | 24.720 | 28.526 | 1.00 | 2.69 | PROT |
| ATOM | 3850 | CA | ASN | 254 | -8.945 | 23.951 | 28.085 | 1.00 | 2.44 | PROT |
| ATOM | 3851 | C | ASN | 254 | -7.183 | 23.231 | 26.753 | 1.00 | 2.45 | PROT |
| ATOM | 3852 | O | ASN | 254 | -8.258 | 23.093 | 25.957 | 1.00 | 2.24 | PROT |
| ATOM | 3853 | CB | ASN | 254 | -6.494 | 22.930 | 29.147 | 1.00 | 2.23 | PROT |
| ATOM | 3854 | CG | ASN | 254 | -6.059 | 23.595 | 30.451 | 1.00 | 2.51 | PROT |
| ATOM | 3855 | OD1 | ASN | 254 | -5.449 | 24.666 | 30.468 | 1.00 | 2.79 | PROT |
| ATOM | 3856 | ND2 | ASN | 254 | -6.361 | 22.950 | 31.548 | 1.00 | 2.76 | PROT |
| ATOM | 3863 | N | ALA | 255 | -8.424 | 22.795 | 26.515 | 1.00 | 2.46 | PROT |
| ATOM | 3864 | CA | ALA | 255 | -8.804 | 22.186 | 25.241 | 1.00 | 2.81 | PROT |
| ATOM | 3865 | C | ALA | 255 | -8.711 | 23.154 | 24.094 | 1.00 | 2.85 | PROT |
| ATOM | 3866 | O | ALA | 255 | -8.192 | 22.827 | 23.022 | 1.00 | 2.52 | PROT |
| ATOM | 3867 | CB | ALA | 255 | -10.236 | 21.690 | 25.313 | 1.00 | 5.00 | PROT |
| ATOM | 3873 | N | GLN | 256 | -9.244 | 24.348 | 24.325 | 1.00 | 3.13 | PROT |
| ATOM | 3874 | CA | GLN | 256 | -9.235 | 25.401 | 23.319 | 1.00 | 3.86 | PROT |
| ATOM | 3875 | C | GLN | 256 | -7.810 | 25.750 | 22.926 | 1.00 | 3.34 | PROT |
| ATOM | 3876 | O | GLN | 256 | -7.515 | 25.312 | 21.745 | 1.00 | 3.84 | PROT |
| ATOM | 3877 | CB | GLN | 256 | -9.893 | 26.632 | 23.806 | 1.00 | 3.76 | PROT |
| ATOM | 3878 | CG | GLN | 256 | -10.183 | 27.719 | 22.733 | 1.00 | 6.52 | PROT |
| ATOM | 3879 | CD | GLN | 256 | -9.205 | 28.876 | 22.876 | 1.00 | 11.19 | PROT |
| ATOM | 3880 | OE1 | GLN | 256 | -8.494 | 29.220 | 21.932 | 1.00 | 16.66 | PROT |
| ATOM | 3881 | NE2 | GLN | 256 | -9.173 | 29.498 | 24.056 | 1.00 | 12.60 | PROT |
| ATOM | 3890 | N | PHE | 257 | -6.938 | 25.945 | 23.930 | 1.00 | 3.06 | PROT |
| ATOM | 3891 | CA | PHE | 257 | -5.518 | 26.084 | 23.721 | 1.00 | 2.83 | PROT |
| ATOM | 3892 | C | PHE | 257 | -4.771 | 24.969 | 23.008 | 1.00 | 2.45 | PROT |
| ATOM | 3893 | O | PHE | 257 | -3.906 | 25.230 | 22.174 | 1.00 | 2.54 | PROT |
| ATOM | 3894 | CB | PHE | 257 | -4.955 | 26.494 | 25.039 | 1.00 | 2.41 | PROT |
| ATOM | 3895 | CG | PHE | 257 | -4.897 | 27.976 | 25.237 | 1.00 | 3.23 | PROT |
| ATOM | 3896 | CD1 | PHE | 257 | -3.770 | 28.738 | 25.098 | 1.00 | 4.55 | PROT |
| ATOM | 3897 | CD2 | PHE | 257 | -6.107 | 28.616 | 25.515 | 1.00 | 3.03 | PROT |
| ATOM | 3898 | CE1 | PHE | 257 | -3.817 | 30.104 | 25.133 | 1.00 | 5.36 | PROT |
| ATOM | 3899 | CE2 | PHE | 257 | -6.167 | 30.009 | 25.620 | 1.00 | 4.80 | PROT |
| ATOM | 3900 | CZ | PHE | 257 | -5.014 | 30.752 | 25.439 | 1.00 | 6.23 | PROT |
| ATOM | 3910 | N | ASP | 258 | -5.131 | 23.730 | 23.311 | 1.00 | 2.85 | PROT |
| ATOM | 3911 | CA | ASP | 258 | -4.570 | 22.589 | 22.579 | 1.00 | 4.03 | PROT |
| ATOM | 3912 | C | ASP | 258 | -4.830 | 22.693 | 21.075 | 1.00 | 3.31 | PROT |
| ATOM | 3913 | O | ASP | 258 | -3.986 | 22.564 | 20.228 | 1.00 | 3.35 | PROT |
| ATOM | 3914 | CB | ASP | 258 | -5.115 | 21.274 | 23.150 | 1.00 | 4.59 | PROT |
| ATOM | 3915 | CG | ASP | 258 | -4.447 | 20.083 | 22.583 | 1.00 | 6.92 | PROT |
| ATOM | 3916 | OD1 | ASP | 258 | -3.209 | 20.056 | 22.405 | 1.00 | 9.90 | PROT |
| ATOM | 3917 | OD2 | ASP | 258 | -5.162 | 19.078 | 22.295 | 1.00 | 11.03 | PROT |
| ATOM | 3922 | N | LEU | 259 | -6.148 | 22.924 | 20.758 | 1.00 | 2.92 | PROT |
| ATOM | 3923 | CA | LEU | 259 | -6.580 | 23.011 | 19.367 | 1.00 | 3.06 | PROT |
| ATOM | 3924 | C | LEU | 259 | -6.055 | 24.234 | 18.626 | 1.00 | 2.87 | PROT |
| ATOM | 3925 | O | LEU | 259 | -5.603 | 24.119 | 17.474 | 1.00 | 3.56 | PROT |
| ATOM | 3926 | CB | LEU | 259 | -8.112 | 22.937 | 19.257 | 1.00 | 3.04 | PROT |
| ATOM | 3927 | CG | LEU | 259 | -8.817 | 21.754 | 19.914 | 1.00 | 3.29 | PROT |
| ATOM | 3928 | CD1 | LEU | 259 | -10.326 | 21.901 | 19.742 | 1.00 | 3.83 | PROT |
| ATOM | 3929 | CD2 | LEU | 259 | -8.321 | 20.431 | 19.354 | 1.00 | 4.84 | PROT |
| ATOM | 3941 | N | MET | 260 | -6.103 | 25.395 | 19.269 | 1.00 | 2.39 | PROT |
| ATOM | 3942 | CA | MET | 260 | -5.763 | 26.644 | 18.596 | 1.00 | 2.81 | PROT |
| ATOM | 3943 | C | MET | 260 | -4.295 | 27.024 | 18.631 | 1.00 | 2.51 | PROT |
| ATOM | 3944 | O | MET | 260 | -3.841 | 27.749 | 17.753 | 1.00 | 2.00 | PROT |
| ATOM | 3945 | CB | MET | 260 | -6.606 | 27.814 | 19.116 | 1.00 | 3.54 | PROT |
| ATOM | 3946 | CG | MET | 260 | -6.103 | 27.734 | 16.625 | 1.00 | 6.15 | PROT |
| ATOM | 3947 | SD | MET | 260 | -6.492 | 27.539 | 17.081 | 1.00 | 12.80 | PROT |

Figure 3 cont.

```
ATOM   3948  CB  MET 260    -0.804  25.905  17.030  1.00  6.34      PROT
ATOM   3958  N   SER 261    -3.564  26.561  19.663  1.00  2.86      PROT
ATOM   3959  CA  SER 261    -2.160  26.953  19.822  1.00  3.70      PROT
ATOM   3960  C   SER 261    -1.148  25.736  19.946  1.00  3.64      PROT
ATOM   3961  O   SER 261     0.011  25.985  19.463  1.00  4.13      PROT
ATOM   3962  CB  SER 261    -1.993  27.824  21.077  1.00  3.66      PROT
ATOM   3963  OG  SER 261    -2.336  26.135  20.898  1.00  5.70      PROT
ATOM   3968  N   ARG 262    -1.557  24.620  20.314  1.00  3.67      PROT
ATOM   3969  CA  ARG 262    -0.639  23.462  20.327  1.00  3.94      PROT
ATOM   3970  C   ARG 262    -0.604  22.654  19.023  1.00  3.73      PROT
ATOM   3971  O   ARG 262     0.438  22.107  18.667  1.00  4.26      PROT
ATOM   3972  CB  ARG 262    -0.868  22.543  21.524  1.00  4.18      PROT
ATOM   3973  CG  ARG 262    -0.745  23.236  22.898  1.00  4.84      PROT
ATOM   3974  CD  ARG 262    -0.292  22.260  23.997  1.00 10.03      PROT
ATOM   3975  NE  ARG 262    -0.792  20.943  23.709  1.00 14.21      PROT
ATOM   3976  CZ  ARG 262    -0.046  19.869  23.432  1.00 14.65      PROT
ATOM   3977  NH1 ARG 262     1.267  19.870  23.435  1.00 14.69      PROT
ATOM   3978  NH2 ARG 262    -0.711  18.769  23.119  1.00 11.65      PROT
ATOM   3992  N   THR 263    -1.734  22.583  18.313  1.00  3.54      PROT
ATOM   3993  CA  THR 263    -1.814  21.914  17.000  1.00  3.69      PROT
ATOM   3994  C   THR 263    -0.519  22.219  16.229  1.00  4.08      PROT
ATOM   3995  O   THR 263    -0.263  23.385  15.366  1.00  4.64      PROT
ATOM   3996  CB  THR 263    -3.055  22.424  16.222  1.00  3.39      PROT
ATOM   3997  OG1 THR 263    -4.246  22.049  16.921  1.00  2.35      PROT
ATOM   3998  CG2 THR 263    -3.114  21.974  14.797  1.00  3.17      PROT
ATOM   4005  N   PRO 264     0.309  21.196  15.917  1.00  4.83      PROT
ATOM   4006  CA  PRO 264     1.659  21.420  15.365  1.00  4.72      PROT
ATOM   4007  C   PRO 264     1.762  22.345  14.132  1.00  4.77      PROT
ATOM   4008  O   PRO 264     2.674  23.182  14.070  1.00  3.58      PROT
ATOM   4009  CB  PRO 264     2.159  20.007  15.042  1.00  5.63      PROT
ATOM   4010  CG  PRO 264     1.429  19.138  16.011  1.00  5.68      PROT
ATOM   4011  CD  PRO 264     0.057  19.746  16.113  1.00  5.12      PROT
ATOM   4019  N   TYR 265     0.844  22.193  13.175  1.00  3.82      PROT
ATOM   4020  CA  TYR 265     0.781  23.105  12.023  1.00  4.05      PROT
ATOM   4021  C   TYR 265     0.718  24.539  12.414  1.00  3.79      PROT
ATOM   4022  O   TYR 265     1.449  25.457  11.965  1.00  3.89      PROT
ATOM   4023  CB  TYR 265    -0.400  22.738  11.118  1.00  4.47      PROT
ATOM   4024  CG  TYR 265    -0.499  23.536   9.882  1.00  5.56      PROT
ATOM   4025  CD1 TYR 265     0.337  23.371   8.795  1.00  5.47      PROT
ATOM   4026  CD2 TYR 265    -1.414  24.631   9.809  1.00  6.44      PROT
ATOM   4027  CE1 TYR 265     0.263  24.163   7.661  1.00  7.13      PROT
ATOM   4028  CE2 TYR 265    -1.494  25.456   8.673  1.00  6.49      PROT
ATOM   4029  CZ  TYR 265    -0.649  25.201   7.604  1.00  6.04      PROT
ATOM   4030  OH  TYR 265    -0.711  25.971   6.467  1.00  6.52      PROT
ATOM   4039  N   ILE 266    -0.162  24.925  13.358  1.00  2.90      PROT
ATOM   4040  CA  ILE 266    -0.339  26.292  13.834  1.00  3.39      PROT
ATOM   4041  C   ILE 266     0.645  26.698  14.751  1.00  2.97      PROT
ATOM   4042  O   ILE 266     1.326  27.826  14.690  1.00  2.90      PROT
ATOM   4043  CB  ILE 266    -1.665  26.493  14.640  1.00  3.05      PROT
ATOM   4044  CG1 ILE 266    -2.862  26.215  13.715  1.00  3.33      PROT
ATOM   4045  CG2 ILE 266    -1.742  27.830  15.357  1.00  3.89      PROT
ATOM   4046  CD  ILE 266    -4.173  25.893  14.426  1.00  3.45      PROT
ATOM   4058  N   ALA 267     1.306  25.756  15.568  1.00  2.97      PROT
ATOM   4059  CA  ALA 267     2.349  26.012  16.563  1.00  3.33      PROT
ATOM   4060  C   ALA 267     3.663  26.407  15.898  1.00  2.90      PROT
ATOM   4061  O   ALA 267     4.337  27.308  16.335  1.00  2.80      PROT
ATOM   4062  CB  ALA 267     2.532  24.794  17.476  1.00  2.96      PROT
ATOM   4068  N   LYS 268     4.039  25.736  14.803  1.00  2.85      PROT
ATOM   4069  CA  LYS 268     5.275  26.063  14.107  1.00  2.85      PROT
ATOM   4070  C   LYS 268     5.215  27.404  13.359  1.00  2.70      PROT
ATOM   4071  O   LYS 268     6.228  28.096  13.236  1.00  2.43      PROT
ATOM   4072  CB  LYS 268     5.715  24.921  13.176  1.00  3.42      PROT
ATOM   4073  CG  LYS 268     4.764  24.663  12.037  1.00  3.26      PROT
ATOM   4074  CD  LYS 268     5.248  23.549  11.110  1.00  3.56      PROT
ATOM   4075  CE  LYS 268     4.413  23.511   9.882  1.00  4.15      PROT
```

Figure 3 cont.

| | | | | | | | | |
|---|---|---|---|---|---|---|---|---|
| ATOM | 4076 | NZ | LYS | 268 | 4.621 | 22.242 | 9.118 | 1.00 | 6.09 | PROT |
| ATOM | 4090 | N | HSD | 269 | 4.034 | 27.763 | 11.857 | 1.00 | 1.47 | PROT |
| ATOM | 4091 | CA | HSD | 269 | 3.842 | 29.035 | 12.149 | 1.00 | 2.69 | PROT |
| ATOM | 4092 | C | HSD | 269 | 3.918 | 30.241 | 13.084 | 1.00 | 2.81 | PROT |
| ATOM | 4093 | O | HSD | 269 | 4.331 | 31.330 | 12.686 | 1.00 | 3.29 | PROT |
| ATOM | 4094 | CB | HSD | 269 | 2.506 | 29.040 | 11.407 | 1.00 | 2.64 | PROT |
| ATOM | 4095 | CG | HSD | 269 | 2.556 | 28.327 | 10.092 | 1.00 | 3.35 | PROT |
| ATOM | 4096 | ND1 | HSD | 269 | 2.302 | 26.981 | 9.973 | 1.00 | 4.72 | PROT |
| ATOM | 4097 | CD2 | HSD | 269 | 2.839 | 28.769 | 8.845 | 1.00 | 4.80 | PROT |
| ATOM | 4098 | CE1 | HSD | 269 | 2.429 | 26.620 | 8.709 | 1.00 | 3.86 | PROT |
| ATOM | 4099 | NE2 | HSD | 269 | 2.751 | 27.688 | 8.003 | 1.00 | 4.94 | PROT |
| ATOM | 4107 | N | ASN | 270 | 3.518 | 30.017 | 14.323 | 1.00 | 2.44 | PROT |
| ATOM | 4108 | CA | ASN | 270 | 3.464 | 31.044 | 15.348 | 1.00 | 3.16 | PROT |
| ATOM | 4109 | C | ASN | 270 | 4.838 | 30.998 | 16.310 | 1.00 | 2.45 | PROT |
| ATOM | 4110 | O | ASN | 270 | 5.032 | 31.025 | 16.879 | 1.00 | 2.07 | PROT |
| ATOM | 4111 | CB | ASN | 270 | 2.151 | 30.893 | 16.130 | 1.00 | 3.29 | PROT |
| ATOM | 4112 | CG | ASN | 270 | 0.974 | 31.496 | 15.405 | 1.00 | 7.11 | PROT |
| ATOM | 4113 | OD1 | ASN | 270 | 0.936 | 32.704 | 15.166 | 1.00 | 11.82 | PROT |
| ATOM | 4114 | ND2 | ASN | 270 | 0.013 | 30.858 | 15.029 | 1.00 | 9.68 | PROT |
| ATOM | 4121 | N | GLY | 271 | 5.202 | 29.809 | 16.492 | 1.00 | 2.29 | PROT |
| ATOM | 4122 | CA | GLY | 271 | 6.252 | 29.630 | 17.496 | 1.00 | 2.63 | PROT |
| ATOM | 4123 | C | GLY | 271 | 7.693 | 29.495 | 17.002 | 1.00 | 2.72 | PROT |
| ATOM | 4124 | O | GLY | 271 | 8.595 | 29.446 | 17.811 | 1.00 | 3.41 | PROT |
| ATOM | 4128 | N | THR | 272 | 7.886 | 29.414 | 15.689 | 1.00 | 2.65 | PROT |
| ATOM | 4129 | CA | THR | 272 | 9.251 | 29.259 | 15.132 | 1.00 | 2.33 | PROT |
| ATOM | 4130 | C | THR | 272 | 10.297 | 30.309 | 15.591 | 1.00 | 2.84 | PROT |
| ATOM | 4131 | O | THR | 272 | 11.384 | 29.317 | 16.034 | 1.00 | 2.14 | PROT |
| ATOM | 4132 | CB | THR | 272 | 9.249 | 29.055 | 13.590 | 1.00 | 2.64 | PROT |
| ATOM | 4133 | OG1 | THR | 272 | 8.799 | 27.726 | 13.293 | 1.00 | 2.09 | PROT |
| ATOM | 4134 | CG2 | THR | 272 | 10.645 | 29.253 | 12.989 | 1.00 | 2.16 | PROT |
| ATOM | 4141 | N | PRO | 273 | 9.989 | 31.631 | 15.472 | 1.00 | 3.18 | PROT |
| ATOM | 4142 | CA | PRO | 273 | 10.929 | 32.636 | 15.991 | 1.00 | 3.00 | PROT |
| ATOM | 4143 | C | PRO | 273 | 11.329 | 32.456 | 17.462 | 1.00 | 2.64 | PROT |
| ATOM | 4144 | O | PRO | 273 | 12.507 | 32.575 | 17.798 | 1.00 | 2.00 | PROT |
| ATOM | 4145 | CB | PRO | 273 | 10.169 | 33.962 | 15.803 | 1.00 | 3.45 | PROT |
| ATOM | 4146 | CG | PRO | 273 | 9.256 | 33.692 | 14.650 | 1.00 | 3.72 | PROT |
| ATOM | 4147 | CD | PRO | 273 | 8.820 | 32.263 | 14.828 | 1.00 | 2.86 | PROT |
| ATOM | 4155 | N | LEU | 274 | 10.357 | 32.191 | 18.328 | 1.00 | 2.00 | PROT |
| ATOM | 4156 | CA | LEU | 274 | 10.648 | 31.979 | 19.741 | 1.00 | 2.18 | PROT |
| ATOM | 4157 | C | LEU | 274 | 11.319 | 30.734 | 20.008 | 1.00 | 2.00 | PROT |
| ATOM | 4158 | O | LEU | 274 | 10.508 | 30.854 | 20.743 | 1.00 | 2.00 | PROT |
| ATOM | 4159 | CB | LEU | 274 | 9.358 | 31.929 | 20.577 | 1.00 | 2.00 | PROT |
| ATOM | 4160 | CG | LEU | 274 | 8.863 | 33.371 | 21.139 | 1.00 | 4.76 | PROT |
| ATOM | 4161 | CD1 | LEU | 274 | 9.874 | 33.724 | 22.199 | 1.00 | 3.36 | PROT |
| ATOM | 4162 | CD2 | LEU | 274 | 7.508 | 33.314 | 21.742 | 1.00 | 6.75 | PROT |
| ATOM | 4174 | N | LEU | 275 | 11.167 | 29.627 | 19.369 | 1.00 | 2.00 | PROT |
| ATOM | 4175 | CA | LEU | 275 | 11.944 | 28.385 | 19.522 | 1.00 | 2.41 | PROT |
| ATOM | 4176 | C | LEU | 275 | 13.389 | 28.541 | 19.063 | 1.00 | 2.73 | PROT |
| ATOM | 4177 | O | LEU | 275 | 14.313 | 28.171 | 19.780 | 1.00 | 2.88 | PROT |
| ATOM | 4178 | CB | LEU | 275 | 11.278 | 27.193 | 18.813 | 1.00 | 2.00 | PROT |
| ATOM | 4179 | CG | LEU | 275 | 11.899 | 25.814 | 19.119 | 1.00 | 2.08 | PROT |
| ATOM | 4180 | CD1 | LEU | 275 | 11.947 | 25.446 | 20.605 | 1.00 | 2.23 | PROT |
| ATOM | 4181 | CD2 | LEU | 275 | 11.316 | 24.665 | 18.251 | 1.00 | 2.25 | PROT |
| ATOM | 4193 | N | GLN | 276 | 13.364 | 29.102 | 17.868 | 1.00 | 3.17 | PROT |
| ATOM | 4194 | CA | GLN | 276 | 14.880 | 29.446 | 17.356 | 1.00 | 3.37 | PROT |
| ATOM | 4195 | C | GLN | 276 | 15.669 | 30.367 | 18.306 | 1.00 | 2.83 | PROT |
| ATOM | 4196 | O | GLN | 276 | 16.851 | 30.146 | 18.549 | 1.00 | 2.03 | PROT |
| ATOM | 4197 | CB | GLN | 276 | 14.782 | 30.019 | 15.935 | 1.00 | 3.63 | PROT |
| ATOM | 4198 | CG | GLN | 276 | 14.378 | 28.934 | 14.893 | 1.00 | 5.11 | PROT |
| ATOM | 4199 | CD | GLN | 276 | 14.282 | 29.439 | 13.469 | 1.00 | 4.81 | PROT |
| ATOM | 4200 | OE1 | GLN | 276 | 14.054 | 30.624 | 13.213 | 1.00 | 5.03 | PROT |
| ATOM | 4201 | NE2 | GLN | 276 | 14.433 | 28.519 | 12.498 | 1.00 | 5.08 | PROT |
| ATOM | 4210 | N | THR | 277 | 15.003 | 31.365 | 18.886 | 1.00 | 3.09 | PROT |
| ATOM | 4211 | CA | THR | 277 | 15.631 | 32.266 | 19.863 | 1.00 | 2.65 | PROT |
| ATOM | 4212 | C | THR | 277 | 16.013 | 31.650 | 21.175 | 1.00 | 2.25 | PROT |

Figure 3 cont.

| | | | | | | | | | |
|---|---|---|---|---|---|---|---|---|---|
| ATOM | 4213 | O | THR | 277 | 17.114 | 31.744 | 21.707 | 1.00 2.00 | PROT |
| ATOM | 4214 | CB | THR | 277 | 14.730 | 33.479 | 20.152 | 1.00 3.05 | PROT |
| ATOM | 4215 | OG1 | THR | 277 | 14.626 | 34.265 | 18.968 | 1.00 4.88 | PROT |
| ATOM | 4216 | CG2 | THR | 277 | 15.294 | 34.323 | 21.300 | 1.00 3.24 | PROT |
| ATOM | 4223 | N | ILE | 278 | 15.099 | 30.744 | 21.700 | 1.00 2.00 | PROT |
| ATOM | 4224 | CA | ILE | 278 | 15.406 | 29.926 | 22.870 | 1.00 2.16 | PROT |
| ATOM | 4225 | C | ILE | 278 | 16.604 | 28.996 | 22.591 | 1.00 2.00 | PROT |
| ATOM | 4226 | O | ILE | 278 | 17.609 | 29.043 | 23.309 | 1.00 2.00 | PROT |
| ATOM | 4227 | CB | ILE | 278 | 14.158 | 29.181 | 23.390 | 1.00 2.52 | PROT |
| ATOM | 4228 | CG1 | ILE | 278 | 13.157 | 30.209 | 23.944 | 1.00 2.00 | PROT |
| ATOM | 4229 | CG2 | ILE | 278 | 14.528 | 28.187 | 24.479 | 1.00 2.43 | PROT |
| ATOM | 4230 | CD | ILE | 278 | 11.727 | 29.693 | 24.176 | 1.00 3.75 | PROT |
| ATOM | 4242 | N | ALA | 279 | 16.502 | 28.202 | 21.522 | 1.00 2.00 | PROT |
| ATOM | 4243 | CA | ALA | 279 | 17.579 | 27.295 | 21.106 | 1.00 2.00 | PROT |
| ATOM | 4244 | C | ALA | 279 | 18.930 | 28.001 | 21.117 | 1.00 2.00 | PROT |
| ATOM | 4245 | O | ALA | 279 | 19.892 | 27.511 | 21.709 | 1.00 2.00 | PROT |
| ATOM | 4246 | CB | ALA | 279 | 17.268 | 26.716 | 19.716 | 1.00 2.00 | PROT |
| ATOM | 4252 | N | HSD | 280 | 18.985 | 29.164 | 20.480 | 1.00 2.25 | PROT |
| ATOM | 4253 | CA | HSD | 280 | 20.245 | 29.874 | 20.276 | 1.00 2.27 | PROT |
| ATOM | 4254 | C | HSD | 280 | 20.811 | 30.381 | 21.605 | 1.00 2.65 | PROT |
| ATOM | 4255 | O | HSD | 280 | 22.013 | 30.268 | 21.833 | 1.00 2.62 | PROT |
| ATOM | 4256 | CB | HSD | 280 | 20.078 | 31.033 | 19.269 | 1.00 2.01 | PROT |
| ATOM | 4257 | CG | HSD | 280 | 21.357 | 31.735 | 18.962 | 1.00 2.59 | PROT |
| ATOM | 4258 | ND1 | HSD | 280 | 21.757 | 32.896 | 19.606 | 1.00 2.93 | PROT |
| ATOM | 4259 | CD2 | HSD | 280 | 22.342 | 31.437 | 18.083 | 1.00 3.83 | PROT |
| ATOM | 4260 | CE1 | HSD | 280 | 22.924 | 33.275 | 19.128 | 1.00 4.17 | PROT |
| ATOM | 4261 | NE2 | HSD | 280 | 23.301 | 32.414 | 19.200 | 1.00 2.85 | PROT |
| ATOM | 4269 | N | ALA | 281 | 19.950 | 30.920 | 22.478 | 1.00 2.95 | PROT |
| ATOM | 4270 | CA | ALA | 281 | 20.386 | 31.358 | 23.816 | 1.00 3.63 | PROT |
| ATOM | 4271 | C | ALA | 281 | 20.961 | 30.195 | 24.639 | 1.00 4.19 | PROT |
| ATOM | 4272 | O | ALA | 281 | 21.894 | 30.380 | 25.434 | 1.00 4.36 | PROT |
| ATOM | 4273 | CB | ALA | 281 | 19.230 | 32.080 | 24.571 | 1.00 3.83 | PROT |
| ATOM | 4279 | N | LEU | 282 | 20.433 | 28.989 | 24.416 | 1.00 5.08 | PROT |
| ATOM | 4280 | CA | LEU | 282 | 20.901 | 27.788 | 25.118 | 1.00 5.36 | PROT |
| ATOM | 4281 | C | LEU | 282 | 22.222 | 27.249 | 24.587 | 1.00 6.17 | PROT |
| ATOM | 4282 | O | LEU | 282 | 22.623 | 26.347 | 25.149 | 1.00 5.73 | PROT |
| ATOM | 4283 | CB | LEU | 282 | 19.822 | 26.691 | 25.163 | 1.00 4.36 | PROT |
| ATOM | 4284 | CG | LEU | 282 | 18.509 | 26.990 | 25.897 | 1.00 3.91 | PROT |
| ATOM | 4285 | CD1 | LEU | 282 | 17.409 | 26.015 | 25.496 | 1.00 3.34 | PROT |
| ATOM | 4286 | CD2 | LEU | 282 | 18.709 | 27.002 | 27.423 | 1.00 2.18 | PROT |
| ATOM | 4298 | N | GLY | 283 | 22.682 | 27.794 | 23.411 | 1.00 7.02 | PROT |
| ATOM | 4299 | CA | GLY | 283 | 23.939 | 27.422 | 22.823 | 1.00 8.72 | PROT |
| ATOM | 4300 | C | GLY | 283 | 23.892 | 26.808 | 21.538 | 1.00 9.89 | PROT |
| ATOM | 4301 | O | GLY | 283 | 24.921 | 26.123 | 21.062 | 1.00 9.62 | PROT |
| ATOM | 4305 | N | SER | 284 | 22.703 | 26.454 | 20.953 | 1.00 11.20 | PROT |
| ATOM | 4306 | CA | SER | 284 | 22.541 | 25.737 | 19.690 | 1.00 12.67 | PROT |
| ATOM | 4307 | C | SER | 284 | 23.297 | 26.428 | 18.528 | 1.00 13.73 | PROT |
| ATOM | 4308 | O | SER | 284 | 23.248 | 27.687 | 18.424 | 1.00 13.58 | PROT |
| ATOM | 4309 | CB | SER | 284 | 21.083 | 25.569 | 19.387 | 1.00 12.83 | PROT |
| ATOM | 4310 | OG | SER | 284 | 20.422 | 24.728 | 20.304 | 1.00 13.58 | PROT |
| ATOM | 4315 | N | ASN | 285 | 23.851 | 25.625 | 17.644 | 1.00 14.88 | PROT |
| ATOM | 4316 | CA | ASN | 285 | 24.564 | 26.133 | 16.462 | 1.00 16.45 | PROT |
| ATOM | 4317 | C | ASN | 285 | 23.593 | 26.578 | 15.364 | 1.00 17.15 | PROT |
| ATOM | 4318 | O | ASN | 285 | 23.823 | 26.368 | 14.169 | 1.00 17.29 | PROT |
| ATOM | 4319 | CB | ASN | 285 | 25.549 | 25.080 | 15.934 | 1.00 16.75 | PROT |
| ATOM | 4320 | CG | ASN | 285 | 26.471 | 25.623 | 14.847 | 1.00 17.87 | PROT |
| ATOM | 4321 | OD1 | ASN | 285 | 26.633 | 25.063 | 13.790 | 1.00 20.17 | PROT |
| ATOM | 4322 | ND2 | ASN | 285 | 27.076 | 26.782 | 15.099 | 1.00 18.67 | PROT |
| ATOM | 4329 | N | ILE | 286 | 22.499 | 27.196 | 15.800 | 1.00 17.97 | PROT |
| ATOM | 4330 | CA | ILE | 286 | 21.437 | 27.676 | 14.942 | 1.00 19.08 | PROT |
| ATOM | 4331 | C | ILE | 286 | 21.742 | 29.139 | 14.579 | 1.00 19.26 | PROT |
| ATOM | 4332 | O | ILE | 286 | 22.673 | 29.737 | 15.129 | 1.00 19.67 | PROT |
| ATOM | 4333 | CB | ILE | 286 | 20.076 | 27.529 | 15.696 | 1.00 19.19 | PROT |
| ATOM | 4334 | CG1 | ILE | 286 | 18.906 | 27.296 | 14.734 | 1.00 20.03 | PROT |
| ATOM | 4335 | CG2 | ILE | 286 | 19.820 | 28.715 | 16.623 | 1.00 19.40 | PROT |

Figure 3 cont.

```
ATOM   4336  CD    ILE   286    17.630  26.813  15.403  1.00  19.77      PROT
ATOM   4348  N     THR   287    20.395  29.692  13.624  1.00  19.35      PROT
ATOM   4349  CA    THR   287    21.047  31.103  13.329  1.00  19.32      PROT
ATOM   4350  C     THR   287    19.746  31.752  13.838  1.00  18.84      PROT
ATOM   4351  O     THR   287    18.862  31.212  13.616  1.00  19.08      PROT
ATOM   4352  CB    THR   287    21.240  31.394  11.810  1.00  19.37      PROT
ATOM   4353  OG1   THR   287    22.487  30.837  11.375  1.00  20.03      PROT
ATOM   4354  CG2   THR   287    21.236  32.894  11.505  1.00  19.77      PROT
ATOM   4361  N     SER   288    19.862  32.871  14.380  1.00  18.17      PROT
ATOM   4362  CA    SER   288    18.680  33.597  15.016  1.00  17.36      PROT
ATOM   4363  C     SER   288    18.910  35.096  15.127  1.00  16.63      PROT
ATOM   4364  O     SER   288    19.949  35.540  15.603  1.00  16.86      PROT
ATOM   4365  CB    SER   288    18.199  33.059  16.364  1.00  17.31      PROT
ATOM   4366  OG    SER   288    16.940  33.645  16.693  1.00  17.47      PROT
ATOM   4371  N     ARG   289    17.916  35.864  14.683  1.00  15.98      PROT
ATOM   4372  CA    ARG   289    17.969  37.313  14.761  1.00  14.97      PROT
ATOM   4373  C     ARG   289    18.319  37.790  16.171  1.00  14.04      PROT
ATOM   4374  O     ARG   289    17.614  37.459  17.134  1.00  13.54      PROT
ATOM   4375  CB    ARG   289    16.665  37.945  14.282  1.00  15.14      PROT
ATOM   4376  CG    ARG   289    16.754  39.458  14.097  1.00  17.07      PROT
ATOM   4377  CD    ARG   289    16.049  39.907  12.837  1.00  18.64      PROT
ATOM   4378  NE    ARG   289    14.655  40.273  13.072  1.00  19.63      PROT
ATOM   4379  CZ    ARG   289    13.719  40.287  12.137  1.00  20.16      PROT
ATOM   4380  NH1   ARG   289    14.014  39.924  10.886  1.00  19.76      PROT
ATOM   4381  NH2   ARG   289    12.477  40.647  12.421  1.00  19.88      PROT
ATOM   4395  N     PRO   290    19.423  38.550  16.291  1.00  12.91      PROT
ATOM   4396  CA    PRO   290    19.926  39.014  17.583  1.00  12.31      PROT
ATOM   4397  C     PRO   290    18.932  39.900  18.338  1.00  11.14      PROT
ATOM   4398  O     PRO   290    18.254  40.727  17.739  1.00  11.04      PROT
ATOM   4399  CB    PRO   290    21.181  39.816  17.208  1.00  12.08      PROT
ATOM   4400  CG    PRO   290    21.575  39.315  15.836  1.00  12.40      PROT
ATOM   4401  CD    PRO   290    20.272  39.015  15.172  1.00  13.25      PROT
ATOM   4409  N     LEU   291    18.860  39.693  19.644  1.00  10.51      PROT
ATOM   4410  CA    LEU   291    18.121  40.643  20.498  1.00   9.58      PROT
ATOM   4411  C     LEU   291    19.109  41.784  20.679  1.00   9.24      PROT
ATOM   4412  O     LEU   291    20.286  41.524  20.916  1.00   8.86      PROT
ATOM   4413  CB    LEU   291    17.760  40.016  21.847  1.00   9.67      PROT
ATOM   4414  CG    LEU   291    16.668  38.937  21.819  1.00   9.62      PROT
ATOM   4415  CD1   LEU   291    15.330  39.536  21.423  1.00   9.83      PROT
ATOM   4416  CD2   LEU   291    16.876  38.239  23.165  1.00   9.61      PROT
ATOM   4428  N     PRO   292    18.660  43.042  20.536  1.00   8.92      PROT
ATOM   4429  CA    PRO   292    19.614  44.143  20.551  1.00   9.07      PROT
ATOM   4430  C     PRO   292    20.261  44.282  21.919  1.00   9.09      PROT
ATOM   4431  O     PRO   292    19.574  44.194  22.937  1.00   8.65      PROT
ATOM   4432  CB    PRO   292    18.749  45.375  20.247  1.00   9.46      PROT
ATOM   4433  CG    PRO   292    17.373  44.990  20.716  1.00   9.59      PROT
ATOM   4434  CD    PRO   292    17.265  43.518  20.377  1.00   8.83      PROT
ATOM   4442  N     ASP   293    21.577  44.473  21.942  1.00   9.25      PROT
ATOM   4443  CA    ASP   293    22.266  44.687  23.187  1.00   9.55      PROT
ATOM   4444  C     ASP   293    22.326  43.614  24.241  1.00   9.31      PROT
ATOM   4445  O     ASP   293    22.404  44.142  25.433  1.00   9.87      PROT
ATOM   4446  CB    ASP   293    21.581  46.138  23.724  1.00  10.30      PROT
ATOM   4447  CG    ASP   293    22.559  47.147  24.229  1.00  12.60      PROT
ATOM   4448  OD1   ASP   293    22.796  48.150  23.509  1.00  16.91      PROT
ATOM   4449  OD2   ASP   293    23.116  46.930  25.328  1.00  13.71      PROT
ATOM   4454  N     ILE   294    22.253  42.549  23.834  1.00   7.89      PROT
ATOM   4455  CA    ILE   294    22.397  41.426  24.752  1.00   7.00      PROT
ATOM   4456  C     ILE   294    23.095  41.048  24.851  1.00   7.00      PROT
ATOM   4457  O     ILE   294    24.625  41.100  23.885  1.00   7.24      PROT
ATOM   4458  CB    ILE   294    21.473  40.217  24.373  1.00   6.93      PROT
ATOM   4459  CG1   ILE   294    21.364  39.322  25.542  1.00   5.67      PROT
ATOM   4460  CG2   ILE   294    21.923  39.541  23.043  1.00   6.07      PROT
ATOM   4461  CD    ILE   294    20.236  38.197  25.417  1.00   5.23      PROT
ATOM   4473  N     SER   295    24.336  40.736  26.062  1.00   6.58      PROT
ATOM   4474  CA    SER   295    25.726  40.403  26.309  1.00   7.30      PROT
```

Figure 3 cont.

```
ATOM   4475  C    SER  295    25.963  39.930  26.006  1.00   7.52    PROT
ATOM   4476  O    SER  295    25.103  39.107  26.307  1.00   6.84    PROT
ATOM   4477  CB   SER  295    26.078  40.699  27.767  1.00   7.35    PROT
ATOM   4478  OG   SER  295    27.398  40.273  28.071  1.00   7.94    PROT
ATOM   4483  N    PRO  296    27.116  39.587  25.385  1.00   8.12    PROT
ATOM   4484  CA   PRO  296    27.460  37.153  25.286  1.00   8.38    PROT
ATOM   4485  C    PRO  296    27.667  36.486  26.653  1.00   8.43    PROT
ATOM   4486  O    PRO  296    27.472  35.263  26.753  1.00   9.10    PROT
ATOM   4487  CB   PRO  296    28.792  37.147  24.612  1.00   8.72    PROT
ATOM   4488  CG   PRO  296    29.289  38.545  24.523  1.00   8.24    PROT
ATOM   4489  CD   PRO  296    28.106  39.463  24.710  1.00   8.34    PROT
ATOM   4497  N    ASP  297    27.853  37.294  27.696  1.00   8.51    PROT
ATOM   4498  CA   ASP  297    27.945  36.795  29.062  1.00   8.73    PROT
ATOM   4499  C    ASP  297    26.585  36.738  29.761  1.00   8.19    PROT
ATOM   4500  O    ASP  297    26.539  36.603  31.002  1.00   9.75    PROT
ATOM   4501  CB   ASP  297    28.933  37.653  29.869  1.00   9.14    PROT
ATOM   4502  CG   ASP  297    30.380  37.489  29.399  1.00  10.18    PROT
ATOM   4503  OD1  ASP  297    30.736  36.412  28.878  1.00  12.04    PROT
ATOM   4504  OD2  ASP  297    31.173  38.445  29.559  1.00  12.86    PROT
ATOM   4509  N    ASN  298    25.489  36.834  29.057  1.00   7.52    PROT
ATOM   4510  CA   ASN  298    24.145  36.730  29.611  1.00   7.12    PROT
ATOM   4511  C    ASN  298    23.886  35.373  30.256  1.00   7.01    PROT
ATOM   4512  O    ASN  298    24.176  34.319  29.664  1.00   7.09    PROT
ATOM   4513  CB   ASN  298    23.055  37.040  28.590  1.00   6.85    PROT
ATOM   4514  CG   ASN  298    21.672  37.156  29.206  1.00   6.67    PROT
ATOM   4515  OD1  ASN  298    21.378  38.114  29.934  1.00   5.83    PROT
ATOM   4516  ND2  ASN  298    20.833  36.161  28.965  1.00   4.59    PROT
ATOM   4523  N    LYS  299    23.319  35.415  31.456  1.00   6.21    PROT
ATOM   4524  CA   LYS  299    23.036  34.216  32.030  1.00   6.05    PROT
ATOM   4525  C    LYS  299    21.547  33.920  32.360  1.00   4.84    PROT
ATOM   4526  O    LYS  299    21.143  32.747  32.471  1.00   4.89    PROT
ATOM   4527  CB   LYS  299    23.689  34.319  33.605  1.00   6.37    PROT
ATOM   4528  CG   LYS  299    25.174  34.024  33.867  1.00   8.71    PROT
ATOM   4529  CD   LYS  299    25.897  34.510  34.806  1.00  12.22    PROT
ATOM   4530  CE   LYS  299    27.416  34.461  34.568  1.00  13.87    PROT
ATOM   4531  NZ   LYS  299    27.915  33.118  34.226  1.00  15.49    PROT
ATOM   4545  N    ILE  300    20.745  34.982  32.344  1.00   3.36    PROT
ATOM   4546  CA   ILE  300    19.298  34.698  32.537  1.00   2.90    PROT
ATOM   4547  C    ILE  300    18.609  35.727  31.435  1.00   2.00    PROT
ATOM   4548  O    ILE  300    18.782  36.953  31.376  1.00   2.00    PROT
ATOM   4549  CB   ILE  300    18.643  35.410  33.915  1.00   3.14    PROT
ATOM   4550  CG1  ILE  300    19.315  34.605  35.041  1.00   3.01    PROT
ATOM   4551  CG2  ILE  300    17.300  35.314  34.070  1.00   3.93    PROT
ATOM   4552  CD   ILE  300    19.366  35.289  36.405  1.00   3.25    PROT
ATOM   4564  N    LEU  301    17.878  35.046  30.567  1.00   2.00    PROT
ATOM   4565  CA   LEU  301    17.060  35.712  29.574  1.00   2.00    PROT
ATOM   4566  C    LEU  301    15.595  35.484  29.918  1.00   2.00    PROT
ATOM   4567  O    LEU  301    15.104  34.346  29.697  1.00   2.47    PROT
ATOM   4568  CB   LEU  301    17.364  35.187  28.164  1.00   2.00    PROT
ATOM   4569  CG   LEU  301    16.419  35.594  27.022  1.00   2.00    PROT
ATOM   4570  CD1  LEU  301    16.352  37.118  26.832  1.00   2.00    PROT
ATOM   4571  CD2  LEU  301    16.886  34.940  25.714  1.00   2.00    PROT
ATOM   4583  N    PHE  302    14.896  36.573  30.195  1.00   2.00    PROT
ATOM   4584  CA   PHE  302    13.492  36.510  30.554  1.00   2.00    PROT
ATOM   4585  C    PHE  302    12.693  37.095  29.385  1.00   2.00    PROT
ATOM   4586  O    PHE  302    12.940  38.232  28.943  1.00   2.00    PROT
ATOM   4587  CB   PHE  302    13.264  37.306  31.836  1.00   2.00    PROT
ATOM   4588  CG   PHE  302    11.838  37.285  32.377  1.00   2.00    PROT
ATOM   4589  CD1  PHE  302    11.450  36.249  33.260  1.00   2.00    PROT
ATOM   4590  CD2  PHE  302    10.904  38.238  32.031  1.00   2.00    PROT
ATOM   4591  CE1  PHE  302    10.133  36.232  33.791  1.00   2.00    PROT
ATOM   4592  CE2  PHE  302     9.602  38.223  32.546  1.02   2.00    PROT
ATOM   4593  CZ   PHE  302     9.213  37.222  33.423  1.00   2.00    PROT
ATOM   4603  N    ILE  303    11.787  36.289  28.859  1.00   2.00    PROT
ATOM   4604  CA   ILE  303    10.963  36.609  27.731  1.00   2.00    PROT
```

Figure 3 cont.

```
ATOM   4605  C    ILE   303       9.525   36.740   28.173  1.00   2.09      PROT
ATOM   4606  O    ILE   303       8.948   35.735   28.589  1.00   2.11      PROT
ATOM   4607  CB   ILE   303      11.197   35.680   26.526  1.00   2.00      PROT
ATOM   4608  CG1  ILE   303      12.608   35.569   26.126  1.00   2.05      PROT
ATOM   4609  CG2  ILE   303      10.273   36.164   25.335  1.00   2.00      PROT
ATOM   4610  CD   ILE   303      12.954   34.372   25.220  1.00   2.00      PROT
ATOM   4622  N    ALA   304       8.974   37.950   28.182  1.00   2.18      PROT
ATOM   4623  CA   ALA   304       7.620   38.236   28.607  1.00   2.00      PROT
ATOM   4624  C    ALA   304       6.622   38.209   27.435  1.00   2.00      PROT
ATOM   4625  O    ALA   304       6.603   39.091   26.574  1.00   2.00      PROT
ATOM   4626  CB   ALA   304       7.363   39.631   29.389  1.00   2.00      PROT
ATOM   4632  N    GLY   305       5.825   37.146   27.402  1.00   2.00      PROT
ATOM   4633  CA   GLY   305       4.877   36.839   26.334  1.00   2.00      PROT
ATOM   4634  C    GLY   305       3.564   36.441   26.825  1.00   2.00      PROT
ATOM   4635  O    GLY   305       3.122   36.901   27.948  1.00   2.00      PROT
ATOM   4639  N    HSD   306       2.962   35.486   26.130  1.00   2.01      PROT
ATOM   4640  CA   HSD   306       1.674   35.092   26.416  1.00   2.20      PROT
ATOM   4641  C    HSD   306       1.423   33.575   26.539  1.00   2.82      PROT
ATOM   4642  O    HSD   306       2.328   32.824   26.165  1.00   2.86      PROT
ATOM   4643  CB   HSD   306       0.718   35.896   25.249  1.00   2.49      PROT
ATOM   4644  CG   HSD   306       0.874   37.070   24.999  1.00   4.73      PROT
ATOM   4645  CD2  HSD   306       1.843   37.583   24.168  1.00   6.93      PROT
ATOM   4646  ND1  HSD   306       0.203   38.134   25.498  1.00   4.07      PROT
ATOM   4647  NE2  HSD   306       1.760   38.900   24.147  1.00   3.76      PROT
ATOM   4648  CE1  HSD   306       0.772   39.258   24.944  1.00   7.37      PROT
ATOM   4656  N    ASP   307       0.265   33.155   27.041  1.00   2.72      PROT
ATOM   4657  CA   ASP   307      -0.140   31.756   27.089  1.00   3.01      PROT
ATOM   4658  C    ASP   307      -0.082   31.060   25.727  1.00   2.89      PROT
ATOM   4659  O    ASP   307       0.321   29.896   25.649  1.00   2.00      PROT
ATOM   4660  CB   ASP   307      -1.525   31.683   27.749  1.00   3.25      PROT
ATOM   4661  CG   ASP   307      -2.620   32.630   27.208  1.00   5.23      PROT
ATOM   4662  OD1  ASP   307      -2.823   33.093   26.084  1.00   5.17      PROT
ATOM   4663  OD2  ASP   307      -3.643   32.683   27.929  1.00   4.48      PROT
ATOM   4668  N    THR   308      -0.470   31.787   24.670  1.00   2.32      PROT
ATOM   4669  CA   THR   308      -0.437   31.079   23.291  1.00   2.98      PROT
ATOM   4670  C    THR   308       1.009   30.906   22.867  1.00   2.42      PROT
ATOM   4671  O    THR   308       1.244   29.875   22.261  1.00   2.00      PROT
ATOM   4672  CB   THR   308      -1.025   32.302   22.273  1.00   3.37      PROT
ATOM   4673  OG1  THR   308      -0.182   33.457   22.222  1.00   5.53      PROT
ATOM   4674  CG2  THR   308      -2.449   32.770   22.679  1.00   3.39      PROT
ATOM   4681  N    ASN   309       1.965   31.764   23.241  1.00   2.00      PROT
ATOM   4682  CA   ASN   309       3.389   31.466   23.045  1.00   2.00      PROT
ATOM   4683  C    ASN   309       3.846   30.191   23.759  1.00   2.00      PROT
ATOM   4684  O    ASN   309       4.525   29.372   23.173  1.00   2.00      PROT
ATOM   4685  CB   ASN   309       4.264   32.651   23.473  1.00   2.00      PROT
ATOM   4686  CG   ASN   309       3.981   33.923   22.683  1.00   2.32      PROT
ATOM   4687  OD1  ASN   309       4.090   33.972   21.456  1.00   5.77      PROT
ATOM   4688  ND2  ASN   309       3.552   34.948   23.383  1.00   2.00      PROT
ATOM   4695  N    ILE   310       3.452   30.008   25.019  1.00   2.00      PROT
ATOM   4696  CA   ILE   310       3.858   28.802   25.753  1.00   2.00      PROT
ATOM   4697  C    ILE   310       3.242   27.561   25.114  1.00   2.00      PROT
ATOM   4698  O    ILE   310       3.902   26.538   24.973  1.00   2.00      PROT
ATOM   4699  CB   ILE   310       3.535   28.917   27.276  1.00   2.00      PROT
ATOM   4700  CG1  ILE   310       4.469   29.946   27.922  1.00   2.00      PROT
ATOM   4701  CG2  ILE   310       3.608   27.555   27.997  1.00   2.00      PROT
ATOM   4702  CD   ILE   310       4.078   30.397   29.287  1.00   4.61      PROT
ATOM   4714  N    ALA   311       1.977   27.668   24.732  1.00   2.00      PROT
ATOM   4715  CA   ALA   311       1.289   26.577   24.052  1.00   2.00      PROT
ATOM   4716  C    ALA   311       1.960   26.246   22.714  1.00   2.00      PROT
ATOM   4717  O    ALA   311       2.153   25.062   22.421  1.00   2.00      PROT
ATOM   4718  CB   ALA   311      -0.175   26.907   23.865  1.00   2.00      PROT
ATOM   4724  N    ASN   312       2.314   27.264   21.921  1.00   2.00      PROT
ATOM   4725  CA   ASN   312       3.052   27.050   20.663  1.00   2.00      PROT
ATOM   4726  C    ASN   312       4.351   26.265   20.861  1.00   2.00      PROT
ATOM   4727  O    ASN   312       4.607   25.260   20.191  1.00   2.00      PROT
```

Figure 3 cont.

| | | | | | | | | | |
|---|---|---|---|---|---|---|---|---|---|
| ATOM | 4728 | CB  | ASN | 312 | 5.385  | 28.366 | 19.947 | 1.00 | 2.00 | PROT |
| ATOM | 4729 | CG  | ASN | 312 | 2.162  | 29.133 | 19.482 | 1.00 | 2.00 | PROT |
| ATOM | 4730 | OD1 | ASN | 312 | 1.107  | 28.570 | 19.212 | 1.00 | 6.00 | PROT |
| ATOM | 4731 | ND2 | ASN | 312 | 2.309  | 30.438 | 19.378 | 1.00 | 2.13 | PROT |
| ATOM | 4738 | N   | ILE | 313 | 5.168  | 26.715 | 21.835 | 1.00 | 2.00 | PROT |
| ATOM | 4739 | CA  | ILE | 313 | 6.433  | 26.028 | 22.162 | 1.00 | 2.05 | PROT |
| ATOM | 4740 | C   | ILE | 313 | 6.194  | 24.579 | 22.595 | 1.00 | 2.22 | PROT |
| ATOM | 4741 | O   | ILE | 313 | 6.874  | 23.662 | 22.136 | 1.00 | 2.00 | PROT |
| ATOM | 4742 | CB  | ILE | 313 | 7.277  | 26.802 | 23.214 | 1.00 | 2.59 | PROT |
| ATOM | 4743 | CG1 | ILE | 313 | 7.717  | 28.170 | 22.671 | 1.00 | 3.03 | PROT |
| ATOM | 4744 | CG2 | ILE | 313 | 6.493  | 26.951 | 23.702 | 1.00 | 2.36 | PROT |
| ATOM | 4745 | CD  | ILE | 313 | 8.462  | 28.102 | 21.848 | 1.00 | 3.79 | PROT |
| ATOM | 4757 | N   | SER | 314 | 5.177  | 24.379 | 23.444 | 1.00 | 3.00 | PROT |
| ATOM | 4758 | CA  | SER | 314 | 4.796  | 23.037 | 23.892 | 1.00 | 3.34 | PROT |
| ATOM | 4759 | C   | SER | 314 | 4.359  | 22.133 | 22.730 | 1.00 | 2.30 | PROT |
| ATOM | 4760 | O   | SER | 314 | 4.749  | 20.976 | 22.670 | 1.00 | 2.00 | PROT |
| ATOM | 4761 | CB  | SER | 314 | 3.693  | 23.169 | 24.952 | 1.00 | 4.25 | PROT |
| ATOM | 4762 | OG  | SER | 314 | 2.461  | 23.528 | 24.397 | 1.00 | 8.68 | PROT |
| ATOM | 4767 | N   | GLY | 315 | 3.544  | 22.677 | 21.831 | 1.00 | 2.41 | PROT |
| ATOM | 4768 | CA  | GLY | 315 | 3.064  | 21.949 | 20.663 | 1.00 | 2.92 | PROT |
| ATOM | 4769 | C   | GLY | 315 | 4.249  | 21.493 | 19.850 | 1.00 | 3.15 | PROT |
| ATOM | 4770 | O   | GLY | 315 | 4.341  | 20.319 | 19.504 | 1.00 | 3.00 | PROT |
| ATOM | 4774 | N   | MET | 316 | 5.102  | 22.426 | 19.579 | 1.00 | 3.27 | PROT |
| ATOM | 4775 | CA  | MET | 316 | 6.360  | 22.178 | 18.762 | 1.00 | 4.09 | PROT |
| ATOM | 4776 | C   | MET | 316 | 7.281  | 21.094 | 19.317 | 1.00 | 4.30 | PROT |
| ATOM | 4777 | O   | MET | 316 | 7.769  | 20.248 | 18.564 | 1.00 | 4.51 | PROT |
| ATOM | 4778 | CB  | MET | 316 | 7.101  | 23.466 | 18.560 | 1.00 | 3.25 | PROT |
| ATOM | 4779 | CG  | MET | 316 | 6.468  | 24.519 | 17.703 | 1.00 | 4.72 | PROT |
| ATOM | 4780 | SD  | MET | 316 | 7.483  | 25.986 | 17.390 | 1.00 | 5.18 | PROT |
| ATOM | 4781 | CE  | MET | 316 | 8.508  | 25.414 | 16.043 | 1.00 | 5.78 | PROT |
| ATOM | 4791 | N   | LEU | 317 | 7.518  | 21.112 | 20.630 | 1.00 | 4.39 | PROT |
| ATOM | 4792 | CA  | LEU | 317 | 8.397  | 20.139 | 21.295 | 1.00 | 4.30 | PROT |
| ATOM | 4793 | C   | LEU | 317 | 7.601  | 18.983 | 21.862 | 1.00 | 4.26 | PROT |
| ATOM | 4794 | O   | LEU | 317 | 8.173  | 18.053 | 22.498 | 1.00 | 3.42 | PROT |
| ATOM | 4795 | CB  | LEU | 317 | 9.161  | 20.828 | 22.413 | 1.00 | 4.11 | PROT |
| ATOM | 4796 | CG  | LEU | 317 | 10.209 | 21.906 | 22.072 | 1.00 | 4.48 | PROT |
| ATOM | 4797 | CD1 | LEU | 317 | 10.573 | 22.683 | 23.320 | 1.00 | 3.44 | PROT |
| ATOM | 4798 | CD2 | LEU | 317 | 11.475 | 21.335 | 21.423 | 1.00 | 4.85 | PROT |
| ATOM | 4810 | N   | GLY | 318 | 6.286  | 18.974 | 21.640 | 1.00 | 4.25 | PROT |
| ATOM | 4811 | CA  | GLY | 318 | 5.385  | 17.911 | 22.083 | 1.00 | 5.16 | PROT |
| ATOM | 4812 | C   | GLY | 318 | 5.388  | 17.667 | 23.591 | 1.00 | 5.53 | PROT |
| ATOM | 4813 | O   | GLY | 318 | 5.188  | 16.569 | 24.056 | 1.00 | 5.23 | PROT |
| ATOM | 4817 | N   | MET | 319 | 5.636  | 18.760 | 24.340 | 1.00 | 5.23 | PROT |
| ATOM | 4818 | CA  | MET | 319 | 5.641  | 18.704 | 25.792 | 1.00 | 5.78 | PROT |
| ATOM | 4819 | C   | MET | 319 | 4.233  | 18.908 | 26.303 | 1.00 | 5.67 | PROT |
| ATOM | 4820 | O   | MET | 319 | 5.516  | 19.776 | 25.823 | 1.00 | 5.41 | PROT |
| ATOM | 4821 | CB  | MET | 319 | 6.554  | 19.775 | 26.382 | 1.00 | 5.89 | PROT |
| ATOM | 4822 | CG  | MET | 319 | 8.022  | 19.570 | 26.068 | 1.00 | 6.35 | PROT |
| ATOM | 4823 | SD  | MET | 319 | 9.054  | 20.829 | 26.820 | 1.00 | 6.72 | PROT |
| ATOM | 4824 | CE  | MET | 319 | 8.272  | 22.359 | 26.304 | 1.00 | 6.72 | PROT |
| ATOM | 4834 | N   | THR | 320 | 5.826  | 18.077 | 27.255 | 1.00 | 5.01 | PROT |
| ATOM | 4835 | CA  | THR | 320 | 3.518  | 18.238 | 27.884 | 1.00 | 5.22 | PROT |
| ATOM | 4836 | C   | THR | 320 | 2.705  | 18.174 | 29.332 | 1.00 | 6.53 | PROT |
| ATOM | 4837 | O   | THR | 320 | 3.753  | 17.739 | 29.070 | 1.00 | 4.49 | PROT |
| ATOM | 4838 | CB  | THR | 320 | 1.502  | 17.176 | 27.410 | 1.00 | 5.50 | PROT |
| ATOM | 4839 | OG1 | THR | 320 | 2.006  | 15.862 | 27.683 | 1.00 | 6.37 | PROT |
| ATOM | 4840 | CG2 | THR | 320 | 1.224  | 17.315 | 25.932 | 1.00 | 6.03 | PROT |
| ATOM | 4847 | N   | TRP | 321 | 1.695  | 18.613 | 30.129 | 1.00 | 3.83 | PROT |
| ATOM | 4848 | CA  | TRP | 321 | 1.779  | 18.677 | 31.569 | 1.00 | 4.01 | PROT |
| ATOM | 4849 | C   | TRP | 321 | 0.425  | 18.980 | 32.189 | 1.00 | 4.34 | PROT |
| ATOM | 4850 | O   | TRP | 321 | -0.502 | 19.424 | 31.513 | 1.00 | 3.81 | PROT |
| ATOM | 4851 | CB  | TRP | 321 | 2.812  | 19.733 | 32.039 | 1.00 | 3.03 | PROT |
| ATOM | 4852 | CG  | TRP | 321 | 2.493  | 21.161 | 31.601 | 1.00 | 3.26 | PROT |
| ATOM | 4853 | CD1 | TRP | 321 | 1.600  | 22.007 | 32.196 | 1.00 | 2.00 | PROT |
| ATOM | 4854 | CD2 | TRP | 321 | 3.097  | 21.906 | 30.528 | 1.00 | 2.02 | PROT |

Figure 3 cont.

```
ATOM    4855  NE1  TRP  321    1.592  23.217  31.855  1.00  2.00  PROT
ATOM    4856  CE2  TRP  321    2.484  23.181  30.515  1.00  2.00  PROT
ATOM    4857  CE3  TRP  321    4.058  21.605  29.546  1.00  2.00  PROT
ATOM    4858  CZ2  TRP  321    2.831  24.174  29.588  1.00  2.00  PROT
ATOM    4859  CZ3  TRP  321    4.396  22.587  28.620  1.00  2.00  PROT
ATOM    4860  CH2  TRP  321    3.788  23.861  28.651  1.00  2.89  PROT
ATOM    4871  N    THR  322    0.392  18.732  33.488  1.00  4.69  PROT
ATOM    4872  CA   THR  322   -0.745  19.169  34.340  1.00  5.33  PROT
ATOM    4873  C    THR  322   -0.082  19.763  35.567  1.00  5.32  PROT
ATOM    4874  O    THR  322    0.306  19.326  36.603  1.00  5.04  PROT
ATOM    4875  CB   THR  322   -1.726  18.000  34.706  1.00  6.24  PROT
ATOM    4876  OG1  THR  322   -2.847  18.815  35.440  1.00  7.87  PROT
ATOM    4877  CG2  THR  322   -1.053  16.913  35.526  1.00  7.29  PROT
ATOM    4884  N    LEU  323   -0.698  20.832  35.112  1.00  4.77  PROT
ATOM    4885  CA   LEU  323   -0.086  21.544  37.222  1.00  4.61  PROT
ATOM    4886  C    LEU  323   -0.847  21.309  38.504  1.00  4.74  PROT
ATOM    4887  O    LEU  323   -1.984  21.761  38.613  1.00  5.05  PROT
ATOM    4888  CB   LEU  323    0.026  23.040  36.919  1.00  3.76  PROT
ATOM    4889  CG   LEU  323    0.633  23.438  35.572  1.00  3.83  PROT
ATOM    4890  CD1  LEU  323    0.529  24.955  35.396  1.00  3.97  PROT
ATOM    4891  CD2  LEU  323    2.086  22.960  35.431  1.00  3.24  PROT
ATOM    4903  N    PRO  324   -0.257  20.559  39.461  1.00  5.15  PROT
ATOM    4904  CA   PRO  324   -0.859  20.425  40.767  1.00  5.43  PROT
ATOM    4905  C    PRO  324   -1.269  21.771  41.385  1.00  5.45  PROT
ATOM    4906  O    PRO  324   -0.434  22.709  41.466  1.00  5.97  PROT
ATOM    4907  CB   PRO  324    0.254  19.760  41.613  1.00  5.87  PROT
ATOM    4908  CG   PRO  324    0.080  18.308  40.620  1.00  5.37  PROT
ATOM    4909  CD   PRO  324    0.975  19.754  39.344  1.00  5.31  PROT
ATOM    4917  N    GLY  325   -2.546  21.892  41.738  1.00  4.92  PROT
ATOM    4918  CA   GLY  325   -3.059  23.084  42.389  1.00  5.21  PROT
ATOM    4919  C    GLY  325   -3.337  24.265  41.475  1.00  4.78  PROT
ATOM    4920  O    GLY  325   -3.784  25.304  41.953  1.00  5.23  PROT
ATOM    4924  N    GLN  326   -3.145  24.094  40.169  1.00  4.76  PROT
ATOM    4925  CA   GLN  326   -3.353  25.140  39.184  1.00  3.97  PROT
ATOM    4926  C    GLN  326   -4.088  24.571  37.960  1.00  4.48  PROT
ATOM    4927  O    GLN  326   -3.447  23.695  37.073  1.00  4.16  PROT
ATOM    4928  CB   GLN  326   -2.001  25.775  38.810  1.00  4.15  PROT
ATOM    4929  CG   GLN  326   -2.030  26.872  37.752  1.00  3.13  PROT
ATOM    4930  CD   GLN  326   -2.969  28.029  38.081  1.00  2.39  PROT
ATOM    4931  OE1  GLN  326   -2.605  26.969  39.300  1.00  3.42  PROT
ATOM    4932  NE2  GLN  326   -4.188  27.995  37.522  1.00  2.00  PROT
ATOM    4941  N    PRO  327   -5.433  24.731  37.901  1.00  4.21  PROT
ATOM    4942  CA   PRO  327   -6.269  24.234  36.839  1.00  4.49  PROT
ATOM    4943  C    PRO  327   -5.943  24.786  35.439  1.00  3.56  PROT
ATOM    4944  O    PRO  327   -6.208  24.104  34.472  1.00  3.33  PROT
ATOM    4945  CB   PRO  327   -7.683  24.643  37.267  1.00  4.40  PROT
ATOM    4946  CG   PRO  327   -7.520  25.726  38.215  1.00  5.15  PROT
ATOM    4947  CD   PRO  327   -6.247  25.423  38.943  1.00  5.18  PROT
ATOM    4955  N    ASP  328   -5.376  25.998  35.339  1.00  3.36  PROT
ATOM    4956  CA   ASP  328   -4.942  26.566  34.056  1.00  3.17  PROT
ATOM    4957  C    ASP  328   -3.544  26.032  33.763  1.00  3.26  PROT
ATOM    4958  O    ASP  328   -2.631  26.208  34.575  1.00  3.41  PROT
ATOM    4959  CB   ASP  328   -4.937  28.120  34.104  1.00  3.03  PROT
ATOM    4960  CG   ASP  328   -4.693  28.793  32.734  1.00  4.77  PROT
ATOM    4961  OD1  ASP  328   -4.506  28.081  31.704  1.00  4.73  PROT
ATOM    4962  OD2  ASP  328   -4.724  30.044  32.657  1.00  5.50  PROT
ATOM    4967  N    ASN  329   -3.398  25.351  32.625  1.00  3.26  PROT
ATOM    4968  CA   ASN  329   -2.104  24.839  32.168  1.00  4.54  PROT
ATOM    4969  C    ASN  329   -1.113  25.933  31.780  1.00  4.26  PROT
ATOM    4970  O    ASN  329    0.106  25.695  31.734  1.00  4.93  PROT
ATOM    4971  CB   ASN  329   -2.285  23.928  30.944  1.00  4.27  PROT
ATOM    4972  CG   ASN  329   -1.903  22.574  31.284  1.00  6.01  PROT
ATOM    4973  OD1  ASN  329   -3.054  32.213  32.447  1.00  6.63  PROT
ATOM    4974  ND2  ASN  329   -3.289  21.810  30.241  1.00  6.33  PROT
ATOM    4981  N    THR  330   -1.641  27.112  31.487  1.00  3.79  PROT
```

Figure 3 cont.

```
ATOM   4982  CA   THR   330     -0.808  28.282  31.137  1.00  3.65      PROT
ATOM   4983  C    THR   330     -1.210  29.481  31.927  1.00  2.93      PROT
ATOM   4984  O    THR   330     -1.678  30.503  31.471  1.00  2.00      PROT
ATOM   4985  CB   THR   330     -0.897  28.655  29.628  1.00  3.63      PROT
ATOM   4986  OG1  THR   330     -2.240  28.583  29.177  1.00  3.40      PROT
ATOM   4987  CG2  THR   330     -0.018  27.722  28.773  1.00  7.14      PROT
ATOM   4994  N    PRO   331     -1.004  29.382  33.329  1.00  2.60      PROT
ATOM   4995  CA   PRO   331     -1.359  30.397  34.203  1.00  3.12      PROT
ATOM   4996  C    PRO   331     -0.781  31.639  34.116  1.00  2.86      PROT
ATOM   4997  O    PRO   331      0.369  31.685  33.568  1.00  2.71      PROT
ATOM   4998  CB   PRO   331     -1.407  29.760  35.594  1.00  2.95      PROT
ATOM   4999  CG   PRO   331     -0.153  28.989  35.483  1.00  2.99      PROT
ATOM   5000  CD   PRO   331     -0.219  28.391  34.096  1.00  3.08      PROT
ATOM   5008  N    PRO   332     -1.319  30.817  34.622  1.00  5.75      PROT
ATOM   5009  CA   PRO   332     -0.616  34.107  34.737  1.00  3.67      PROT
ATOM   5010  C    PRO   332      0.665  33.936  35.550  1.00  3.37      PROT
ATOM   5011  O    PRO   332      0.655  33.484  36.693  1.00  3.55      PROT
ATOM   5012  CB   PRO   332     -1.606  35.003  35.477  1.00  6.18      PROT
ATOM   5013  CG   PRO   332     -2.632  34.074  36.042  1.00  5.00      PROT
ATOM   5014  CD   PRO   332     -2.837  32.969  35.132  1.00  3.74      PROT
ATOM   5022  N    GLY   333      1.755  34.476  34.956  1.00  2.28      PROT
ATOM   5023  CA   GLY   333      3.074  34.313  35.529  1.00  2.91      PROT
ATOM   5024  C    GLY   333      3.583  32.921  35.423  1.00  2.99      PROT
ATOM   5025  O    GLY   333      4.781  32.721  35.906  1.00  3.97      PROT
ATOM   5029  N    GLY   334      2.960  31.965  34.837  1.00  2.83      PROT
ATOM   5030  CA   GLY   334      3.486  30.616  34.583  1.00  2.33      PROT
ATOM   5031  C    GLY   334      4.519  30.738  33.484  1.00  2.69      PROT
ATOM   5032  O    GLY   334      4.343  31.540  32.588  1.00  2.36      PROT
ATOM   5036  N    ALA   335      5.613  29.991  33.594  1.00  2.62      PROT
ATOM   5037  CA   ALA   335      6.739  30.111  32.662  1.00  3.34      PROT
ATOM   5038  C    ALA   335      7.379  28.773  32.364  1.00  3.69      PROT
ATOM   5039  O    ALA   335      7.595  27.943  33.268  1.00  4.06      PROT
ATOM   5040  CB   ALA   335      7.793  31.093  33.210  1.00  3.15      PROT
ATOM   5046  N    LEU   336      7.734  28.592  31.095  1.00  4.32      PROT
ATOM   5047  CA   LEU   336      8.668  27.550  30.667  1.00  4.62      PROT
ATOM   5048  C    LEU   336     10.112  27.992  30.943  1.00  4.80      PROT
ATOM   5049  O    LEU   336     10.581  29.035  30.427  1.00  3.97      PROT
ATOM   5050  CB   LEU   336      8.487  27.274  29.174  1.00  4.66      PROT
ATOM   5051  CG   LEU   336      7.859  26.018  28.576  1.00  6.34      PROT
ATOM   5052  CD1  LEU   336      6.997  26.265  27.544  1.00  6.16      PROT
ATOM   5053  CD2  LEU   336      7.132  26.390  27.236  1.00  5.98      PROT
ATOM   5065  N    VAL   337     10.812  27.196  31.750  1.00  3.62      PROT
ATOM   5066  CA   VAL   337     12.170  27.524  32.177  1.00  3.27      PROT
ATOM   5067  C    VAL   337     13.123  26.521  31.550  1.00  3.62      PROT
ATOM   5068  O    VAL   337     13.119  25.339  31.910  1.00  3.55      PROT
ATOM   5069  CB   VAL   337     12.286  27.585  33.734  1.00  3.42      PROT
ATOM   5070  CG1  VAL   337     13.702  27.977  34.189  1.00  2.29      PROT
ATOM   5071  CG2  VAL   337     11.302  28.669  34.298  1.00  3.28      PROT
ATOM   5081  N    PHE   338     13.893  27.003  30.572  1.00  3.31      PROT
ATOM   5082  CA   PHE   338     14.894  26.213  29.896  1.00  4.21      PROT
ATOM   5083  C    PHE   338     16.239  26.483  30.544  1.00  4.44      PROT
ATOM   5084  O    PHE   338     16.561  27.633  30.691  1.00  4.06      PROT
ATOM   5085  CB   PHE   338     14.970  26.590  28.402  1.00  3.55      PROT
ATOM   5086  CG   PHE   338     13.682  26.364  27.641  1.00  4.01      PROT
ATOM   5087  CD1  PHE   338     13.530  25.256  26.819  1.00  5.16      PROT
ATOM   5088  CD2  PHE   338     12.633  27.281  27.736  1.00  4.22      PROT
ATOM   5089  CE1  PHE   338     12.334  25.043  26.098  1.00  6.41      PROT
ATOM   5090  CE2  PHE   338     11.441  27.086  27.024  1.00  3.64      PROT
ATOM   5091  CZ   PHE   338     11.294  25.968  26.208  1.00  4.82      PROT
ATOM   5101  N    GLU   339     16.907  25.421  30.944  1.00  4.45      PROT
ATOM   5102  CA   GLU   339     18.198  25.554  31.610  1.00  5.03      PROT
ATOM   5103  C    GLU   339     19.276  24.840  30.808  1.00  4.78      PROT
ATOM   5104  O    GLU   339     19.076  23.695  30.411  1.00  4.66      PROT
ATOM   5105  CB   GLU   339     18.119  24.961  33.004  1.00  5.11      PROT
ATOM   5106  CG   GLU   339     17.179  25.691  33.935  1.00  7.80      PROT
```

Figure 3 cont.

```
ATOM   5107  CD   GLU   339      16.869  24.916  35.197  1.00  12.08           PROT
ATOM   5108  OE1  GLU   339      17.192  23.712  35.272  1.00  14.47           PROT
ATOM   5109  OE2  GLU   339      16.300  25.518  36.125  1.00  13.95           PROT
ATOM   5116  N    ARG   340      20.400  25.522  30.978  1.00   4.68           PROT
ATOM   5117  CA   ARG   340      21.614  24.910  30.021  1.00   5.03           PROT
ATOM   5118  C    ARG   340      22.499  24.410  31.164  1.00   4.37           PROT
ATOM   5119  O    ARG   340      22.938  25.193  32.022  1.00   3.21           PROT
ATOM   5120  CB   ARG   340      21.388  25.893  29.153  1.00   4.36           PROT
ATOM   5121  CG   ARG   340      23.591  25.300  28.391  1.00   7.01           PROT
ATOM   5122  CD   ARG   340      24.611  26.363  27.982  1.00   7.23           PROT
ATOM   5123  NE   ARG   340      25.615  25.927  26.893  1.00  12.53           PROT
ATOM   5124  CZ   ARG   340      26.723  25.399  27.081  1.00  14.36           PROT
ATOM   5125  NH1  ARG   340      27.204  25.238  28.300  1.00  17.14           PROT
ATOM   5126  NH2  ARG   340      27.465  25.026  26.048  1.00  15.00           PROT
ATOM   5140  N    TRP   341      22.737  23.096  31.174  1.00   3.97           PROT
ATOM   5141  CA   TRP   341      23.539  22.439  32.202  1.00   4.03           PROT
ATOM   5142  C    TRP   341      24.771  21.841  31.559  1.00   4.50           PROT
ATOM   5143  O    TRP   341      24.704  21.367  30.423  1.00   4.22           PROT
ATOM   5144  CB   TRP   341      22.742  21.315  32.880  1.00   4.51           PROT
ATOM   5145  CG   TRP   341      21.699  21.773  33.856  1.00   3.65           PROT
ATOM   5146  CD1  TRP   341      20.376  22.013  33.533  1.00   4.03           PROT
ATOM   5147  CD2  TRP   341      21.885  22.034  35.252  1.00   4.22           PROT
ATOM   5148  NE1  TRP   341      19.738  22.408  34.789  1.00   3.92           PROT
ATOM   5149  CE2  TRP   341      20.637  22.430  35.771  1.00   3.81           PROT
ATOM   5150  CE3  TRP   341      22.983  21.969  36.121  1.00   3.82           PROT
ATOM   5151  CZ2  TRP   341      20.457  22.769  37.119  1.00   4.76           PROT
ATOM   5152  CZ3  TRP   341      22.810  22.295  37.453  1.00   4.30           PROT
ATOM   5153  CH2  TRP   341      21.554  22.696  37.940  1.00   4.15           PROT
ATOM   5164  N    VAL   342      25.898  21.875  32.271  1.00   4.71           PROT
ATOM   5165  CA   VAL   342      27.070  21.083  31.867  1.00   5.12           PROT
ATOM   5166  C    VAL   342      27.494  20.129  32.956  1.00   4.93           PROT
ATOM   5167  O    VAL   342      27.492  20.469  34.177  1.00   5.09           PROT
ATOM   5168  CB   VAL   342      28.282  21.943  31.422  1.00   5.51           PROT
ATOM   5169  CG1  VAL   342      28.807  22.845  32.553  1.00   6.56           PROT
ATOM   5170  CG2  VAL   342      27.933  22.760  30.202  1.00   6.74           PROT
ATOM   5180  N    ASP   343      27.870  18.912  32.612  1.00   4.45           PROT
ATOM   5181  CA   ASP   343      28.392  17.949  33.572  1.00   4.24           PROT
ATOM   5182  C    ASP   343      29.908  18.082  33.748  1.00   4.62           PROT
ATOM   5183  O    ASP   343      30.526  18.397  33.192  1.00   4.72           PROT
ATOM   5184  CB   ASP   343      28.005  16.516  33.174  1.00   3.93           PROT
ATOM   5185  CG   ASP   343      28.663  16.036  31.899  1.00   2.84           PROT
ATOM   5186  OD1  ASP   343      29.624  16.682  31.383  1.00   2.00           PROT
ATOM   5187  OD2  ASP   343      28.265  14.974  31.385  1.00   3.69           PROT
ATOM   5192  N    ASN   344      30.458  17.157  34.540  1.00   4.90           PROT
ATOM   5193  CA   ASN   344      31.889  16.376  34.747  1.00   5.40           PROT
ATOM   5194  C    ASN   344      32.784  17.568  33.513  1.00   5.27           PROT
ATOM   5195  O    ASN   344      33.895  17.606  33.617  1.00   5.66           PROT
ATOM   5196  CB   ASN   344      32.001  15.396  35.166  1.00   5.75           PROT
ATOM   5197  CG   ASN   344      32.744  15.197  36.464  1.00   7.06           PROT
ATOM   5198  OD1  ASN   344      33.976  15.180  36.498  1.00  11.04           PROT
ATOM   5199  ND2  ASN   344      31.908  14.097  37.541  1.00   6.19           PROT
ATOM   5206  N    ALA   345      32.308  16.592  32.372  1.00   4.45           PROT
ATOM   5207  CA   ALA   345      33.108  16.536  31.151  1.00   4.03           PROT
ATOM   5208  C    ALA   345      32.771  17.660  30.178  1.00   3.98           PROT
ATOM   5209  O    ALA   345      33.197  17.636  29.018  1.00   4.09           PROT
ATOM   5210  CB   ALA   345      32.924  15.186  30.479  1.00   4.00           PROT
ATOM   5216  N    GLY   346      31.995  18.635  30.644  1.00   3.89           PROT
ATOM   5217  CA   GLY   346      31.602  19.773  29.821  1.00   3.87           PROT
ATOM   5218  C    GLY   346      30.577  19.464  28.766  1.00   4.15           PROT
ATOM   5219  O    GLY   346      30.397  20.244  27.822  1.00   4.55           PROT
ATOM   5223  N    LYS   347      29.882  18.336  28.912  1.00   3.35           PROT
ATOM   5224  CA   LYS   347      28.781  18.033  28.006  1.00   3.39           PROT
ATOM   5225  C    LYS   347      27.571  18.878  28.390  1.00   2.53           PROT
ATOM   5226  O    LYS   347      27.125  18.620  29.536  1.00   2.10           PROT
ATOM   5227  CB   LYS   347      28.430  16.541  28.007  1.00   3.15           PROT
```

Figure 3 cont.

| | | | | | | | | |
|---|---|---|---|---|---|---|---|---|
| ATOM | 5228 | CG | LYS | 347 | 27.390 | 16.179 | 26.962 | 1.00 | 3.71 | PROT |
| ATOM | 5229 | CD | LYS | 347 | 27.065 | 14.686 | 26.935 | 1.00 | 4.66 | PROT |
| ATOM | 5230 | CE | LYS | 347 | 25.818 | 14.395 | 26.080 | 1.00 | 7.37 | PROT |
| ATOM | 5231 | NZ | LYS | 347 | 26.052 | 14.673 | 24.628 | 1.00 | 7.31 | PROT |
| ATOM | 5245 | N | PRO | 348 | 27.054 | 19.684 | 27.439 | 1.00 | 2.45 | PROT |
| ATOM | 5246 | CA | PRO | 348 | 25.890 | 20.527 | 27.717 | 1.00 | 2.33 | PROT |
| ATOM | 5247 | C | PRO | 348 | 24.598 | 19.793 | 27.532 | 1.00 | 2.32 | PROT |
| ATOM | 5248 | O | PRO | 348 | 24.384 | 19.019 | 26.577 | 1.00 | 2.07 | PROT |
| ATOM | 5249 | CB | PRO | 348 | 26.029 | 21.666 | 26.705 | 1.00 | 2.65 | PROT |
| ATOM | 5250 | CG | PRO | 348 | 26.777 | 21.056 | 25.545 | 1.00 | 2.31 | PROT |
| ATOM | 5251 | CD | PRO | 348 | 27.040 | 19.652 | 26.056 | 1.00 | 2.61 | PROT |
| ATOM | 5259 | N | TYR | 349 | 23.646 | 20.040 | 28.465 | 1.00 | 2.47 | PROT |
| ATOM | 5260 | CA | TYR | 349 | 22.294 | 19.502 | 28.436 | 1.00 | 2.44 | PROT |
| ATOM | 5261 | C | TYR | 349 | 21.293 | 20.640 | 28.847 | 1.00 | 2.33 | PROT |
| ATOM | 5262 | O | TYR | 349 | 21.630 | 21.753 | 28.990 | 1.00 | 2.00 | PROT |
| ATOM | 5263 | CB | TYR | 349 | 22.063 | 18.346 | 29.604 | 1.00 | 3.09 | PROT |
| ATOM | 5264 | CG | TYR | 349 | 23.063 | 17.426 | 29.735 | 1.00 | 4.05 | PROT |
| ATOM | 5265 | CD1 | TYR | 349 | 22.768 | 16.156 | 29.257 | 1.00 | 4.11 | PROT |
| ATOM | 5266 | CD2 | TYR | 349 | 24.293 | 17.629 | 30.357 | 1.00 | 4.39 | PROT |
| ATOM | 5267 | CE1 | TYR | 349 | 23.678 | 15.118 | 29.376 | 1.00 | 5.80 | PROT |
| ATOM | 5268 | CE2 | TYR | 349 | 25.212 | 16.596 | 30.482 | 1.00 | 4.72 | PROT |
| ATOM | 5269 | CZ | TYR | 349 | 24.895 | 15.342 | 29.988 | 1.00 | 5.06 | PROT |
| ATOM | 5270 | OH | TYR | 349 | 25.785 | 14.304 | 30.108 | 1.00 | 4.73 | PROT |
| ATOM | 5279 | N | VAL | 350 | 20.063 | 20.336 | 29.131 | 1.00 | 2.23 | PROT |
| ATOM | 5280 | CA | VAL | 350 | 18.900 | 21.165 | 29.329 | 1.00 | 2.90 | PROT |
| ATOM | 5281 | C | VAL | 350 | 17.926 | 20.446 | 29.261 | 1.00 | 3.29 | PROT |
| ATOM | 5282 | O | VAL | 350 | 17.685 | 19.239 | 29.149 | 1.00 | 3.46 | PROT |
| ATOM | 5283 | CB | VAL | 350 | 18.191 | 21.529 | 26.994 | 1.00 | 3.06 | PROT |
| ATOM | 5284 | CG1 | VAL | 350 | 16.988 | 22.418 | 27.254 | 1.00 | 2.59 | PROT |
| ATOM | 5285 | CG2 | VAL | 350 | 19.157 | 22.243 | 26.037 | 1.00 | 3.39 | PROT |
| ATOM | 5295 | N | SER | 351 | 17.392 | 21.208 | 30.195 | 1.00 | 3.62 | PROT |
| ATOM | 5296 | CA | SER | 351 | 16.367 | 20.751 | 31.102 | 1.00 | 4.47 | PROT |
| ATOM | 5297 | C | SER | 351 | 15.225 | 21.750 | 30.974 | 1.00 | 4.38 | PROT |
| ATOM | 5298 | O | SER | 351 | 15.465 | 22.947 | 30.789 | 1.00 | 4.62 | PROT |
| ATOM | 5299 | CB | SER | 351 | 16.914 | 20.760 | 32.528 | 1.00 | 4.82 | PROT |
| ATOM | 5300 | OG | SER | 351 | 16.158 | 19.869 | 33.342 | 1.00 | 7.33 | PROT |
| ATOM | 5305 | N | VAL | 352 | 13.989 | 21.272 | 31.065 | 1.00 | 4.04 | PROT |
| ATOM | 5306 | CA | VAL | 352 | 12.833 | 22.160 | 30.959 | 1.00 | 3.57 | PROT |
| ATOM | 5307 | C | VAL | 352 | 11.847 | 21.916 | 32.097 | 1.00 | 3.71 | PROT |
| ATOM | 5308 | O | VAL | 352 | 11.481 | 20.780 | 32.373 | 1.00 | 3.29 | PROT |
| ATOM | 5309 | CB | VAL | 352 | 12.084 | 22.039 | 29.604 | 1.00 | 3.51 | PROT |
| ATOM | 5310 | CG1 | VAL | 352 | 11.158 | 23.215 | 29.448 | 1.00 | 2.69 | PROT |
| ATOM | 5311 | CG2 | VAL | 352 | 13.056 | 21.942 | 28.460 | 1.00 | 2.63 | PROT |
| ATOM | 5321 | N | ASN | 353 | 11.471 | 23.006 | 32.751 | 1.00 | 3.66 | PROT |
| ATOM | 5322 | CA | ASN | 353 | 10.466 | 22.973 | 33.788 | 1.00 | 4.40 | PROT |
| ATOM | 5323 | C | ASN | 353 | 9.306 | 23.943 | 33.530 | 1.00 | 4.77 | PROT |
| ATOM | 5324 | O | ASN | 353 | 9.545 | 25.045 | 32.997 | 1.00 | 4.34 | PROT |
| ATOM | 5325 | CB | ASN | 353 | 11.095 | 23.315 | 35.131 | 1.00 | 4.68 | PROT |
| ATOM | 5326 | CG | ASN | 353 | 12.036 | 22.242 | 35.613 | 1.00 | 6.13 | PROT |
| ATOM | 5327 | OD1 | ASN | 353 | 13.196 | 22.183 | 35.199 | 1.00 | 9.71 | PROT |
| ATOM | 5328 | ND2 | ASN | 353 | 11.554 | 21.404 | 36.523 | 1.00 | 6.41 | PROT |
| ATOM | 5335 | N | MET | 354 | 8.121 | 23.551 | 33.941 | 1.00 | 4.16 | PROT |
| ATOM | 5336 | CA | MET | 354 | 7.034 | 24.521 | 34.035 | 1.00 | 4.54 | PROT |
| ATOM | 5337 | C | MET | 354 | 6.885 | 25.013 | 35.470 | 1.00 | 4.11 | PROT |
| ATOM | 5338 | O | MET | 354 | 6.540 | 24.262 | 36.374 | 1.00 | 3.99 | PROT |
| ATOM | 5339 | CB | MET | 354 | 5.717 | 23.973 | 33.484 | 1.00 | 4.79 | PROT |
| ATOM | 5340 | CG | MET | 354 | 4.601 | 25.003 | 33.467 | 1.00 | 6.37 | PROT |
| ATOM | 5341 | SD | MET | 354 | 4.709 | 26.307 | 32.235 | 1.00 | 9.36 | PROT |
| ATOM | 5342 | CE | MET | 354 | 3.182 | 27.060 | 32.366 | 1.00 | 7.20 | PROT |
| ATOM | 5352 | N | VAL | 355 | 7.160 | 26.296 | 35.657 | 1.00 | 4.58 | PROT |
| ATOM | 5353 | CA | VAL | 355 | 7.235 | 26.917 | 36.977 | 1.00 | 4.86 | PROT |
| ATOM | 5354 | C | VAL | 355 | 6.042 | 27.849 | 37.104 | 1.00 | 4.65 | PROT |
| ATOM | 5355 | O | VAL | 355 | 5.778 | 28.631 | 36.196 | 1.00 | 5.49 | PROT |
| ATOM | 5356 | CB | VAL | 355 | 8.566 | 27.699 | 37.132 | 1.00 | 5.10 | PROT |
| ATOM | 5357 | CG1 | VAL | 355 | 8.686 | 28.303 | 38.516 | 1.00 | 5.69 | PROT |

Figure 3 cont.

| | | | | | | | | | |
|---|---|---|---|---|---|---|---|---|---|
| ATOM | 5358 | CG2 | VAL | 355 | 9.766 | 26.762 | 36.859 | 1.00 | 6.13 | PROT |
| ATOM | 5368 | N | TYR | 356 | 5.326 | 27.780 | 38.224 | 1.00 | 4.58 | PROT |
| ATOM | 5369 | CA | TYR | 356 | 4.031 | 28.448 | 38.314 | 1.00 | 3.94 | PROT |
| ATOM | 5370 | C | TYR | 356 | 3.638 | 28.697 | 39.759 | 1.00 | 3.64 | PROT |
| ATOM | 5371 | O | TYR | 356 | 4.162 | 28.053 | 40.678 | 1.00 | 4.24 | PROT |
| ATOM | 5372 | CB | TYR | 356 | 2.952 | 27.586 | 37.619 | 1.00 | 3.46 | PROT |
| ATOM | 5373 | CG | TYR | 356 | 2.690 | 26.099 | 38.360 | 1.00 | 2.83 | PROT |
| ATOM | 5374 | CD1 | TYR | 356 | 3.535 | 25.204 | 38.204 | 1.00 | 3.31 | PROT |
| ATOM | 5375 | CD2 | TYR | 356 | 1.613 | 26.167 | 39.239 | 1.00 | 3.22 | PROT |
| ATOM | 5376 | CE1 | TYR | 356 | 3.314 | 24.037 | 38.699 | 1.00 | 3.12 | PROT |
| ATOM | 5377 | CE2 | TYR | 356 | 1.384 | 25.029 | 39.940 | 1.00 | 2.03 | PROT |
| ATOM | 5378 | CZ | TYR | 356 | 2.243 | 23.957 | 39.766 | 1.00 | 4.66 | PROT |
| ATOM | 5379 | OH | TYR | 356 | 2.036 | 22.797 | 40.458 | 1.00 | 3.09 | PROT |
| ATOM | 5388 | N | GLN | 357 | 2.731 | 29.643 | 39.984 | 1.00 | 2.58 | PROT |
| ATOM | 5389 | CA | GLN | 357 | 2.007 | 29.792 | 41.222 | 1.00 | 2.87 | PROT |
| ATOM | 5390 | C | GLN | 357 | 0.717 | 28.962 | 41.186 | 1.00 | 2.10 | PROT |
| ATOM | 5391 | O | GLN | 357 | -0.037 | 29.034 | 40.221 | 1.00 | 2.00 | PROT |
| ATOM | 5392 | CB | GLN | 357 | 1.687 | 31.267 | 41.486 | 1.00 | 2.00 | PROT |
| ATOM | 5393 | CG | GLN | 357 | 2.910 | 32.094 | 41.953 | 1.00 | 3.39 | PROT |
| ATOM | 5394 | CD | GLN | 357 | 2.903 | 33.836 | 41.467 | 1.00 | 2.38 | PROT |
| ATOM | 5395 | OE1 | GLN | 357 | 3.076 | 34.478 | 42.261 | 1.00 | 4.96 | PROT |
| ATOM | 5396 | NE2 | GLN | 357 | 2.702 | 33.724 | 40.172 | 1.00 | 2.00 | PROT |
| ATOM | 5405 | N | THR | 358 | 0.478 | 28.168 | 42.234 | 1.00 | 2.00 | PROT |
| ATOM | 5406 | CA | THR | 358 | -0.805 | 27.477 | 42.393 | 1.00 | 2.02 | PROT |
| ATOM | 5407 | C | THR | 358 | -1.901 | 28.516 | 42.437 | 1.00 | 2.14 | PROT |
| ATOM | 5408 | O | THR | 358 | -1.620 | 29.707 | 42.630 | 1.00 | 2.00 | PROT |
| ATOM | 5409 | CB | THR | 358 | -0.690 | 26.640 | 43.687 | 1.00 | 2.00 | PROT |
| ATOM | 5410 | OG1 | THR | 358 | -0.745 | 27.498 | 44.827 | 1.00 | 2.00 | PROT |
| ATOM | 5411 | CG2 | THR | 358 | 0.203 | 25.585 | 43.701 | 1.00 | 2.00 | PROT |
| ATOM | 5418 | N | LEU | 359 | -3.144 | 28.092 | 42.240 | 1.00 | 2.55 | PROT |
| ATOM | 5419 | CA | LEU | 359 | -4.249 | 29.050 | 42.275 | 1.00 | 3.53 | PROT |
| ATOM | 5420 | C | LEU | 359 | -4.381 | 29.698 | 43.665 | 1.00 | 3.50 | PROT |
| ATOM | 5421 | O | LEU | 359 | -4.690 | 30.903 | 43.775 | 1.00 | 3.18 | PROT |
| ATOM | 5422 | CB | LEU | 359 | -5.558 | 28.415 | 41.773 | 1.00 | 3.89 | PROT |
| ATOM | 5423 | CG | LEU | 359 | -6.908 | 29.096 | 41.563 | 1.00 | 3.74 | PROT |
| ATOM | 5424 | CD1 | LEU | 359 | -6.568 | 30.456 | 40.609 | 1.00 | 3.16 | PROT |
| ATOM | 5425 | CD2 | LEU | 359 | -7.991 | 28.401 | 41.128 | 1.00 | 4.92 | PROT |
| ATOM | 5437 | N | ALA | 360 | -4.129 | 28.915 | 44.717 | 1.00 | 2.90 | PROT |
| ATOM | 5438 | CA | ALA | 360 | -4.097 | 29.457 | 46.076 | 1.00 | 3.11 | PROT |
| ATOM | 5439 | C | ALA | 360 | -2.933 | 30.430 | 46.309 | 1.00 | 2.80 | PROT |
| ATOM | 5440 | O | ALA | 360 | -3.097 | 31.424 | 46.996 | 1.00 | 3.30 | PROT |
| ATOM | 5441 | CB | ALA | 360 | -4.108 | 28.338 | 47.139 | 1.00 | 3.28 | PROT |
| ATOM | 5447 | N | GLN | 361 | -1.770 | 30.172 | 45.703 | 1.00 | 3.29 | PROT |
| ATOM | 5448 | CA | GLN | 361 | -0.633 | 31.106 | 45.810 | 1.00 | 3.37 | PROT |
| ATOM | 5449 | C | GLN | 361 | -0.933 | 32.486 | 45.191 | 1.00 | 3.34 | PROT |
| ATOM | 5450 | O | GLN | 361 | -0.459 | 33.509 | 45.677 | 1.00 | 3.39 | PROT |
| ATOM | 5451 | CB | GLN | 361 | 0.638 | 30.500 | 45.224 | 1.00 | 3.24 | PROT |
| ATOM | 5452 | CG | GLN | 361 | 1.375 | 29.569 | 46.208 | 1.00 | 3.85 | PROT |
| ATOM | 5453 | CD | GLN | 361 | 2.460 | 28.749 | 45.555 | 1.00 | 3.80 | PROT |
| ATOM | 5454 | OE1 | GLN | 361 | 2.383 | 28.433 | 44.365 | 1.00 | 2.00 | PROT |
| ATOM | 5455 | NE2 | GLN | 361 | 3.486 | 28.402 | 46.352 | 1.00 | 4.40 | PROT |
| ATOM | 5464 | N | LEU | 362 | -1.729 | 32.495 | 44.127 | 1.00 | 3.01 | PROT |
| ATOM | 5465 | CA | LEU | 362 | -2.152 | 33.731 | 43.473 | 1.00 | 3.73 | PROT |
| ATOM | 5466 | C | LEU | 362 | -3.194 | 34.452 | 44.298 | 1.00 | 3.56 | PROT |
| ATOM | 5467 | O | LEU | 362 | -3.110 | 35.661 | 44.484 | 1.00 | 3.77 | PROT |
| ATOM | 5468 | CB | LEU | 362 | -2.733 | 33.437 | 42.095 | 1.00 | 3.02 | PROT |
| ATOM | 5469 | CG | LEU | 362 | -1.761 | 32.331 | 41.543 | 1.00 | 4.31 | PROT |
| ATOM | 5470 | CD1 | LEU | 362 | -2.539 | 31.456 | 39.851 | 1.00 | 3.00 | PROT |
| ATOM | 5471 | CD2 | LEU | 362 | -0.758 | 34.040 | 40.678 | 1.00 | 3.22 | PROT |
| ATOM | 5483 | N | HSD | 363 | -4.177 | 33.703 | 44.795 | 1.00 | 3.82 | PROT |
| ATOM | 5484 | CA | HSD | 363 | -5.260 | 34.263 | 45.584 | 1.00 | 4.30 | PROT |
| ATOM | 5485 | C | HSD | 363 | -6.730 | 34.839 | 46.899 | 1.00 | 4.44 | PROT |
| ATOM | 5486 | O | HSD | 363 | -5.135 | 35.915 | 47.338 | 1.00 | 4.87 | PROT |
| ATOM | 5487 | CB | HSD | 363 | -6.363 | 33.254 | 45.837 | 1.00 | 4.13 | PROT |
| ATOM | 5488 | CG | HSD | 363 | -7.606 | 33.843 | 46.387 | 1.00 | 3.66 | PROT |

Figure 3 cont.

| | | | | | | | | | |
|---|---|---|---|---|---|---|---|---|---|
| ATOM | 5489 | ND1 | HSD | 363 | -8.036 | 33.643 | 47.690 | 1.00 7.86 | PROT |
| ATOM | 5490 | CE2 | HSD | 363 | -8.564 | 34.634 | 45.814 | 1.00 6.16 | PROT |
| ATOM | 5491 | CE1 | HSD | 363 | -9.178 | 34.275 | 47.890 | 1.00 7.35 | PROT |
| ATOM | 5492 | NE2 | HSD | 363 | -9.520 | 34.881 | 46.766 | 1.00 7.63 | PROT |
| ATOM | 5500 | N | ASP | 364 | -3.793 | 34.109 | 47.505 | 1.00 4.67 | PROT |
| ATOM | 5501 | CA | ASP | 364 | -3.238 | 34.475 | 48.783 | 1.00 4.76 | PROT |
| ATOM | 5502 | C | ASP | 364 | -2.037 | 33.420 | 48.662 | 1.00 4.40 | PROT |
| ATOM | 5503 | O | ASP | 364 | -1.551 | 33.928 | 43.667 | 1.00 4.17 | PROT |
| ATOM | 5504 | CB | ASP | 364 | -2.856 | 33.208 | 49.580 | 1.00 5.41 | PROT |
| ATOM | 5505 | CG | ASP | 364 | -4.054 | 32.287 | 49.637 | 1.00 7.09 | PROT |
| ATOM | 5506 | OD1 | ASP | 364 | -5.207 | 32.692 | 49.573 | 1.00 8.62 | PROT |
| ATOM | 5507 | OD2 | ASP | 364 | -3.840 | 31.140 | 50.281 | 1.00 9.49 | PROT |
| ATOM | 5512 | H | GLN | 365 | -1.587 | 33.664 | 47.436 | 1.00 4.26 | PROT |
| ATOM | 5513 | CA | GLN | 365 | -0.345 | 36.403 | 47.163 | 1.00 3.68 | PROT |
| ATOM | 5514 | C | GLN | 365 | 0.869 | 35.861 | 48.021 | 1.00 2.79 | PROT |
| ATOM | 5515 | O | GLN | 365 | 1.556 | 36.622 | 48.620 | 1.00 2.38 | PROT |
| ATOM | 5516 | CB | GLN | 365 | -0.536 | 37.917 | 47.360 | 1.00 3.68 | PROT |
| ATOM | 5517 | CG | GLN | 365 | -1.497 | 38.582 | 46.378 | 1.00 5.70 | PROT |
| ATOM | 5518 | CD | GLN | 365 | -1.630 | 40.074 | 46.651 | 1.00 6.77 | PROT |
| ATOM | 5519 | OE1 | GLN | 365 | -2.239 | 40.491 | 47.649 | 1.00 10.89 | PROT |
| ATOM | 5520 | NE2 | GLN | 365 | -1.040 | 40.880 | 45.789 | 1.00 9.97 | PROT |
| ATOM | 5529 | N | ALA | 366 | 0.936 | 34.535 | 48.058 | 1.00 2.21 | PROT |
| ATOM | 5530 | CA | ALA | 366 | 1.917 | 33.853 | 48.910 | 1.00 2.51 | PROT |
| ATOM | 5531 | C | ALA | 366 | 3.365 | 34.193 | 48.557 | 1.00 2.38 | PROT |
| ATOM | 5532 | O | ALA | 366 | 3.704 | 34.194 | 47.372 | 1.00 2.00 | PROT |
| ATOM | 5533 | CB | ALA | 366 | 1.712 | 32.347 | 48.643 | 1.00 2.00 | PROT |
| ATOM | 5539 | N | PRO | 367 | 4.190 | 34.527 | 49.577 | 1.00 2.69 | PROT |
| ATOM | 5540 | CA | PRO | 367 | 5.641 | 34.702 | 49.376 | 1.00 3.01 | PROT |
| ATOM | 5541 | C | PRO | 367 | 6.263 | 33.411 | 48.830 | 1.00 3.62 | PROT |
| ATOM | 5542 | O | PRO | 367 | 5.872 | 32.308 | 49.231 | 1.00 4.03 | PROT |
| ATOM | 5543 | CB | PRO | 367 | 6.153 | 35.017 | 50.791 | 1.00 3.66 | PROT |
| ATOM | 5544 | CG | PRO | 367 | 4.879 | 35.617 | 51.474 | 1.00 3.72 | PROT |
| ATOM | 5545 | CD | PRO | 367 | 3.816 | 34.796 | 50.980 | 1.00 2.86 | PROT |
| ATOM | 5553 | H | LEU | 368 | 7.176 | 33.550 | 47.875 | 1.00 3.23 | PROT |
| ATOM | 5554 | CA | LEU | 368 | 7.784 | 32.406 | 47.219 | 1.00 3.42 | PROT |
| ATOM | 5555 | C | LEU | 368 | 9.275 | 32.358 | 47.529 | 1.00 3.81 | PROT |
| ATOM | 5556 | O | LEU | 368 | 10.034 | 33.263 | 47.149 | 1.00 4.15 | PROT |
| ATOM | 5557 | CB | LEU | 368 | 7.535 | 32.450 | 45.706 | 1.00 2.79 | PROT |
| ATOM | 5558 | CG | LEU | 368 | 6.082 | 32.498 | 45.215 | 1.00 2.23 | PROT |
| ATOM | 5559 | CD1 | LEU | 368 | 6.036 | 31.595 | 43.692 | 1.00 2.00 | PROT |
| ATOM | 5560 | CD2 | LEU | 368 | 5.253 | 31.289 | 45.674 | 1.00 2.00 | PROT |
| ATOM | 5572 | N | THR | 369 | 9.677 | 31.300 | 48.229 | 1.00 3.36 | PROT |
| ATOM | 5573 | CA | THR | 369 | 11.042 | 31.162 | 48.740 | 1.00 3.13 | PROT |
| ATOM | 5574 | C | THR | 369 | 11.492 | 29.717 | 48.552 | 1.00 2.98 | PROT |
| ATOM | 5575 | O | THR | 369 | 10.683 | 28.881 | 48.258 | 1.00 3.03 | PROT |
| ATOM | 5576 | CB | THR | 369 | 11.084 | 31.448 | 50.247 | 1.00 2.50 | PROT |
| ATOM | 5577 | OG1 | THR | 369 | 10.268 | 30.486 | 50.919 | 1.00 3.94 | PROT |
| ATOM | 5578 | CG2 | THR | 369 | 10.583 | 32.865 | 50.577 | 1.00 2.02 | PROT |
| ATOM | 5585 | N | LEU | 370 | 12.778 | 29.419 | 48.753 | 1.00 3.81 | PROT |
| ATOM | 5586 | CA | LEU | 370 | 13.270 | 28.034 | 48.642 | 1.00 4.43 | PROT |
| ATOM | 5587 | C | LEU | 370 | 12.571 | 27.065 | 49.603 | 1.00 4.26 | PROT |
| ATOM | 5588 | O | LEU | 370 | 12.362 | 25.891 | 49.282 | 1.00 4.08 | PROT |
| ATOM | 5589 | CB | LEU | 370 | 14.786 | 27.993 | 48.855 | 1.00 5.24 | PROT |
| ATOM | 5590 | CG | LEU | 370 | 15.699 | 27.988 | 47.614 | 1.00 6.30 | PROT |
| ATOM | 5591 | CD1 | LEU | 370 | 17.010 | 28.858 | 47.960 | 1.00 8.65 | PROT |
| ATOM | 5592 | CD2 | LEU | 370 | 15.075 | 26.601 | 46.351 | 1.00 9.02 | PROT |
| ATOM | 5604 | N | GLN | 371 | 12.263 | 27.571 | 50.775 | 1.00 4.01 | PROT |
| ATOM | 5605 | CA | GLN | 371 | 11.483 | 26.774 | 51.753 | 1.00 4.81 | PROT |
| ATOM | 5606 | C | GLN | 371 | 9.999 | 26.714 | 51.444 | 1.00 4.40 | PROT |
| ATOM | 5607 | O | GLN | 371 | 9.319 | 25.751 | 51.820 | 1.00 4.04 | PROT |
| ATOM | 5608 | CB | GLN | 371 | 11.724 | 27.304 | 53.172 | 1.00 5.33 | PROT |
| ATOM | 5609 | CG | GLN | 371 | 13.171 | 27.165 | 53.648 | 1.00 8.93 | PROT |
| ATOM | 5610 | CD | GLN | 371 | 13.546 | 25.747 | 54.110 | 1.00 13.11 | PROT |
| ATOM | 5611 | OE1 | GLN | 371 | 13.183 | 24.746 | 53.480 | 1.00 16.05 | PROT |
| ATOM | 5612 | NE2 | GLN | 371 | 14.293 | 25.067 | 55.208 | 1.00 14.36 | PROT |

Figure 3 cont.

| | | | | | | | | | |
|---|---|---|---|---|---|---|---|---|---|
| ATOM | 5621 | H | HSD | 372 | 9.498 | 27.737 | 50.753 | 1.00 | 3.76 | PROT |
| ATOM | 5622 | CA | HSD | 372 | 8.087 | 27.785 | 50.368 | 1.00 | 4.03 | PROT |
| ATOM | 5623 | C | HSD | 372 | 7.926 | 29.118 | 49.893 | 1.00 | 3.57 | PROT |
| ATOM | 5624 | O | HSD | 372 | 7.416 | 29.181 | 48.548 | 1.00 | 3.41 | PROT |
| ATOM | 5625 | CB | HSD | 372 | 7.358 | 26.792 | 51.297 | 1.00 | 3.91 | PROT |
| ATOM | 5626 | CG | HSD | 372 | 7.399 | 28.419 | 52.747 | 1.00 | 4.12 | PROT |
| ATOM | 5627 | ND1 | HSD | 372 | 8.234 | 29.032 | 53.639 | 1.00 | 2.79 | PROT |
| ATOM | 5628 | CD2 | HSD | 372 | 6.737 | 27.460 | 53.437 | 1.00 | 3.90 | PROT |
| ATOM | 5629 | CE1 | HSD | 372 | 8.068 | 28.487 | 54.844 | 1.00 | 2.26 | PROT |
| ATOM | 5630 | NE2 | HSD | 372 | 7.171 | 27.526 | 54.737 | 1.00 | 4.03 | PROT |
| ATOM | 5638 | N | PRO | 373 | 8.346 | 27.188 | 48.013 | 1.00 | 3.63 | PROT |
| ATOM | 5639 | CA | PRO | 373 | 8.498 | 27.508 | 46.690 | 1.00 | 3.77 | PROT |
| ATOM | 5640 | C | PRO | 373 | 7.228 | 27.606 | 45.754 | 1.00 | 3.68 | PROT |
| ATOM | 5641 | O | PRO | 373 | 6.155 | 27.149 | 46.159 | 1.00 | 3.95 | PROT |
| ATOM | 5642 | CB | PRO | 373 | 9.347 | 26.345 | 46.068 | 1.00 | 3.82 | PROT |
| ATOM | 5643 | CG | PRO | 373 | 9.013 | 25.223 | 46.944 | 1.00 | 4.08 | PROT |
| ATOM | 5644 | CD | PRO | 373 | 8.712 | 25.795 | 48.296 | 1.00 | 3.70 | PROT |
| ATOM | 5652 | N | ALA | 374 | 7.390 | 28.172 | 44.565 | 1.00 | 3.31 | PROT |
| ATOM | 5653 | CA | ALA | 374 | 6.408 | 28.044 | 43.516 | 1.00 | 3.58 | PROT |
| ATOM | 5654 | C | ALA | 374 | 6.356 | 26.580 | 43.064 | 1.00 | 4.02 | PROT |
| ATOM | 5655 | O | ALA | 374 | 7.326 | 25.821 | 43.266 | 1.00 | 4.05 | PROT |
| ATOM | 5656 | CB | ALA | 374 | 6.773 | 28.936 | 42.339 | 1.00 | 4.40 | PROT |
| ATOM | 5662 | N | GLY | 375 | 5.203 | 26.174 | 42.575 | 1.00 | 4.07 | PROT |
| ATOM | 5663 | CA | GLY | 375 | 5.072 | 24.922 | 41.860 | 1.00 | 4.15 | PROT |
| ATOM | 5664 | C | GLY | 375 | 6.081 | 24.790 | 40.732 | 1.00 | 4.33 | PROT |
| ATOM | 5665 | O | GLY | 375 | 6.528 | 25.782 | 40.107 | 1.00 | 2.99 | PROT |
| ATOM | 5669 | N | SER | 376 | 6.443 | 23.550 | 40.439 | 1.00 | 4.62 | PROT |
| ATOM | 5670 | CA | SER | 376 | 7.384 | 23.267 | 39.372 | 1.00 | 5.54 | PROT |
| ATOM | 5671 | C | SER | 376 | 7.186 | 21.843 | 38.873 | 1.00 | 6.07 | PROT |
| ATOM | 5672 | O | SER | 376 | 7.109 | 20.919 | 39.678 | 1.00 | 6.63 | PROT |
| ATOM | 5673 | CB | SER | 376 | 8.819 | 23.479 | 39.885 | 1.00 | 5.74 | PROT |
| ATOM | 5674 | OG | SER | 376 | 9.754 | 23.504 | 38.814 | 1.00 | 7.31 | PROT |
| ATOM | 5679 | N | VAL | 377 | 7.099 | 21.677 | 37.553 | 1.00 | 6.61 | PROT |
| ATOM | 5680 | CA | VAL | 377 | 6.932 | 20.362 | 36.912 | 1.00 | 6.56 | PROT |
| ATOM | 5681 | C | VAL | 377 | 8.094 | 20.149 | 35.932 | 1.00 | 6.45 | PROT |
| ATOM | 5682 | O | VAL | 377 | 8.270 | 20.926 | 34.969 | 1.00 | 6.93 | PROT |
| ATOM | 5683 | CB | VAL | 377 | 5.538 | 20.214 | 36.195 | 1.00 | 6.43 | PROT |
| ATOM | 5684 | CG1 | VAL | 377 | 5.432 | 18.880 | 35.398 | 1.00 | 7.12 | PROT |
| ATOM | 5685 | CG2 | VAL | 377 | 4.398 | 20.318 | 37.194 | 1.00 | 6.19 | PROT |
| ATOM | 5695 | N | ARG | 378 | 8.869 | 19.107 | 36.181 | 1.00 | 5.91 | PROT |
| ATOM | 5696 | CA | ARG | 378 | 9.903 | 18.676 | 35.268 | 1.00 | 6.08 | PROT |
| ATOM | 5697 | C | ARG | 378 | 9.319 | 18.088 | 33.985 | 1.00 | 5.72 | PROT |
| ATOM | 5698 | O | ARG | 378 | 8.396 | 17.260 | 34.055 | 1.00 | 5.14 | PROT |
| ATOM | 5699 | CB | ARG | 378 | 10.796 | 17.622 | 35.958 | 1.00 | 6.73 | PROT |
| ATOM | 5700 | CG | ARG | 378 | 12.109 | 17.390 | 35.267 | 1.00 | 9.58 | PROT |
| ATOM | 5701 | CD | ARG | 378 | 13.167 | 18.281 | 35.836 | 1.00 | 14.74 | PROT |
| ATOM | 5702 | NE | ARG | 378 | 14.408 | 18.145 | 35.057 | 1.00 | 17.47 | PROT |
| ATOM | 5703 | CZ | ARG | 378 | 15.622 | 18.010 | 35.578 | 1.00 | 16.90 | PROT |
| ATOM | 5704 | NH1 | ARG | 378 | 15.794 | 17.996 | 36.891 | 1.00 | 21.63 | PROT |
| ATOM | 5705 | NH2 | ARG | 378 | 16.664 | 17.886 | 34.776 | 1.00 | 18.67 | PROT |
| ATOM | 5719 | N | LEU | 379 | 9.835 | 18.491 | 32.802 | 1.00 | 5.09 | PROT |
| ATOM | 5720 | CA | LEU | 379 | 9.181 | 18.131 | 31.547 | 1.00 | 5.73 | PROT |
| ATOM | 5721 | C | LEU | 379 | 9.942 | 17.157 | 30.644 | 1.00 | 5.89 | PROT |
| ATOM | 5722 | O | LEU | 379 | 11.123 | 17.357 | 30.356 | 1.00 | 6.76 | PROT |
| ATOM | 5723 | CB | LEU | 379 | 8.800 | 19.389 | 30.750 | 1.00 | 5.56 | PROT |
| ATOM | 5724 | CG | LEU | 379 | 7.840 | 20.425 | 31.366 | 1.00 | 6.20 | PROT |
| ATOM | 5725 | CD1 | LEU | 379 | 7.630 | 21.578 | 30.402 | 1.00 | 6.28 | PROT |
| ATOM | 5726 | CD2 | LEU | 379 | 6.497 | 19.784 | 31.708 | 1.00 | 5.49 | PROT |
| ATOM | 5738 | N | ASN | 380 | 9.243 | 16.120 | 30.191 | 1.00 | 5.83 | PROT |
| ATOM | 5739 | CA | ASN | 380 | 9.754 | 15.207 | 29.167 | 1.00 | 6.00 | PROT |
| ATOM | 5740 | C | ASN | 380 | 9.600 | 15.835 | 27.793 | 1.00 | 6.13 | PROT |
| ATOM | 5741 | O | ASN | 380 | 8.567 | 16.467 | 27.494 | 1.00 | 6.05 | PROT |
| ATOM | 5742 | CB | ASN | 380 | 9.011 | 13.857 | 29.191 | 1.00 | 5.83 | PROT |
| ATOM | 5743 | CG | ASN | 380 | 9.539 | 12.866 | 28.147 | 1.00 | 5.84 | PROT |
| ATOM | 5744 | OD1 | ASN | 380 | 8.851 | 12.318 | 27.174 | 1.00 | 4.66 | PROT |

Figure 3 cont.

| | | | | | | | | | |
|---|---|---|---|---|---|---|---|---|---|
| ATOM | 5748 | HD2 | ASN | 380 | 10.764 | 12.412 | 23.344 | 1.00 5.73 | PROT |
| ATOM | 5752 | N | ILE | 381 | 10.639 | 15.684 | 25.976 | 1.00 5.95 | PROT |
| ATOM | 5753 | CA | ILE | 381 | 10.571 | 16.031 | 25.561 | 1.00 6.63 | PROT |
| ATOM | 5754 | C | ILE | 381 | 10.529 | 14.693 | 24.801 | 1.00 6.61 | PROT |
| ATOM | 5755 | O | ILE | 381 | 11.562 | 14.064 | 24.641 | 1.00 6.72 | PROT |
| ATOM | 5756 | CB | ILE | 381 | 11.794 | 16.915 | 25.147 | 1.00 6.28 | PROT |
| ATOM | 5757 | CG1 | ILE | 381 | 11.793 | 18.281 | 25.915 | 1.00 6.46 | PROT |
| ATOM | 5758 | CG2 | ILE | 381 | 11.829 | 17.159 | 23.627 | 1.00 6.84 | PROT |
| ATOM | 5759 | CD | ILE | 381 | 13.184 | 18.806 | 26.014 | 1.00 5.79 | PROT |
| ATOM | 5771 | N | PRO | 382 | 9.336 | 14.249 | 24.340 | 1.00 7.23 | PROT |
| ATOM | 5772 | CA | PRO | 382 | 9.205 | 12.900 | 23.738 | 1.00 7.48 | PROT |
| ATOM | 5773 | C | PRO | 382 | 10.175 | 12.652 | 22.585 | 1.00 7.62 | PROT |
| ATOM | 5774 | O | PRO | 382 | 10.711 | 11.551 | 22.451 | 1.00 7.64 | PROT |
| ATOM | 5775 | CB | PRO | 382 | 7.781 | 12.854 | 23.243 | 1.00 7.39 | PROT |
| ATOM | 5776 | CG | PRO | 382 | 7.037 | 13.871 | 24.093 | 1.00 8.31 | PROT |
| ATOM | 5777 | CD | PRO | 382 | 8.043 | 14.964 | 24.347 | 1.00 6.99 | PROT |
| ATOM | 5785 | N | GLY | 383 | 10.418 | 13.675 | 21.769 | 1.00 7.96 | PROT |
| ATOM | 5786 | CA | GLY | 383 | 11.341 | 13.567 | 20.639 | 1.00 8.59 | PROT |
| ATOM | 5787 | C | GLY | 383 | 12.773 | 13.268 | 21.044 | 1.00 8.98 | PROT |
| ATOM | 5788 | O | GLY | 383 | 13.519 | 12.365 | 20.682 | 1.00 9.10 | PROT |
| ATOM | 5792 | N | CYS | 384 | 13.193 | 13.699 | 22.245 | 1.00 9.77 | PROT |
| ATOM | 5793 | CA | CYS | 384 | 14.560 | 13.468 | 22.759 | 1.00 9.74 | PROT |
| ATOM | 5794 | C | CYS | 384 | 14.619 | 12.043 | 23.298 | 1.00 9.29 | PROT |
| ATOM | 5795 | O | CYS | 384 | 14.267 | 11.760 | 24.446 | 1.00 9.55 | PROT |
| ATOM | 5796 | CB | CYS | 384 | 14.865 | 14.492 | 23.827 | 1.00 10.14 | PROT |
| ATOM | 5797 | SG | CYS | 384 | 16.631 | 14.411 | 24.265 | 1.00 11.38 | PROT |
| ATOM | 5802 | N | SER | 385 | 15.101 | 11.153 | 22.434 | 1.00 8.36 | PROT |
| ATOM | 5803 | CA | SER | 385 | 15.206 | 9.721 | 22.730 | 1.00 8.15 | PROT |
| ATOM | 5804 | C | SER | 385 | 16.287 | 9.392 | 23.757 | 1.00 7.30 | PROT |
| ATOM | 5805 | O | SER | 385 | 16.030 | 8.398 | 24.419 | 1.00 6.87 | PROT |
| ATOM | 5806 | CB | SER | 385 | 15.459 | 8.913 | 21.446 | 1.00 7.99 | PROT |
| ATOM | 5807 | OG | SER | 385 | 14.250 | 8.710 | 20.746 | 1.00 10.17 | PROT |
| ATOM | 5812 | N | ASP | 386 | 17.271 | 10.278 | 23.878 | 1.00 6.44 | PROT |
| ATOM | 5813 | CA | ASP | 386 | 18.367 | 10.067 | 24.820 | 1.00 5.92 | PROT |
| ATOM | 5814 | C | ASP | 386 | 18.277 | 10.955 | 26.071 | 1.00 5.20 | PROT |
| ATOM | 5815 | O | ASP | 386 | 19.279 | 11.196 | 26.765 | 1.00 4.61 | PROT |
| ATOM | 5816 | CB | ASP | 386 | 19.731 | 10.180 | 24.115 | 1.00 6.01 | PROT |
| ATOM | 5817 | CG | ASP | 386 | 19.822 | 11.379 | 23.173 | 1.00 6.66 | PROT |
| ATOM | 5818 | OD1 | ASP | 386 | 18.944 | 12.263 | 23.206 | 1.00 7.37 | PROT |
| ATOM | 5819 | OD2 | ASP | 386 | 20.790 | 11.435 | 22.389 | 1.00 7.73 | PROT |
| ATOM | 5824 | N | GLN | 387 | 17.076 | 11.469 | 26.361 | 1.00 4.94 | PROT |
| ATOM | 5825 | CA | GLN | 387 | 16.821 | 10.022 | 27.590 | 1.00 4.68 | PROT |
| ATOM | 5826 | C | GLN | 387 | 16.969 | 11.301 | 28.791 | 1.00 4.74 | PROT |
| ATOM | 5827 | O | GLN | 387 | 16.480 | 10.173 | 28.780 | 1.00 4.93 | PROT |
| ATOM | 5828 | CB | GLN | 387 | 15.423 | 12.871 | 27.578 | 1.00 4.41 | PROT |
| ATOM | 5829 | CG | GLN | 387 | 15.206 | 13.904 | 28.659 | 1.00 4.24 | PROT |
| ATOM | 5830 | CD | GLN | 387 | 13.846 | 14.669 | 28.562 | 1.00 4.94 | PROT |
| ATOM | 5831 | OE1 | GLN | 387 | 12.965 | 14.260 | 27.606 | 1.00 4.19 | PROT |
| ATOM | 5832 | NE2 | GLN | 387 | 13.677 | 15.739 | 29.344 | 1.00 5.87 | PROT |
| ATOM | 5841 | N | THR | 388 | 17.728 | 11.763 | 29.795 | 1.00 4.48 | PROT |
| ATOM | 5842 | CA | THR | 388 | 18.066 | 10.947 | 30.963 | 1.00 4.71 | PROT |
| ATOM | 5843 | C | THR | 388 | 16.843 | 10.764 | 31.870 | 1.00 5.00 | PROT |
| ATOM | 5844 | O | THR | 388 | 15.926 | 11.590 | 31.826 | 1.00 4.77 | PROT |
| ATOM | 5845 | CB | THR | 388 | 19.215 | 11.588 | 31.771 | 1.00 4.92 | PROT |
| ATOM | 5846 | OG1 | THR | 388 | 18.774 | 12.854 | 32.284 | 1.00 4.89 | PROT |
| ATOM | 5847 | CG2 | THR | 388 | 20.441 | 11.796 | 30.899 | 1.00 4.53 | PROT |
| ATOM | 5854 | N | PRO | 389 | 16.810 | 9.678 | 32.662 | 1.00 5.07 | PROT |
| ATOM | 5855 | CA | PRO | 389 | 15.705 | 9.010 | 33.637 | 1.00 5.23 | PROT |
| ATOM | 5856 | C | PRO | 389 | 15.464 | 10.712 | 34.956 | 1.00 5.19 | PROT |
| ATOM | 5857 | O | PRO | 389 | 14.327 | 10.937 | 34.974 | 1.00 5.28 | PROT |
| ATOM | 5858 | CB | PRO | 389 | 16.123 | 8.275 | 34.441 | 1.00 5.17 | PROT |
| ATOM | 5859 | CG | PRO | 389 | 16.951 | 7.501 | 33.465 | 1.00 5.57 | PROT |
| ATOM | 5860 | CD | PRO | 389 | 17.740 | 8.536 | 32.741 | 1.00 5.08 | PROT |
| ATOM | 5868 | N | ASP | 390 | 16.511 | 11.488 | 34.645 | 1.00 5.01 | PROT |
| ATOM | 5869 | CA | ASP | 390 | 16.349 | 12.715 | 35.620 | 1.00 5.06 | PROT |

Figure 3 cont.

```
ATOM   5870  C    ASP   390      19.107  13.981  34.779  1.00  4.87      PROT
ATOM   5871  O    ASP   390      16.172  15.091  35.303  1.00  5.02      PROT
ATOM   5872  CB   ASP   390      17.498  12.912  36.828  1.00  5.78      PROT
ATOM   5873  CG   ASP   390      18.867  12.656  36.031  1.00  5.29      PROT
ATOM   5874  OD1  ASP   390      19.835  12.632  36.808  1.00  5.95      PROT
ATOM   5875  OD2  ASP   390      18.982  12.459  34.803  1.00  7.08      PROT
ATOM   5880  N    GLY   391      15.830  13.808  33.484  1.00  4.09      PROT
ATOM   5881  CA   GLY   391      15.252  14.876  32.654  1.00  3.89      PROT
ATOM   5882  C    GLY   391      16.194  15.745  31.831  1.00  3.62      PROT
ATOM   5883  O    GLY   391      15.782  16.791  31.315  1.00  3.66      PROT
ATOM   5887  N    TYR   392      17.446  15.322  31.687  1.00  3.83      PROT
ATOM   5888  CA   TYR   392      18.433  16.088  30.926  1.00  4.36      PROT
ATOM   5889  C    TYR   392      18.512  15.652  29.461  1.00  4.81      PROT
ATOM   5890  O    TYR   392      18.603  14.490  29.149  1.00  3.99      PROT
ATOM   5891  CB   TYR   392      19.810  16.061  31.618  1.00  4.00      PROT
ATOM   5892  CG   TYR   392      19.763  16.650  33.013  1.00  4.79      PROT
ATOM   5893  CD1  TYR   392      19.632  15.830  34.135  1.00  5.39      PROT
ATOM   5894  CD2  TYR   392      19.804  18.038  33.208  1.00  3.59      PROT
ATOM   5895  CE1  TYR   392      19.572  16.378  35.425  1.00  5.47      PROT
ATOM   5896  CE2  TYR   392      19.739  18.585  34.478  1.00  5.43      PROT
ATOM   5897  CZ   TYR   392      19.623  17.752  35.590  1.00  4.30      PROT
ATOM   5898  OH   TYR   392      19.564  18.318  36.828  1.00  6.19      PROT
ATOM   5907  N    CYS   393      18.215  16.664  28.579  1.00  5.83      PROT
ATOM   5908  CA   CYS   393      18.265  16.413  27.140  1.00  5.86      PROT
ATOM   5909  C    CYS   393      19.394  16.941  26.582  1.00  5.26      PROT
ATOM   5910  O    CYS   393      19.868  18.141  26.676  1.00  5.53      PROT
ATOM   5911  CB   CYS   393      17.078  17.140  26.485  1.00  6.12      PROT
ATOM   5912  SG   CYS   393      17.124  17.179  24.676  1.00  9.15      PROT
ATOM   5917  N    PRO   394      20.427  16.056  25.999  1.00  4.67      PROT
ATOM   5918  CA   PRO   394      21.677  16.517  25.383  1.00  4.87      PROT
ATOM   5919  C    PRO   394      21.414  17.734  24.474  1.00  4.30      PROT
ATOM   5920  O    PRO   394      20.415  17.751  23.762  1.00  4.43      PROT
ATOM   5921  CB   PRO   394      22.128  15.307  24.561  1.00  4.74      PROT
ATOM   5922  CG   PRO   394      21.544  14.133  25.252  1.00  4.83      PROT
ATOM   5923  CD   PRO   394      20.242  14.596  25.869  1.00  4.82      PROT
ATOM   5931  N    LEU   395      22.272  18.753  24.526  1.00  3.97      PROT
ATOM   5932  CA   LEU   395      22.039  19.979  23.751  1.00  3.62      PROT
ATOM   5933  C    LEU   395      22.063  19.707  22.247  1.00  3.36      PROT
ATOM   5934  O    LEU   395      21.242  20.248  21.495  1.00  3.43      PROT
ATOM   5935  CB   LEU   395      23.037  21.092  24.118  1.00  3.07      PROT
ATOM   5936  CG   LEU   395      23.039  22.367  23.249  1.00  3.92      PROT
ATOM   5937  CD1  LEU   395      21.669  23.083  23.230  1.00  2.70      PROT
ATOM   5938  CD2  LEU   395      24.134  23.334  23.680  1.00  2.81      PROT
ATOM   5950  N    SER   396      22.999  18.859  21.820  1.00  4.70      PROT
ATOM   5951  CA   SER   396      23.127  18.506  20.409  1.00  5.32      PROT
ATOM   5952  C    SER   396      21.857  17.859  19.869  1.00  5.80      PROT
ATOM   5953  O    SER   396      21.424  18.145  18.754  1.00  6.19      PROT
ATOM   5954  CB   SER   396      24.386  17.663  20.152  1.00  5.48      PROT
ATOM   5955  OG   SER   396      24.323  16.613  21.085  1.00  5.67      PROT
ATOM   5960  N    THR   397      21.233  16.954  20.664  1.00  6.11      PROT
ATOM   5961  CA   THR   397      19.929  16.336  20.342  1.00  6.16      PROT
ATOM   5962  C    THR   397      18.635  17.457  20.379  1.00  6.05      PROT
ATOM   5963  O    THR   397      17.970  17.471  19.493  1.00  6.21      PROT
ATOM   5964  CB   THR   397      19.806  15.270  21.301  1.00  6.31      PROT
ATOM   5965  OG1  THR   397      20.538  14.287  21.405  1.00  4.48      PROT
ATOM   5966  CG2  THR   397      18.211  14.534  20.836  1.00  7.29      PROT
ATOM   5973  N    PHE   398      18.657  18.359  21.380  1.00  5.32      PROT
ATOM   5974  CA   PHE   398      17.865  19.415  21.465  1.00  5.36      PROT
ATOM   5975  C    PHE   398      17.907  20.276  20.200  1.00  5.41      PROT
ATOM   5976  O    PHE   398      16.845  20.576  19.663  1.00  5.23      PROT
ATOM   5977  CB   PHE   398      18.082  20.266  22.734  1.00  5.11      PROT
ATOM   5978  CG   PHE   398      18.976  21.270  22.981  1.00  4.66      PROT
ATOM   5979  CD1  PHE   398      15.787  20.691  23.509  1.00  3.01      PROT
ATOM   5980  CD2  PHE   398      17.143  22.599  22.623  1.00  5.20      PROT
ATOM   5981  CE1  PHE   398      14.769  21.825  23.833  1.00  4.07      PROT
```

Figure 3 cont.

```
ATOM   5982  CE2  PHE  398    16.148  23.543  22.661  1.00   5.56      PROT
ATOM   5983  CZ   PHE  398    14.949  23.154  23.462  1.00   4.23      PROT
ATOM   5993  N    SER  399    19.106  20.634  19.726  1.00   5.44      PROT
ATOM   5994  CA   SER  399    19.283  21.418  18.489  1.00   6.85      PROT
ATOM   5995  C    SER  399    18.640  20.758  17.263  1.00   6.95      PROT
ATOM   5996  O    SER  399    18.081  21.440  16.401  1.00   6.93      PROT
ATOM   5997  CB   SER  399    20.769  21.646  18.176  1.00   6.34      PROT
ATOM   5998  OG   SER  399    21.012  22.043  19.308  1.00   7.08      PROT
ATOM   6003  N    ARG  400    18.751  19.433  17.186  1.00   7.76      PROT
ATOM   6004  CA   ARG  400    18.214  18.661  16.069  1.00   8.83      PROT
ATOM   6005  C    ARG  400    16.701  18.664  16.079  1.00   9.30      PROT
ATOM   6006  O    ARG  400    16.073  19.776  15.024  1.00   9.29      PROT
ATOM   6007  CB   ARG  400    18.710  17.206  16.104  1.00   8.37      PROT
ATOM   6008  CG   ARG  400    20.199  17.037  16.328  1.00  10.19      PROT
ATOM   6009  CD   ARG  400    21.027  17.679  15.220  1.00  13.32      PROT
ATOM   6010  NE   ARG  400    20.692  17.123  13.912  1.00  14.23      PROT
ATOM   6011  CZ   ARG  400    21.390  16.180  13.283  1.00  15.63      PROT
ATOM   6012  NH1  ARG  400    22.488  15.672  13.832  1.00  17.67      PROT
ATOM   6013  NH2  ARG  400    20.991  15.751  12.098  1.00  15.05      PROT
ATOM   6027  N    LEU  401    16.124  18.507  17.276  1.00  10.33      PROT
ATOM   6028  CA   LEU  401    14.673  18.522  17.441  1.00  11.29      PROT
ATOM   6029  C    LEU  401    14.067  19.845  17.021  1.00  12.10      PROT
ATOM   6030  O    LEU  401    13.060  19.874  16.304  1.00  12.54      PROT
ATOM   6031  CB   LEU  401    14.264  18.163  18.876  1.00  13.30      PROT
ATOM   6032  CG   LEU  401    13.523  16.825  19.065  1.00  12.19      PROT
ATOM   6033  CD1  LEU  401    14.360  15.844  18.565  1.00  13.72      PROT
ATOM   6034  CD2  LEU  401    12.160  16.834  18.376  1.00  11.84      PROT
ATOM   6046  N    VAL  402    14.790  20.934  17.453  1.00  12.79      PROT
ATOM   6047  CA   VAL  402    14.286  22.276  17.052  1.00  13.12      PROT
ATOM   6048  C    VAL  402    14.356  22.433  15.525  1.00  13.49      PROT
ATOM   6049  O    VAL  402    13.367  22.797  14.889  1.00  12.87      PROT
ATOM   6050  CB   VAL  402    15.133  23.351  17.774  1.00  13.15      PROT
ATOM   6051  CG1  VAL  402    14.949  24.723  17.144  1.00  12.99      PROT
ATOM   6052  CG2  VAL  402    14.725  23.371  19.264  1.00  12.46      PROT
ATOM   6062  N    SER  403    15.503  22.136  14.982  1.00  14.58      PROT
ATOM   6063  CA   SER  403    15.744  22.289  13.510  1.00  15.62      PROT
ATOM   6064  C    SER  403    14.692  21.407  12.699  1.00  16.00      PROT
ATOM   6065  O    SER  403    14.274  21.960  11.639  1.00  16.66      PROT
ATOM   6066  CB   SER  403    17.155  21.819  13.143  1.00  16.07      PROT
ATOM   6067  OG   SER  403    18.167  22.481  13.874  1.00   0.00      PROT
ATOM   6072  N    HSD  404    14.243  20.355  13.219  1.00  16.33      PROT
ATOM   6073  CA   HSD  404    13.199  19.565  12.556  1.00  16.35      PROT
ATOM   6074  C    HSD  404    11.779  20.086  12.604  1.00  16.52      PROT
ATOM   6075  O    HSD  404    10.880  19.815  12.011  1.00  16.80      PROT
ATOM   6076  CB   HSD  404    13.205  18.092  12.944  1.00  17.22      PROT
ATOM   6077  CG   HSD  404    14.505  17.393  12.447  1.00  19.47      PROT
ATOM   6078  ND1  HSD  404    15.230  16.488  13.215  1.00  21.57      PROT
ATOM   6079  CE2  HSD  404    15.176  17.469  11.261  1.00  21.25      PROT
ATOM   6080  CE1  HSD  404    16.264  16.039  12.523  1.00  22.36      PROT
ATOM   6081  NE2  HSD  404    16.256  16.620  11.336  1.00  22.83      PROT
ATOM   6089  N    SER  405    11.584  20.838  13.891  1.00  16.43      PROT
ATOM   6090  CA   SER  405    10.234  21.321  14.281  1.00  16.43      PROT
ATOM   6091  C    SER  405     9.863  22.657  13.645  1.00  16.09      PROT
ATOM   6092  O    SER  405     8.696  22.994  13.353  1.00  16.13      PROT
ATOM   6093  CB   SER  405    10.148  21.423  15.808  1.00  16.58      PROT
ATOM   6094  OG   SER  405    10.437  20.169  16.410  1.00  16.84      PROT
ATOM   6099  N    VAL  406    10.844  23.529  13.430  1.00  16.25      PROT
ATOM   6100  CA   VAL  406    10.600  24.863  12.918  1.00  16.19      PROT
ATOM   6101  C    VAL  406    10.043  24.958  11.490  1.00  16.82      PROT
ATOM   6102  O    VAL  406    10.262  23.911  10.717  1.00  15.71      PROT
ATOM   6103  CB   VAL  406    11.873  25.758  13.009  1.00  16.37      PROT
ATOM   6104  CG1  VAL  406    12.234  26.015  14.480  1.00  15.56      PROT
ATOM   6105  CG2  VAL  406    13.045  25.135  12.261  1.00  16.53      PROT
ATOM   6115  N    GLU  407     9.274  25.001  11.179  1.00  16.82      PROT
ATOM   6116  CA   GLU  407     8.667  26.200   9.816  1.00  16.87      PROT
```

Figure 3 cont.

```
ATOM   6117 C    GLU  407      9.833  27.246   9.246  1.00 17.18      PROT
ATOM   6118 O    GLU  407      9.886  26.380   9.738  1.00 17.41      PROT
ATOM   6119 CB   GLU  407      7.412  26.703   9.792  1.00 15.59      PROT
ATOM   6120 CG   GLU  407      6.890  27.167   8.411  1.00 16.45      PROT
ATOM   6121 CD   GLU  407      7.909  26.995   7.330  1.00 16.08      PROT
ATOM   6122 OE1  GLU  407      8.931  26.961   7.542  1.00 15.69      PROT
ATOM   6123 OE2  GLU  407      7.591  26.393   6.267  1.00 16.92      PROT
ATOM   6130 N    PRO  408     10.827  26.868   8.213  1.00 17.40      PROT
ATOM   6131 CA   PRO  408     11.398  27.764   7.566  1.00 17.31      PROT
ATOM   6132 C    PRO  408     11.019  29.086   7.050  1.00 17.08      PROT
ATOM   6133 O    PRO  408     11.693  30.112   7.124  1.00 16.93      PROT
ATOM   6134 CB   PRO  408     12.130  26.925   6.394  1.00 17.56      PROT
ATOM   6135 CG   PRO  408     11.932  25.522   6.815  1.00 17.56      PROT
ATOM   6136 CD   PRO  408     10.650  25.522   7.603  1.00 17.68      PROT
ATOM   6144 N    ALA  409      9.792  29.059   6.535  1.00 17.22      PROT
ATOM   6145 CA   ALA  409      9.133  30.265   6.022  1.00 17.67      PROT
ATOM   6146 C    ALA  409      8.824  31.282   7.124  1.00 17.95      PROT
ATOM   6147 O    ALA  409      8.596  32.455   6.834  1.00 18.07      PROT
ATOM   6148 CB   ALA  409      7.857  29.960   5.271  1.00 17.40      PROT
ATOM   6154 N    CYS  410      8.908  30.617   8.375  1.00 18.41      PROT
ATOM   6155 CA   CYS  410      8.511  31.667   9.535  1.00 18.68      PROT
ATOM   6156 C    CYS  410      9.747  32.035  10.361  1.00 19.34      PROT
ATOM   6157 O    CYS  410      9.622  32.549  11.463  1.00 19.62      PROT
ATOM   6158 CB   CYS  410      7.464  31.010  10.436  1.00 19.18      PROT
ATOM   6159 SG   CYS  410      5.961  30.531   9.596  1.00 17.28      PROT
ATOM   6164 N    GLN  411     10.929  31.774   9.798  1.00 20.10      PROT
ATOM   6165 CA   GLN  411     12.186  32.186  10.410  1.00 21.33      PROT
ATOM   6166 C    GLN  411     12.343  33.699  10.335  1.00 21.81      PROT
ATOM   6167 O    GLN  411     11.879  34.330   9.385  1.00 21.94      PROT
ATOM   6168 CB   GLN  411     13.372  31.533   9.699  1.00 21.35      PROT
ATOM   6169 CG   GLN  411     13.505  30.036   9.901  1.00 21.83      PROT
ATOM   6170 CD   GLN  411     14.706  29.462   9.166  1.00 22.12      PROT
ATOM   6171 OE1  GLN  411     14.681  29.291   7.946  1.00 23.89      PROT
ATOM   6172 NE2  GLN  411     15.769  29.161   9.913  1.00 22.55      PROT
ATOM   6181 N    LEU  412     12.965  34.269  11.351  1.00 22.23      PROT
ATOM   6182 CA   LEU  412     13.408  35.664  11.332  1.00 23.01      PROT
ATOM   6183 C    LEU  412     14.792  35.752  10.702  1.00 23.67      PROT
ATOM   6184 O    LEU  412     15.744  35.167  11.224  1.00 24.29      PROT
ATOM   6185 CB   LEU  412     13.453  36.243  12.754  1.00 22.85      PROT
ATOM   6186 CG   LEU  412     12.241  37.017  13.278  1.00 22.87      PROT
ATOM   6187 CD1  LEU  412     10.969  36.233  13.090  1.00 20.93      PROT
ATOM   6188 CD2  LEU  412     12.417  37.398  14.742  1.00 22.61      PROT
ATOM   6200 N    PRO  413     14.913  36.467   9.573  1.00 24.80      PROT
ATOM   6201 CA   PRO  413     13.866  37.110   8.773  1.00 24.96      PROT
ATOM   6202 C    PRO  413     13.308  36.203   7.670  1.00 25.63      PROT
ATOM   6203 O    PRO  413     13.784  35.041   7.563  1.00  0.00      PROT
ATOM   6204 CB   PRO  413     14.606  38.303   8.145  1.00 25.21      PROT
ATOM   6205 CG   PRO  413     16.079  38.179   8.604  1.00 24.76      PROT
ATOM   6206 CD   PRO  413     16.240  36.765   9.014  1.00 24.83      PROT
END
ATOM   6276 OH2  TIP3   1     -3.972  26.428  28.319  1.00  5.13      XWAT
ATOM   6279 OH2  TIP3   2     19.235  31.249  47.659  1.00  7.39      XWAT
ATOM   6282 OH2  TIP3   4     -7.692  42.917  44.597  1.00 17.68      XWAT
ATOM   6285 OH2  TIP3   5    -23.906  40.436  31.657  1.00 10.85      XWAT
ATOM   6288 OH2  TIP3   6     -3.436  35.420  25.094  1.00 16.60      XWAT
ATOM   6291 OH2  TIP3   7     -4.285  20.702  37.337  1.00 13.56      XWAT
ATOM   6294 OH2  TIP3   8      6.238  18.106  30.958  1.00 34.49      XWAT
ATOM   6297 OH2  TIP3   9     -4.338  26.003  44.389  1.00  2.00      XWAT
ATOM   6300 OH2  TIP3  10     17.982  53.263  34.416  1.00 22.49      XWAT
ATOM   6303 OH2  TIP3  11    -15.336  45.435  40.806  1.00 24.08      XWAT
ATOM   6306 OH2  TIP3  12     -6.979  30.022  48.903  1.00  2.31      XWAT
ATOM   6309 OH2  TIP3  13    -24.617  39.602  20.934  1.00 16.08      XWAT
ATOM   6312 OH2  TIP3  14      5.228  44.028  12.852  1.00 11.14      XWAT
ATOM   6315 OH2  TIP3  15     16.987  43.790  30.477  1.00  2.00      XWAT
ATOM   6318 OH2  TIP3  16    -36.889  20.833  26.995  1.00 19.97      XWAT
```

Figure 3 cont.

```
ATOM   6321 OH2  TIP3  17     0.894  31.821  38.110  1.00   2.00      XWAT
ATOM   6324 OH2  TIP3  18     8.773  43.753  21.839  1.00   2.00      XWAT
ATOM   6327 OH2  TIP3  19     7.471  32.852  17.803  1.00   3.87      XWAT
ATOM   6330 OH2  TIP3  20     3.475  41.387  19.104  1.00   3.12      XWAT
ATOM   6333 OH2  TIP3  21    -8.051  51.464  41.465  1.00  31.31      XWAT
ATOM   6336 OH2  TIP3  22    13.604  18.554  31.108  1.00   2.85      XWAT
ATOM   6339 OH2  TIP3  23    -5.028  22.234  35.106  1.00   2.00      XWAT
ATOM   6342 OH2  TIP3  24     1.275  29.082   3.627  1.00  30.13      XWAT
ATOM   6345 OH2  TIP3  25    15.270  51.303  36.584  1.00  18.00      XWAT
ATOM   6348 OH2  TIP3  26    -6.265  44.031  24.876  1.00  23.60      XWAT
ATOM   6351 OH2  TIP3  27     1.627  35.581  38.617  1.00   2.00      XWAT
ATOM   6354 OH2  TIP3  29     8.932  35.977  46.472  1.00   4.06      XWAT
ATOM   6357 OH2  TIP3  30     0.500  33.893  44.957  1.00   2.00      XWAT
ATOM   6360 OH2  TIP3  31     7.257  34.269  35.602  1.00   6.65      XWAT
ATOM   6363 OH2  TIP3  32    -2.565  56.534  31.190  1.00   8.52      XWAT
ATOM   6366 OH2  TIP3  33    11.674  31.203  53.645  1.00  34.76      XWAT
ATOM   6369 OH2  TIP3  34    -4.341  29.841  16.524  1.00  19.11      XWAT
ATOM   6372 OH2  TIP3  35     1.964  33.926  17.971  1.00  11.95      XWAT
ATOM   6375 OH2  TIP3  36    -0.660  19.756  29.302  1.00  22.93      XWAT
ATOM   6378 OH2  TIP3  37    10.179  13.731  26.347  1.00  14.01      XWAT
ATOM   6381 OH2  TIP3  38   -17.095  31.454  43.045  1.00  11.14      XWAT
ATOM   6384 OH2  TIP3  39    -0.485  29.218  49.363  1.00  36.91      XWAT
ATOM   6387 OH2  TIP3  41     0.389  15.294  30.657  1.00  25.38      XWAT
ATOM   6390 OH2  TIP3  42    -6.704  35.930  21.602  1.00  14.76      XWAT
ATOM   6393 OH2  TIP3  43    30.781  22.813  27.685  1.00  21.61      XWAT
ATOM   6396 OH2  TIP3  44     0.034  36.216  15.196  1.00  15.47      XWAT
ATOM   6399 OH2  TIP3  45     4.915  31.645  19.808  1.00   2.00      XWAT
ATOM   6402 OH2  TIP3  46     0.519  36.968   7.747  1.00  11.79      XWAT
ATOM   6405 OH2  TIP3  47     1.766  30.262  31.734  1.00   2.00      XWAT
ATOM   6408 OH2  TIP3  49    36.537  43.971  43.066  1.00  50.80      XWAT
ATOM   6411 OH2  TIP3  50    -1.358  30.272  18.762  1.00   7.06      XWAT
ATOM   6414 OH2  TIP3  51    -1.917  46.015  21.194  1.00  32.76      XWAT
ATOM   6417 OH2  TIP3  52   -17.005  17.710  30.167  1.00  10.08      XWAT
ATOM   6420 OH2  TIP3  53    22.332  45.965  39.049  1.00  27.83      XWAT
ATOM   6423 OH2  TIP3  54   -27.895  26.164  23.213  1.00  10.74      XWAT
ATOM   6426 OH2  TIP3  55     0.457  38.134  38.069  1.00   2.00      XWAT
ATOM   6429 OH2  TIP3  56    27.614  44.494  33.182  1.00  18.11      XWAT
ATOM   6432 OH2  TIP3  58    20.048  39.345  42.697  1.00  20.36      XWAT
ATOM   6435 OH2  TIP3  59     4.963  26.985  48.456  1.00  17.72      XWAT
ATOM   6438 OH2  TIP3  60   -22.589  26.968  40.936  1.00  19.68      XWAT
ATOM   6441 OH2  TIP3  61   -31.306  26.064  23.725  1.00  27.75      XWAT
ATOM   6444 OH2  TIP3  62    -1.660  48.684  35.094  1.00  19.22      XWAT
ATOM   6447 OH2  TIP3  63    -4.789  42.329  17.037  1.00  30.85      XWAT
ATOM   6450 OH2  TIP3  64    -3.544  16.729  22.218  1.00  16.97      XWAT
ATOM   6453 OH2  TIP3  65   -26.106  31.745  38.820  1.00  22.55      XWAT
ATOM   6456 OH2  TIP3  67     3.982  21.585  41.813  1.00  10.93      XWAT
ATOM   6459 OH2  TIP3  68   -19.846  33.120  16.435  1.00   6.34      XWAT
ATOM   6462 OH2  TIP3  69    -6.752  40.793  21.739  1.00  39.90      XWAT
ATOM   6465 OH2  TIP3  70   -11.460  47.040  33.436  1.00  11.07      XWAT
ATOM   6468 OH2  TIP3  71    -3.054  17.405  26.030  1.00  42.00      XWAT
ATOM   6471 OH2  TIP3  72   -13.347  16.579  37.333  1.00  15.39      XWAT
ATOM   6474 OH2  TIP3  73    -4.140  30.490  29.711  1.00   2.00      XWAT
ATOM   6477 OH2  TIP3  74   -18.238  44.937  33.599  1.00  20.78      XWAT
ATOM   6480 OH2  TIP3  76    27.325  13.037  33.206  1.00   9.23      XWAT
ATOM   6483 OH2  TIP3  77    -4.034  22.356  26.702  1.00  30.41      XWAT
ATOM   6486 OH2  TIP3  78   -14.602  37.028  17.414  1.00  21.94      XWAT
ATOM   6489 OH2  TIP3  80    14.572  33.851  52.173  1.00  18.48      XWAT
ATOM   6492 OH2  TIP3  81   -20.946  22.901  44.365  1.00  46.27      XWAT
ATOM   6495 OH2  TIP3  82   -14.181  39.792  35.249  1.00   6.94      XWAT
ATOM   6498 OH2  TIP3  83     3.039  52.630  13.502  1.00  24.18      XWAT
ATOM   6501 OH2  TIP3  86    -4.365  55.903  33.584  1.00  49.46      XWAT
ATOM   6504 OH2  TIP3  87   -26.511  23.171  33.160  1.00  14.13      XWAT
ATOM   6507 OH2  TIP3  88   -23.934  29.146  27.983  1.00  10.91      XWAT
ATOM   6510 OH2  TIP3  89     7.308  49.733  39.638  1.00  12.68      XWAT
ATOM   6513 OH2  TIP3  90     5.993  16.030  29.077  1.00  13.56      XWAT
```

Figure 3 cont.

| | | | | | | | | | |
|---|---|---|---|---|---|---|---|---|---|
| ATOM | 6516 | OH2 | TIP3 | 91 | -34.683 | 29.557 | 29.050 | 1.00 18.32 | XWAT |
| ATOM | 6519 | OH2 | TIP3 | 92 | 14.499 | 50.037 | 39.004 | 1.00 17.43 | XWAT |
| ATOM | 6522 | OH2 | TIP3 | 94 | 27.474 | 20.025 | 41.171 | 1.00 22.72 | XWAT |
| ATOM | 6525 | OH2 | TIP3 | 95 | -3.921 | 20.857 | 5.122 | 1.00 26.03 | XWAT |
| ATOM | 6528 | OH2 | TIP3 | 96 | 10.644 | 43.991 | 45.229 | 1.00 34.20 | XWAT |
| ATOM | 6531 | OH2 | TIP3 | 97 | 19.673 | 46.568 | 45.681 | 1.00 22.99 | XWAT |
| ATOM | 6534 | OH2 | TIP3 | 98 | -6.934 | 15.771 | 9.670 | 1.00 2.00 | XWAT |
| ATOM | 6537 | OH2 | TIP3 | 99 | -34.305 | 25.894 | 30.628 | 1.00 35.79 | XWAT |
| ATOM | 6540 | OH2 | TIP3 | 102 | 8.909 | 37.371 | 48.431 | 1.00 20.01 | XWAT |
| ATOM | 6543 | OH2 | TIP3 | 103 | 25.430 | 17.781 | 24.059 | 1.00 14.21 | XWAT |
| ATOM | 6546 | OH2 | TIP3 | 104 | -5.648 | 19.701 | 27.080 | 1.00 30.94 | XWAT |
| ATOM | 6549 | OH2 | TIP3 | 106 | 19.471 | 43.314 | 50.752 | 1.00 31.75 | XWAT |
| ATOM | 6552 | OH2 | TIP3 | 107 | -15.487 | 31.506 | 46.327 | 1.00 34.41 | XWAT |
| ATOM | 6555 | OH2 | TIP3 | 108 | -36.738 | 30.101 | 32.179 | 1.00 38.94 | XWAT |
| ATOM | 6558 | OH2 | TIP3 | 109 | -13.179 | 17.086 | 39.913 | 1.00 18.15 | XWAT |
| ATOM | 6561 | OH2 | TIP3 | 110 | -25.214 | 22.785 | 28.115 | 1.00 25.10 | XWAT |
| ATOM | 6564 | OH2 | TIP3 | 111 | 7.243 | 38.052 | 49.987 | 1.00 20.89 | XWAT |
| ATOM | 6567 | OH2 | TIP3 | 112 | -10.404 | 18.789 | 7.035 | 1.00 43.30 | XWAT |
| ATOM | 6570 | OH2 | TIP3 | 113 | -20.034 | 22.773 | 48.104 | 1.00 47.65 | XWAT |
| ATOM | 6573 | OH2 | TIP3 | 114 | -27.218 | 19.793 | 28.993 | 1.00 27.43 | XWAT |
| ATOM | 6576 | OH2 | TIP3 | 115 | -24.538 | 16.997 | 30.259 | 1.00 32.69 | XWAT |
| ATOM | 6579 | OH2 | TIP3 | 116 | 30.246 | 23.359 | 39.108 | 1.00 10.67 | XWAT |
| ATOM | 6582 | OH2 | TIP3 | 118 | 12.424 | 46.084 | 46.210 | 1.00 46.05 | XWAT |
| ATOM | 6585 | OH2 | TIP3 | 121 | -1.291 | 47.033 | 25.727 | 1.00 14.74 | XWAT |
| ATOM | 6588 | OH2 | TIP3 | 123 | -6.585 | 21.401 | 34.879 | 1.00 23.63 | XWAT |
| ATOM | 6591 | OH2 | TIP3 | 124 | -16.531 | 27.349 | 9.704 | 1.00 12.22 | XWAT |
| ATOM | 6594 | OH2 | TIP3 | 126 | 12.221 | 49.090 | 32.006 | 1.00 5.05 | XWAT |
| ATOM | 6597 | OH2 | TIP3 | 127 | -7.897 | 31.181 | 18.670 | 1.00 17.92 | XWAT |
| ATOM | 6600 | OH2 | TIP3 | 129 | -13.867 | 38.591 | 44.834 | 1.00 15.14 | XWAT |
| ATOM | 6603 | OH2 | TIP3 | 130 | -1.782 | 45.132 | 27.800 | 1.00 2.00 | XWAT |
| ATOM | 6606 | OH2 | TIP3 | 131 | -15.595 | 41.861 | 34.028 | 1.00 10.51 | XWAT |
| ATOM | 6609 | OH2 | TIP3 | 132 | 6.298 | 16.130 | 30.368 | 1.00 6.49 | XWAT |
| ATOM | 6612 | OH2 | TIP3 | 133 | 11.512 | 47.236 | 37.606 | 1.00 2.00 | XWAT |
| ATOM | 6615 | OH2 | TIP3 | 134 | 19.286 | 46.897 | 32.567 | 1.00 12.95 | XWAT |
| ATOM | 6618 | OH2 | TIP3 | 135 | 0.742 | 51.629 | 31.304 | 1.00 11.89 | XWAT |
| ATOM | 6621 | OH2 | TIP3 | 136 | -4.689 | 32.032 | 19.571 | 1.00 25.46 | XWAT |
| ATOM | 6624 | OH2 | TIP3 | 137 | 31.574 | 16.202 | 26.472 | 1.00 30.19 | XWAT |
| ATOM | 6627 | OH2 | TIP3 | 138 | -0.787 | 26.277 | 47.192 | 1.00 11.50 | XWAT |
| ATOM | 6630 | OH2 | TIP3 | 140 | -9.298 | 44.508 | 42.115 | 1.00 14.23 | XWAT |
| ATOM | 6633 | OH2 | TIP3 | 141 | 16.066 | 48.886 | 28.032 | 1.00 4.97 | XWAT |
| ATOM | 6636 | OH2 | TIP3 | 142 | -10.378 | 19.463 | 22.500 | 1.00 13.44 | XWAT |
| ATOM | 6639 | OH2 | TIP3 | 144 | 2.471 | 39.135 | 49.063 | 1.00 4.79 | XWAT |
| ATOM | 6642 | OH2 | TIP3 | 146 | -8.932 | 13.766 | 28.573 | 1.00 10.19 | XWAT |
| ATOM | 6645 | OH2 | TIP3 | 147 | 8.960 | 52.000 | 26.374 | 1.00 6.77 | XWAT |
| ATOM | 6648 | OH2 | TIP3 | 148 | -20.203 | 45.043 | 25.034 | 1.00 13.56 | XWAT |
| ATOM | 6651 | OH2 | TIP3 | 149 | 7.339 | 23.005 | 44.068 | 1.00 21.49 | XWAT |
| ATOM | 6654 | OH2 | TIP3 | 150 | 2.056 | 46.463 | 42.157 | 1.00 5.58 | XWAT |
| ATOM | 6657 | OH2 | TIP3 | 151 | -20.167 | 21.286 | 18.362 | 1.00 3.46 | XWAT |
| ATOM | 6660 | OH2 | TIP3 | 153 | -5.961 | 33.846 | 27.750 | 1.00 23.52 | XWAT |
| ATOM | 6663 | OH2 | TIP3 | 154 | -17.904 | 24.775 | 9.675 | 1.00 19.85 | XWAT |
| ATOM | 6666 | OH2 | TIP3 | 155 | 15.834 | 45.800 | 39.877 | 1.00 5.85 | XWAT |
| ATOM | 6669 | OH2 | TIP3 | 156 | 12.144 | 12.644 | 36.966 | 1.00 25.76 | XWAT |
| ATOM | 6672 | OH2 | TIP3 | 157 | 14.679 | 36.773 | 17.184 | 1.00 19.22 | XWAT |
| ATOM | 6675 | OH2 | TIP3 | 158 | 10.044 | 49.744 | 35.900 | 1.00 7.82 | XWAT |
| ATOM | 6678 | OH2 | TIP3 | 159 | -20.447 | 28.489 | 16.163 | 1.00 18.20 | XWAT |
| ATOM | 6681 | OH2 | TIP3 | 160 | -0.818 | 19.485 | 12.849 | 1.00 4.63 | XWAT |
| ATOM | 6684 | OH2 | TIP3 | 162 | 2.211 | 16.727 | 34.304 | 1.00 9.36 | XWAT |
| ATOM | 6687 | OH2 | TIP3 | 163 | -13.231 | 19.447 | 11.509 | 1.00 14.57 | XWAT |
| ATOM | 6690 | OH2 | TIP3 | 165 | 5.819 | 44.206 | 44.472 | 1.00 8.37 | XWAT |
| ATOM | 6693 | OH2 | TIP3 | 166 | -6.133 | 27.178 | 49.829 | 1.00 36.92 | XWAT |
| ATOM | 6696 | OH2 | TIP3 | 167 | 0.356 | 30.575 | 50.390 | 1.00 14.30 | XWAT |
| ATOM | 6699 | OH2 | TIP3 | 168 | 18.338 | 48.456 | 29.679 | 1.00 3.36 | XWAT |
| ATOM | 6702 | OH2 | TIP3 | 169 | 6.046 | 45.172 | 41.025 | 1.00 12.76 | XWAT |
| ATOM | 6705 | OH2 | TIP3 | 170 | 7.146 | 46.493 | 33.067 | 1.00 3.87 | XWAT |
| ATOM | 6708 | OH2 | TIP3 | 171 | -1.163 | 43.404 | 45.762 | 1.00 14.81 | XWAT |

Figure 3 cont.

```
ATOM   6711  OH2  TIP3  172     -28.499  22.397  16.783  1.00  29.73      XWAT
ATOM   6714  OH2  TIP3  173      -7.665  18.904  23.197  1.00  22.44      XWAT
ATOM   6717  OH2  TIP3  175     -16.670  25.977  20.457  1.00   2.00      XWAT
ATOM   6720  OH2  TIP3  176       4.855  16.351  33.003  1.00  22.98      XWAT
ATOM   6723  OH2  TIP3  178      -7.681  20.427  32.270  1.00  36.55      XWAT
ATOM   6726  OH2  TIP3  180      28.558  31.447  41.569  1.00  14.65      XWAT
ATOM   6729  OH2  TIP3  181      12.783  49.008  35.551  1.00   7.97      XWAT
ATOM   6732  OH2  TIP3  182      -4.556  20.016  33.170  1.00  11.43      XWAT
ATOM   6735  OH2  TIP3  183      -4.759  45.391  41.806  1.00   2.00      XWAT
ATOM   6738  OH2  TIP3  184     -27.103  40.457  30.822  1.00  10.55      XWAT
ATOM   6741  OH2  TIP3  185      -4.549  46.166  26.507  1.00  24.95      XWAT
ATOM   6744  OH2  TIP3  186     -21.132  23.788  13.743  1.00  20.95      XWAT
ATOM   6747  OH2  TIP3  187      -5.074  44.959  44.622  1.00  13.48      XWAT
ATOM   6750  OH2  TIP3  188     -19.351  14.781  26.745  1.00   8.84      XWAT
ATOM   6753  OH2  TIP3  189      26.364  39.235  36.443  1.00  20.41      XWAT
ATOM   6756  OH2  TIP3  190     -20.159  31.629  14.171  1.00  10.67      XWAT
ATOM   6759  OH2  TIP3  191      32.938  17.064  39.436  1.00   2.00      XWAT
ATOM   6762  OH2  TIP3  192     -15.939  45.997  31.794  1.00  23.45      XWAT
ATOM   6765  OH2  TIP3  193       5.674  46.420  36.745  1.00   2.00      XWAT
ATOM   6768  OH2  TIP3  194     -13.733  10.283  15.149  1.00  30.03      XWAT
ATOM   6771  OH2  TIP3  195     -14.451  45.075  24.982  1.00  12.08      XWAT
ATOM   6774  OH2  TIP3  196      13.881  30.053  51.927  1.00   5.72      XWAT
ATOM   6777  OH2  TIP3  198       7.109  31.694  36.151  1.00  11.31      XWAT
ATOM   6780  OH2  TIP3  199      -9.531  13.910  13.314  1.00  18.42      XWAT
ATOM   6783  OH2  TIP3  200     -24.408  29.511  17.439  1.00   9.70      XWAT
ATOM   6786  OH2  TIP3  201     -15.380  24.117  11.361  1.00   9.69      XWAT
ATOM   6789  OH2  TIP3  202     -16.234  47.171  27.156  1.00  14.70      XWAT
ATOM   6792  OH2  TIP3  203      19.601  44.019  30.049  1.00   6.62      XWAT
ATOM   6795  OH2  TIP3  204     -27.869  25.450  33.153  1.00   9.51      XWAT
ATOM   6798  OH2  TIP3  205     -11.449  16.320  21.174  1.00  20.73      XWAT
ATOM   6801  OH2  TIP3  206      -4.001  14.317  19.529  1.00  34.99      XWAT
ATOM   6804  OH2  TIP3  207     -11.053  14.430  23.403  1.00  30.27      XWAT
END
```

HAFNIA PHYTASE

CROSS-REFERENCE TO RELATED APPLICATIONS

This application claims priority or the benefit under 35 U.S.C. 119 of European application no. EP07104870.6 filed Mar. 26, 2007 and U.S. provisional application No. 60/908,705 filed Mar. 29, 2007, the contents of which are fully incorporated herein by reference.

SEQUENCE LISTING AND DEPOSITED MICROORGANISMS

Sequence Listing

The present application contains a computer readable form of a sequence listing. The contents of the computer readable form are fully incorporated herein by reference.

Deposit of Biological Material

A phytase producing bacterial strain was isolated from Danish soil. The strain was demonstrated to produce a phytase with acidic pH optimum and high thermostability. The strain was identified as *Hafnia alvei* and it was deposited on Mar. 21, 2007, under the terms of the Budapest Treaty with Deutsche Sammlung von Mikroorganismen und Zellkulturen (DSMZ) and given the following accession number:

| Deposit | Accession Number | Date of Deposit |
| --- | --- | --- |
| *Hafnia alvei* NN020125 | DSM 19197 | March 21, 2007 |

FIELD OF THE INVENTION

The present invention relates to isolated polypeptides having phytase activity and isolated polynucleotides encoding the polypeptides. The polypeptides are related to a phytase derived from *Hafnia alvei*, the amino acid sequence of which is shown in the appended sequence listing as SEQ ID NO: 10. The invention also relates to nucleic acid constructs, vectors, and host cells comprising the polynucleotides as well as methods for producing and using the polypeptides, in particular within animal feed.

BACKGROUND OF THE INVENTION

Phytases are well-known enzymes, as are the advantages of adding them to foodstuffs for animals, including humans. Phytases have been isolated from very many sources, including a number of fungal and bacterial strains.

It is an object of the present invention to provide alternative polypeptides having phytase activity and polynucleotides encoding the polypeptides. The polypeptides of the invention are preferably of amended, more preferably improved, properties, for example of a different substrate specificity, of a higher specific activity, of an increased stability (such as acid-stability, heat-stability, and/or protease stability, in particular pepsin stability), of an altered pH optimum (such as a lower, or higher pH optimum) and/or of an improved performance in animal feed (such as an improved release and/or degradation of phytate).

SUMMARY OF THE INVENTION

The present invention relates to polypeptides having phytase activity, selected from the group consisting of: (a) a polypeptide having an amino acid sequence which has at least 75% identity with (i) amino acids 1 to 413 of SEQ ID NO: 10, and/or (ii) the mature polypeptide part of SEQ ID NO: 10; (b) a variant comprising a deletion, insertion, and/or conservative substitution of one or more amino acids of (i) amino acids 1 to 413 of SEQ ID NO: 10, and/or (ii) the mature polypeptide part of SEQ ID NO: 10; and/or (c) a fragment of (i) amino acids 1 to 413 of SEQ ID NO: 10, and/or (ii) the mature polypeptide part of SEQ ID NO: 10.

The invention also relates to isolated polynucleotides encoding a polypeptide having phytase activity, selected from the group consisting of: (a) a polynucleotide encoding a polypeptide having an amino acid sequence which has at least 75% identity with amino acids 1 to 413 of SEQ ID NO: 10; and (b) a polynucleotide having at least 75% identity with nucleotides 100 to 1338 of SEQ ID NO: 9.

The invention also relates to nucleic acid constructs, recombinant expression vectors, and recombinant host cells comprising the polynucleotides.

The invention also relates to methods for producing such polypeptides having phytase activity comprising (a) cultivating a recombinant host cell comprising a nucleic acid construct comprising a polynucleotide encoding the polypeptide under conditions conducive for production of the polypeptide; and (b) recovering the polypeptide.

The invention further relates to a nucleic acid construct comprising a gene encoding a protein operably linked to a nucleotide sequence encoding a signal peptide consisting of (i) nucleotides 1 to 99 of SEQ ID NO: 11.

The invention also relates to methods of using the phytases of the invention in animal feed, as well as animal feed and animal feed additive compositions containing the polypeptides.

The invention also relates to methods of using the phytases of the invention in producing a fermentation product, such as, e.g., ethanol, beer, wine, wherein the fermentation is carried out in the presence of a phytase of the present invention.

The present invention relates to methods for treating proteins, including vegetable proteins, with the phytases of the present invention.

BRIEF DESCRIPTION OF FIGURES

FIG. 3 shows the Appendix of the structural coordinates for the solved crystal three dimensional structure of the *Hafnia alvei* phytase.

DEFINITIONS

Figure 1:
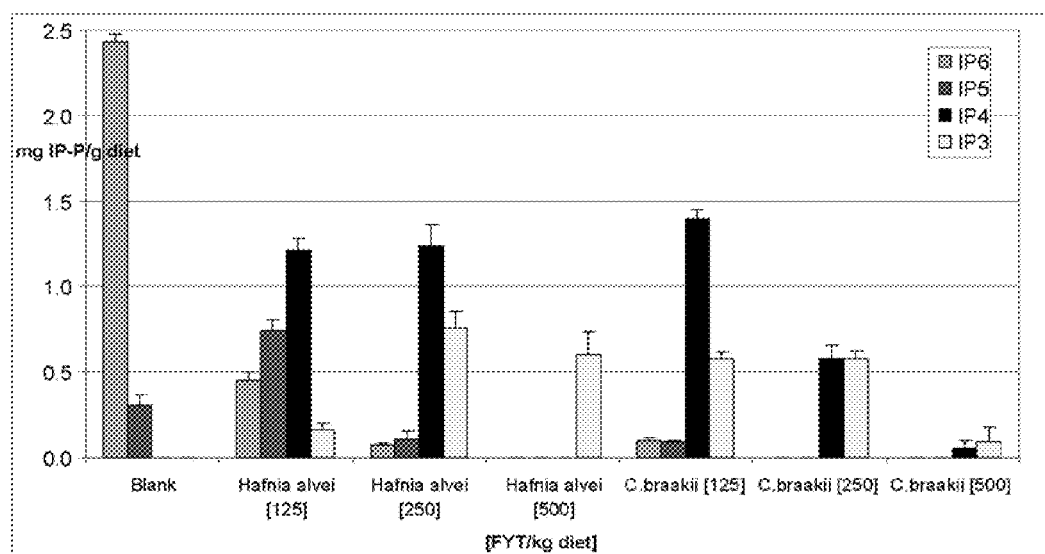
FIG. 1 shows the residual inositol-phosphate bound phosphorous after in vitro incubation in a comparison between the *Hafnia alvei* phytase and a *Citrobacter braakii* phytase dosed from 125 to 500 FYT/kg Feed.

Phytase activity: In the present context a polypeptide having phytase activity (a phytase) is an enzyme which catalyzes the hydrolysis of phytate (myo-inositol hexakis-phosphate) to (1) myo-inositol and/or (2) mono-, di-, tri-, tetra- and/or penta-phosphates thereof and (3) inorganic phosphate.

The ENZYME site at the internet (www.expasy.ch/enzyme/) is a repository of information relative to the nomenclature of enzymes. It is primarily based on the recommendations of the Nomenclature Committee of the International Union of Biochemistry and Molecular Biology (IUB-MB)

and it describes each type of characterized enzyme for which an EC (Enzyme Commission) number has been provided (Bairoch A. The ENZYME database, 2000, Nucleic Acids Res 28:304-305). See also the handbook Enzyme Nomenclature from NC-IUBMB, 1992).

According to the ENZYME site, three different types of phytases are known: A 3-phytase (myo-inositol hexaphosphate 3-phosphohydrolase, EC 3.1.3.8), a 6-phytase (myo-inositol hexaphosphate 6-phosphohydrolase, EC 3.1.3.26), and a 5-phytase (EC 3.1.3.72). For the purposes of the present invention, all types are included in the definition of phytase.

In a particular embodiment, the phytases of the invention belong to the family of acid histidine phosphatases, which includes the *Escherichia coli* pH 2.5 acid phosphatase (gene appA) as well as fungal phytases such as *Aspergillus awamorii* phytases A and B (EC: 3.1.3.8) (gene phyA and phyB). The histidine acid phosphatases share two regions of sequence similarity, each centered around a conserved histidine residue. These two histidines seem to be involved in the enzymes' catalytic mechanism. The first histidine is located in the N-terminal section and forms a phosphor-histidine intermediate while the second is located in the C-terminal section and possibly acts as proton donor.

In a further particular embodiment, the phytases of the invention have a conserved active site motif, viz. R-H-G-X-R-X-P, wherein X designates any amino acid (see amino acids 18 to 24 of the mature phytase shown in SEQ ID NO: 10).

For the purposes of the present invention the phytase activity is determined in the unit of FYT, one FYT being the amount of enzyme that liberates 1 micro-mol inorganic orthophosphate per min. under the following conditions: pH 5.5; temperature 37° C.; substrate: sodium phytate ($C_6H_6O_{24}P_6Na_{12}$) in a concentration of 0.0050 mol/l. Suitable phytase assays are the FYT and FTU assays described in Example 1 of WO 00/20569. FTU is for determining phytase activity in feed and premix. Phytase activity may also be determined using the phytase assays of the examples herein.

pH optimum: The pH-optimum of a polypeptide of the invention is determined by incubating the phytase at various pH-values, using a substrate in a pre-determined concentration and a fixed incubation temperature. The pH-optimum is then determined from a graphical representation of phytase activity versus pH. In a particular embodiment, the FYT assay is used, viz. the substrate is 5 mM sodium phytate, the reaction temperature 37° C., and the activity is determined in FYT units at various pH-values, as done in the examples below. In another particular embodiment, the phytase assay of any one of the examples is used. A relatively low pH-optimum means a pH-optimum below pH 5.0, for example below pH 4.5, 4.0, 3.5, 3.0, 2.5, or even below 2.0. A relatively high pH-optimum means a pH-optimum above pH 5.0, for example above pH 5.5, 6.0, 6.5, 7.0, 7.5, 8.0, 8.5, or even above 9.0.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences, as well as the degree of identity between two nucleotide sequences, is determined by the program "align" which is a Needleman-Wunsch alignment (i.e. global alignment), useful for both protein and DNA alignments. The default scoring matrix BLOSUM50 and the default identity matrix are used for protein and DNA alignments respectively. The penalty for the first residue in a gap is −12 for proteins and −16 for DNA. While the penalties for additional residues in a gap are −2 for proteins and −4 for DNA.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183: 63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

The Needleman-Wunsch algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17.

The degree of identity between the target (or sample, or test) sequence and a specified sequence (e.g. amino acids 1 to 413 of the mature phytase shown in SEQ ID NO: 10) may also be determined as follows: The sequences are aligned using the program "align." The number of perfect matches ("N-perfect-match") in the alignment is determined (a perfect match means same amino acid residue in same position of the alignment, usually designated with a "|" in the alignment). The length of the specified sequence (the number of amino acid residues) is determined ("N-specified", in the example mentioned above=413). The degree of identity is calculated as the ratio between "N-perfect-match" and "N-specified" (for conversion to percentage identity, multiply by 100).

In an alternative embodiment, the degree of identity between a target (or sample, or test) sequence and the specified sequence (e.g. amino acids 1 to 413 of SEQ ID NO: 10) is determined as follows: The two sequences are aligned using the program "align." The number of perfect matches ("N-perfect-match") in the alignment is determined (a perfect match means same amino acid residue in same position of the alignment, usually designated with a "|" in the alignment).

The common length of the two aligned sequences is also determined, viz. the total number of amino acids in the overlapping part of the alignment ("N-overlap"). The degree of identity is calculated as the ratio between "N-perfect-match" and "N-overlap" (for conversion to percentage identity, multiply by 100). In one embodiment, N-overlap includes trailing and leading gaps created by the alignment, if any. In another embodiment, N-overlap excludes trailing and leading gaps created by the alignment, if any.

In another alternative embodiment, the degree of identity between a target (or sample, or test) sequence and a specified sequence (e.g. amino acids 1 to 413 of SEQ ID NO: 10) is determined as follows: The sequences are aligned using the program "align." The number of perfect matches ("N-perfect-match") in the alignment is determined (a perfect match means same amino acid residue in same position of the alignment, usually designated with a "|" in the alignment). The length of the target sequence (the number of amino acid residues) is determined ("N-target"). The degree of identity is calculated as the ratio between "N-perfect-match" and "N-target" (for conversion to percentage identity, multiply by 100).

Preferably, the overlap is at least 20% of the specified sequence ("N-overlap" as defined above, divided by the number of the amino acids in the specified sequence ("N-specified"), and multiplied by 100), more preferably at least 25%, 30%, 35%, 40%, 45%, 50%, 55%, 60%, 65%, 70%, 75%, 80%, 85%, 90%, or at least 95%. This means that at least 20% (preferably 25-95%) of the amino acids of the specified sequence end up being included in the overlap, when the sample sequence is aligned to the specified sequence.

In the alternative, the overlap is at least 20% of the target (or sample, or test) sequence ("N-overlap" as defined above, divided by "N-target" as defined above, and multiplied by 100), more preferably at least 25%, 30%, 35%, 40%, 45%, 50%, 55%, 60%, 65%, 70%, 75%, 80%, 85%, 90%, or at least 95%. This means that at least 20% (preferably 25-95%) of the amino acids of the target sequence end up being included in the overlap, when aligned against the specified sequence).

Polypeptide Fragment: The term "polypeptide fragment" is defined herein as a polypeptide having one or more amino acids deleted from the amino and/or carboxyl terminus of the mature peptide part of the specified sequence, e.g. SEQ ID NO: 10, or a homologous sequence thereof, wherein the fragment has phytase activity. In particular embodiments, the fragment contains at least 350, 360, 370, 380, 390, 400, 405, or at least 410 amino acid residues.

Subsequence: The term "subsequence" is defined herein as a nucleotide sequence having one or more nucleotides deleted from the 5' and/or 3' end of the mature peptide encoding part of the specified sequence, e.g. SEQ ID NO: 9, or a homologous sequence thereof, wherein the subsequence encodes a polypeptide fragment having phytase activity. In particular embodiments, the subsequence contains at least 1050, 1080, 1110, 1140, 1170, 1200, 1215, 1230, 1245, 1260, 1275, 1290, 1305, 1320, or at least 1335 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Mature polypeptide part: When used herein the terms "mature polypeptide part" or "mature peptide part" refer to that part of the polypeptide which is secreted by a cell which contains, as part of its genetic equipment, a polynucleotide encoding the polypeptide. In other words, the mature polypeptide part refers to that part of the polypeptide which remains after the signal peptide part is cleaved off once it has fulfilled its function of directing the encoded polypeptide into the cell's secretory pathway. The predicted signal peptide part of SEQ ID NO: 10 is amino acids −33 to −1 thereof, which means that the predicted mature polypeptide part of SEQ ID NO: 10 corresponds to amino acids 1 to 413 thereof. However, a slight variation may occur from host cell to host cell, and therefore the expression mature polypeptide part is preferred.

Mature polypeptide encoding part: When used herein the term "mature polypeptide encoding part" or "mature polypeptide coding sequence" refers to that part of the polynucleotide encoding the polypeptide which encodes the mature polypeptide part. For example, for SEQ ID NO: 9, the predicted mature polypeptide encoding part corresponds to nucleotides 100 to 1338 (encoding amino acids 1 to 413 of SEQ ID NO: 10).

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the specified polypeptide, e.g. the polypeptide consisting of the amino acids 1 to 413 of SEQ ID NO: 10, as well as genetic manipulation of the DNA encoding that polypeptide. The modification(s) can be substitution(s), deletion(s) and/or insertions(s) of the amino acid(s) as well as replacement(s) of amino acid side chain(s).

Artificial variant: When used herein, the term "artificial variant" means a polypeptide having phytase activity produced by an organism expressing a modified nucleotide sequence of mature phytase encoding part of SEQ ID NO: 9. The modified nucleotide sequence is obtained through human intervention by modification of the mature phytase encoding part of the nucleotide sequence disclosed in SEQ ID NO: 9.

DETAILED DESCRIPTION OF THE INVENTION

Polypeptides Having Phytase Activity

In a first aspect, the present invention relates to isolated polypeptides having phytase activity and having an amino acid sequence which has a degree of identity to amino acids 1 to 413 of SEQ ID NO: 10 (i.e., the mature polypeptide) of at least 75%.

In particular embodiments, the degree of identity is at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%, which have phytase activity (hereinafter "homologous polypeptides").

In other particular embodiments, the homologous polypeptides have an amino acid sequence which differs by 20, 19, 18, 17, 16, 15, 14, 13, 12, 11, 10, 9, 8, 7, 6, 5, 4, 3, 2, or 1 amino acid from amino acids 1 to 413 of SEQ ID NO: 10.

In particular embodiments, the polypeptide of the present invention comprises the mature part of the amino acid sequence of SEQ ID NO: 10, or is an allelic variant thereof; or a fragment thereof that has phytase activity. In still further particular embodiments, the polypeptide comprises amino acids 1 to 413 of SEQ ID NO: 10, or an allelic variant thereof; or a fragment thereof that has phytase activity.

In a second aspect, the present invention relates to isolated polypeptides having phytase activity which are encoded by polynucleotides which hybridize under at least medium, preferably medium, stringency conditions with (i) nucleotides 100 to 1338 of SEQ ID NO: 9, (ii) the mature polypeptide encoding part of SEQ ID NO: 9, and/or (iii) a complementary strand of any one of (i), and (ii), and/or (iv) a subsequence of (i), (ii), or (iii) (J. Sambrook, E. F. Fritsch, and T. Maniatus, 1989, Molecular Cloning, A Laboratory Manual, 2d edition, Cold Spring Harbor, N.Y.). A subsequence of SEQ ID NO: 9 contains at least 100 contiguous nucleotides or preferably at least 200 contiguous nucleotides. Moreover, the subsequence may encode a polypeptide fragment which has phytase activity.

In particular embodiments, the hybridization takes place under at least medium-high, at least high, or at least very high stringency conditions; preferably under medium-high, high, or very high stringency conditions.

In alternative embodiments, the hybridization is conducted under very low, or low stringency conditions.

The nucleotide sequence of SEQ ID NO: 9, or a subsequence thereof, as well as the amino acid sequence of SEQ ID NO: 10, or a fragment thereof, may be used to design a nucleic acid probe to identify and clone DNA encoding polypeptides having phytase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from such other organisms may, therefore, be screened for DNA which hybridizes with the probes described above and which encodes a polypeptide having phytase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 9, or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 9, the complementary strand thereof, or a subsequence thereof, under very low to very high stringency conditions. Molecules to which the nucleic acid probe hybridizes under these conditions can be detected using X-ray film.

In a particular embodiment, the nucleic acid probe is any one of SEQ ID NOs: 1-8. In another particular embodiment, the nucleic acid probe is the complementary strand of nucleotides 100 to 450, nucleotides 450 to 900, or nucleotides 900 to 1338 of SEQ ID NO: 9. In a further particular embodiment, the nucleic acid probe is a polynucleotide sequence which encodes the mature part of the polypeptide of SEQ ID NO: 10, or a subsequence thereof. In a still further particular embodiment, the nucleic acid probe is SEQ ID NO: 9, in particular any one of the mature polypeptide coding regions thereof.

For long probes of at least 100 nucleotides in length, very low to very high stringency conditions are defined as prehybridization and hybridization at 42° C. in 5×SSPE, 0.3% SDS, 200 microgram/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[\text{Na}^+]) + 0.41(\% \ G+C) - 0.72(\% \text{ formamide})$$

(See www.ndsu.nodak.edu/instruct/mcclean/plsc731/dna/dna6.htm)

"G+C" designates the content of nucleotides G and T in the probe. For medium stringency, for example, the formamide is 35% and the Na$^+$ concentration for 5×SSPE is 0.75 M.

In one aspect, the present invention relates to isolated polypeptides having phytase activity, and the following physicochemical properties (as analyzed on the substantially pure polypeptides):

(i) a high specific activity, such as a specific activity on phytate of at least 50% of the specific activity of *E. coli* appA (SPTREMBL:Q8GN88), the specific activity being preferably measured in the units of FYT per mg phytase enzyme protein;

(ii) acid-stability; such as (a) at least 60%, preferably at least 65%, at least 70%, or at least 75%, residual activity after incubation over night at 37° C. in glycine/hydrochloric acid buffer pH 2.2, relative to the residual activity after incubation over night at 37° C. in HEPES buffer pH 7.0;

(b) at least 80%, preferably at least 85%, at least 90%, or at least 95%, residual activity after incubation over night at 370° C. in glycine/hydrochloric acid buffer pH 3.0, relative to the residual activity after incubation over night at 37° C. in HEPES buffer pH 7.0; and/or (c) a residual phytase activity after 2 hours incubation at a temperature of 25, 30, 35, or 37° C., preferably 370° C., and a pH of 2.2, 2.4, 2.5, 2.6, 2.8, 3.0, 3.2, 3.4, or 3.5, preferably glycine/hydrochloric acid buffers of pH 2.2, or 3.0, of at least 50%, compared to the residual activity of *E. coli* appA (SPTREMBL:Q8GN88);

(iii) heat-stability, such as a residual phytase activity after 0.5, 1, 1.5, or 2 hours, preferably 0.5 hours, of incubation at a pH of 5.5 and a temperature of 55, 60, 65, 70, 75, 80, 85 or 95° C., preferably 70° C., of at least 50%, compared to the residual activity of *E. coli* appA (SPTREMBL:Q8GN88);

In the alternative, Differential Scanning Calorimetry (DSC) measurements may be used to determine the denaturation temperature, Td, of the purified phytase protein. The Td is indicative of the heat-stability of the protein: The higher the Td, the higher the heat-stability. DSC measurements may be performed at various pH values, e.g. using the VP-DSC from Micro Cal. Scans are performed at a constant scan rate of 1.5° C./min from 20-90° C. Preferred pH values are 4.0 and 5.5, preferably 4.0. Before running the DSC, the phytases are desalted, e.g. using NAP-5 columns (Pharmacia) equilibrated in appropriate buffers (e.g. 25 mM sodium acetate pH 4.0; 0.1M sodium acetate, pH5.5). Data-handling is performed using the MicroCal Origin software (version 4.10), and the denaturation temperature, Td (also called the melting temperature, Tm) is defined as the temperature at the apex of the peak in the thermogram.

(iv) protease-stability, such as a residual phytase activity after 0.5, 1, 1.5, or 2 hours, preferably 1 hour, incubation at a temperature of 20, 25, 30, 35, or 37° C., preferably 37° C., and a pH of 5.5, in the presence of 0.1 mg/ml pepsin, of at least 50%, compared to the residual activity of *E. coli* appA (SPTREMBL:Q8GN88); and/or (v) a pH-optimum below pH 5.0, for example below pH 4.5, 4.0, 3.5, 3.0, 2.5, or even below 2.0, determined using the FYT assay, and/or using the assay of Example 4, as described hereinbefore.

In particular embodiments of aspect (i) above, the specific activity is at least 60, 70, 80, 90, 100, 110, 120, 130, 140, or at least 150% of the specific activity of *E. coli* appA. In particular embodiments of each of aspects (ii) to (iv) above, the residual activity is at least 60, 70, 80, 90, 100, 110, 120, 130, 140, or at least 150% of the residual activity of *E. coli* appA.

In a fifth aspect, the activity of the enzyme of the invention, at pH 5.0 and 37° C., measured on the substrate pNP-phosphate is less than 11% of the activity of the enzyme measured on the substrate phytate. Preferably, the ratio is less than 10%, 9%, 8%, 7%, 6%, or less than 5%. The ratio of pNP to phytate hydrolysis is indicative of the true phytase nature of the enzyme. A high ratio of activity on pNP relative to activity on phytate may indicate that the enzyme in question is a phosphatase with relatively low substrate specificity, whereas a low ratio indicates that this is an enzyme more specifically accepting phytate as a substrate.

In a sixth aspect, the phytase of the invention has a higher release of phosphorous (P) in an in vitro model, as compared to the phytase from *Peniophora lycii*, preferably at least 110% thereof, more preferably at least 120%, 130%, or at least 140% thereof. In one embodiment, the phytase of the invention, dosed 0.25 FYT/g feed, releases at least 150% phosphorous (P), relative to the phosphorous released by the phytase from *Peniophora lycii*, also dosed 0.25 FYT/g feed, in the in vitro model. Preferably, the release is at least 155%, 160%, 165%, 170%, 175%, or at least 180%. In another embodiment, the phytase of the invention, dosed 0.75 FYT/g feed, releases at least 150% phosphorous (P), relative to the phosphorous released by the phytase from *Peniophora lycii*, also dosed 0.75 FYT/g feed, in the in vitro model. Preferably, the release is at least 155%, 160%, 165%, 170%, 175%, 180%, 185%, or at least 190%.

In a seventh aspect, the phytase of the invention has a residual activity following incubation at 37° C. and in a 0.1M Glycine/HCl buffer, pH 2.0, for 4 hours of at least 20%, as compared to the activity at time, t=0, the activity (and the residual activity) being assayed at 37° C. and pH 5.5 on 1% (w/v) Na-phytate, using a 0.25 M Na-acetate buffer pH 5.5, buffer blind subtracted. In preferred embodiments, the residual activity is at least 25%, 30%, 35%, 40%, 45%, 50%, 55%, 60%, 65%, 70%, 75%, or at least 80%. In another embodiment, the phytase of the invention has a residual activity following incubation at 37° C. and in a 0.1M Glycine/HCl buffer, pH 2.5, for 1 day (24 hours) of at least 20%, as compared to the activity at time, t=0, the activity (and the residual activity) being assayed at 37° C. and pH 5.5 on 1% (w/v) Na-phytate, using a 0.25 M Na-acetate buffer pH 5.5, buffer blind subtracted. In preferred embodiments, the residual activity is at least 25%, 30%, 35%, 40%, 45%, 50%, 55%, 60%, 65%, 70%, 75%, or at least 80%.

In an eighth aspect, the present invention relates to artificial variants comprising a conservative substitution, deletion, and/or insertion of one or more amino acids of SEQ ID NO: 10, or the mature polypeptide thereof. An insertion can be inside the molecule, and/or at the N- and/or C-terminal end of the molecule in which case it is also designated extension. Preferably, amino acid changes are of a minor nature, that is conservative amino acid substitutions; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain—in other words: Changes that do not significantly affect the folding and/or activity of the protein.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine).

Other examples of conservative substitutions are substitutions of the 20 standard amino acids with non-standard amino acids (such as 4-hydroxyproline, 6-N-methyl lysine, 2-aminoisobutyric acid, isovaline, and alpha-methyl serine). Conservative substitutions may also include a substitution into amino acids that are not encoded by the genetic code, and unnatural amino acids. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., phytase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include errorprone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions (preferably conservative substitutions), deletions and/or insertions in the sequence of amino acids 1 to 413 of SEQ ID NO: 10 is at most 10, preferably at most 9, more preferably at most 8, more preferably at most 7, more preferably at most 6, more preferably at most 5, more preferably at most 4, even more preferably at most 3, most preferably at most 2, and even most preferably 1.

The total number of amino acid substitutions, deletions and/or insertions of amino acids 1 to 413 of SEQ ID NO: 10 is 10, preferably 9, more preferably 8, more preferably 7, more preferably at most 6, more preferably at most 5, more preferably 4, even more preferably 3, most preferably 2, and even most preferably 1. In the alternative, the total number of amino acid substitutions (preferably conservative substitutions), deletions and/or insertions in the sequence of amino acids 1 to 413 of SEQ ID NO: 10 is at most 50, 45, 40, 35, 30, 25, 20, 19, 18, 17, 16, 15, 14, 13, 12, or at most 11.

In a specific embodiment, the polypeptide of the invention is a low-allergenic variant, designed to invoke a reduced immunological response when exposed to animals, including man. The term immunological response is to be understood as any reaction by the immune system of an animal exposed to the polypeptide. One type of immunological response is an allergic response leading to increased levels of IgE in the exposed animal. Low-allergenic variants may be prepared using techniques known in the art. For example the polypeptide may be conjugated with polymer moieties shielding portions or epitopes of the polypeptide involved in an immunological response. Conjugation with polymers may involve in vitro chemical coupling of polymer to the polypeptide, e.g. as described in WO 96/17929, WO98/30682, WO98/35026, and/or WO99/00489. Conjugation may in addition or alternatively thereto involve in vivo coupling of polymers to the polypeptide. Such conjugation may be achieved by genetic engineering of the nucleotide sequence encoding the polypeptide, inserting consensus sequences encoding additional glycosylation sites in the polypeptide and expressing the polypeptide in a host capable of glycosylating the polypeptide, see e.g. WO00/26354. Another way of providing low-allergenic variants is genetic engineering of the nucleotide sequence encoding the polypeptide so as to cause the polypeptide to self-oligomerize, effecting that polypeptide monomers may shield the epitopes of other polypeptide monomers and thereby lowering the antigenicity of the oligomers. Such products and their preparation is described e.g. in WO96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the polypeptide by known gene manipulation techniques such as site directed mutagenesis (see e.g. WO 00/26230, WO 00/26354 and/or WO00/22103) and/or conjugation of a polymer may be done in sufficient proximity to the epitope for the polymer to shield the epitope.

Three Dimensional Structure of a *Hafnia alvei* Phytase

The three-dimensional structure of a *Hafnia alvei* phytase (amino acids 1 to 413 of SEQ ID NO:10) is provided in the Appendix. The structure was solved in accordance with the principles for x-ray crystallographic methods, for example, as given in X-Ray Structure Determinations, Stout, G. K. and Jensen, L. H., John Wiley and Sons, Inc. NY 1989. The structural coordinates for the solved crystal structure of *Hafnia alvei* phytase are given in standard PDB format (Protein Database Bank, Brookhaven National Laboratory, Brookhaven, Conn.) as set forth in the Appendix. It is to be understood that the Appendix forms part of the present application. The Appendix provides the coordinates of the heavy atoms, excluding the hydrogen atoms. The first three residues of the enzyme were not visible in the crystal structure as well as the amino acid residues between amino acids 180 and 189. However, the structure between 180 and 189 was built using modelling combining the homology modelling (see, for example, Marti-Renom et al., 2000) program NEST from the JACKAL package (wiki.c2b2.columbia.edu/honiglab_public/index.php/Software:Jackal) and the simulation software called CHARMm (//accelrys.com/products/scitegic/component-collections/charmm.html).

Sources of Polypeptides Having Phytase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, or a *Streptomyces* polypeptide; or a gram negative bacterial polypeptide, e.g., an *Escherichia coli, Yersinia, Klebsiella, Citrobacter*, or a *Pseudomonas* polypeptide. In a particular embodiment, the polypeptide is derived from Proteobacteria, such as Gammaproteobacteria, for example Enterobacteriales, such as Enterobacteriaceae.

In a particular aspect, the polypeptide derived from Enterobacteriaceae is a *Hafnia* polypeptide, such as a *Hafnia alvei* species polypeptide.

A polypeptide of the present invention may also be a fungal polypeptide, such as a yeast polypeptide or a filamentous fungal polypeptide.

Strains of the above microorganisms are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter (s) and terminator.

Polynucleotides

The present invention also relates to isolated polynucleotides having a nucleotide sequence which encodes a polypeptide of the present invention. In a preferred aspect, the nucleotide sequence is set forth in SEQ ID NO: 9. In another preferred aspect, the nucleotide sequence is the mature polypeptide coding region of SEQ ID NO: 9. The present invention also encompasses nucleotide sequences which encode a polypeptide having the amino acid sequence of SEQ ID NO: 10, or the mature polypeptides thereof, which differ from SEQ ID NO: 9, by virtue of the degeneracy of the genetic code. The present invention also relates to subsequences of SEQ ID NO: 9, which encode fragments of SEQ ID NO: 10, that have phytase activity.

The present invention also relates to mutant polynucleotides comprising at least one mutation in the mature polypeptide coding sequence of any one of SEQ ID NO: 9, in which the mutant nucleotide sequence encodes a polypeptide which consists of amino acids 1 to 413 of SEQ ID NO: 10.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Hafnia*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 9 (i.e., nucleotides 100 to 1338) of at least 75%, and which encode a polypeptide having phytase activity. In particular embodiments, the degree of identity is at least In particular embodiments, the degree of identity is at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%. In alternative embodiments, the degree of identity is at least 75%, 80%, 85%, 90%, 94, 97, 98, 98.0, 98.1, 98.2, or at least 98.3%.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH-optimum, or the like. The variant sequence may be constructed on the basis of the nucleotide sequence presented as the polypeptide encoding region of SEQ ID NO: 9, e.g., a subsequence thereof, and/or by introduction of nucleotide substitutions which do not give rise to another amino acid sequence of the polypeptide encoded by the nucleotide sequence, but which correspond to the codon usage of the host organism intended for production of the polypeptide, or by introduction of nucleotide substitutions which may give rise to a different amino acid sequence. For a general description of nucleotide substitution, see, e.g., Ford et al., 1991, Protein Expression and Purification 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for phytase activity to identify amino acid residues that are critical to the activity of the molecule. Sites of substrate-polypeptide interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The present invention also relates to isolated polynucleotides encoding a polypeptide of the present invention, which hybridize under medium stringency conditions, more preferably medium-high stringency conditions, even more preferably high stringency conditions, and most preferably very high stringency conditions with (i) nucleotides 100 to 1338 of SEQ ID NO: 9, (ii) the mature polypeptide encoding part of SEQ ID NO: 9, and/or (iii) a complementary strand of any one of (i), and/or (ii); or allelic variants and subsequences thereof (Sambrook et al., 1989, supra), as defined herein. In alternative embodiments the hybridization is conducted under very low, or low, stringency conditions.

The present invention also relates to isolated polynucleotides obtained, or obtainable, by (a) hybridizing a population of DNA under very low, low, medium, medium-high, high, or very high stringency conditions with (i) nucleotides 100 to 1338 of SEQ ID NO: 9, (ii) the mature polypeptide encoding part of SEQ ID NO: 9, and/or (iii) a complementary strand of any one of (i), and/or (ii); and (b) isolating the hybridizing polynucleotide, which encodes a polypeptide having phytase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), Bacillus amyloliquefaciens alpha-amylase gene (amyQ), Bacillus licheniformis penicillinase gene (penP), Bacillus subtilis xylA and xylB genes, and prokaryotic beta-lactamase gene (VIIIa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase II, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), *Saccharomyces cerevisiae* 3-phosphoglycerate kinase, and *Pichia pastoris* alcohol oxidase (AOX1). Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra, and by Xiong et al in Journal of Applied Microbiology 2005, 98, 418-428.

In a preferred aspect, the signal peptide coding region is nucleotides 1 to 99 of SEQ ID NO: 9, which encode amino acids 1 to 33 of SEQ ID NO: 10. In another preferred aspect, the signal peptide coding region is nucleotides 1 to 81 of SEQ ID NO: 11, which encode amino acids 1 to 27 of SEQ ID NO: 12.

The control sequence may also be a propeptide coding region that codes for an amino acid sequence positioned at the amino terminus of a polypeptide. The resultant polypeptide is known as a propolypeptide or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis*, *Bacillus licheniformis*, or other Bacilli, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, Gene 98:61-67; Cullen et al., 1987, Nucleic Acids Research 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Pichia pastoris, Pichia methanolica, Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa*, or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Hafnia*, and more preferably *Hafnia alvei*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of any one of SEQ ID NO: 9, wherein the mutant nucleotide sequence encodes a polypeptide which consists of amino acids 1 to 413 of SEQ ID NO: 10, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of a polypeptide product, or disappearance of an polypeptide substrate. For example, an polypeptide assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Transgenic Plants

The present invention also relates to a transgenic plant, plant part, or plant cell which has been transformed with a nucleotide sequence encoding a polypeptide having phytase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and Theological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, triticale (stabilized hybrid of wheat (Triticum) and rye (Secale), and maize (corn). Examples of dicot plants are tobacco, legumes, such as sunflower (Helianthus), cotton (Gossypium), lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. No. 5,689,054 and U.S. Pat. No. 6,111,168 are examples of engineered plants.

Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, Plant Physiology 86: 506.

For constitutive expression, the following promoters may be used: The 35S-CaMV promoter (Franck et al., 1980, Cell 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol. 18, 675-689; Zhang W, McElroy D. and Wu R 1991, Analysis of rice Act1 5' region activity in transgenic rice plants. Plant Cell 3, 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the *chlorella* virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may be inducible by abiotic treatments such as temperature, drought or alterations in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the polypeptide in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using e.g. co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having phytase activity of the present invention under conditions conducive for production of the polypeptide; and (b) recovering the polypeptide.

Transgenic Animals

The present invention also relates to a transgenic, non-human animal and products or elements thereof, examples of which are body fluids such as milk and blood, organs, flesh, and animal cells. Techniques for expressing proteins, e.g. in mammalian cells, are known in the art, see e.g. the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having phytase activity of the present invention so as to express and produce the polypeptide. The polypeptide may be recovered from the animal, e.g. from the milk of female animals, or the polypeptide may be expressed to the benefit of the animal itself, e.g. to assist the animal's digestion. Examples of animals are mentioned below in the section headed Animal Feed.

To produce a transgenic animal with a view to recovering the polypeptide from the milk of the animal, a gene encoding the polypeptide may be inserted into the fertilized eggs of an animal in question, e.g. by use of a transgene expression vector which comprises a suitable milk protein promoter, and the gene encoding the polypeptide. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see e.g. Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the polypeptide, the transgene may be operably linked to a first regulatory sequence for salivary gland specific expression of the polypeptide, as disclosed in WO 00/064247.

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. For instance, the polypeptide composition may be in the form of granulates or microgranulates. The polypeptide to be included in the composition may be stabilized in accordance with methods known in the art.

The phytase of the invention can be used for degradation, in any industrial context, of, for example, phytate, phytic acid, and/or the mono-, di-, tri-, tetra- and/or penta-phosphates of myo-inositol. It is well known that the phosphate moieties of these compounds chelates divalent and trivalent cations such as metal ions, i.a. the nutritionally essential ions of calcium, iron, zinc and magnesium as well as the trace minerals manganese, copper and molybdenum. Besides, the phytic acid also to a certain extent binds proteins by electrostatic interaction.

Accordingly, preferred uses of the polypeptides of the invention are in animal feed preparations (including human food) or in additives for such preparations.

In a particular embodiment, the polypeptide of the invention can be used for improving the nutritional value of an animal feed. Non-limiting examples of improving the nutritional value of animal feed (including human food), are: Improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating the need for adding supplemental phosphate, trace minerals, and/or macro minerals; and/or improving egg shell quality. The nutritional value of the feed is therefore increased, and the growth rate and/or weight gain and/or feed conversion (i.e. the weight of ingested feed relative to weight gain) of the animal may be improved.

Furthermore, the polypeptide of the invention can be used for reducing phytate level of manure.

Animals, Animal Feed, and Animal Feed Additives

The term animal includes all animals, including human beings. Examples of animals are non-ruminants, and ruminants. Ruminant animals include, for example, animals such as sheep, goats, horses, and cattle, e.g. beef cattle, cows, and young calves. In a particular embodiment, the animal is a non-ruminant animal. Non-ruminant animals include monogastric animals, e.g. pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the polypeptide can be fed to the animal before, after, or simultaneously with the diet. The latter is preferred.

In a particular embodiment, the polypeptide, in the form in which it is added to the feed, or when being included in a feed additive, is substantially pure. In a particular embodiment it is well-defined. The term "well-defined" means that the phytase preparation is at least 50% pure as determined by Size-exclusion chromatography (see Example 12 of WO 01/58275). In other particular embodiments the phytase preparation is at least 60, 70, 80, 85, 88, 90, 92, 94, or at least 95% pure as determined by this method.

A substantially pure, and/or well-defined polypeptide preparation is advantageous. For instance, it is much easier to dose correctly to the feed a polypeptide that is essentially free from interfering or contaminating other polypeptides. The term dose correctly refers in particular to the objective of obtaining consistent and constant results, and the capability of optimising dosage based upon the desired effect.

For the use in animal feed, however, the phytase polypeptide of the invention need not be that pure; it may e.g. include other polypeptides, in which case it could be termed a phytase preparation.

The phytase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

Polypeptide preparations with purities of this order of magnitude are in particular obtainable using recombinant methods of production, whereas they are not so easily obtained and also subject to a much higher batch-to-batch variation when the polypeptide is produced by traditional fermentation methods.

Such polypeptide preparation may of course be mixed with other polypeptides.

The polypeptide can be added to the feed in any form, be it as a relatively pure polypeptide, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the polypeptide of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g. carotenoids such as beta-carotene, astaxanthin, and lutein; aroma compounds; stabilisers; antimicrobial peptides; polyunsaturated fatty acids; reactive oxygen generating species; and/or at least one other polypeptide selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other polypeptides are well-defined (as defined above for phytase preparations).

In a particularly preferred embodiment, the phytase of the invention having a relatively low pH-optimum is combined with at least one phytase having a higher pH-optimum. Preferred examples of phytases of higher pH-optimum are *Bacillus* phytases, such as the phytases from *Bacillus licheniformis* and *Bacillus subtilis*, as well as derivatives, variants, or fragments thereof having phytase activity.

The phytase of the invention may also be combined with other phytases, for example ascomycete phytases such as *Aspergillus* phytases, for example derived from *Aspergillus ficuum, Aspergillus niger*, or *Aspergillus awamori*; or basidiomycete phytases, for example derived from *Peniophora lycii, Agrocybe pediades, Trametes pubescens*, or *Paxillus involutus*; or derivatives, fragments or variants thereof which have phytase activity.

Thus, in preferred embodiments of the use in animal feed of the invention, and in preferred embodiments of the animal feed additive and the animal feed of the invention, the phytase of the invention is combined with such phytases.

The above-mentioned ascomycete and basidiomycete phytases, in particular the RONOZYME P phytase derived from *Peniophora lycii* as well as derivatives, variants, and fragments thereof, may also be combined with *Bacillus* phytases, in particular the *B. licheniformis* phytase as well as with a derivative, fragment or variant thereof, in particular for animal feed purposes.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a synthethase.

Usually fat- and water-soluble vitamins, as well as trace minerals form part of a so-called premix intended for addition to the feed, whereas macro minerals are usually separately added to the feed. Either of these composition types, when enriched with a polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning 9 additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-0 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Polypeptides can be added as solid or liquid polypeptide formulations. For example, a solid polypeptide formulation is typically added before or during the mixing step; and a liquid polypeptide preparation is typically added after the pelleting step. The polypeptide may also be incorporated in a feed additive or premix.

The final polypeptide concentration in the diet is within the range of 0.01-200 mg polypeptide protein per kg diet, for example in the range of 0.1-10 mg/kg animal diet (typical dosage is in the range of 250 to 2000 FYT/kg animal diet).

The phytase of the invention should of course be applied in an effective amount, i.e. in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10—all these ranges being in mg phytase polypeptide protein per kg feed (ppm).

For determining mg phytase polypeptide protein per kg feed, the phytase is purified from the feed composition, and the specific activity of the purified phytase is determined using a relevant assay. The phytase activity of the feed composition as such is also determined using the same assay, and on the basis of these two determinations, the dosage in mg phytase protein per kg feed is calculated.

The same principles apply for determining mg phytase polypeptide protein in feed additives. Of course, if a sample is available of the phytase used for preparing the feed additive or the feed, the specific activity is determined from this sample (no need to purify the phytase from the feed composition or the additive).

Methods for Producing Fermentation Products

Yet another aspect of the present invention relates to the methods for producing a fermentation product, such as, e.g., ethanol, beer, wine, distillers dried grains (DDG), wherein the fermentation is carried out in the presence of a phytase of the present invention. Examples of fermentation processes include, for example, the processes described in WO 01/62947. Fermentation is carried out using a fermenting microorganism, such as, yeast.

In a particular embodiment, the present invention provides methods for producing fermentation product, comprising (a) fermenting (using a fermenting microorganism, such as yeast) a carbohydrate containing material (e.g., starch) in the presence of a phytase of the present invention and (b) producing the fermentation product from the fermented carbohydrate containing material.

In a particular embodiment, the present invention provides methods for producing ethanol, comprising fermenting (using a fermenting microorganism, such as yeast) a carbohydrate containing material (e.g., starch) in the presence of a phytase of the present invention and producing or recovering ethanol from the fermented carbohydrate containing material.

In another embodiment, the present invention provides methods for producing ethanol comprising a) hydrolyzing starch, e.g., by a liquefaction and/or saccharification process, a raw starch hydrolysis process, b) fermenting the resulting starch in the presence of a phytase of the present invention, and c) producing ethanol.

The phytase may be added to the fermentation process at any suitable stage and in any suitable composition, including alone or in combination with other enzymes, such as, one or more alpha-amylases, glucoamylases, proteases, and/or cellulases.

In another embodiment, the present invention provides methods for producing ethanol comprising hydrolyzing biomass, and fermenting (using a fermenting microorganism, such as yeast) the resulting biomass in the presence of a phytase of the present invention.

Signal Peptide

The present invention also relates to nucleic acid constructs comprising a gene encoding a protein operably linked to a first nucleotide sequence consisting of nucleotides 1 to 99 of SEQ ID NO: 9, encoding a signal peptide consisting of amino acids 1 to 33 of SEQ ID NO: 10, wherein the gene is foreign to the first nucleotide sequences.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The first nucleotide sequences may be operably linked to foreign genes individually with other control sequences or in combination with other control sequences. Such other control sequences are described supra.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, polypeptide, e.g., enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic polypeptide, peroxidase, phytase, polyphenoloxidase, proteolytic polypeptide, ribonuclease, transglutaminase or xylanase.

The gene may be obtained from any prokaryotic, eukaryotic, or other source.

Various Embodiments

The following are additional embodiments of the present invention. Also included herein are the corresponding aspects relating to nucleic acid sequences, nucleic acid constructs, recombinant expression vectors, recombinant host cells, methods for production of the polypeptides, transgenic plants and animals, and the various uses, methods of use and feed compositions/additives, all as claimed.

An isolated polypeptide having phytase activity and a residual activity following incubation at 37° C. and in a 0.1M Glycine/HCl buffer, pH 2.0, for 4 hours of at least 20%, as compared to the activity at time, t=0, the activity being assayed at 37° C. and pH 5.5 on 1% (w/v) Na-phytate, using a 0.25 M Na-acetate buffer pH 5.5, buffer blind subtracted; preferably with an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity and a residual activity following incubation at 37° C. and in a 0.1M Glycine/HCl buffer, pH 2.5, for 24 hours of at least 20%, as compared to the activity at time, t=0, the activity being assayed at 37° C. and pH 5.5 on 1% (w/v) Na-phytate, using a 0.25 M Na-acetate buffer pH 5.5, buffer blind subtracted; preferably with an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity, wherein the activity of the polypeptide, at pH 5.0 and 37° C., measured on the substrate pNP-phosphate is less than 11% of the activity of the polypeptide measured on the substrate phytate; preferably with an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity, wherein the polypeptide has a higher release of phosphorous (P), as compared to the phytase from *Peniophora lycii*; preferably as measured in the in vitro model; and/or, wherein the polypeptide preferably has an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity, wherein the polypeptide, dosed 0.25 FYT/g feed, releases at least 150% phosphorous (P), relative to the phosphorous released by the phytase from *Peniophora lycii*, also dosed 0.25 FYT/g feed; and/or, wherein the polypeptide preferably has an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity, wherein the polypeptide, dosed 0.75 FYT/g feed, releases at least 150% phosphorous (P), relative to the phosphorous released by the phytase from *Peniophora lycii*, also dosed 0.75 FYT/g feed; and/or, wherein the polypeptide preferably has an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

I. An isolated polypeptide having phytase activity, selected from the group consisting of: (a) a polypeptide having an amino acid sequence which has at least 75% identity with (i) amino acids 1 to 413 of SEQ ID NO: 10, and/or (ii) the mature polypeptide part of SEQ ID NO: 10, (b) a polypeptide which is encoded by a polynucleotide which hybridizes under at least medium stringency conditions with (i) nucleotides 100 to 1338 of SEQ ID NO: 9, (ii) the mature polypeptide encoding part of SEQ ID NO: 9, and/or (iii) a complementary strand of any one of (i), or (ii); (c) a variant of any one of the polypeptides of (a)(i)-(a)(ii), comprising a conservative substitution, deletion, and/or insertion of one or more amino acids; and (d) a fragment of any one of the polypeptides of (a)(i)-(a)(ii).

II. An isolated polynucleotide comprising a nucleotide sequence which encodes the polypeptide of section I.

III. An isolated polynucleotide encoding a polypeptide having phytase activity, selected from the group consisting of: (a) a polynucleotide encoding a polypeptide having an amino acid sequence which has at least 75% identity, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9% identity with amino acids 1 to 413 of SEQ ID NO: 10; (b) a polynucleotide having at least 75% identity, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9% identity with nucleotides 100 to 1338 of SEQ ID NO: 9; and (c) a polynucleotide which hybridizes under at least medium stringency conditions with (i) nucleotides 100 to 1338 of SEQ ID NO: 9, (ii) the mature polypeptide encoding part of SEQ ID NO: 9, (iii) a complementary strand of any one of (i), or (ii).

IV. The isolated polynucleotide of any one of sections II and III, having at least one mutation in the mature polypeptide coding sequence of SEQ ID NO: 9, in which the mutant nucleotide sequence encodes a polypeptide comprising amino acids 1 to 413 of SEQ ID NO: 10.

V. A nucleic acid construct comprising the polynucleotide of any one of sections II-IV operably linked to one or more control sequences that direct the production of the polypeptide in an expression host.

VI. A recombinant expression vector comprising the nucleic acid construct of section V.

VII. A recombinant host cell comprising the nucleic acid construct of section V.

VII. A method for producing the polypeptide of section I comprising (a) cultivating a cell, which in its wild-type form is capable of producing the polypeptide, under conditions conducive for production of the polypeptide; and (b) recovering the polypeptide.

IX. A method for producing the polypeptide of section I comprising (a) cultivating a recombinant host cell comprising a nucleic acid construct comprising a nucleotide sequence encoding the polypeptide under conditions conducive for production of the polypeptide; and (b) recovering the polypeptide.

X. A transgenic plant, plant part or plant cell, which has been transformed with a polynucleotide encoding the polypeptide of section I.

XI. A transgenic, non-human animal, or products, or elements thereof, being capable of expressing the polypeptide of section 1.

XII. Use of at least one polypeptide of section I in animal feed.

XIII. Use of at least one polypeptide of section I in the preparation of a composition for use in animal feed.

XIV. A method for improving the nutritional value of an animal feed, wherein at least one polypeptide of section I is added to the feed.

XV. An animal feed additive comprising (a) at least one polypeptide of section I; and (b) at least one fat soluble vitamin, (c) at least one water soluble vitamin, and/or (d) at least one trace mineral.

XVI. The animal feed additive of section XV, which further comprises at least one amylase, at least one additional phytase, at least one xylanase, at least one galactanase, at least one alpha-galactosidase, at least one protease, at least one phospholipase, and/or at least one beta-glucanase.

XVII. The animal feed additive of section XVI, wherein the additional phytase has a pH-optimum which is higher than the pH-optimum of the polypeptide having the amino acid sequence of amino acids 1 to 413 of SEQ ID NO: 10.

IIXX. An animal feed composition having a crude protein content of 50 to 800 g/kg and comprising at least one polypeptide of section I.

A polypeptide having phytase activity which comprises, preferably has or consists of, an amino acid sequence which has at least 75% identity, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9% identity with amino acids 1 to 413 of SEQ ID NO: 10.

A polypeptide having phytase activity which comprises, preferably has, the sequence of
(i) amino acids 1 to 413 of SEQ ID NO: 10, and/or
(ii) the mature polypeptide part of SEQ ID NO: 10; or which polypeptide
(a) is a variant of any one of the polypeptides of (i)-(ii), comprising a deletion, insertion, and/or conservative substitution of one or more amino acids; or
(b) is a fragment of any one of the polypeptides of (i)-(ii).

The present invention is further described by the following examples which should not be construed as limiting the scope of the invention.

EXAMPLES

Example 1

Cloning of a *Hafnia alvei* Phytase Gene

A multiple alignment was made of the following histidine acid phosphatases (HAP): appA *Escherichia coli* (SP-TREMBL:Q8GN88), *Citrobacter gillenii* DSM 13694 phytase (geneseqp:aeh04533), *Citrobacter amalonaticus* ATCC 25407 phytase (geneseqp:aeh04535), *Citrobacter braakii* phytase (geneseqp:aeh04827), and ypo1648 *Yersinia pestis* CO92 (SPTREMBL:Q8ZFP6). Two degenerate oligonucleotide primers were designed on the basis of consensus sequences:

```
2123FW:
5'-CATGGTGTGCGNGCNCCNACNAA-3'          (SEQ ID NO:1)

2065rev:
5'-CCCACCAGGNGGNGTRTTTRTCNGGYTG-3',    (SEQ ID NO:2)
``` wherein Y designates T or C, R designates A or G, and N designates A, C, G or T.

The primers were used for PCR screening of a number of bacterial species at annealing temperatures between 40 and 50° C. but typical as touch down program starting with 50° C. and then reduced the annealing temperature with 1° C. for each cycle over the next 10 cycles before conducting standard PCR.

A partial phytase gene in the form of an approximately 950 bp PCR fragment was identified in *Hafnia alvei* (DSM 19197).

The PCR fragment was isolated from agarose gel and the fragment was sequenced using the same PCR primers the fragment was generated with. By translation of the nucleotide sequence, it was confirmed that the DNA fragment was part of a HAP phytase gene.

For obtaining the full length nucleotide sequence of the gene, the DNA WALKING SPEEDUP™ Kit (DWSK-V102 from Seegene, Inc., 2nd Fl., Myungji Bldg., 142-21, Samsung-dong, Kangnam-gu, Seoul, 135-090, Korea) was used, which is designed to capture unknown target sites. For this purpose, 6 specific oligonucleotides were designed and used with the kit.

```
2328 TSP1dw:
5'-ACTTGCATCGACGTTGGCTG        (SEQ ID NO: 3)

2329 TSP2dw:
5'-ACTGAGCAGCAATGGAACTCTCTG    (SEQ ID NO: 4)

2330 TSP3dw:
5'-ACTGGGTTCCAATATCACGAGTC     (SEQ ID NO: 5)

2331 TSP1up:
5'-ATGGTGGATCGCTAAATCACACTG    (SEQ ID NO: 6)

2332 TSP2up:
5'-ACGTCTGCCCAAACATACACG       (SEQ ID NO: 7)

2333 TSP3up:
5'-ACCGCCCATCAGGCTAATC         (SEQ ID NO: 8)
```

The full length nucleotide sequence encoding the phytase from *Hafnia alvei* DSM 19197 is shown in the sequence listing as SEQ ID NO: 9, and the corresponding encoded amino acid sequence is shown in SEQ ID NO: 10. The first 33 amino acids of SEQ ID NO:10 (i.e. amino acids −33 to −1) are a signal peptide, as predicted by the software Signal P V3.0 (see www.cbs.dtu.dk/services/SignalP/).

Example 2

Expression of the *Hafnia alvei* Phytase Gene

A 27 amino-acid signal peptide encoding polynucleotide of a native protease, Savinase™, from *Bacillus licheniformis* was fused by PCR in frame to the gene encoding the mature phytase from *Hafnia alvei*. The signal peptide coding sequence is shown in SEQ ID NO: 11, encoding the signal peptide of SEQ ID NO: 12.

The DNA coding for the fusion polypeptide was integrated by homologous recombination on a *Bacillus subtilis* host cell genome. The gene construct was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including the mRNA stabilizing sequence. The gene coding for Chloramphenicol acetyl-transferase was used as marker, as described in, e.g., Diderichsen et al., A useful cloning vector for *Bacillus subtilis*. Plasmid, 30, p. 312, 1993.

Chloramphenicol resistant transformants was cultured in PS-1 medium (10% sucrose, 4% soybean flour, 1% $Na_3PO_4 \cdot 12H_2O$, 0.5% $CaCO_3$, and 0.01% pluronic acid) shaken at 250 RPM at 30° C. After 2-5 days of incubation the supernatant was removed and the phytase activity was identified by applying 20 microliter of the supernatant into 4 mm diameter holes punched out in 1% LSB-agarose plates containing 0.1M Sodium acetate pH 4.5 and 0.1% Inositol hexaphosphoric acid. The plates were left over night at 37° C. and a buffer consisting of 0.25M $CaCl_2$ and 500 mM MES (adjusted to pH 6.5 with 4N NaOH) was poured over the plates. The plates were left at room temperature for 1 h and the inositolphosphate phosphatase, or phytase, activity was then identified as a clear zone.

Several phytase positive transformants were analyzed by DNA sequencing to ensure the correct DNA sequence of the constructs. One correct clone was selected.

Example 3

Fermentation of the *Hafnia* NN020125 Phytase Host

The selected clone of *Bacillus subtilis*, which was harboring the *Hafnia alvei* phytase construct and was capable of expressing the phytase (mature part) was cultivated at 30° C. and with 250 rpm for 6 days in SK-1M medium (Sodium Caseinate (Miprodan 30 from Aria) 40 g, Maltodextrin 01 (Glucidex 6, catalogue no. 332203 from Roquette), 200 g, Soybean Meal 50 g, Dowfax 63N10 (a non-ionic surfactant from Dow) 0.1 ml, tap water up to 1000 ml, $CaCO_3$ tablet 0.5 g/100 ml).

Example 4

Purification of *Hafnia alvei* Phytase

The fermentation supernatant with the phytase was first centrifuged at 7200 rpm and 5° C. for one hour and filtered through a sandwich of four Whatman glass microfibre filters (2.7, 1.6, 1.2 and 0.7 micrometer). Following this the solution was sterile filtered through a Seitz-EKS depth filter using pressure. Next, the filtered supernatant was pre-treated as follows:

The sample solution was washed with water and concentrated using an ultrafiltration unit (Filtron, from Filtron Technology Corporation) equipped with a 10 kDa cut-off ultrafiltration membrane. Then pH was adjusted to 4.5 with 10% (w/v) acetic acid, which caused a minor precipitation. No activity was found in the precipitate and it was removed by filtration through a Fast PES bottle top filter with a 0.22 micrometer cut-off.

After pretreatment the phytase was purified by chromatography on S Sepharose, approximately 50 ml in a XK26 column, using as buffer A 50 mM sodium acetate pH 4.5, and as buffer B 50 mM sodium acetate+1 M NaCl pH 4.5. The fractions from the column were analyzed for activity using the phosphatase assay (see below) and fractions with activity were pooled.

The solution was added solid ammonium sulfate giving a final concentration of 1.5 M and the pH was adjusted to 6.0 using 6 M HCl. The phytase-containing solution was applied to a butyl-sepharose column, approximately 30 ml in a XK26 column, using as buffer A 25 mM bis-tris (Bis-(2-hydroxyethyl)imino-tris(hydroxymethyl)methan))+1.5 M ammonium sulfate pH 6.0, and as buffer B 25 mM bis-tris pH 6.0. The fractions from the column were analyzed for activity using the phosphatase assay (see below) and fractions with activity were pooled. Finally, the solution containing the purified phytase was buffer-changed into 50 mM sodium acetate+ 0.1 M NaCl, pH 4.5 and concentrated using an Amicon ultra-15 filtering device with a 30 kDa cut-off membrane.

The molecular weight, as estimated from SDS-PAGE, was approximately 40 kDa and the purity was >95%.

Example 5

Activity Assays

Determination of Phosphatase Activity 75 microliter phytase-containing enzyme solution is dispensed in a microtiter plate well, e.g. NUNC 269620 and 75 microliter substrate is added (for preparing the substrate, two 5 mg p-nitrophenyl phosphate tablets (Sigma, Cat. No. N-9389) are dissolved in 10 ml 0.1 M Na-acetate buffer, pH 5.5). The plate is sealed and incubated 15 min., shaken with 750 rpm at 37° C. After the incubation time 75 microliter stop reagent is added (the stop reagent is 0.1 M di-sodiumtetraborate in water) and the absorbance at 405 nm is measured in a microtiter plate spectrophotometer.

Determination of Phytase Activity 75 microliter phytase-containing enzyme solution, appropriately diluted in 0.25M sodium acetate, 0.005% (w/v) Tween-20. pH5.5, is dispensed in a microtiter plate well, e.g. NUNC 269620, and 75 microliter substrate is added (prepared by dissolving 100 mg sodium phytate from rice (Aldrich Cat. No. 274321) in 10 ml 0.25M sodium acetate buffer, pH5.5). The plate is sealed and incubated 15 min. shaken with 750 rpm at 37° C. After incubation, 75 microliter stop reagent is added (the stop reagent being prepared by mixing 10 ml molybdate solution (10% (w/v) ammonium hepta-molybdate in 0.25% (w/v) ammonia solution), 10 ml ammonium vanadate (0.24% commercial product from Bie&Berntsen, Cat. No. LAB17650), and 20 ml 21.7% (w/v) nitric acid), and the absorbance at 405 nm is measured in a microtiter plate spectrophotometer. The phytase activity is expressed in the unit of FYT, one FYT being the amount of enzyme that liberates 1 micromole inorganic ortho-phosphate per minute under the conditions above. An absolute value for the measured phytase activity may be obtained by reference to a standard curve prepared from appropriate dilutions of inorganic phosphate, or by reference to a standard curve made from dilutions of a phytase enzyme preparation with known activity (such standard enzyme preparation with a known activity is available on request from Novozymes A/S, Krogshoejvej 36, DK-2880 Bagsvaerd).

Determination of Specific Phytase Activity

The specific activity of the phytase was determined in sodium acetate buffer, pH 5.5. The phytase was highly purified as described above, i.e. only one component was identified on an SDS poly acryl amide gel.

The protein concentration was determined by amino acid analysis as follows: An aliquot of the sample was hydrolyzed in 6M HCl, 0.1% phenol for 16 h at 110° C. in an evacuated glass tube. The resulting amino acids were quantified using an Applied Biosystems 420A amino acid analysis system operated according to the manufacturer's instructions. From the amounts of the amino acids the total mass—and thus also the concentration—of protein in the hydrolyzed aliquot was calculated.

The phytase activity was determined in the units of FYT as described above and the specific activity was calculated as the phytase activity measured in FYT units per mg phytase enzyme protein.

The resulting specific activity was 980 FYT/mg protein. The specific activity was determined on sodium phytate at pH5.5 and 37° C.

Example 6

Determination of the Phytase pH Profile

The pH profile was determined at 37° C. in the pH range of 2.0 to 7.5 (in 0.5 pH-unit steps) as described above in the section "Determination of phytase activity", except that a buffer cocktail (50 mM glycine, 50 mM acetic acid and 50 mM Bis-Tris was used instead of the 0.25M sodium acetate pH5.5 buffer. The results are summarized in table 1 below. The values given for each pH in the range of 2.0-7.5 are the relative activity in % normalized to the value at optimum.

TABLE 1

| pH profile | | | | | | | | | | | | |
|---|---|---|---|---|---|---|---|---|---|---|---|---|
| | pH | | | | | | | | | | | |
| Phytase | 2.0 | 2.5 | 3.0 | 3.5 | 4.0 | 4.5 | 5.0 | 5.5 | 6.0 | 6.5 | 7.0 | 7.5 |
| Hafnia alvei | 46 | 61 | 83 | 95 | 100 | 100 | 88 | 71 | 43 | 18 | 3 | 0 |

Example 7

Determination of the Phytase Isoelectric Point

The isoelectric point, pI, for the phytase was determined using isoelectric focusing gels (Novex pH 3 10 IEF gel from Invitrogen, catalog number EC6655A2) run as described by the manufacturer. The pI for the *Hafnia alvei* phytase is about 7.4.

Example 8

Phytase Temperature Profile

The temperature profile (phytase activity as a function of temperature) was determined for the *Hafnia alvei* phytase in the temperature range of 20-90° C. essentially as described above ("Determination of phytase activity"). However, the enzymatic reactions (100 microliter phytase-containing enzyme solution+100 microliter substrate) were performed in PCR tubes instead of microtiter plates. After a 15 minute reaction period at desired temperature the tubes were cooled to 20° C. for 20 seconds and 150 microliter of each reaction mixture was transferred to a microtiter plate. 75 microliter stop reagent was added and the absorbance at 405 nm was measured in a microtiter plate spectrophotometer. The results are summarized in Table 2 below. The numbers given for each temperature are relative activity (in %) normalized to the value at optimum.

TABLE 2

| Temperature profile | | | | | | | | | |
|---|---|---|---|---|---|---|---|---|---|
| | Temperature ° C. | | | | | | | | |
| | 20 | 30 | 40 | 50 | 55 | 60 | 65 | 70 | 80 | 90 |
| Relative activity | 17 | 27 | 45 | 69 | 79 | 85 | 100 | 95 | 7 | 0 |

Example 9

Phytase Thermostability

*Hafnia alvei* phytase expressed in both *Aspergillus oryzae* and *Bacillus subtilis* were subjected to thermostability measurements by Differential Scanning Calorimetry (DSC) and compared to the *E. coli* phytase (commercially available as PHYZYME XP from Danisco A/S).

An aliquot of the protein sample of *Hafnia alvei* phytase (purified as described in Example 4) was dialysed against 2×500 ml 20 mM Na-acetate, pH 4.0 at 4° C. in a 2-3 h step followed by an overnight step. The sample was 0.45 μm filtered and diluted with buffer to approx. 2 A280 units. The exact absorbance values measured are given in the results table shown below. The dialysis buffer was used as reference in Differential Scanning Calorimetry (DSC). The samples were degassed using vacuum suction and stirring for approx. 10 minutes. An aliquot of the *E. coli* phytase from the commercial product PHYZYME XP was purified in a similar fashion as described in Example 4.

A DSC scan was performed at a constant scan rate of 1.5° C./min from 20-80° C. Filtering period: 16 s. Before running the DSC, the phytases were dialyzed against the appropriate buffers (e.g. 0.1M glycine-HCl, pH 2.5 or 3.0; 20 mM sodium acetate pH 4.0; 0.1 M sodium acetate, pH 5.5; 0.1M Tris-HCl, pH 7.0). Data-handling was performed using the MicroCal Origin software (version 4.10), and the denaturation temperature, Td (also called the melting temperature, Tm) is defined as the temperature at the apex of the peak in the thermogram. To probe the reversibility of the unfolding process, a second scan was performed immediately after a short cooling phase. For the second scan the peak area (the area between the peak and the baseline=enthalpy of unfolding which is compared) is compared to the peak area of the first scan. A large peak (between 75-100% of the peak area of the first scan) is interpreted as a reversible unfolding/folding process.

The results of DSC for *Hafnia alvei* phytase expressed in both *Aspergillus oryzae* and *Bacillus subtilis* and the *E. coli* phytase are summarized in the Table 3 below.

TABLE 3

Comparative Thermostability of *Hafnia alvei* Phytase and *E. coli* Phytase

| Phytase | Buffer | A280 | Td 1st Scan (° C.) | TD 2nd Scan (° C.) | Relative peak size (actual area) on 2 scans |
|---|---|---|---|---|---|
| *Aspergillus* expressed *H. alvei* | 20 nM NaAc ph 4.0 | 3.2 | 70.2 | 70.3 | large |
| *Bacillus* expressed *H. alvei* | 20 nM NaAc pH 4.0 | 1.6 | 70.1 | 70.3 | large |
| *E. coli* | 20 nM NaAc pH 4.0 | 2.4 | 62.6 | 62.9 | medium |

As illustrated in the above table, the *Hafnia alvei* phytase had greater thermostability than the *E. coli* phytase. It is also clear that the thermostability of the *Hafnia alvei* phytase was not affected by the expression host.

Example 10

Gastric Proteolytic Resistance of *Hafnia alvei* Phytase and *E. coli* Phytase

Samples of *H. alvei* phytase and *E. coli* phytase (PHYZYME XP, available from Danisco) were treated with pepsin (Pepsin 1:60000 from Porcine Stomach Mucosa, Wako 162-18721, 2900 Units/mg, Lot SDK5232) in 250 mM glycine buffer pH 3.0 (approx. 1000 pepsin Units/mg phytase). Incubation for 30 minutes at 40° C. with shaking (750 rpm). Following incubation with pepsin, the phytase activity was determined as described in Example 5 and compared to the activity of a sample treated in the same way, but without addition of pepsin. The results are summarized in Table 4 below.

TABLE 4

Gastric Proteolytic Resistance of *Hafnia alvei* Phytase and *E. coli* Phytase

| Phytase | Mean (res. act. %) | |
|---|---|---|
| *E. coli* | 96 | result of two runs with results of 95% and 97% residual activity. |
| *H. alvei* | 95.5 | result of two runs with results of 97% and 94% residual activity. |

Thus, the *E. coli* phytase and *H. alvei* phytase had very similar gastro proteolytic resistance properties.

Example 11

Performance in Animal Feed in an In Vitro Model for the *Hafnia alvei* Phytase and *Citrobacter braakii* Phytase The performance in animal feed of the *Hafnia alvei* phytase was compared, in an in vitro model, to the performance of a *Citrobacter braakii* phytase. The in vitro model simulates gastro-intestinal conditions in a monogastric animal and correlates well with results obtained in animal trials in vivo. Phytase activity in the sample is determined as described in Example 5 under "Determination of phytase activity". The comparison was performed as follows:

Feed samples composed of 30% soybean meal and 70% maize meal with added $CaCl_2$ to a concentration of 5 g calcium per kg feed are then prepared and pre-incubated at 40° C. and pH 3.0 for 30 minutes followed by addition of pepsin (3000 U/g feed) and suitable dosages of the phytases (identical dosages are used for all phytases to be tested to allow comparison), for example between 0.1 to 1.0 phytase units FYT/g feed. A blank with no phytase activity was also included as reference. The samples was then incubated at 40° C. and pH 3.0 for 60 minutes followed by pH 4.0 for 30 minutes.

The reactions were stopped and phytic acid and inositol-phosphates extracted by addition of HCl to a final concentration of 0.5 M and incubation at 40° C. for 2 hours, followed by one freeze-thaw cycle and 1 hour incubation at 40° C.

Phytic acid and inositol-phosphates were separated by high performance ion chroma¬tography as described by Chen et al in Journal of Chromatography A (2003) vol. 1018, pp. 41-52 and quantified as described by Skog¬lund et al in J. Agric. Food Chem. (1997), vol. 45, pp. 431-436.

FIG. 1 shows a dose-response of the *Hafnia alvei* phytase compared to a *Citrobacter braakii* phytase at dosing of 125 FYT/kg feed, 250 FYT/kg feed and 500 FYT/kg feed. The effects of phytases in vitro are shown as the residual inositol-phosphate bound phosphorous (IP-P) remaining in a sample after in vitro incubation and compared to the residual IP-P remaining in a control sample without phytase. All numbers given are average and standard deviation of 4 or 5 replica (in vitro incubations). Dosing 250 FYT/kg of the *Hafnia* phytase reduced the amount of residual IP-P in the in vitro sample to about the same degree as 125 FYT/kg of the *Citrobacter* phytase.

Accordingly, the *Hafnia* phytase was able to obtain a very good reduction in the amount of residual inositol-phosphate bound phosphorous.

Example 12

Figure 2:
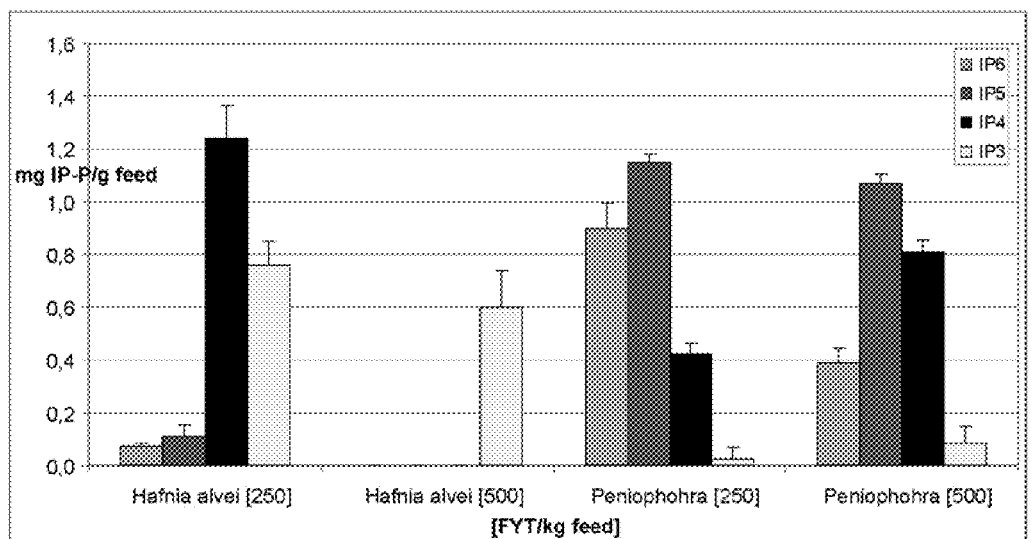
FIG. 2 shows a comparison of the residual inositol-phosphate bound phosphorous after in vitro incubation between the *Hafnia alvei* phytase and a *Peniophora lycii* phytase dosed at 250 FYT/kg Feed and 500 FYT/kg Feed.

Performance in Animal Feed in an In Vitro Model for the *Hafnia alvei* Phytase and *Peniophora lycii* Phytase The performance in animal feed of the *Hafnia alvei* phytase in an in vitro model was also compared to the performance of a *Peniophora lycii* phytase at dosing of 250 FYT/kg and 500 FYT/kg feed. The results were obtained following the experimental protocol as described in Example 11. As shown in FIG. 2, the *Hafnia alvei* phytase reduced the amount of residual IP-P in the in vitro sample better than the *Peniophora lycii* phytase.

---

The invention claimed is:

1. An isolated polypeptide having phytase activity selected from the group consisting of:
   (a) a polypeptide with at least 95% identity with (i) amino acids 1 to 413 of SEQ ID NO: 10, and/or (ii) the mature polypeptide part of SEQ ID NO: 10; or
   (b) a fragment of any one of the polypeptides of (a)(i)-(a)(ii);
   wherein the polypeptide has phytase activity.

2. The polypeptide of claim 1, which has at least 97% identity with the sequence of amino acids 1 to 413 of SEQ ID NO: 10.

3. The polypeptide of claim 1, which has at least 99% identity with the sequence of amino acids 1 to 413 of SEQ ID NO: 10.

4. The polypeptide of claim 1, which comprises the sequence of amino acids 1 to 413 of SEQ ID NO: 10.

5. The polypeptide of claim 1, which is a fragment of the sequence of amino acids 1 to 413 of SEQ ID NO: 10.

6. An animal feed additive comprising
   (a) at least one polypeptide of claim 1; and
   (b) at least one fat soluble vitamin, at least one water soluble vitamin, at least one trace mineral or combinations thereof.

7. The animal feed additive of claim 6, which further comprises at least one amylase, at least one additional phytase, at least one xylanase, at least one galactanase, at least one alpha-galactosidase, at least one protease, at least one phospholipase, and/or at least one beta-glucanase.

8. An animal feed composition having a crude protein content of 50 to 800 g/kg and comprising at least one polypeptide of claim 1.

9. A method for improving the nutritional value of an animal feed, comprising adding at least one polypeptide of claim 1 to the animal feed.

10. A method for producing a fermentation product, comprising
   (a) fermenting using a fermenting microorganism a carbohydrate containing material in the presence of a polypeptide of claim 1 and
   (b) producing the fermentation product or fermentation coproduct from the fermented carbohydrate containing material.

11. The method of claim 10, wherein the fermentation product is ethanol, beer, wine, or distillers dried grains (DDG).

* * * * *

```
SEQUENCE LISTING

<160> NUMBER OF SEQ ID NOS: 12

<210> SEQ ID NO 1
<211> LENGTH: 23
<212> TYPE: DNA
<213> ORGANISM: Artificial sequence
<220> FEATURE:
<223> OTHER INFORMATION: Primer 2123fw
<220> FEATURE:
<221> NAME/KEY: misc_feature
<222> LOCATION: (12)..(12)
<223> OTHER INFORMATION: N designates A, C, G or T.
<220> FEATURE:
<221> NAME/KEY: misc_feature
<222> LOCATION: (15)..(15)
<223> OTHER INFORMATION: N designates A, C, G or T.
<220> FEATURE:
<221> NAME/KEY: misc_feature
<222> LOCATION: (18)..(18)
<223> OTHER INFORMATION: N designates A, C, G or T.
<220> FEATURE:
<221> NAME/KEY: misc_feature
<222> LOCATION: (21)..(21)
<223> OTHER INFORMATION: N designates A, C, G or T.

<400> SEQUENCE: 1
catggtgtgc gngcnccnac naa                                          23

<210> SEQ ID NO 2
<211> LENGTH: 27
<212> TYPE: DNA
<213> ORGANISM: Artificial sequence
<220> FEATURE:
<223> OTHER INFORMATION: Primer 2065rev
<220> FEATURE:
<221> NAME/KEY: misc_feature
<222> LOCATION: (10)..(10)
<223> OTHER INFORMATION: N designates A, C, G or T.
<220> FEATURE:
<221> NAME/KEY: misc_feature
<222> LOCATION: (13)..(13)
<223> OTHER INFORMATION: N designates A, C, G or T.
<220> FEATURE:
<221> NAME/KEY: misc_feature
<222> LOCATION: (16)..(16)
<223> OTHER INFORMATION: R designates A or G.
<220> FEATURE:
<221> NAME/KEY: misc_feature
<222> LOCATION: (19)..(19)
<223> OTHER INFORMATION: R designates A or G.
<220> FEATURE:
<221> NAME/KEY: misc_feature
<222> LOCATION: (22)..(22)
<223> OTHER INFORMATION: N designates A, C, G or T.
<220> FEATURE:
<221> NAME/KEY: misc_feature
<222> LOCATION: (25)..(25)
<223> OTHER INFORMATION: Y designates T or C.

<400> SEQUENCE: 2
cccaccaggn ggngtrttrt cnggytg                                      27
```

```
<210> SEQ ID NO 3
<211> LENGTH: 20
<212> TYPE: DNA
<213> ORGANISM: Artificial sequence
<220> FEATURE:
<223> OTHER INFORMATION: Primer 2328 TSP1dw

<400> SEQUENCE: 3
acttgcatcg acgttggctg                                                      20

<210> SEQ ID NO 4
<211> LENGTH: 24
<212> TYPE: DNA
<213> ORGANISM: Artificial sequence
<220> FEATURE:
<223> OTHER INFORMATION: Primer 2329 TSP2dw

<400> SEQUENCE: 4
actgagcagc aatggaactc tctg                                                 24

<210> SEQ ID NO 5
<211> LENGTH: 23
<212> TYPE: DNA
<213> ORGANISM: Artificial sequence
<220> FEATURE:
<223> OTHER INFORMATION: Primer 2330 TSP3dw

<400> SEQUENCE: 5
actgggttcc aatatcacga gtc                                                  23

<210> SEQ ID NO 6
<211> LENGTH: 24
<212> TYPE: DNA
<213> ORGANISM: Artificial sequence
<220> FEATURE:
<223> OTHER INFORMATION: Primer 2331 TSP1up

<400> SEQUENCE: 6
atggtggatc gctaaatcac actg                                                 24

<210> SEQ ID NO 7
<211> LENGTH: 21
<212> TYPE: DNA
<213> ORGANISM: Artificial sequence
<220> FEATURE:
<223> OTHER INFORMATION: Primer 2332 TSP2up

<400> SEQUENCE: 7
acgtctgccc aaacatacac g                                                    21

<210> SEQ ID NO 8
<211> LENGTH: 19
<212> TYPE: DNA
<213> ORGANISM: Artificial sequence
<220> FEATURE:
<223> OTHER INFORMATION: Primer 2333 TSP3up

<400> SEQUENCE: 8
accgcccatc aggctaatc                                                       19

<210> SEQ ID NO 9
<211> LENGTH: 1338
<212> TYPE: DNA
<213> ORGANISM: Hafnia alvei
<220> FEATURE:
<221> NAME/KEY: CDS
<222> LOCATION: (1)..(1338)
```

```
<220> FEATURE:
<221> NAME/KEY: sig_peptide
<222> LOCATION: (1)..(99)
<220> FEATURE:
<221> NAME/KEY: mat_peptide
<222> LOCATION: (100)..(1338)

<400> SEQUENCE: 9 atg aca atc tct ctg ttt aac cgt aat aaa ccc gct att gca cag cgt      48
Met Thr Ile Ser Leu Phe Asn Arg Asn Lys Pro Ala Ile Ala Gln Arg
            -30                 -25                 -20 att tta tgt cct ctg atc gtg gct tta ttc tca ggt tta ccg gca tac      96
Ile Leu Cys Pro Leu Ile Val Ala Leu Phe Ser Gly Leu Pro Ala Tyr
        -15                 -10                  -5 gcc agt gat acc gcc cct gct ggg ttc cag ttg gaa aag gtt gtt atc     144
Ala Ser Asp Thr Ala Pro Ala Gly Phe Gln Leu Glu Lys Val Val Ile
 -1   1              5                  10                  15 cta agc aga cat ggt gta cgc gcg cca acc aaa atg aca caa acg atg     192
Leu Ser Arg His Gly Val Arg Ala Pro Thr Lys Met Thr Gln Thr Met
                 20                  25                  30 cgc gac gtc aca cct cac cag tgg cct gaa tgg ccg gta aaa ctc ggc     240
Arg Asp Val Thr Pro His Gln Trp Pro Glu Trp Pro Val Lys Leu Gly
             35                  40                  45 tat atc acg cca cgc ggc gaa cat ctg att agc ctg atg ggc ggt ttt     288
Tyr Ile Thr Pro Arg Gly Glu His Leu Ile Ser Leu Met Gly Gly Phe
         50                  55                  60 tat cga gag cgc ttt cag caa caa ggt tta tta cct aag gat aac tgt     336
Tyr Arg Glu Arg Phe Gln Gln Gln Gly Leu Leu Pro Lys Asp Asn Cys
 65                  70                  75 cct aca cca gat gcc gtg tat gtt tgg gca gac gtc gat caa cgc aca     384
Pro Thr Pro Asp Ala Val Tyr Val Trp Ala Asp Val Asp Gln Arg Thr
 80                  85                  90                  95 cgt aaa acc ggc gag gct ttc tta gca ggt ctt gct ccc cag tgt gat     432
Arg Lys Thr Gly Glu Ala Phe Leu Ala Gly Leu Ala Pro Gln Cys Asp
                100                 105                 110 tta gcg atc cac cat cag caa aac act cag cag gcc gat ccg ctg ttc     480
Leu Ala Ile His His Gln Gln Asn Thr Gln Gln Ala Asp Pro Leu Phe
             115                 120                 125 cac cct gtg aaa gcc ggt att tgt tcg atg gat aaa tca cag gta cac     528
His Pro Val Lys Ala Gly Ile Cys Ser Met Asp Lys Ser Gln Val His
         130                 135                 140 gcc gcg gtt gaa aag cag gca ggc aca ccg att gag acg ctc aat caa     576
Ala Ala Val Glu Lys Gln Ala Gly Thr Pro Ile Glu Thr Leu Asn Gln
145                 150                 155 cgc tat caa gcc tct tta gcg ctg atg agt tcg gta ctc gat ttt cca     624
Arg Tyr Gln Ala Ser Leu Ala Leu Met Ser Ser Val Leu Asp Phe Pro
160                 165                 170                 175 aaa tcc ccc tat tgt cag cag cac aac att ggc aaa ctc tgc gat ttt     672
Lys Ser Pro Tyr Cys Gln Gln His Asn Ile Gly Lys Leu Cys Asp Phe
                180                 185                 190 tca cag gcg atg cct agc aga ctg gcg ata aat gac gac ggt aat aaa     720
Ser Gln Ala Met Pro Ser Arg Leu Ala Ile Asn Asp Asp Gly Asn Lys
             195                 200                 205 gtg gct ctc gaa ggt gcc gtg gga ctt gca tcg acg ttg gct gaa att     768
Val Ala Leu Glu Gly Ala Val Gly Leu Ala Ser Thr Leu Ala Glu Ile
         210                 215                 220 ttc ctg ctg gaa cac gct cag gga atg cct aaa gtg gct tgg ggg aat     816
Phe Leu Leu Glu His Ala Gln Gly Met Pro Lys Val Ala Trp Gly Asn
225                 230                 235 att cac act gag cag caa tgg aac tct ctg ttg aaa ttg cat aat gcg     864
Ile His Thr Glu Gln Gln Trp Asn Ser Leu Leu Lys Leu His Asn Ala
240                 245                 250                 255
```

```
cag ttt gac ttg atg tcg cgc acg ccc tat atc gcc aag cat aac ggt    912
Gln Phe Asp Leu Met Ser Arg Thr Pro Tyr Ile Ala Lys His Asn Gly
            260                 265                 270 act cca ctg ctg caa acc atc gcc cac gca ctg ggt tcc aat atc acg    960
Thr Pro Leu Leu Gln Thr Ile Ala His Ala Leu Gly Ser Asn Ile Thr
        275                 280                 285 agt cgc cca ctg ccg gat att tcg cca gac aat aag atc ctg ttt att    1008
Ser Arg Pro Leu Pro Asp Ile Ser Pro Asp Asn Lys Ile Leu Phe Ile
    290                 295                 300 gcc ggt cac gac acc aat att gcc aat att tct ggc atg tta ggg atg    1056
Ala Gly His Asp Thr Asn Ile Ala Asn Ile Ser Gly Met Leu Gly Met
305                 310                 315 aca tgg aca ctt ccg gga caa cca gat aac acg cct ccg ggt ggc gct    1104
Thr Trp Thr Leu Pro Gly Gln Pro Asp Asn Thr Pro Pro Gly Gly Ala
320                 325                 330                 335 ttg gtg ttt gaa cgc tgg gta gat aac gcg ggg aaa ccg tat gtt agc    1152
Leu Val Phe Glu Arg Trp Val Asp Asn Ala Gly Lys Pro Tyr Val Ser
                340                 345                 350 gtg aat atg gtg tat caa aca ctg gca cag ttg cac gac cag gcg ccg    1200
Val Asn Met Val Tyr Gln Thr Leu Ala Gln Leu His Asp Gln Ala Pro
            355                 360                 365 cta acg ttg cag cat cct gcg ggc agc gta cga cta aac ata ccg ggt    1248
Leu Thr Leu Gln His Pro Ala Gly Ser Val Arg Leu Asn Ile Pro Gly
        370                 375                 380 tgc agc gat caa acg ccc gat ggc tat tgc ccg ctc tcc acc ttc agc    1296
Cys Ser Asp Gln Thr Pro Asp Gly Tyr Cys Pro Leu Ser Thr Phe Ser
    385                 390                 395 cgc tta gtc agc cac agc gtt gag cct gcg tgc cag ctt cct            1338
Arg Leu Val Ser His Ser Val Glu Pro Ala Cys Gln Leu Pro
400                 405                 410

<210> SEQ ID NO 10
<211> LENGTH: 446
<212> TYPE: PRT
<213> ORGANISM: Hafnia alvei

<400> SEQUENCE: 10

Met Thr Ile Ser Leu Phe Asn Arg Asn Lys Pro Ala Ile Ala Gln Arg
            -30                 -25                 -20

Ile Leu Cys Pro Leu Ile Val Ala Leu Phe Ser Gly Leu Pro Ala Tyr
        -15                 -10                 -5

Ala Ser Asp Thr Ala Pro Ala Gly Phe Gln Leu Glu Lys Val Val Ile
-1   1               5                  10                  15

Leu Ser Arg His Gly Val Arg Ala Pro Thr Lys Met Thr Gln Thr Met
            20                  25                  30

Arg Asp Val Thr Pro His Gln Trp Pro Glu Trp Pro Val Lys Leu Gly
        35                  40                  45

Tyr Ile Thr Pro Arg Gly Glu His Leu Ile Ser Leu Met Gly Gly Phe
    50                  55                  60

Tyr Arg Glu Arg Phe Gln Gln Gln Gly Leu Leu Pro Lys Asp Asn Cys
65                  70                  75

Pro Thr Pro Asp Ala Val Tyr Val Trp Ala Asp Val Asp Gln Arg Thr
80                  85                  90                  95

Arg Lys Thr Gly Glu Ala Phe Leu Ala Gly Leu Ala Pro Gln Cys Asp
                100                 105                 110

Leu Ala Ile His His Gln Gln Asn Thr Gln Gln Ala Asp Pro Leu Phe
            115                 120                 125

His Pro Val Lys Ala Gly Ile Cys Ser Met Asp Lys Ser Gln Val His
        130                 135                 140
```

```
Ala Ala Val Glu Lys Gln Ala Gly Thr Pro Ile Glu Thr Leu Asn Gln
        145                 150                 155

Arg Tyr Gln Ala Ser Leu Ala Leu Met Ser Ser Val Leu Asp Phe Pro
160                 165                 170                 175

Lys Ser Pro Tyr Cys Gln Gln His Asn Ile Gly Lys Leu Cys Asp Phe
                180                 185                 190

Ser Gln Ala Met Pro Ser Arg Leu Ala Ile Asn Asp Asp Gly Asn Lys
            195                 200                 205

Val Ala Leu Glu Gly Ala Val Gly Leu Ala Ser Thr Leu Ala Glu Ile
        210                 215                 220

Phe Leu Leu Glu His Ala Gln Gly Met Pro Lys Val Ala Trp Gly Asn
    225                 230                 235

Ile His Thr Glu Gln Gln Trp Asn Ser Leu Leu Lys Leu His Asn Ala
240                 245                 250                 255

Gln Phe Asp Leu Met Ser Arg Thr Pro Tyr Ile Ala Lys His Asn Gly
                260                 265                 270

Thr Pro Leu Leu Gln Thr Ile Ala His Ala Leu Gly Ser Asn Ile Thr
            275                 280                 285

Ser Arg Pro Leu Pro Asp Ile Ser Pro Asp Asn Lys Ile Leu Phe Ile
        290                 295                 300

Ala Gly His Asp Thr Asn Ile Ala Asn Ile Ser Gly Met Leu Gly Met
    305                 310                 315

Thr Trp Thr Leu Pro Gly Gln Pro Asp Asn Thr Pro Pro Gly Gly Ala
320                 325                 330                 335

Leu Val Phe Glu Arg Trp Val Asp Asn Ala Gly Lys Pro Tyr Val Ser
                340                 345                 350

Val Asn Met Val Tyr Gln Thr Leu Ala Gln Leu His Asp Gln Ala Pro
            355                 360                 365

Leu Thr Leu Gln His Pro Ala Gly Ser Val Arg Leu Asn Ile Pro Gly
        370                 375                 380

Cys Ser Asp Gln Thr Pro Asp Gly Tyr Cys Pro Leu Ser Thr Phe Ser
    385                 390                 395

Arg Leu Val Ser His Ser Val Glu Pro Ala Cys Gln Leu Pro
400                 405                 410

<210> SEQ ID NO 11
<211> LENGTH: 81
<212> TYPE: DNA
<213> ORGANISM: Bacillus licheniformis
<220> FEATURE:
<221> NAME/KEY: CDS
<222> LOCATION: (1)..(81)
<223> OTHER INFORMATION: Savinase signal peptide

<400> SEQUENCE: 11 atg aag aaa ccg ttg ggg aaa att gtc gca agc acc gca cta ctc att    48
Met Lys Lys Pro Leu Gly Lys Ile Val Ala Ser Thr Ala Leu Leu Ile
1               5                   10                  15 tct gtt gct ttt agt tca tcg atc gca tcg gct                        81
Ser Val Ala Phe Ser Ser Ser Ile Ala Ser Ala
            20                  25

<210> SEQ ID NO 12
<211> LENGTH: 27
<212> TYPE: PRT
<213> ORGANISM: Bacillus licheniformis
```

```
<400> SEQUENCE: 12

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20              25
```